United States Patent
Brnardic et al.

(10) Patent No.: US 11,229,623 B2
(45) Date of Patent: *Jan. 25, 2022

(54) TRPV4 ANTAGONISTS

(71) Applicant: GlaxoSmithKline Intellectual Property (No.2) Limited, Middlesex (GB)

(72) Inventors: Edward J. Brnardic, Collegeville, PA (US); Carl A. Brooks, Collegeville, PA (US); Brian Griffin Lawhorn, Collegeville, PA (US); Guosen Ye, Collegeville, PA (US); Linda S. Barton, Collegeville, PA (US); Brian W. Budzik, Collegeville, PA (US); Jay M. Matthews, Collegeville, PA (US); John Jeffrey McAtee, Collegeville, PA (US); Jaclyn R. Patterson, Collegeville, PA (US); Joseph E. Pero, Collegeville, PA (US); Robert Sanchez, Collegeville, PA (US); Matthew Robert Sender, Collegeville, PA (US); Lamont Roscoe Terrell, Collegeville, PA (US); David J. Behm, Collegeville, PA (US); James V. Thomas, Collegeville, PA (US)

(73) Assignee: GLAXOSMITHKLINE INTELLECTUAL PROPERTY (NO. 2) LIMITED, Brentford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/796,989

(22) Filed: Feb. 21, 2020

(65) Prior Publication Data
US 2020/0261411 A1 Aug. 20, 2020

Related U.S. Application Data

(63) Continuation of application No. 16/334,391, filed as application No. PCT/IB2017/055700 on Sep. 20, 2017, now Pat. No. 10,588,891.

(Continued)

(51) Int. Cl.
| | |
|---|---|
| *A61K 31/40* | (2006.01) |
| *A61K 31/695* | (2006.01) |
| *A61K 31/424* | (2006.01) |
| *A61K 31/4155* | (2006.01) |
| *A61K 31/4025* | (2006.01) |

(Continued)

(52) U.S. Cl.
CPC ............ *A61K 31/40* (2013.01); *A61K 9/0019* (2013.01); *A61K 9/0053* (2013.01); *A61K 9/0073* (2013.01); *A61K 9/2059* (2013.01); *A61K 9/4866* (2013.01); *A61K 31/407* (2013.01); *A61K 31/4025* (2013.01); *A61K 31/4155* (2013.01); *A61K 31/424* (2013.01); *A61K 31/427* (2013.01); *A61K 31/429* (2013.01); *A61K 31/4245* (2013.01); *A61K 31/4439* (2013.01); *A61K 31/501* (2013.01); *A61K 31/506* (2013.01); *A61K 31/5386* (2013.01); *A61K 31/695* (2013.01); *A61K 45/06* (2013.01); *C07D 207/48* (2013.01); *C07D 401/12* (2013.01); *C07D 403/12* (2013.01); *C07D 409/12* (2013.01); *C07D 413/12* (2013.01); *C07D 417/12* (2013.01);

(Continued)

(58) Field of Classification Search
CPC .... A61K 31/40; A61K 31/695; A61K 31/424; A61K 31/4155; A61K 31/4025; A61K 31/4439; A61K 31/429; A61K 31/4245; A61K 31/501; A61K 31/506; A61K 31/5386; A61K 31/427; A61K 31/407; A61K 45/06; A61K 9/0053; A61K 9/0073; A61K 9/2059; A61K 9/4866; A61K 9/0019; C07D 207/48; C07D 513/04; C07D 401/12; C07D 409/12; C07D 498/10; C07D 403/12; C07D 491/07; C07D 413/12; C07F 7/0812; A61P 7/10; A61P 29/00; A61P 19/00; A61P 15/00; A61P 1/16; A61P 1/10; A61P 31/04; A61P 17/00; A61P 17/04; A61P 37/06; A61P 27/02; A61P 27/06; A61P 1/00; A61P 43/00; A61P 37/04; A61P 13/12; A61P 13/10; A61P 25/06; A61P 25/28; A61P 25/01; A61P 11/06; A61P 11/14; A61P 11/02; A61P 1/04; A61P 1/18; A61P 3/04; A61P 3/00; A61P 19/02; A61P 9/04; A61P 9/00; A61P 3/10
See application file for complete search history.

(56) References Cited

U.S. PATENT DOCUMENTS

| | | |
|---|---|---|
| 6,417,219 B1 | 7/2002 | Natchus et al. |
| 10,588,891 B2 * | 3/2020 | Brnardic ................ A61P 19/00 |

(Continued)

FOREIGN PATENT DOCUMENTS

| | | |
|---|---|---|
| AU | 2005237500 | 4/2005 |
| CA | 2263928 A1 | 8/1997 |

(Continued)

OTHER PUBLICATIONS

Rios et al., 2021, https://pubmed.ncbi.nlm.nih.gov/31048895/.*

(Continued)

*Primary Examiner* — Sun Jae Yoo
(74) *Attorney, Agent, or Firm* — Shan Liu; J. Scott Young

(57) ABSTRACT

The present invention relates to pyrrolidine sulfonamide analogs, pharmaceutical compositions containing them and their use as TRPV4 antagonists.

21 Claims, No Drawings

Related U.S. Application Data

(60) Provisional application No. 62/396,991, filed on Sep. 20, 2016, provisional application No. 62/482,296, filed on Apr. 6, 2017.

(51) Int. Cl.

| | | |
|---|---|---|
| A61K 31/4439 | (2006.01) | |
| A61K 31/429 | (2006.01) | |
| A61K 31/4245 | (2006.01) | |
| A61K 31/501 | (2006.01) | |
| A61K 31/506 | (2006.01) | |
| A61K 31/5386 | (2006.01) | |
| A61K 31/427 | (2006.01) | |
| A61K 31/407 | (2006.01) | |
| A61K 45/06 | (2006.01) | |
| C07D 207/48 | (2006.01) | |
| C07D 513/04 | (2006.01) | |
| C07D 401/12 | (2006.01) | |
| C07D 409/12 | (2006.01) | |
| C07D 498/10 | (2006.01) | |
| C07D 403/12 | (2006.01) | |
| C07D 413/12 | (2006.01) | |
| A61P 7/10 | (2006.01) | |
| A61P 29/00 | (2006.01) | |
| A61P 19/00 | (2006.01) | |
| A61P 15/00 | (2006.01) | |
| A61P 1/16 | (2006.01) | |
| A61P 1/10 | (2006.01) | |
| A61P 31/04 | (2006.01) | |
| A61P 17/00 | (2006.01) | |
| A61P 17/04 | (2006.01) | |
| A61P 37/06 | (2006.01) | |
| A61P 27/02 | (2006.01) | |
| A61P 27/06 | (2006.01) | |
| A61P 1/00 | (2006.01) | |
| A61P 43/00 | (2006.01) | |
| A61P 37/04 | (2006.01) | |
| A61P 13/12 | (2006.01) | |
| A61P 13/10 | (2006.01) | |
| A61P 25/06 | (2006.01) | |
| A61P 25/28 | (2006.01) | |
| A61P 11/06 | (2006.01) | |
| A61P 11/14 | (2006.01) | |
| A61P 11/02 | (2006.01) | |
| A61P 1/04 | (2006.01) | |
| A61P 1/18 | (2006.01) | |
| A61P 3/04 | (2006.01) | |
| A61P 3/00 | (2006.01) | |
| A61P 9/00 | (2006.01) | |
| A61P 3/10 | (2006.01) | |
| A61K 9/00 | (2006.01) | |
| A61K 9/20 | (2006.01) | |
| A61K 9/48 | (2006.01) | |
| C07D 417/12 | (2006.01) | |
| C07D 491/107 | (2006.01) | |
| C07F 7/08 | (2006.01) | |

(52) U.S. Cl.
CPC ....... *C07D 491/107* (2013.01); *C07D 498/10* (2013.01); *C07D 513/04* (2013.01); *C07F 7/0812* (2013.01)

(56) References Cited

U.S. PATENT DOCUMENTS

| | | |
|---|---|---|
| 2006/0155129 A1 | 7/2006 | Gharbaoui et al. |
| 2007/0142394 A1 | 6/2007 | Solomon et al. |
| 2008/0004287 A1 | 1/2008 | Ma et al. |
| 2008/0176861 A1 | 7/2008 | Guha et al. |
| 2011/0021487 A1 | 1/2011 | Hübsch et al. |
| 2016/0024049 A1 | 1/2016 | Koike et al. |

FOREIGN PATENT DOCUMENTS

| | | |
|---|---|---|
| CA | 2567343 A1 | 12/2005 |
| CA | 2891551 A1 | 5/2014 |
| CA | 2904393 A1 | 9/2014 |
| EP | 1760079 A1 | 3/2007 |
| JP | 2009523176 A | 6/2009 |
| WO | WO03/050154 A2 | 6/2003 |
| WO | WO2004/086865 A1 | 10/2004 |
| WO | WO2005/115983 A1 | 12/2005 |
| WO | WO2006005551 A1 | 1/2006 |
| WO | 2007082262 A2 | 7/2007 |
| WO | WO2009091941 A1 | 7/2009 |
| WO | WO10008739 A2 | 1/2010 |
| WO | 2014101295 A2 | 7/2014 |
| WO | WO14140310 A1 | 9/2014 |
| WO | WO2016016370 A1 | 2/2016 |
| WO | 2018055526 A1 | 3/2018 |
| WO | 2018055527 A1 | 3/2018 |

OTHER PUBLICATIONS

Ryskamp et al., 2016, Scientific Reports, 6:30583, pp. 1-15.*
Zamarripa et al., 201, Scientic Reports, 7:13094, pp. 1-16.*
Willette, et al., J. Pharmacol. Exp. Ther., 325:466-474 (2008).
Xu et al., Oncotarget, 7(25), 37622-37635 (Year: 2016).
Yang, et al., Am. J Physiol., 290:L1267-L1276 (2006).
Ye, et al., Cell, 151:96-110 (2012).
Yin, et al., Am J Respir Cell Mol Biol, 54: 370-383 (2016).
Zhu, et al., Hum Mol Genetics, 18: 2053-2062 (2009).
Zsomboketal et al., "TRP Channels as Therapeutic Targets in Diabetes and Obesity", Pharmaceuticals, 9(3): 50; 2016.
Achanta et al., https://www.atsjournals.org/doi/pdf/10.1164/ajrccm-conference.2019.199.1_MeetingAbstracts.A1017 (Year: 2019).
Akiyama, et al., J Invest Dermatol, 136:154-60; 2016.
Alessandri-Haber, et al., J Neurosci., 26: 3864-3874 (2006).
Alvarez, et al., Circ. Res., 99:988-985 (2006).
Auer-Grumbach, et al., Nat Genet. PMID: 20037588 (2009).
Balakrishna, et al., Am J Physiol Lung Cell Mol Physiol, 307: LI58-LI 72 (2014).
Basoglu Ok, et al., Chest., 148(2):430-435 (2015).
Belvisi et al., https://erj.ersjournals.com/content/50/2/1601357 (Year: 2017).
Bhargave, et al., Am J Rhinol, 22:7-12 (2008).
Bonvini, et al., J Allergy Clin Immunol, 138: 249-261 (2016).
Celiac, "Future Therapies for Celiac Disease", https://celiac.org/about-celiac-disease/future-therapies-for-celiac-disease (Year: 2019).
Chen, et al., J Biol Chem, 291: 10252-10262 (2016).
Corwin et al., https://www.atsjournals.org/doi/abs/10.1164/ajrccm-conference.2016.193.1_MeetingAbstracts.A1358 (Year: 2016).
Delany, et al., Physiol. Genomics, 4:165-174 (2001).
Deng, et al., Nat Genet PMID: 20037587 (2009).
Duan, et al., Mol Genet Genomics, 290: 1357-1365 (2015).
Earley, et al., Circ Res 97: 1270-1279 (2005).
Everaerts, et al., Proc Natl Acad Sci US A, 107: 19084-19089 (2010).
Fan, et al., J Biol. Chem., 284:27884-27891 (2009).
Grant, et al., J Physiol, 578: 715-733 (2007).
Guler, et al., J Neurosci, 22:6408-6414 (2002).
Hamanaka, et al., Am J Physiol., 293: L923-L932 (2007).
Hilfiker, et al.,ACSMed. Chem. Lett., 4: 293-296 (2013).
Hinata et al., "Sensitization of transient receptor potential vanilloid 4 and increasing its endogenous ligand 5,6-epoxyeicosatrienoic acid

(56) References Cited

OTHER PUBLICATIONS in rats with monoiodoacetate-induced osteoarthritis", Pain, May 2018; 159(5):939-947. https://www.ncbi.nlm.nih.gov/pubmed/29438227.
Huebsch, et al., 2009, caplus an 2009:1014102 (Year: 2009).
Jian, et al., Am. J Respir. Cell Mol. Biol., 38:386-392 (2008).
Jie, et al., Front Cell Neurosci, 9: 141 (2015).
Jo, et al., Proc Natl Acad Sci US A, 113: 3885-3890 (2016).
Krakow, etal.,AmJ Hum Genet, 84: 307-315 (2009).
Kuriyama, et al., Copper (II)-Catalyzed Monoarylation of Vicinal Diols with Diaryliodonium Salts, Chemistry A European Journal, 18(6): 1591-1594; 2012.
Landoure, et al., Nat Genet. PMID: 20037586 (2009).
Li, et al., Front Cell Neurosci, 7: 17 (2013).
Liedtke & Simon, Am J Physiol, 287: 269-271 (2004).
Liu, et al., "TRPV4 Inhibition Improved Myelination and Reduced Glia Reactivity and Inflammation in a Cuprizone-Induced Mouse Model of Demyelination", Frontiers in Cellular Neuroscience; vol. 12; pp. 1-12; 2019; URL: https://www.frontiersin.org/articles/10.3389/fncel.2018.00392/full.
Masuyama, et al., Cell Metab, 8: 257-265 (2008).
Matsunaga et al. full article, J. Am. Chem. Soc., 122, 10, 2000, 2252-2260.
Matsunaga et al., 2000, caplus an 2000:135981 (Year: 2000).
Monaghan, et al., PloS One, 10: e0128359 (2015).
Morty, et al., Am J Physiol Lung Cell Mol Physiol, 307: L817-L821 (2014).
Muramatsu, et al., J Biol. Chem., 282: 32158-32167 (2007).
Rahaman, et al., J Clin Invest, 124: 5225-5238 (2014).
Rock, et al., Nat Genet, 40: 999-1003 (2008).
Skerratt, et al., Identification of false positives in 'HTS hits to lead': The application of Bayesian models in HTS triage to rapidly deliver a series of selective TRPV4 antagonists, MEDCHEMCOMM, 4(1):244-251 (2013).
Strotmann, et al., Nat. Cell Biol., 2:695-702 (2000).
Thornelone, et al., Sci. Transl. Med., 4:159ra148 (2012).
Todaka, et al., J Biol Chem, 279: 35133-35138 (2004).
Vergnolle, Biochem Pharmacol, 89: 157-161 (2014.).
Vincent, et al., Biochem Biophys Res Commun, 389: 490-494 (2009).
Vriens, et al., Proc. Atl. Acad. Sci. USA, 101:396-401 (2004).
Wegierski, et al., J Biol. Chem., 284:2923-2933 (2009).

* cited by examiner ations.

TRPV4 ANTAGONISTS

CROSS-REFERENCE TO RELATED APPLICATIONS

This application is a continuation of U.S. application Ser. No. 16/334,391, filed on 19 Mar. 2019, which is a 371 of PCT/IB2017/055700, filed on 20 Sep. 2017, which claims priority to U.S. 62/396,991 filed on 20 Sep. 2016, and claims priority to U.S. 62/482,296 filed on 6 Apr. 2017, all of which are incorporated herein as though set forth in their entireties.

FIELD OF THE INVENTION

The present invention relates to pyrrolidine sulfonamide analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at physiological temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101:396-401). In addition, amongst other mechanisms proposed, tyrosine kinase activity, as well as protein kinase A and C, may also regulate TRPV4 (Wegierski et al., 2009. *J Biol Chem.* 284: 2923-33; Fan et al., 2009. *J Biol Chem* 284: 27884-91).

Heart failure results in the decreased ability of the left ventricle to pump blood into the peripheral circulation as indicated by a reduced ejection fraction and/or left ventricular dilation. This increases the left ventricular end diastolic pressure resulting in enhanced pulmonary blood pressures. This places the septal barrier, which separates the circulatory aqueous environment and the alveolar airspaces of the lung, at risk. Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and its level of expression is up-regulated in individuals with congestive heart failure (Thorneloe et al., 2012. *Sci Transl Med* 4: 159ra148). TRPV4 has been shown to mediate $Ca^{2+}$ entry in isolated endothelial cells and in intact lungs (Jian et al., 2009. *Am J Respir Cell Mol Biol* 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008. *J Pharmacol Exp Ther* 325: 466-74), at least partially due to the enhanced filtration at the septal barrier evoking lung edema and hemorrage (Alvarez et al., 2006. *Circ Res* 99: 988-95). Indeed, filtration at the septal barrier is increased in response to increased vascular and/or airway pressures and this response is dependent on the activity of TRPV4 channels (Jian et al., 2008. *Am J Respir Cell Mol Biol* 38:386-92). Consistent with these observations, TRPV4 antagonists prevent and resolve pulmonary edema in heart failure models (Thorneloe et al., 2012. *Sci Transl Med* 4: 159ra148). Overall this suggests a clinical benefit of inhibiting TRPV4 function in the treatment of acute and/or chronic heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis (Rahaman et al., 2014. *J Clin Invest* 124: 5225-38), cough (Bonvini et al., 2016 *J Allergy Clin Immunol* 138: 249-61) and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

TRPV4 has been shown to be involved in acute lung injury (ALI). Chemical activation of TRPV4 disrupts the alvelor septal blood barrier potentially leading to pulmonary edema (Alvarez et al, *Circ Res.* 2006 Oct. 27; 99(9):988-95). In animal models, TRPV4 antagonism attenuates lung damage induced by chemical agents and biological toxins such as HCl, chlorine gas, and platelet activating factor (Balakrishna et al., 2014. *Am J Physiol Lung Cell Mol Physiol* 307: L158-72; Morty et al., 2014. *Am J Physiol Lung Cell Mol Physiol* 307: L817-21; Yin et al., 2016. *Am J Respir Cell Mol Biol* 54: 370-83). In addition, TRPV4 is necessary in a process known to cause or worsen ALI in humans (Hamanaka et al, *Am J Physiol Lung Cell Mol Physiol.* 2007 October; 293(4):L923-32). Overall this suggests a clinical benefit of inhibiting TRPV4 function in the treatment of ARDS and ALI.

Furthermore, TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat Genet.* PMID: 20037588; Deng et al., 2009. *Nat Genet* PMID: 20037587; Landoure et al., 2009. *Nat Genet.* PMID: 20037586), cardiovascular disease (Earley et al., 2005. *Circ Res* 97: 1270-9; Yang et al., 2006. *Am. J Physiol.* 290: L1267-L1276), bone related disorders [including osteoarthritis (Muramatsu et al., 2007. *J. Biol. Chem.* 282: 32158-67), genetic gain-of function mutations (Krakow et al., 2009. *Am J Hum Genet* 84: 307-15; Rock et al., 2008 *Nat Genet* 40: 999-1003) and osteoclast differentiation (Masuyama et al. 2008. *Cell Metab* 8: 257-65)], itch (Akiyama et al., 2016. *J Invest Dermatol* 136: 154-60; Chen et al., 2016. *J Biol Chem* 291: 10252-62), stroke and disorders associated with cerebral edema (Li et al., 2013. *Front Cell Neurosci* 7: 17; Jie et al., 2015. *Front Cell Neurosci* 9: 141), inflammatory bowel disorders (Vergnolle, 2014. *Biochem Pharmacol* 89: 157-61), various diseases of the eye including glaucoma and retinopathy (Monaghan et al., 2015. *PloS One* 10: e0128359; Jo et al., 2016. *Proc Natl Acad Sci USA* 113:

3885-90), and metabolic syndrome including obestiy and diabetes (Ye et al., 2012. *Cell* 151: 96-110; Duan et al., 2015. *Mol Genet Genomics* 290: 1357-65).

Thornelone et al., 2012. *Sci Trans Med* 4:159ra148; Balakrishna et al., 2014 *Am J Physiol Lung Cell Mol Physiol.* 307:L158-L172; Hilfiker et al., 2013 *ACS Med. Chem. Lett.* 4: 293-296; Skerratt et al., 2013 Med. *Chem. Commun.* 4: 244-251; Everaerts et al., 2010, *Proc Natl Acad Sci USA* 107: 19084-19089; and Vincent et al., 2009 *Biochem Biophys Res Commun* 389: 490-494, describe antagonists of TRPV4.

Chronic cough is highly prevalent worldwide and is highly impactful on the quality of life for suffers, with typical cough rates of 10-50 coughs per hour, during waking hours. It is hypothesized that chronic cough reflects a state of neuronal hypersensitivity involving exaggerated spinal and cortical responses to afferent sensory signals in a manner similar to chronic pain. Activation of TRPV4 channels in vivo causes ATP release and triggers afferent sensory signals from the lung through binding of ATP to P2X3 channels, resulting in cough (Bonvini S J, et al., J Allergy Clin Immunol. 2016 July; 138(1):249-261.e12). ATP levels are increased in exhaled breath of patients with diseases associated with cough, for example COPD (Basoglu O K, et al., Chest. 2015 August; 148(2):430-5). Recently a P2X3 anatagonist has demonstrated high level efficacy in reducing chronic cough and improving quality of life scores in a phase 2 clinical trial (Abdulqawi R, et al. *Lancet.* 2015 Mar. 28; 385(9974):1198-1205). These clinical data along with data from pre-clinical models suggests a role for TRPV4 receptors in generating cough. TRPV4 receptors are expressed in airway smooth muscle cells (McAlexander M A, et al., *J Pharmacol Exp Ther.* 2014 April; 349(1):118-25), in airway epithelial cells (Delany N S, et al., *Physiol Genomics.* 2001 Jan. 19; 4(3):165-74), and in sensory neurons in the lung, including Ad-fibers from airway specific afferent neurons (Bonvini S J, et al., *J Allergy Clin Immunol.* 2016 July; 138(1):249-261.e12). Taken together, these data suggest a potential therapeutic role for TRPV4 antagonists in cough; including acute cough, sub-acute cough and chronic cough.

SUMMARY OF THE INVENTION

In one aspect this invention provides for pyrrolidine sulfonamide compounds of Formula (I), pharmaceutically acceptable salts thereof, and pharmaceutical compositions containing them.

In a second aspect, this invention provides for the use of the compounds of Formula (I) as TRPV4 antagonists.

In another aspect, this invention provides for compounds of Formula (I) for use in therapy.

In another aspect, this invention provides for the use of the compounds of Formula (I) for treating conditions associated with TRPV4 imbalance.

In yet another aspect, this invention provides for a method of treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence, which method comprises administering to a subject, suitably a human subject, in need thereof a therapeutically effective amount of a compound of Formula (I) or a pharmaceutically acceptable salt thereof.

In yet another aspect, this invention provides for the use of the compounds of Formula (I), and pharmaceutically acceptable salts thereof, for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

In yet another aspect, this invention provides for compounds of Formula (I), and pharmaceutically acceptable salts thereof, for use in the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

In yet another aspect, this invention provides for the use of the compounds of Formula (I), and pharmaceutically acceptable salts thereof, in the manufacture of a medicament for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, acute, chronic and polycystic kidney disease, stroke, glaucoma, retinopathy, endometriosis, preterm labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence.

The TRPV4 antagonist may be administered alone or in conjunction with one or more other therapeutic agents, eg. agents selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blockers, aldosterone antagonists, inotropes, NSAIDS, nitric oxide donors, calcium channel modulators, muscarinic antagonists, steroidal anti-inflammatory drugs, bronchodilators, antihistamines, leukotriene antagonist, HMG-CoA reductase inhibitors, dual non-selective Padrenoceptor and nq-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

This invention relates to compounds of Formula (I):

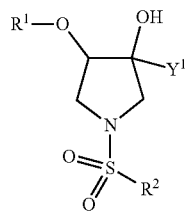

(I)

wherein:
R$^1$ is selected from:
  aryl,
  aryl substituted from 1 to 4 times by R$^a$,
  heteroaryl,
  heteroaryl substituted from 1 to 4 times by R$^a$
  bicycloheteroaryl, and
  bicycloheteroaryl substituted from 1 to 4 times by R$^a$;
R$^2$ is selected from:
  aryl,
  aryl substituted from 1 to 4 times by R$^b$,
  heteroaryl,
  heteroaryl substituted from 1 to 4 times by R$^b$
  bicycloheteroaryl, and
  bicycloheteroaryl substituted from 1 to 4 times by R$^b$,
  and
Y$^1$ is selected from:
  C$_{1-6}$alkyl, and
  C$_{1-6}$alkyl substituted with from: 1 to 9 substitutents independently selected
  from:
    fluoro,
    chloro,
    bromo,
    iodo,
    —OC$_{1-6}$alkyl,
    —OC$_{1-6}$alkyl substituted with from 1 to 6 substituents independently selected from: fluoro, oxo, —OH, —NH$_2$, and —CN,
    mercapto,
    —S(O)H,
    —S(O)$_2$H,
    oxo,
    hydroxy,
    amino,
    —NHR$^{x11}$,
      where R$^{x11}$ is selected from C$_{1-6}$alkyl, and C$_{1-6}$alkyl substituted with from 1 to 6 substituents independently selected from: fluoro, oxo, —OH, —NH$_2$, —CN, —OC$_{1-5}$alkyl,
      —OC$_{1-5}$alkyl substituted from 1 to 6 times by fluoro and —NH$_2$,
    —NR$^{x12}$R$^{x13}$
      where R$^{x12}$ and R$^{x13}$ are each independently selected from C$_{1-6}$alkyl, and C$_{1-6}$alkyl substituted with from 1 to 6 substituents independently selected from: fluoro, oxo, —OH, —NH$_2$, and —CN,
    —C(O)NH$_2$,
    aryl,
    —Oaryl,
    heteroaryl,
    —Oheteroaryl,
    —S(O)$_2$NH$_2$,
    —NHS(O)$_2$H,
    nitro, and
    cyano, or
  Y$^1$ is taken together with the adjacent —OH to form a heterocyclic ring selected from:
    morpholinyl,
    morpholinyl substituted by —CH$_3$, and
    oxazolidin-2-one;
each R$^a$ is independently selected from:
  fluoro,
  chloro,
  bromo,
  iodo,
  —OH,
  C$_{1-6}$alkyl,
  C$_{1-6}$alkyl substituted with from 1 to 5 substituents independently selected from: fluoro, chloro, bromo, iodo, C$_{1-4}$alkoxy, —OH, C$_{1-4}$alkyl, phenyl, oxo, —NO$_2$, —NH$_2$ and —CN,
  cyano,
  —OC$_{1-6}$alkyl,
  —OC$_{1-6}$alkyl substituted with from 1 to 5 substituents independently selected from: fluoro, chloro, bromo, iodo, C$_{1-4}$alkoxy, —OH, C$_{1-4}$alkyl, phenyl, oxo, —NO$_2$, —NH$_2$ and —CN,
  —Ophenyl, —C(O)OC$_{1-6}$alkyl,
—C(O)OC$_{1-6}$alkyl substituted 1 to 5 times by fluoro, and
—Ocycloalkyl; and
each R$^b$ is independently selected from:
  fluoro,
  chloro,
  bromo,
  iodo,
  —OH,
  C$_{1-6}$alkyl,
  C$_{1-6}$alkyl substituted with from 1 to 5 substituents independently selected from: fluoro, chloro, bromo, iodo, C$_{1-4}$alkoxy, —OH, C$_{1-4}$alkyl, phenyl, oxo, —NO$_2$, —NH$_2$ and —CN,
  cyano,
  —OC$_{1-6}$alkyl,
  —OC$_{1-6}$alkyl substituted with from 1 to 5 substituents independently selected from: fluoro, chloro, bromo, iodo, C$_{1-4}$alkoxy, —OH, C$_{1-4}$alkyl, phenyl, oxo, —NO$_2$, —NH$_2$ and —CN,
  phenyl,
  C$_{1-4}$alkylphenyl,
  C≡C—Si(CH$_3$)$_3$, and
  C≡C-cycloalkyl;
and pharmaceutically acceptable salts thereof.

Suitably, in the compounds of Formula (I), R$^1$ is selected from:
  aryl,
  aryl substituted from 1 to 4 times by R$^a$,
  heteroaryl,
  heteroaryl substituted from 1 to 4 times by R$^a$,
  bicycloheteroaryl, and
  bicycloheteroaryl substituted from 1 to 4 times by R$^a$.

Suitably, in the compounds of Formula (I), R$^2$ is selected from:
  aryl,
  aryl substituted from 1 to 4 times by R$^b$,
  heteroaryl,
  heteroaryl substituted from 1 to 4 times by R$^b$
  bicycloheteroaryl, and
  bicycloheteroaryl substituted from 1 to 4 times by R$^b$.

Suitably, in the compounds of Formula (I), Y$^1$ is selected from:
  C$_{1-6}$alkyl, and
  C$_{1-6}$alkyl substituted with from: 1 to 9 substitutents independently selected from:
    fluoro,
    chloro,
    bromo,
    iodo,
    —OC$_{1-6}$alkyl,
    —OC$_{1-6}$alkyl substituted with from 1 to 6 substituents independently selected from: fluoro, oxo, —OH, —NH$_2$, and —CN,
    mercapto,
    —S(O)H,
    —S(O)$_2$H,
    oxo,
    hydroxy,
    amino,
    —NHR$^{x11}$,
      where R$^{x11}$ is selected from C$_{1-6}$alkyl, and C$_{1-6}$alkyl substituted with from 1 to 6 substituents independently selected from: fluoro, oxo, —OH, —NH$_2$, —CN, —OC$_{1-5}$alkyl, —OC$_{1-5}$alkyl substituted from 1 to 6 times by fluoro and —NH$_2$,
    —NR$^{x12}$R$^{x13}$
      where R$^{x12}$ and R$^{x13}$ are each independently selected from C$_{1-6}$alkyl, and C$_{1-6}$alkyl substituted with from 1 to 6 substituents independently selected from: fluoro, oxo, —OH, —COOH, —NH$_2$, and —CN,
    —C(O)NH$_2$,
    aryl,
    —Oaryl,
    heteroaryl,
    —Oheteroaryl,
    —S(O)$_2$NH$_2$,
    —NHS(O)$_2$H,
    nitro, and
    cyano, or
  Y$^1$ is taken together with the adjacent —OH to form a heterocyclic ring selected from:
    morpholinyl,
    morpholinyl substituted by —CH$_3$, and
    oxazolidin-2-one.

Suitably, in the compounds of Formula (I), R$^a$ is selected from:
  fluoro,
  chloro,
  bromo,
  iodo,
  —OH,
  C$_{1-6}$alkyl,
  cyano,
  —CF$_3$,
  —C$_{1-5}$alkylCF$_3$,
  —CHF$_2$,
  —CH$_2$F,
  —OC$_{1-5}$alkyl,
  —OCF$_3$,
  —OC$_{1-5}$alkylCF$_3$,
  —Ophenyl,
  —Obenzyl,
  C$_{1-5}$alkylCN,
  —C(O)OC$_{1-5}$alkyl,
  —C(O)OH, and
  —Ocycloalkyl.

Suitably, in the compounds of Formula (I), R$^b$ is selected from:
  fluoro,
  chloro,
  bromo,
  iodo,
  —OH,
  C$_{1-6}$alkyl,
  cyano,
  —CF$_3$,
  —C$_{1-5}$alkylCF$_3$,
  —CHF$_2$,
  —CH$_2$F,
  —OC$_{1-5}$alkyl,
  —OCF$_3$,
  —OC$_{1-5}$alkylCF$_3$,
  —C(O)CH$_3$,
  —OCHF$_2$,
  phenyl,
  —C≡C—Si(CH$_3$)$_3$,
  —C≡C-cycloalkyl, and
  —C≡C-phenyl.

Included in the compounds of Formula (I) are compounds of Formula (II):

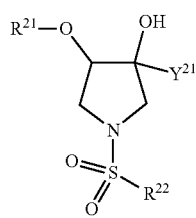

(II)

wherein:
R²¹ is selected from:
aryl,
aryl substituted from 1 to 3 times by $R^{a2}$,
heteroaryl,
heteroaryl substituted from 1 to 3 times by $R^{a2}$
bicycloheteroaryl, and
bicycloheteroaryl substituted from 1 to 3 times by $R^{a2}$;
R²² is selected from:
aryl,
aryl substituted from 1 to 3 times by $R^{b2}$,
bicycloheteroaryl,
bicycloheteroaryl substituted from 1 to 3 times by $R^{b2}$;
heteroaryl, and
heteroaryl substituted from 1 to 3 times by $R^{b2}$, and
Y²¹ is selected from:
$C_{1-6}$alkyl, and
$C_{1-6}$alkyl substituted with from: 1 to 9 substitutents independently selected from:
fluoro,
chloro,
bromo,
iodo,
—O$C_{1-6}$alkyl,
—O$C_{1-6}$alkyl substituted with from 1 to 6 substituents independently selected from: fluoro, oxo, —OH, —NH₂, and —CN,
mercapto,
—S(O)H,
—S(O)₂H,
oxo,
hydroxy,
amino,
—NHR$^{x21}$,
where $R^{x21}$ is selected from $C_{1-6}$alkyl, and $C_{1-6}$alkyl substituted with from 1 to 6 substituents independently selected from: fluoro, oxo, —OH, —NH₂, and —CN,
—NR$^{x22}$R$^{x23}$
where $R^{x22}$ and $R^{x23}$ are each independently selected from $C_{1-6}$alkyl, and $C_{1-6}$alkyl substituted with from 1 to 6 substituents independently selected from: fluoro, oxo, —OH, —NH₂, and —CN,
—C(O)NH₂,
aryl,
—Oaryl,
heteroaryl,
—Oheteroaryl,
—S(O)₂NH₂,
—NHS(O)₂H,
nitro, and
cyano, or
Y²¹ is taken together with the adjacent —OH to form a heterocyclic ring selected from:

morpholinyl,
morpholinyl substituted by —CH₃, and
oxazolidin-2-one;
each $R^{a2}$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO₂, —NH₂ and —CN,
cyano,
—O$C_{1-6}$alkyl,
—O$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO₂, —NH₂ and —CN,
—Ophenyl,
—C(O)O$C_{1-5}$alkyl,
—C(O)O$C_{1-5}$alkyl substituted 1 to 5 times by fluoro, and
—Ocycloalkyl; and
each $R^{b2}$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO₂, —NH₂ and —CN,
cyano,
—O$C_{1-6}$alkyl,
—O$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO₂, —NH₂ and —CN,
phenyl,
$C_{1-4}$alkylphenyl,
—C≡C—Si(CH₃)₃, and
—C≡C-cycloalkyl;
and pharmaceutically acceptable salts thereof.
Suitably, in the compounds of Formula (II), R²¹ is selected from:
aryl,
aryl substituted from 1 to 3 times by $R^{a2}$,
heteroaryl,
heteroaryl substituted from 1 to 3 times by $R^{a2}$
bicycloheteroaryl, and
bicycloheteroaryl substituted from 1 to 3 times by $R^{a2}$.
Suitably, in the compounds of Formula (II), R²² is selected from:
aryl,
aryl substituted from 1 to 3 times by $R^{b2}$,
bicycloheteroaryl,
bicycloheteroaryl substituted from 1 to 3 times by $R^{b2}$;
heteroaryl, and
heteroaryl substituted from 1 to 3 times by $R^{b2}$.
Suitably, in the compounds of Formula (II), Y²¹ is selected from:
$C_{1-6}$alkyl, and
$C_{1-6}$alkyl substituted with from: 1 to 9 substitutents independently selected from:

fluoro,
chloro,
bromo,
iodo,
—OC$_{1-6}$alkyl,
—OC$_{1-6}$alkyl substituted with from 1 to 6 substituents independently selected from: fluoro, oxo, —OH, —NH$_2$, and —CN,
mercapto,
—S(O)H,
—S(O)$_2$H,
oxo,
hydroxy,
amino,
—NHR$^{x21}$,
  where R$^{x21}$ is selected from C$_{1-6}$alkyl, and C$_{1-6}$alkyl substituted with from 1 to 6 substituents independently selected from: fluoro, oxo, —OH, —NH$_2$, and —CN,
—NR$^{x22}$R$^{x23}$
  where R$^{x22}$ and R$^{x23}$ are each independently selected from C$_{1-6}$alkyl, and C$_{1-6}$alkyl substituted with from 1 to 6 substituents independently selected from: fluoro, oxo, —OH, —NH$_2$, and —CN,
—C(O)NH$_2$,
aryl,
—Oaryl,
heteroaryl,
—Oheteroaryl,
—S(O)$_2$NH$_2$,
—NHS(O)$_2$H,
nitro, and
cyano, or
Y$^{21}$ is taken together with the adjacent —OH to form a heterocyclic ring selected from:
morpholinyl,
morpholinyl substituted by —CH$_3$, and
oxazolidin-2-one.
Suitably, in the compounds of Formula (II), R$^{a2}$ is selected from:
  fluoro,
  chloro,
  bromo,
  iodo,
  —OH,
  C$_{1-6}$alkyl,
  cyano,
  —CF$_3$,
  —C$_{1-5}$alkylCF$_3$,
  —CHF$_2$,
  —CH$_2$F,
  —OC$_{1-5}$alkyl,
  —OCF$_3$,
  —OC$_{1-5}$alkylCF$_3$,
  —Ophenyl,
  —Obenzyl,
  C$_{1-5}$alkylCN,
  —C(O)OC$_{1-5}$alkyl,
  —C(O)OH, and
  —Ocycloalkyl.
Suitably, in the compounds of Formula (II), R$^{b2}$ is selected from:
  fluoro,
  chloro,
  bromo,
  iodo,
  —OH,
  C$_{1-6}$alkyl,
  cyano,
  —CF$_3$,
  —C$_{1-5}$alkylCF$_3$,
  —CHF$_2$,
  —CH$_2$F,
  —OC$_{1-5}$alkyl,
  —OCF$_3$,
  —OC$_{1-5}$alkylCF$_3$,
  —C(O)CH$_3$,
  —OCHF$_2$,
  phenyl,
  —C≡C—Si(CH$_3$)$_3$,
  —C≡C-cycloalkyl, and
  —C≡C-phenyl.
Included in the compounds of Formula (I) are compounds of Formula (III):

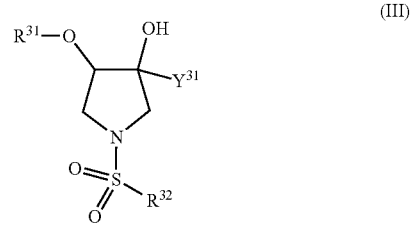

(III)

wherein:
  R$^{31}$ is selected from:
    phenyl,
    phenyl substituted from 1 to 3 times by R$^{a3}$
    benzo[c][1,2,5]oxadiazole,
    benzo[c][1,2,5]oxadiazole substituted from 1 to 3 times by R$^{a3}$
    pyrimidine,
    pyrimidine substituted from 1 to 3 times by R$^{a3}$
    naphthalene,
    naphthalene substituted from 1 to 3 times by R$^{a3}$
    pyridine, and
    pyridine substituted from 1 to 3 times by R$^{a3}$;
  R$^{32}$ is selected from:
    phenyl,
    phenyl substituted from 1 to 3 times by R$^{b3}$
    pyridine,
    pyridine substituted from 1 to 3 times by R$^{b3}$
    benzo[c][1,2,5]oxadiazole,
    benzo[c][1,2,5]oxadiazole substituted from 1 to 3 times by R$^{b3}$
    thiophene,
    thiophene substituted from 1 to 3 times by R$^{b3}$
    thiazole,
    thiazole substituted from 1 to 3 times by R$^{b3}$
    pyrazole,
    pyrazole substituted from 1 to 3 times by R$^{b3}$
    imidazo[2,1-b]thiazole,
    imidazo[2,1-b]thiazole substituted from 1 to 3 times by R$^{b3}$
    pyrimidine,
    pyrimidine substituted from 1 to 3 times by R$^{b3}$
    pyridazine, and
    pyridazine substituted from 1 to 3 times by R$^{b3}$; and
  Y$^{31}$ is selected from:
    —CH$_2$OH,
    —CH(OH)CH$_3$, —CH(OH)CH$_2$CH$_3$,
—CH(OH)CH$_2$CH$_2$CH$_3$,
—CH(OH)CH$_2$CH(CH$_3$)$_2$,
—C(OH)(CH$_3$)$_2$,
—CH$_2$NH$_2$,
—CH$_2$NHR$^{x30}$,
—CH$_2$NR$^{x30}$R$^{x30}$,
—CH(NH$_2$)CH$_3$, or
Y$^{31}$ is taken together with the adjacent —OH to form a heterocyclic ring selected from:
morpholinyl,
morpholinyl substituted by —CH$_3$, and
oxazolidin-2-one,
where each R$^{x30}$ is independently selected from: C$_{1-6}$alkyl, and C$_{1-6}$alkyl substituted with from 1 to 6 substituents independently selected from: fluoro, oxo, —OH, —NH$_2$, and —CN;
each R$^{a3}$ is independently selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—Ophenyl,
—Obenzyl,
C$_{1-5}$alkylCN,
—C(O)OC$_{1-5}$alkyl,
—C(O)OH, and
—Ocycloalkyl; and
each R$^{b3}$ is independently selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—C(O)CH$_3$,
—OCHF$_2$,
phenyl,
—C≡C—Si(CH$_3$)$_3$,
—C≡C-cycloalkyl, and
—C≡C-phenyl;
and pharmaceutically acceptable salts thereof.
Suitably, in the compounds of Formula (III), R$^{31}$ is selected from:
phenyl,
phenyl substituted from 1 to 3 times by R$^{a3}$
benzo[c][1,2,5]oxadiazole,
benzo[c][1,2,5]oxadiazole substituted from 1 to 3 times by R$^{a3}$ pyrimidine,
pyrimidine substituted from 1 to 3 times by R$^{a3}$,
naphthalene,
naphthalene substituted from 1 to 3 times by R$^{a3}$,
pyridine, and
pyridine substituted from 1 to 3 times by R$^{a3}$.
Suitably, in the compounds of Formula (III), R$^{32}$ is selected from:
phenyl,
phenyl substituted from 1 to 3 times by R$^{b3}$,
pyridine,
pyridine substituted from 1 to 3 times by R$^{b3}$,
benzo[c][1,2,5]oxadiazole,
benzo[c][1,2,5]oxadiazole substituted from 1 to 3 times by R$^{b3}$
thiophene,
thiophene substituted from 1 to 3 times by R$^{b3}$,
thiazole,
thiazole substituted from 1 to 3 times by R$^{b3}$,
pyrazole,
pyrazole substituted from 1 to 3 times by R$^{b3}$,
imidazo[2,1-b]thiazole,
imidazo[2,1-b]thiazole substituted from 1 to 3 times by R$^{b3}$
pyrimidine,
pyrimidine substituted from 1 to 3 times by R$^{b3}$
pyridazine, and
pyridazine substituted from 1 to 3 times by R$^{b3}$.
Suitably, in the compounds of Formula (III), Y$^{31}$ is selected from:
—CH$_2$OH,
—CH(OH)CH$_3$,
—CH(OH)CH$_2$CH$_3$,
—CH(OH)CH$_2$CH$_2$CH$_3$,
—CH(OH)CH$_2$CH(CH$_3$)$_2$,
—C(OH)(CH$_3$)$_2$,
—CH$_2$NH$_2$,
—CH$_2$NHR$^{x30}$,
—CH$_2$NR$^{x30}$R$^{x30}$,
—CH(NH$_2$)CH$_3$, or
Y$^{31}$ is taken together with the adjacent —OH to form a heterocyclic ring selected from:
morpholinyl,
morpholinyl substituted by —CH$_3$, and
oxazolidin-2-one,
where each R$^{x30}$ is independently selected from: C$_{1-6}$alkyl, and C$_{1-6}$alkyl substituted with from 1 to 6 substituents independently selected from: fluoro, oxo, —OH, —NH$_2$, and —CN.
Suitably, in the compounds of Formula (III), R$^{a3}$ is selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—Ophenyl,
—Obenzyl, C$_{1-5}$alkylCN,
—C(O)OC$_{1-5}$alkyl,
—C(O)OH, and
—Ocycloalkyl.

Suitably, in the compounds of Formula (III), R$^{b3}$ is selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—C(O)CH$_3$,
—OCHF$_2$,
phenyl,
—C≡C—Si(CH$_3$)$_3$,
—C≡C-cycloalkyl, and
—C≡C-phenyl.

Included in the compounds of Formula (I) are compounds of Formula (IV):

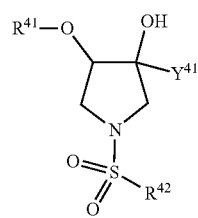

(IV)

wherein:
R$^{41}$ is selected from:
  phenyl, and
  phenyl substituted from 1 to 3 times by R$^{a4}$;
R$^{42}$ is selected from:
  phenyl,
  phenyl substituted from 1 to 3 times by R$^{b4}$
  pyridine, and
  pyridine substituted from 1 to 3 times by R$^{b4}$; and
Y$^{41}$ is selected from:
  —CH$_2$OH,
  —CH$_2$NH$_2$,
  —CH$_2$NHR$^{x40}$,
  —CH$_2$NR$^{x40}$R$^{x40}$, and
  —CH(NH$_2$)CH$_3$, or
Y$^{41}$ is taken together with the adjacent —OH to form a heterocyclic ring selected from:
  morpholinyl,
  morpholinyl substituted by —CH$_3$, and
  oxazolidin-2-one,
    where each R$^{x40}$ is independently selected from:
      C$_{1-6}$alkyl, and C$_{1-6}$alkyl substituted with from 1 to 6 substituents independently selected from: fluoro, oxo, —OH, —NH$_2$, and —CN;
each R$^{a4}$ is independently selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—Ophenyl,
—Obenzyl,
C$_{1-5}$alkylCN,
—C(O)OC$_{1-5}$alkyl,
—C(O)OH, and
—Ocycloalkyl; and
each R$^{b4}$ is independently selected from:
fluoro,
chloro,
bromo,
iodo,
—OH,
C$_{1-6}$alkyl,
cyano,
—CF$_3$,
—C$_{1-5}$alkylCF$_3$,
—CHF$_2$,
—CH$_2$F,
—OC$_{1-5}$alkyl,
—OCF$_3$,
—OC$_{1-5}$alkylCF$_3$,
—C(O)CH$_3$,
—OCHF$_2$,
phenyl,
—C≡C—Si(CH$_3$)$_3$,
—C≡C-cycloalkyl, and
—C≡C-phenyl;
and pharmaceutically acceptable salts thereof.

Suitably, in the compounds of Formula (IV), R$^{41}$ is selected from:
  phenyl, and
  phenyl substituted from 1 to 3 times by R$^{a4}$.

Suitably, in the compounds of Formula (IV), R$^{42}$ is selected from:
  phenyl,
  phenyl substituted from 1 to 3 times by R$^{b4}$
  pyridine, and
  pyridine substituted from 1 to 3 times by R$^{b4}$.

Suitably, in the compounds of Formula (IV), Y$^{41}$ is selected from:
  —CH$_2$OH,
  —CH$_2$NH$_2$,
  —CH$_2$NHR$^{x40}$,
  —CH$_2$NR$^{x40}$R$^{x40}$, and
  —CH(NH$_2$)CH$_3$, or
Y$^{41}$ is taken together with the adjacent —OH to form a heterocyclic ring selected from:
  morpholinyl,
  morpholinyl substituted by —CH$_3$, and
  oxazolidin-2-one,
    where each R$^{x40}$ is independently selected from: C$_{1-6}$alkyl, and C$_{1-6}$alkyl substituted with from 1 to 6 substituents independently selected from: fluoro, oxo, —OH, —NH$_2$, and —CN.

Suitably, in the compounds of Formula (IV), $R^{a4}$ is selected from:
fluoro,
chloro,
bromo,
iodo,
—OH,
$C_{1-6}$alkyl,
cyano,
—$CF_3$,
—$C_{1-5}$alkyl$CF_3$,
—$CHF_2$,
—$CH_2F$,
—$OC_{1-5}$alkyl,
—$OCF_3$,
—$OC_{1-5}$alkyl$CF_3$,
—Ophenyl,
—Obenzyl,
$C_{1-5}$alkylCN,
—C(O)O$C_{1-5}$alkyl,
—C(O)OH, and
—Ocycloalkyl.

Suitably, in the compounds of Formula (IV), $R^{b4}$ is selected from:
fluoro,
chloro,
bromo,
iodo,
—OH,
$C_{1-6}$alkyl,
cyano,
—$CF_3$,
—$C_{1-5}$alkyl$CF_3$,
—$CHF_2$,
—$CH_2F$,
—$OC_{1-5}$alkyl,
—$OCF_3$,
—$OC_{1-5}$alkyl$CF_3$,
—C(O)$CH_3$,
—$OCHF_2$,
phenyl,
—C≡C—Si$(CH_3)_3$,
—C≡C-cycloalkyl, and
—C≡C-phenyl.

Suitably, in the compounds of Formula (I), $R^1$ is phenyl independently substituted from 1 to 3 times by cyano and/or fluoro.

Suitably, in the compounds of Formula (I), $R^2$ is a substituted phenyl or a substituted pyridine.

Suitably, in the compounds of Formula (I), $Y^1$ is selected from: —$CH_2OH$, —$CH_2NH_2$, and —$CH_2NHCH_3$.

Representative compounds of the invention include the specific compounds described herein, e.g., the compounds of Formula (I) of the Examples, as well as any alternative stereoisomeric forms, free acid/base forms, salt forms, and alternative salt forms thereof (particularly pharmaceutically acceptable salt or alternative salt forms thereof), as applicable. Accordingly, in some embodiments the compound of the invention is a compound of Formula (I) selected from:

4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((2,4-dichlorophenyl)sulfonyl)-4-hydroxy-4-(hydroxymethyl)pyrrolidin-3-yl)oxy)-2-fluorobenzonitrile;

4-(((3S,4R)-1-((4-chloro-2-cyanophenyl)sulfonyl)-4-hydroxy-4-(hydroxymethyl)pyrrolidin-3-yl)oxy)-2-fluorobenzonitrile;

(3R,4S)-1-((2,4-dichlorophenyl)sulfonyl)-4-(3,4-difluorophenoxy)-3-(hydroxymethyl) pyrrolidin-3-ol;

2-fluoro-4-(((3S,4R)-4-hydroxy-4-(hydroxymethyl)-1-((6-(trifluoromethyl)pyridin-3-yl)sulfonyl)pyrrolidin-3-yl)oxy)benzonitrile;

2-(((3R,4S)-4-(4-chlorophenoxy)-3-hydroxy-3-(hydroxymethyl)pyrrolidin-1-yl)sulfonyl)-5-(trifluoromethyl)benzonitrile;

2-(((3R,4S)-4-(benzo[c][1,2,5]oxadiazol-5-yloxy)-3-hydroxy-3-(hydroxymethyl)pyrrolidin-1-yl)sulfonyl)-5-(trifluoromethyl)benzonitrile;

5-chloro-2-(((3R,4S)-4-(3,4-difluorophenoxy)-3-hydroxy-3-(hydroxymethyl) pyrrolidin-1-yl)sulfonyl)benzonitrile;

2-(((3R,4S)-4-(4-cyano-2-fluorophenoxy)-3-hydroxy-3-(hydroxymethyl) pyrrolidin-1-yl)sulfonyl)-5-(trifluoromethyl)benzonitrile;

2-(((3R,4S)-4-(4-cyano-2-methoxyphenoxy)-3-hydroxy-3-(hydroxymethyl)pyrrolidin-1-yl)sulfonyl)-5-(trifluoromethyl)benzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethyl)benzonitrile;

2-(((3R,4S)-4-(4-cyano-2-ethoxyphenoxy)-3-hydroxy-3-(hydroxymethyl)pyrrolidin-1-yl)sulfonyl)-5-(trifluoromethyl)benzonitrile;

5-(((3S,4R)-1-((2-cyano-4-(trifluoromethyl)phenyl)sulfonyl)-4-hydroxy-4-(hydroxymethyl)pyrrolidin-3-yl)oxy) pyrimidine-2-carbonitrile;

2-(((3R,4S)-4-(2-chloro-4-cyanophenoxy)-3-hydroxy-3-(hydroxymethyl)pyrrolidin-1-yl)sulfonyl)-5-(trifluoromethyl)benzonitrile;

4-(((3S,4R)-1-((2-cyano-4-(trifluoromethyl)phenyl)sulfonyl)-4-hydroxy-4-(hydroxymethyl) pyrrolidin-3-yl)oxy)-2,3-difluorobenzonitrile;

2-(((3R,4S)-4-(4-cyano-2-methylphenoxy)-3-hydroxy-3-(hydroxymethyl)pyrrolidin-1-yl)sulfonyl)-5-(trifluoromethyl)benzonitrile;

2-(((3R,4S)-4-(4-cyano-2-(trifluoromethyl)phenoxy)-3-hydroxy-3-(hydroxymethyl) pyrrolidin-1-yl)sulfonyl)-5-(trifluoromethyl)benzonitrile;

6-(((3S,4R)-1-((2-cyano-4-(trifluoromethyl)phenyl)sulfonyl)-4-hydroxy-4-(hydroxymethyl) pyrrolidin-3-yl)oxy)-2-naphthonitrile;

4-(((3S,4R)-1-((2-cyano-4-(trifluoromethyl)phenyl)sulfonyl)-4-hydroxy-4-(hydroxymethyl) pyrrolidin-3-yl)oxy)-2,5-difluorobenzonitrile;

4-(((3S,4R)-1-((2-cyano-4-(trifluoromethyl)phenyl)sulfonyl)-4-hydroxy-4-(hydroxymethyl) pyrrolidin-3-yl)oxy)-2,6-difluorobenzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethoxy)benzonitrile;

5-chloro-2-(((3R,4S)-3-hydroxy-3-(hydroxymethyl)-4-(3,4,5-trifluorophenoxy)pyrrolidin-1-yl)sulfonyl)benzonitrile;

5-chloro-2-(((3R,4S)-3-hydroxy-3-(hydroxymethyl)-4-(2,3,4-trifluorophenoxy)pyrrolidin-1-yl)sulfonyl)benzonitrile;

5-chloro-2-(((3R,4S)-3-hydroxy-3-(hydroxymethyl)-4-(2,4,5-trifluorophenoxy)pyrrolidin-1-yl)sulfonyl)benzonitrile;

2-(((3R,4S)-4-(3,4-difluorophenoxy)-3-hydroxy-3-(hydroxymethyl)pyrrolidin-1-yl)sulfonyl)-5-(trifluoromethyl)benzonitrile;

2-(((3R,4S)-3-hydroxy-3-(hydroxymethyl)-4-(3,4,5-trifluorophenoxy)pyrrolidin-1-yl)sulfonyl)-5-(trifluoromethyl)benzonitrile;

2-(((3R,4S)-3-hydroxy-3-(hydroxymethyl)-4-(2,4,5-trifluorophenoxy)pyrrolidin-1-yl)sulfonyl)-5-(trifluoromethyl) benzonitrile;
2-(((3R,4S)-3-hydroxy-3-(hydroxymethyl)-4-(2,3,4-trifluorophenoxy) pyrrolidin-1-yl) sulfonyl)-5-(trifluoromethyl) benzonitrile;
2-(((3R,4S)-4-(4-cyanophenoxy)-3-hydroxy-3-(hydroxymethyl)pyrrolidin-1-yl)sulfonyl)-5-(trifluoromethyl)benzonitrile;
2-(((3R,4S)-4-(4-chloro-3-fluorophenoxy)-3-hydroxy-3-(hydroxymethyl)pyrrolidin-1-yl)sulfonyl)-5-(trifluoromethyl)benzonitrile;
2-(((3R,4S)-4-(3-fluoro-4-(trifluoromethyl)phenoxy)-3-hydroxy-3-(hydroxymethyl)pyrrolidin-1-yl)sulfonyl)-5-(trifluoromethyl)benzonitrile;
2-(((3R,4S)-4-(4-(cyanomethyl) phenoxy)-3-hydroxy-3-(hydroxymethyl)pyrrolidin-1-yl)sulfonyl)-5-(trifluoromethyl)benzonitrile;
2-(((3R,4S)-4-(3-(cyanomethyl) phenoxy)-3-hydroxy-3-(hydroxymethyl)pyrrolidin-1-yl)sulfonyl)-5-(trifluoromethyl)benzonitrile;
methyl 5-cyano-2-(((3S,4R)-1-((2-cyano-4-(trifluoromethyl)phenyl) sulfonyl)-4-hydroxy-4-(hydroxymethyl) pyrrolidin-3-yl)oxy)benzoate;
(3R,4S)-1-((2,4-dichlorophenyl)sulfonyl)-3-(hydroxymethyl)-4-((6-(trifluoromethyl)pyridin-3-yl)oxy)pyrrolidin-3-ol;
5-(((3S,4R)-1-((2,4-dichlorophenyl)sulfonyl)-4-hydroxy-4-(hydroxymethyl)pyrrolidin-3-yl)oxy)-3-fluoropicolinonitrile;
2-(((3R,4S)-3-hydroxy-3-(hydroxymethyl)-4-(4-(trifluoromethyl)phenoxy)pyrrolidin-1-yl)sulfonyl)-5-(trifluoromethyl)benzonitrile;
2-(((3R,4S)-4-(4-fluoro-3-(trifluoromethyl)phenoxy)-3-hydroxy-3-(hydroxymethyl) pyrrolidin-1-yl)sulfonyl)-5-(trifluoromethyl)benzonitrile;
2-(((3R,4S)-4-(3,4-dichlorophenoxy)-3-hydroxy-3-(hydroxymethyl)pyrrolidin-1-yl)sulfonyl)-5-(trifluoromethyl)benzonitrile;
2-(((3R,4S)-4-(3-fluoro-4-(trifluoromethoxy)phenoxy)-3-hydroxy-3-(hydroxymethyl)pyrrolidin-1-yl)sulfonyl)-5-(trifluoromethyl)benzonitrile;
2-(((3R,4S)-4-(3-chloro-4-fluorophenoxy)-3-hydroxy-3-(hydroxymethyl)pyrrolidin-1-yl)sulfonyl)-5-(trifluoromethyl)benzonitrile;
2-(((3R,4S)-3-hydroxy-3-(hydroxymethyl)-4-((6-(trifluoromethyl)pyridin-3-yl)oxy) pyrrolidin-1-yl)sulfonyl)-5-(trifluoromethyl)benzonitrile;
2-(((3R,4S)-4-(3-fluoro-4-methoxyphenoxy)-3-hydroxy-3-(hydroxymethyl)pyrrolidin-1-yl)sulfonyl)-5-(trifluoromethyl)benzonitrile;
2-(((3R,4S)-4-(4-cyano-2-isopropoxyphenoxy)-3-hydroxy-3-(hydroxymethyl) pyrrolidin-1-yl)sulfonyl)-5-(trifluoromethyl)benzonitrile;
2-(((3R,4S)-4-(4-cyano-2-cyclopropoxyphenoxy)-3-hydroxy-3-(hydroxymethyl) pyrrolidin-1-yl)sulfonyl)-5-(trifluoromethyl)benzonitrile;
2-(((3R,4S)-3-hydroxy-3-(hydroxymethyl)-4-phenoxypyrrolidin-1-yl)sulfonyl)-5-(trifluoromethyl)benzonitrile;
2-(((3R,4S)-4-(4-fluorophenoxy)-3-hydroxy-3-(hydroxymethyl) pyrrolidin-1-yl)sulfonyl)-5-(trifluoromethyl)benzonitrile;
2-(((3R,4S)-4-(4-chloro-2-methoxyphenoxy)-3-hydroxy-3-(hydroxymethyl)pyrrolidin-1-yl)sulfonyl)-5-(trifluoromethyl)benzonitrile;
4-(((3S,4R)-1-((2-chloro-4-(trifluoromethyl)phenyl)sulfonyl)-4-hydroxy-4-(hydroxymethyl) pyrrolidin-3-yl)oxy)benzonitrile;
2-(((3R,4S)-3-hydroxy-3-(hydroxymethyl)-4-(4-(trifluoromethoxy)phenoxy)pyrrolidin-1-yl)sulfonyl)-5-(trifluoromethyl)benzonitrile;
2-(((3R,4S)-3-hydroxy-3-(hydroxymethyl)-4-(p-tolyloxy) pyrrolidin-1-yl)sulfonyl)-5-(trifluoromethyl)benzonitrile;
2-(((3R,4S)-3-hydroxy-3-(hydroxymethyl)-4-(4-methoxyphenoxy)pyrrolidin-1-yl)sulfonyl)-5-(trifluoromethyl)benzonitrile;
2-(((3R,4S)-4-(3-cyanophenoxy)-3-hydroxy-3-(hydroxymethyl) pyrrolidin-1-yl)sulfonyl)-5-(trifluoromethyl)benzonitrile;
2-(((3R,4S)-4-(5-cyano-2-methoxyphenoxy)-3-hydroxy-3-(hydroxymethyl)pyrrolidin-1-yl)sulfonyl)-5-(trifluoromethyl)benzonitrile;
2-(((3R,4S)-3-hydroxy-3-(hydroxymethyl)-4-((2-(trifluoromethyl)pyrimidin-5-yl)oxy)pyrrolidin-1-yl)sulfonyl)-5-(trifluoromethyl)benzonitrile;
2-(((3R,4S)-3-hydroxy-3-(hydroxymethyl)-4-(4-(trifluoromethyl)phenoxy)pyrrolidin-1-yl)sulfonyl)benzonitrile;
4-(((3S,4R)-1-((5-chloropyridin-2-yl)sulfonyl)-4-hydroxy-4-(hydroxymethyl)pyrrolidin-3-yl)oxy)-1-naphthonitrile;
4-(((3S,4R)-1-((5-chloropyridin-2-yl)sulfonyl)-4-hydroxy-4-(hydroxymethyl)pyrrolidin-3-yl)oxy)-2-fluorobenzonitrile;
4-(((3S,4R)-1-((7-chlorobenzo[c][1,2,5]oxadiazol-4-yl) sulfonyl)-4-hydroxy-4-(hydroxymethyl)pyrrolidin-3-yl)oxy)-2-fluorobenzonitrile;
4-(((3S,4R)-1-(benzo[c][1,2,5]oxadiazol-5-ylsulfonyl)-4-hydroxy-4-(hydroxymethyl)pyrrolidin-3-yl)oxy)-2-fluorobenzonitrile;
4-(((3S,4R)-1-((2-cyanophenyl)sulfonyl)-4-hydroxy-4-(hydroxymethyl) pyrrolidin-3-yl)oxy)-2-fluorobenzonitrile;
3-(((3R,4S)-4-(4-cyano-3-fluorophenoxy)-3-hydroxy-3-(hydroxymethyl) pyrrolidin-1-yl)sulfonyl)picolinonitrile;
4-(((3S,4R)-1-((2-chloro-4-(trifluoromethyl)phenyl)sulfonyl)-4-hydroxy-4-(hydroxymethyl)pyrrolidin-3-yl)oxy)-2-fluorobenzonitrile;
4-(((3S,4R)-1-((2-bromo-4-methoxyphenyl)sulfonyl)-4-hydroxy-4-(hydroxymethyl)pyrrolidin-3-yl)oxy)-2-fluorobenzonitrile;
4-(((3S,4R)-1-((2-bromo-4-(trifluoromethoxy)phenyl)sulfonyl)-4-hydroxy-4-(hydroxymethyl)pyrrolidin-3-yl)oxy)-2-fluorobenzonitrile;
4-(((3S,4R)-1-((2-chloro-4-(trifluoromethoxy)phenyl)sulfonyl)-4-hydroxy-4-(hydroxymethyl)pyrrolidin-3-yl)oxy)-2-fluorobenzonitrile;
4-(((3S,4R)-1-((4-bromo-2-cyanophenyl)sulfonyl)-4-hydroxy-4-(hydroxymethyl)pyrrolidin-3-yl)oxy)-2-fluorobenzonitrile;
4-(((3S,4R)-1-((4-cyano-2-(trifluoromethyl)phenyl)sulfonyl)-4-hydroxy-4-(hydroxymethyl)pyrrolidin-3-yl)oxy)-2-fluorobenzonitrile;
5-(((3S,4R)-1-((2-cyano-4-(trifluoromethyl)phenyl)sulfonyl)-4-hydroxy-4-(hydroxymethyl) pyrrolidin-3-yl)oxy) picolinonitrile;
2-fluoro-4-(((3S,4R)-4-hydroxy-4-(hydroxymethyl)-1-((4-(trifluoromethyl)phenyl)sulfonyl)pyrrolidin-3-yl)oxy) benzonitrile;
4-(((3S,4R)-1-((4-cyanophenyl)sulfonyl)-4-hydroxy-4-(hydroxymethyl)pyrrolidin-3-yl)oxy)-2-fluorobenzonitrile;
4-(((3S,4R)-1-((4-acetyl-2-cyanophenyl)sulfonyl)-4-hydroxy-4-(hydroxymethyl) pyrrolidin-3-yl)oxy)-2-fluorobenzonitrile;

5-(((3S,4R)-1-((2,4-dichlorphenyl)sulfonyl)-4-hydroxy-4-(hydroxymethyl)pyrrolidin-3-yl)oxy)picolinonitrile;

5-(((3S,4R)-1-((2-chloro-4-(trifluoromethyl)phenyl)sulfonyl)-4-hydroxy-4-(hydroxymethyl) pyrrolidin-3-yl)oxy)picolinonitrile;

5-(((3S,4R)-1-((2-chloro-4-methylphenyl)sulfonyl)-4-hydroxy-4-(hydroxymethyl) pyrrolidin-3-yl)oxy)picolinonitrile;

5-(((3S,4R)-4-hydroxy-4-(hydroxymethyl)-1-((2,4,6-trichlorophenyl)sulfonyl) pyrrolidin-3-yl)oxy)picolinonitrile;

2-fluoro-4-(((3S,4R)-4-hydroxy-4-(hydroxymethyl)-1-((2,4,6-trichlorophenyl)sulfonyl)pyrrolidin-3-yl)oxy)benzonitrile;

4-(((3S,4R)-1-((2-chloro-4-methylphenyl)sulfonyl)-4-hydroxy-4-(hydroxymethyl) pyrrolidin-3-yl)oxy)-2-fluorobenzonitrile;

5-(((3R,4S)-4-(4-cyano-3-fluorophenoxy)-3-hydroxy-3-(hydroxymethyl) pyrrolidin-1-yl)sulfonyl)picolinonitrile;

4-(((3S,4R)-1-((4-cyano-2-methylphenyl)sulfonyl)-4-hydroxy-4-(hydroxymethyl) pyrrolidin-3-yl)oxy)-2-fluorobenzonitrile;

2-fluoro-4-(((3S,4R)-4-hydroxy-4-(hydroxymethyl)-1-((2-methyl-4-(trifluoromethyl)phenyl)sulfonyl)pyrrolidin-3-yl)oxy)benzonitrile;

5-(((3R,4S)-4-(4-cyano-2,5-difluorophenoxy)-3-hydroxy-3-(hydroxymethyl)pyrrolidin-1-yl)sulfonyl)picolinonitrile;

2-fluoro-4-(((3S,4R)-4-hydroxy-4-(hydroxymethyl)-1-((2-methyl-6-(trifluoromethyl)pyridin-3-yl)sulfonyl)pyrrolidin-3-yl)oxy)benzonitrile;

2-fluoro-4-(((3S,4R)-4-hydroxy-4-(hydroxymethyl)-1-((5-(trifluoromethyl)pyridin-2-yl)sulfonyl)pyrrolidin-3-yl)oxy)benzonitrile;

4-(((3S,4R)-1-((2-chlorophenyl)sulfonyl)-4-hydroxy-4-(hydroxymethyl)pyrrolidin-3-yl)oxy)-2-fluorobenzonitrile;

4-(((3S,4R)-1-((5-chlorothiophen-2-yl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((2-methyl-4-(trifluoromethyl)thiazol-5-yl)sulfonyl)pyrrolidin-3-yl)oxy)benzonitrile;

4-(((3S,4R)-1-((2,4-dichlorothiazol-5-yl)sulfonyl)-4-hydroxy-4-(hydroxymethyl) pyrrolidin-3-yl)oxy)-2-fluorobenzonitrile;

4-(((3S,4R)-1-((4-chloro-1-methyl-1H-pyrazol-5-yl)sulfonyl)-4-hydroxy-4-(hydroxymethyl)pyrrolidin-3-yl)oxy)-2-fluorobenzonitrile;

4-(((3S,4R)-1-((6-chloroimidazo[2,1-b]thiazol-5-yl)sulfonyl)-4-hydroxy-4-(hydroxymethyl)pyrrolidin-3-yl)oxy)-2-fluorobenzonitrile;

4-(((3S,4R)-1-((6-chloropyridin-3-yl)sulfonyl)-4-hydroxy-4-(hydroxymethyl)pyrrolidin-3-yl)oxy)-2-fluorobenzonitrile;

4-(((3S,4R)-1-((2,6-dichloropyridin-3-yl)sulfonyl)-4-hydroxy-4-(hydroxymethyl)pyrrolidin-3-yl)oxy)-2-fluorobenzonitrile;

4-(((3S,4R)-1-((2-ethynylphenyl)sulfonyl)-4-hydroxy-4-(hydroxymethyl)pyrrolidin-3-yl)oxy)-2-fluorobenzonitrile;

4-(((3S,4R)-1-((2,3-dichlorophenyl)sulfonyl)-4-hydroxy-4-(hydroxymethyl) pyrrolidin-3-yl)oxy)-2-fluorobenzonitrile;

4-(((3S,4R)-1-((3-chloro-2-cyanophenyl)sulfonyl)-4-hydroxy-4-(hydroxymethyl)pyrrolidin-3-yl)oxy)-2-fluorobenzonitrile;

4-(((3S,4R)-1-((2,6-dichloro-4-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((2-chloro-4-cyanophenyl)sulfonyl)-4-hydroxy-4-(hydroxymethyl)pyrrolidin-3-yl)oxy)-2-fluorobenzonitrile;

4-(((3S,4R)-1-((4-(difluoromethyl)phenyl)sulfonyl)-4-hydroxy-4-(hydroxymethyl) pyrrolidin-3-yl)oxy)-2-fluorobenzonitrile;

4-(((3S,4R)-1-((6-bromopyridin-3-yl)sulfonyl)-4-hydroxy-4-(hydroxymethyl) pyrrolidin-3-yl)oxy)-2-fluorobenzonitrile;

4-(((3S,4R)-1-((2-chloro-6-(trifluoromethyl)pyridin-3-yl)sulfonyl)-4-hydroxy-4-(hydroxymethyl)pyrrolidin-3-yl)oxy)-2-fluorobenzonitrile;

4-(((3S,4R)-1-((4-chlorophenyl)sulfonyl)-4-hydroxy-4-(hydroxymethyl)pyrrolidin-3-yl)oxy)-2-fluorobenzonitrile;

4-(((3S,4R)-1-((4-bromophenyl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((4-iodophenyl)sulfonyl)pyrrolidin-3-yl)oxy)benzonitrile;

4-(((3S,4R)-1-((4-cyano-2-methoxyphenyl)sulfonyl)-4-hydroxy-4-(hydroxymethyl)pyrrolidin-3-yl)oxy)-2-fluorobenzonitrile;

4-(((3S,4R)-1-((5-bromopyridin-2-yl)sulfonyl)-4-hydroxy-4-(hydroxymethyl) pyrrolidin-3-yl)oxy)-2-fluorobenzonitrile;

3-chloro-4-(((3R,4S)-4-(4-chlorophenoxy)-3-hydroxy-3-(hydroxymethyl) pyrrolidin-1-yl)sulfonyl)benzonitrile;

2-(((3R,4S)-4-(4-chlorophenoxy)-3-hydroxy-3-(hydroxymethyl) pyrrolidin-1-yl)sulfonyl)benzonitrile;

3-bromo-4-(((3R,4S)-4-(4-chlorophenoxy)-3-hydroxy-3-(hydroxymethyl)pyrrolidin-1-yl)sulfonyl)benzonitrile;

5-(((3R,4S)-4-(4-chlorophenoxy)-3-hydroxy-3-(hydroxymethyl) pyrrolidin-1-yl)sulfonyl)picolinonitrile;

3-(((3R,4S)-4-(4-chlorophenoxy)-3-hydroxy-3-(hydroxymethyl) pyrrolidin-1-yl)sulfonyl)picolinonitrile;

2-fluoro-4-(((3S,4R)-4-hydroxy-4-(hydroxymethyl)-1-((4-(2,2,2-trifluoroethyl)phenyl)sulfonyl)pyrrolidin-3-yl)oxy)benzonitrile;

2-fluoro-4-(((3S,4R)-4-hydroxy-4-(hydroxymethyl)-1-((5-(trifluoromethyl)thiophen-2-yl)sulfonyl)pyrrolidin-3-yl)oxy)benzonitrile;

4-(((3S,4R)-1-((4-cyano-2-fluorophenyl)sulfonyl)-4-hydroxy-4-(hydroxymethyl)pyrrolidin-3-yl)oxy)-2-fluorobenzonitrile;

4-(((3S,4R)-1-((2-cyano-4-iodophenyl)sulfonyl)-4-hydroxy-4-(hydroxymethyl)pyrrolidin-3-yl)oxy)-2-fluorobenzonitrile;

4-(((3S,4R)-1-((2-chloro-4-iodophenyl)sulfonyl)-4-hydroxy-4-(hydroxymethyl) pyrrolidin-3-yl)oxy)-2-fluorobenzonitrile;

2-fluoro-4-(((3S,4R)-1-((3-fluoro-4-(trifluoromethyl)phenyl)sulfonyl)-4-hydroxy-4-(hydroxymethyl) pyrrolidin-3-yl)oxy)benzonitrile;

4-(((3S,4R)-1-((2-bromophenyl)sulfonyl)-4-hydroxy-4-(hydroxymethyl)pyrrolidin-3-yl)oxy)-2-fluorobenzonitrile;

2-fluoro-4-(((3S,4R)-1-((3-fluoro-4-methylphenyl)sulfonyl)-4-hydroxy-4-(hydroxymethyl) pyrrolidin-3-yl)oxy)benzonitrile;

2-fluoro-4-(((3S,4R)-4-hydroxy-4-(hydroxymethyl)-1-((2-iodophenyl)sulfonyl)pyrrolidin-3-yl)oxy)benzonitrile;

4-(((3S,4R)-1-((2-bromo-4-chlorophenyl)sulfonyl)-4-hydroxy-4-(hydroxymethyl) pyrrolidin-3-yl)oxy)-2-fluorobenzonitrile;

4-(((3S,4R)-1-((4-bromo-2-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((2-(difluoromethoxy)pyridin-3-yl)sulfonyl)-4-hydroxy-4-(hydroxymethyl)pyrrolidin-3-yl)oxy)-2-fluorobenzonitrile;

4-(((3S,4R)-1-((4-bromo-1-methyl-1H-pyrazol-5-yl)sulfonyl)-4-hydroxy-4-(hydroxymethyl) pyrrolidin-3-yl)oxy)-2-fluorobenzonitrile;

4-(((3S,4R)-1-((4-chloro-1,3-dimethyl-1H-pyrazol-5-yl)sulfonyl)-4-hydroxy-4-(hydroxymethyl) pyrrolidin-3-yl)oxy)-2-fluorobenzonitrile;

(3R,4S)-4-(benzo[c][1,2,5]oxadiazol-5-yloxy)-1-((2-fluoro-4-(trifluoromethyl)phenyl)sulfonyl)-3-(hydroxymethyl)pyrrolidin-3-ol;

4-(((3S,4R)-1-((6-(difluoromethoxy)pyridin-3-yl)sulfonyl)-4-hydroxy-4-(hydroxymethyl) pyrrolidin-3-yl)oxy)-2-fluorobenzonitrile;

2-fluoro-4-(((3S,4R)-4-hydroxy-4-(hydroxymethyl)-1-((5-(trifluoromethoxy)pyridin-2-yl)sulfonyl)pyrrolidin-3-yl)oxy)benzonitrile;

2-fluoro-4-(((3S,4R)-4-hydroxy-4-(hydroxymethyl)-1-((2-(trifluoromethyl)pyrimidin-5-yl)sulfonyl)pyrrolidin-3-yl)oxy)benzonitrile;

4-(((3S,4R)-1-((4-chloro-3-(trifluoromethoxy)phenyl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((5-iodopyridin-2-yl)sulfonyl)pyrrolidin-3-yl)oxy)benzonitrile;

5-(((3R,4S)-4-(4-cyano-3-fluorophenoxy)-3-hydroxy-3-(hydroxymethyl) pyrrolidin-1-yl)sulfonyl)-6-methylpicolinonitrile;

2-fluoro-4-(((3S,4R)-4-hydroxy-4-(hydroxymethyl)-1-((6-(trifluoromethoxy)pyridin-2-yl)sulfonyl)pyrrolidin-3-yl)oxy)benzonitrile;

2-fluoro-4-(((3S,4R)-4-hydroxy-4-(hydroxymethyl)-1-((6-(2,2,2-trifluoroethoxy)pyridazin-3-yl)sulfonyl)pyrrolidin-3-yl)oxy)benzonitrile;

4-(((3S,4R)-1-((6-(difluoromethoxy)pyridin-2-yl)sulfonyl)-4-hydroxy-4-(hydroxymethyl)pyrrolidin-3-yl)oxy)-2-fluorobenzonitrile;

4-(((3S,4S)-1-((2-cyano-4-(trifluoromethyl)phenyl)sulfonyl)-4-hydroxy-4-(hydroxymethyl)pyrrolidin-3-yl)oxy)-2-fluorobenzonitrile;

4-(((3S,4S)-1-((5-chloropyridin-2-yl)sulfonyl)-4-hydroxy-4-(hydroxymethyl)pyrrolidin-3-yl)oxy)-2-fluorobenzonitrile;

4-(((3S,4S)-1-((2-cyanophenyl)sulfonyl)-4-hydroxy-4-(hydroxymethyl) pyrrolidin-3-yl)oxy)-2-fluorobenzonitrile;

4-(((3S,4S)-1-((2-cyano-4-fluorophenyl)sulfonyl)-4-hydroxy-4-(hydroxymethyl) pyrrolidin-3-yl)oxy)-2-fluorobenzonitrile;

4-(((3S,4S)-1-((4-chloro-2-cyanophenyl)sulfonyl)-4-hydroxy-4-(hydroxymethyl)pyrrolidin-3-yl)oxy)-2-fluorobenzonitrile;

3-(((3S,4S)-4-(4-cyano-3-fluorophenoxy)-3-hydroxy-3-(hydroxymethyl)pyrrolidin-1-yl)sulfonyl)picolinonitrile;

4-(((3S,4S)-1-((2-chloro-4-cyanophenyl)sulfonyl)-4-hydroxy-4-(hydroxymethyl)pyrrolidin-3-yl)oxy)-2-fluorobenzonitrile;

4-(((3S,4S)-1-((2,4-dichlorophenyl)sulfonyl)-4-hydroxy-4-(hydroxymethyl)pyrrolidin-3-yl)oxy)-2-fluorobenzonitrile;

4-(((3S,4S)-1-((4-bromo-2-cyanophenyl)sulfonyl)-4-hydroxy-4-(hydroxymethyl)pyrrolidin-3-yl)oxy)-2-fluorobenzonitrile;

4-(((3S,4S)-1-((2-bromo-4-fluorophenyl)sulfonyl)-4-hydroxy-4-(hydroxymethyl)pyrrolidin-3-yl)oxy)-2-fluorobenzonitrile;

4-(((3S,4S)-1-((2-cyano-4-methoxyphenyl)sulfonyl)-4-hydroxy-4-(hydroxymethyl)pyrrolidin-3-yl)oxy)-2-fluorobenzonitrile;

2-(((3S,4S)-4-(4-chlorophenoxy)-3-hydroxy-3-(hydroxymethyl)pyrrolidin-1-yl)sulfonyl)-5-(trifluoromethyl)benzonitrile;

2-(((3S,4S)-4-(4-chlorophenoxy)-3-hydroxy-3-(hydroxymethyl)pyrrolidin-1-yl)sulfonyl)-5-fluorobenzonitrile;

2-(((3S,4S)-3-hydroxy-3-(hydroxymethyl)-4-(4-(trifluoromethyl)phenoxy)pyrrolidin-1-yl)sulfonyl)-5-(trifluoromethyl)benzonitrile;

5-fluoro-2-(((3S,4S)-3-hydroxy-3-(hydroxymethyl)-4-(4-(trifluoromethyl) phenoxy)pyrrolidin-1-yl)sulfonyl)benzonitrile;

3-chloro-4-(((3R,4S)-3-hydroxy-3-(hydroxymethyl)-4-(4-(trifluoromethyl) phenoxy)pyrrolidin-1-yl)sulfonyl)benzonitrile;

5-chloro-2-(((3S,4S)-4-(4-chlorophenoxy)-3-hydroxy-3-(hydroxymethyl) pyrrolidin-1-yl)sulfonyl)benzonitrile;

5-chloro-2-(((3S,4S)-3-hydroxy-3-(hydroxymethyl)-4-(4-(trifluoromethyl)phenoxy) pyrrolidin-1-yl)sulfonyl)benzonitrile;

5-fluoro-2-(((3R,4S)-3-hydroxy-3-(hydroxymethyl)-4-(4-(trifluoromethyl)phenoxy)pyrrolidin-1-yl)sulfonyl)benzonitrile;

5-chloro-2-(((3R,4S)-4-(4-chlorophenoxy)-3-hydroxy-3-(hydroxymethyl) pyrrolidin-1-yl)sulfonyl)benzonitrile;

2-(((3R,4S)-4-(4-chlorophenoxy)-3-hydroxy-3-(hydroxymethyl)pyrrolidin-1-yl)sulfonyl)-5-fluorobenzonitrile;

5-chloro-2-(((3R,4S)-3-hydroxy-3-(hydroxymethyl)-4-(4-(trifluoromethyl) phenoxy)pyrrolidin-1-yl)sulfonyl)benzonitrile;

4-(((3S,4R)-1-((2-cyano-4-(trifluoromethyl)phenyl)sulfonyl)-4-hydroxy-4-(hydroxymethyl) pyrrolidin-3-yl)oxy)-2-fluoro-5-(2,2,2-trifluoroethoxy)benzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-methoxybenzonitrile;

4-(((3S,4R)-1-((2-cyano-4-(trifluoromethyl)phenyl)sulfonyl)-4-hydroxy-4-(hydroxymethyl) pyrrolidin-3-yl)oxy)-5-ethoxy-2-fluorobenzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-propoxybenzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-isopropoxybenzonitrile;

4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-hydroxybenzonitrile;

5-(benzyloxy)-4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile;

5-butoxy-4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((2-cyano-4-(trifluoromethyl)phenyl)sulfonyl)-4-hydroxy-4-(hydroxymethyl) pyrrolidin-3-yl)oxy)-2-fluoro-5-isobutoxybenzonitrile;

2-(((3R,4S)-4-(4-cyano-2-propoxyphenoxy)-3-hydroxy-3-(hydroxymethyl)pyrrolidin-1-yl)sulfonyl)-5-(trifluoromethyl)benzonitrile;

2-(((3R,4S)-4-(4-cyano-2-(2,2,2-trifluoroethoxy)phenoxy)-3-hydroxy-3-(hydroxymethyl)pyrrolidin-1-yl)sulfonyl)-5-(trifluoromethyl)benzonitrile;

2-(((3R,4S)-4-(4-cyano-2-hydroxyphenoxy)-3-hydroxy-3-(hydroxymethyl)pyrrolidin-1-yl)sulfonyl)-5-(trifluoromethyl)benzonitrile;

2-(((3R,4S)-4-(2-butoxy-4-cyanophenoxy)-3-hydroxy-3-(hydroxymethyl)pyrrolidin-1-yl)sulfonyl)-5-(trifluoromethyl)benzonitrile;

2-(((3R,4S)-4-(4-cyano-2-isobutoxyphenoxy)-3-hydroxy-3-(hydroxymethyl)pyrrolidin-1-yl)sulfonyl)-5-(trifluoromethyl)benzonitrile;

2-(((3R,4S)-4-(2-(benzyloxy)-4-cyanophenoxy)-3-hydroxy-3-(hydroxymethyl) pyrrolidin-1-yl)sulfonyl)-5-(trifluoromethyl)benzonitrile;

4-(((3S,4R)-1-((4-cyanophenyl)sulfonyl)-4-hydroxy-4-(hydroxymethyl)pyrrolidin-3-yl)oxy)-3-(2,2,2-trifluoroethoxy)benzonitrile;

4-(((3S,4R)-1-((2-cyanophenyl)sulfonyl)-4-hydroxy-4-(hydroxymethyl)pyrrolidin-3-yl)oxy)-2-fluoro-5-(2,2,2-trifluoroethoxy)benzonitrile;

5-(((3R,4S)-4-(4-cyano-5-fluoro-2-(2,2,2-trifluoroethoxy)phenoxy)-3-hydroxy-3-(hydroxymethyl)pyrrolidin-1-yl)sulfonyl)picolinonitrile;

2-fluoro-4-(((3S,4R)-4-hydroxy-4-(hydroxymethyl)-1-((6-(trifluoromethyl)pyridin-3-yl)sulfonyl) pyrrolidin-3-yl)oxy)-5-(2,2,2-trifluoroethoxy)benzonitrile;

2-fluoro-4-(((3S,4R)-4-hydroxy-4-(hydroxymethyl)-1-(phenylsulfonyl) pyrrolidin-3-yl)oxy)-5-(2,2,2-trifluoroethoxy)benzonitrile;

4-(((3S,4R)-1-((2,4-dichlorophenyl)sulfonyl)-4-hydroxy-4-(hydroxymethyl) pyrrolidin-3-yl)oxy)-2-fluoro-5-(2,2,2-trifluoroethoxy)benzonitrile;

4-(((3S,4R)-1-((4-cyanophenyl)sulfonyl)-4-hydroxy-4-(hydroxymethyl)pyrrolidin-3-yl)oxy)-2-fluoro-5-(2,2,2-trifluoroethoxy)benzonitrile;

4-(((3S,4R)-1-((2-cyanophenyl)sulfonyl)-4-hydroxy-4-(hydroxymethyl)pyrrolidin-3-yl)oxy)-2-fluoro-5-isobutoxybenzonitrile;

4-(((3S,4R)-1-((4-cyanophenyl)sulfonyl)-4-hydroxy-4-(hydroxymethyl)pyrrolidin-3-yl)oxy)-2-fluoro-5-isobutoxybenzonitrile;

5-(((3R,4S)-4-(4-cyano-5-fluoro-2-isobutoxyphenoxy)-3-hydroxy-3-(hydroxymethyl)pyrrolidin-1-yl)sulfonyl)picolinonitrile;

2-fluoro-4-(((3S,4R)-4-hydroxy-4-(hydroxymethyl)-1-((4-(trifluoromethyl)phenyl)sulfonyl)pyrrolidin-3-yl)oxy)-5-isobutoxybenzonitrile;

2-fluoro-4-(((3S,4R)-4-hydroxy-4-(hydroxymethyl)-1-((6-(trifluoromethyl)pyridin-3-yl)sulfonyl)pyrrolidin-3-yl)oxy)-5-isobutoxybenzonitrile;

5-(((3R,4S)-4-(4-cyano-2-(2,2,2-trifluoroethoxy)phenoxy)-3-hydroxy-3-(hydroxymethyl)pyrrolidin-1-yl)sulfonyl)picolinonitrile;

4-(((3S,4R)-1-((2-cyanophenyl)sulfonyl)-4-hydroxy-4-(hydroxymethyl)pyrrolidin-3-yl)oxy)-3-(2,2,2-trifluoroethoxy)benzonitrile;

4-(((3S,4R)-1-((5-chloropyridin-2-yl)sulfonyl)-4-hydroxy-4-(hydroxymethyl)pyrrolidin-3-yl)oxy)-3-(2,2,2-trifluoroethoxy)benzonitrile;

4-(((3S,4R)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile;

2-fluoro-4-(((3S,4R)-4-hydroxy-4-(hydroxymethyl)-1-((6-methylpyridazin-3-yl)sulfonyl)pyrrolidin-3-yl)oxy)-5-isobutoxybenzonitrile;

4-(((3S,4R)-1-((5-chloropyridin-2-yl)sulfonyl)-4-hydroxy-4-((S)-1-hydroxybutyl) pyrrolidin-3-yl)oxy)-2-fluorobenzonitrile;

4-(((3S,4R)-1-((2-cyano-4-(trifluoromethyl)phenyl)sulfonyl)-4-hydroxy-4-((R)-1-hydroxyethyl)pyrrolidin-3-yl)oxy)-2-fluorobenzonitrile;

4-(((3S,4R)-1-((5-chloropyridin-2-yl)sulfonyl)-4-hydroxy-4-(1-hydroxyethyl)pyrrolidin-3-yl)oxy)-2-fluorobenzonitrile;

4-(((3S,4R)-1-((5-chloropyridin-2-yl)sulfonyl)-4-hydroxy-4-((S)-1-hydroxy-3-methylbutyl)pyrrolidin-3-yl)oxy)-2-fluorobenzonitrile;

4-(((3S,4R)-1-((2-cyano-4-(trifluoromethyl)phenyl)sulfonyl)-4-hydroxy-4-(1-hydroxyethyl)pyrrolidin-3-yl)oxy)-2-fluorobenzonitrile;

4-(((3S,4S)-1-((2-cyano-4-(trifluoromethyl)phenyl)sulfonyl)-4-hydroxy-4-((S)-1-hydroxyethyl)pyrrolidin-3-yl)oxy)-2-fluorobenzonitrile;

4-(((3S,4R)-1-((5-chloropyridin-2-yl)sulfonyl)-4-hydroxy-4-((R)-1-methoxyethyl)pyrrolidin-3-yl)oxy)-2-fluorobenzonitrile;

4-(((3S,4R)-1-((5-chloropyridin-2-yl)sulfonyl)-4-hydroxy-4-((R)-1-hydroxypropyl)pyrrolidin-3-yl)oxy)-2-fluorobenzonitrile;

4-(((3S,4R)-1-((5-chloropyridin-2-yl)sulfonyl)-4-hydroxy-4-((R)-1-hydroxy-3-methylbutyl)pyrrolidin-3-yl)oxy)-2-fluorobenzonitrile;

4-(((3S,4R)-1-((5-chloropyridin-2-yl)sulfonyl)-4-hydroxy-4-((R)-1-hydroxybutyl)pyrrolidin-3-yl)oxy)-2-fluorobenzonitrile;

4-(((3S,4R)-1-((2-cyano-4-methoxyphenyl)sulfonyl)-4-hydroxy-4-((S)-1-hydroxyethyl)pyrrolidin-3-yl)oxy)-2-fluorobenzonitrile;

4-(((3S,4R)-1-((2-cyanophenyl)sulfonyl)-4-hydroxy-4-((S)-1-hydroxyethyl) pyrrolidin-3-yl)oxy)-2-fluorobenzonitrile;

4-(((3S,4R)-1-((2-cyano-4-fluorophenyl)sulfonyl)-4-hydroxy-4-((S)-1-hydroxyethyl)pyrrolidin-3-yl)oxy)-2-fluorobenzonitrile;

4-(((3S,4R)-1-((4-chloro-2-cyanophenyl)sulfonyl)-4-hydroxy-4-((S)-1-hydroxyethyl)pyrrolidin-3-yl)oxy)-2-fluorobenzonitrile;

3-(((3R,4S)-4-(4-cyano-3-fluorophenoxy)-3-hydroxy-3-((S)-1-hydroxyethyl)pyrrolidin-1-yl)sulfonyl)picolinonitrile;

4-(((3S,4R)-1-((2,4-dichlorophenyl)sulfonyl)-4-hydroxy-4-((S)-1-hydroxyethyl)pyrrolidin-3-yl)oxy)-2-fluorobenzonitrile;

4-(((3S,4R)-1-((2-chloro-4-cyanophenyl)sulfonyl)-4-hydroxy-4-((S)-1-hydroxyethyl)pyrrolidin-3-yl)oxy)-2-fluorobenzonitrile;

2-fluoro-4-(((3S,4R)-4-hydroxy-4-((R)-1-hydroxyethyl)-1-((6-(trifluoromethyl)pyridin-3-yl)sulfonyl)pyrrolidin-3-yl)oxy)benzonitrile;

2-fluoro-4-(((3S,4R)-1-((5-fluoropyridin-2-yl)sulfonyl)-4-hydroxy-4-((R)-1-hydroxyethyl)pyrrolidin-3-yl)oxy)benzonitrile;

2-fluoro-4-(((3S,4R)-4-hydroxy-4-((R)-1-hydroxyethyl)-1-((6-(trifluoromethoxy)pyridin-3-yl)sulfonyl)pyrrolidin-3-yl)oxy)benzonitrile;

2-fluoro-4-(((3S,4R)-4-hydroxy-4-((R)-1-hydroxyethyl)-1-((4-iodophenyl)sulfonyl)pyrrolidin-3-yl)oxy)benzonitrile;

2-fluoro-4-(((3S,4R)-4-hydroxy-4-((R)-1-hydroxyethyl)-1-((5-(trifluoromethoxy)pyridin-2-yl)sulfonyl)pyrrolidin-3-yl)oxy)benzonitrile;

4-(((3S,4R)-1-((5-(difluoromethyl)pyridin-2-yl)sulfonyl)-4-hydroxy-4-((R)-1-hydroxyethyl)pyrrolidin-3-yl)oxy)-2-fluorobenzonitrile;

4-(((3S,4R)-1-((6-(difluoromethyl)pyridin-3-yl)sulfonyl)-4-hydroxy-4-((R)-1-hydroxyethyl)pyrrolidin-3-yl)oxy)-2-fluorobenzonitrile;

4-(((3S,4R)-1-((6-(difluoromethoxy)pyridin-3-yl)sulfonyl)-4-hydroxy-4-((R)-1-hydroxyethyl)pyrrolidin-3-yl)oxy)-2-fluorobenzonitrile;

4-(((3S,4S)-1-((5-chloropyridin-2-yl)sulfonyl)-4-hydroxy-4-(2-hydroxypropan-2-yl) pyrrolidin-3-yl)oxy)-2-fluorobenzonitrile;

4-(((3S,4S)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile;

4-(((3S,4R)-1-((2-cyano-4-methylphenyl)sulfonyl)-4-hydroxy-4-(hydroxymethyl) pyrrolidin-3-yl)oxy)-2-fluorobenzonitrile;

4-(((3S,4R)-1-((2-cyano-4-ethylphenyl)sulfonyl)-4-hydroxy-4-(hydroxymethyl)pyrrolidin-3-yl)oxy)-2-fluorobenzonitrile;

4-(((3R,4S)-4-(4-cyano-3-fluorophenoxy)-3-hydroxy-3-(hydroxymethyl) pyrrolidin-1-yl)sulfonyl)-[1,1'-biphenyl]-3-carbonitrile;

4-(((3S,4R)-1-((2-cyano-4-(prop-1-yn-1l-yl)phenyl)sulfonyl)-4-hydroxy-4-(hydroxymethyl)pyrrolidin-3-yl)oxy)-2-fluorobenzonitrile;

4-(((3S,4R)-1-((2-cyano-4-ethynylphenyl)sulfonyl)-4-hydroxy-4-(hydroxymethyl)pyrrolidin-3-yl)oxy)-2-fluorobenzonitrile;

4-(((3S,4R)-1-((2-cyano-4-((trimethylsilyl)ethynyl)phenyl)sulfonyl)-4-hydroxy-4-(hydroxymethyl) pyrrolidin-3-yl)oxy)-2-fluorobenzonitrile;

2-fluoro-4-(((3S,4R)-4-hydroxy-4-(hydroxymethyl)-1-((4-(prop-1-yn-1-yl)phenyl)sulfonyl)pyrrolidin-3-yl)oxy)benzonitrile;

2-fluoro-4-(((3S,4R)-4-hydroxy-4-(hydroxymethyl)-1-((6-(prop-1-yn-1-yl)pyridin-3-yl)sulfonyl)pyrrolidin-3-yl)oxy)benzonitrile;

4-(((3S,4R)-1-((4-cyano-2-(prop-1-yn-1-yl)phenyl)sulfonyl)-4-hydroxy-4-(hydroxymethyl) pyrrolidin-3-yl)oxy)-2-fluorobenzonitrile;

4-(((3S,4R)-1-((2-ethynyl-4-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((6-(cyclopropylethynyl)pyridin-3-yl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((5-(prop-1-yn-1-yl)pyridin-2-yl)sulfonyl)pyrrolidin-3-yl)oxy)benzonitrile;

4-(((3S,4R)-1-((5-ethynylpyridin-2-yl)sulfonyl)-4-hydroxy-4-(hydroxymethyl)pyrrolidin-3-yl)oxy)-2-fluorobenzonitrile;

4-(((3S,4R)-1-((5-(3,3-dimethylbut-1-yn-1-yl)pyridin-2-yl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((5-(phenylethynyl)pyridin-2-yl)sulfonyl)pyrrolidin-3-yl)oxy)benzonitrile;

6-(((3R,4S)-4-(4-cyano-3-fluorophenoxy)-3-hydroxy-3-(hydroxymethyl) pyrrolidin-1-yl)sulfonyl)nicotinonitrile;

4-(((3S,4R)-1-((2-cyano-4-(trifluoromethoxy)phenyl)sulfonyl)-4-hydroxy-4-(hydroxymethyl)pyrrolidin-3-yl)oxy)-2-fluorobenzonitrile;

4-(((3S,4S)-4-(aminomethyl)-1-((5-chloropyridin-2-yl)sulfonyl)-4-hydroxypyrrolidin-3-yl)oxy)-2-fluorobenzonitrile;

4-(((3S,4R)-4-(aminomethyl)-1-((5-chloropyridin-2-yl)sulfonyl)-4-hydroxypyrrolidin-3-yl)oxy)-2-fluorobenzonitrile;

4-(((3S,4R)-4-(aminomethyl)-1-((4-chloro-2-cyanophenyl)sulfonyl)-4-hydroxypyrrolidin-3-yl)oxy)-2-fluorobenzonitrile;

4-(((3S,4R)-1-((4-chloro-2-cyanophenyl)sulfonyl)-4-hydroxy-4-(((2-hydroxyethyl)amino)methyl)pyrrolidin-3-yl)oxy)-2-fluorobenzonitrile;

4-(((3S,4S)-1-((2-cyano-4-(trifluoromethyl)phenyl)sulfonyl)-4-hydroxy-4-((methylamino)methyl) pyrrolidin-3-yl)oxy)-2-fluorobenzonitrile;

4-(((3S,4S)-1-((2-cyano-4-(trifluoromethyl)phenyl)sulfonyl)-4-((ethylamino)methyl)-4-hydroxypyrrolidin-3-yl)oxy)-2-fluorobenzonitrile;

4-(((3S,4S)-1-((2-cyano-4-(trifluoromethyl)phenyl)sulfonyl)-4-hydroxy-4-((isopropylamino)methyl)pyrrolidin-3-yl)oxy)-2-fluorobenzonitrile;

4-(((3S,4S)-4-(aminomethyl)-1-((4-chloro-2-cyanophenyl)sulfonyl)-4-hydroxypyrrolidin-3-yl)oxy)-2-fluorobenzonitrile;

4-(((3S,4S)-4-(aminomethyl)-1-((4-chloro-1-methyl-1H-pyrazol-5-yl)sulfonyl)-4-hydroxypyrrolidin-3-yl)oxy)-2-fluorobenzonitrile;

4-(((3S,4S)-4-(aminomethyl)-1-((5-fluoropyridin-2-yl)sulfonyl)-4-hydroxypyrrolidin-3-yl)oxy)-2-fluorobenzonitrile;

5-(((3S,4S)-3-(aminomethyl)-4-(4-cyano-3-fluorophenoxy)-3-hydroxypyrrolidin-1-yl)sulfonyl)picolinonitrile;

4-(((3S,4S)-4-(aminomethyl)-1-((5-(difluoromethyl)pyridin-2-yl)sulfonyl)-4-hydroxypyrrolidin-3-yl)oxy)-2-fluorobenzonitrile;

4-(((3S,4S)-4-(aminomethyl)-4-hydroxy-1-((6-(trifluoromethyl)pyridin-3-yl)sulfonyl)pyrrolidin-3-yl)oxy)-2-fluorobenzonitrile;

4-(((3S,4S)-4-(aminomethyl)-1-((5-chloropyridin-2-yl)sulfonyl)-4-hydroxypyrrolidin-3-yl)oxy)benzonitrile;

4-(((3S,4S)-4-(aminomethyl)-1-((5-(difluoromethoxy)pyridin-2-yl)sulfonyl)-4-hydroxypyrrolidin-3-yl)oxy)-2-fluorobenzonitrile;

4-(((3S,4S)-4-(aminomethyl)-4-hydroxy-1-((5-(trifluoromethoxy)pyridin-2-yl)sulfonyl)pyrrolidin-3-yl)oxy)-2-fluorobenzonitrile;

4-(((3S,4S)-4-(aminomethyl)-4-hydroxy-1-((6-(trifluoromethoxy)pyridin-3-yl)sulfonyl)pyrrolidin-3-yl)oxy)-2-fluorobenzonitrile;

4-(((3S,4S)-4-(aminomethyl)-4-hydroxy-1-((5-iodopyridin-2-yl)sulfonyl)pyrrolidin-3-yl)oxy)-2-fluorobenzonitrile, 2,2,2-trifluoroacetate;

4-(((3S,4S)-4-(aminomethyl)-1-((5-bromopyridin-2-yl)sulfonyl)-4-hydroxypyrrolidin-3-yl)oxy)-2-fluorobenzonitrile, 2,2,2-trifluoroacetate;

4-(((4S,5R)-2-((4-chloro-2-cyanophenyl)sulfonyl)-9-methyl-6-oxa-2,9-diazaspiro[4.5]decan-4-yl)oxy)-2-fluorobenzonitrile;

4-(((4S,5S)-2-((4-chloro-2-cyanophenyl)sulfonyl)-6-oxa-2,9-diazaspiro[4.5]decan-4-yl)oxy)-2-fluorobenzonitrile;

4-(((5S,9S)-7-((4-chloro-2-cyanophenyl)sulfonyl)-2-oxo-1-oxa-3,7-diazaspiro[4.4]nonan-9-yl)oxy)-2-fluorobenzonitrile;

4-(((5R,9S)-7-((4-chloro-2-cyanophenyl)sulfonyl)-2-oxo-1-oxa-3,7-diazaspiro[4.4]nonan-9-yl)oxy)-2-fluorobenzonitrile;

4-(((3S,4R)-4-((R)-1-aminoethyl)-1-((5-chloropyridin-2-yl)sulfonyl)-4-hydroxypyrrolidin-3-yl)oxy)-2-fluorobenzonitrile;

4-(((3S,4R)-4-((S)-1-aminoethyl)-1-((5-chloropyridin-2-yl)sulfonyl)-4-hydroxypyrrolidin-3-yl)oxy)-2-fluorobenzonitrile; and ((3R,4S)-1-((5-chloropyridin-2-yl)sulfonyl)-4-(4-cyano-3-fluorophenoxy)-3-hydroxypyrrolidin-3-yl)methyl 2-aminoacetate;

or a pharmaceutically acceptable salt thereof.

The skilled artisan will appreciate that salts, including pharmaceutically acceptable salts, of the compounds according to Formula (I) may be prepared. Indeed, in certain embodiments of the invention, salts including pharmaceutically-acceptable salts of the compounds according to Formula (I) may be preferred over the respective free or unsalted compound. Accordingly, the invention is further directed to salts, including pharmaceutically-acceptable salts, of the compounds according to Formula (I).

The salts, including pharmaceutically acceptable salts, of the compounds of the invention are readily prepared by those of skill in the art.

Typically, the salts of the present invention are pharmaceutically acceptable salts.

Salts encompassed within the term "pharmaceutically acceptable salts" refer to non-toxic salts of the compounds of this invention.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate. Suitably the pharmaceutically acceptable salt is the esylate salt. Suitably the pharmaceutically acceptable salt is the mesylate salt.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidinyl, potassium, procaine, quinine, quinoline, sodium, strontium, t-butylamine, and zinc.

The compounds according to Formula I may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula I, or in any chemical structure illustrated herein, if not specified the structure is intended to encompass all individual stereoisomers and all mixtures thereof. Thus, compounds according to Formula I containing one or more chiral centers may be used as racemic mixtures, enantiomerically or diastereomerically enriched mixtures, or as enantiomerically or diastereomerically pure individual stereoisomers.

The compounds according to Formula (I) and pharmaceutically acceptable salts thereof may be in the form of isotopically-labelled compounds, wherein one or more atoms of Formula (I) are replaced by an atom having an atomic mass or mass number different from the atomic mass or mass number usually found in nature. Examples of such isotopes include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Isotopically-labelled compounds, for example those into which radioactive isotopes such as $^3H$ or $^{14}C$ are incorporated, are useful in drug and/or substrate tissue distribution assays. Tritium, i.e., $^3H$, and carbon-14, i.e., $^{14}O$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), both are useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds can generally be prepared by substituting a readily available isotopically labelled reagent for a non-isotopically labelled reagent.

The compounds according to Formula (I) may also contain double bonds or other centers of geometric asymmetry. Where the stereochemistry of a center of geometric asymmetry present in Formula (I), or in any chemical structure illustrated herein, is not specified, the structure is intended to encompass the trans (E) geometric isomer, the cis (Z) geometric isomer, and all mixtures thereof. Likewise, all tautomeric forms are also included in Formula (I) whether such tautomers exist in equilibrium or predominately in one form.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism ("polymorphs"). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may exist in solvated and unsolvated forms. As used herein, the term "solvate" refers to a complex of variable stoichiometry formed by a solute (in this invention, a compound of Formula (I) or a salt) and a solvent. Such solvents, for the purpose of the invention, may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice structures incorporated with water molecules are typically referred to as "hydrates". Hydrates include stoichiometric hydrates as well as compositions containing variable amounts of water.

It is also noted that the compounds of Formula (I) may form tautomers. 'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention.

While aspects for each variable have generally been listed above separately for each variable this invention includes those compounds in which several or each aspect in Formula (I) is selected from each of the aspects listed above. Therefore, this invention is intended to include all combinations of aspects for each variable.

Definitions

"Alkyl" refers to a hydrocarbon chain having the specified number of "member atoms". For example, $C_1$-$C_6$ alkyl refers to an alkyl group having from 1 to 6 member atoms. Alkyl groups may be saturated, unsaturated, straight or branched. Representative branched alkyl groups have one, two, or three branches. Alkyl includes but is not limited to: methyl, ethyl, ethylene, ethynyl, propyl (n-propyl and isopropyl), butene, butyl (n-butyl, isobutyl, and t-butyl), pentyl and hexyl.

"Alkoxy" refers to an —O-alkyl group wherein "alkyl" is as defined herein. For example, $C_1$-$C_4$alkoxy refers to an alkoxy group having from 1 to 4 carbon member atoms. Examples of such groups include but is not limited to: methoxy, ethoxy, propoxy, isopropoxy, butoxy, and t-butoxy.

"Aryl" refers to an aromatic hydrocarbon ring system. Aryl groups are monocyclic, bicyclic, and tricyclic ring systems having a total of five to fourteen ring member atoms, wherein at least one ring system is aromatic and wherein each ring in the system contains 3 to 7 member atoms, such as but no limited to: phenyl, dihydroindene, naphthalene, tetrahydronaphthalene and biphenyl. Suitably aryl is phenyl.

"Cycloalkyl", unless otherwise defined, refers to a saturated or unsaturated non aromatic hydrocarbon ring having from three to seven carbon atoms. Cycloalkyl groups are monocyclic ring systems. For example, $C_3$-$C_7$ cycloalkyl refers to a cycloalkyl group having from 3 to 7 member atoms. Examples of cycloalkyl as used herein include but is not limited to: cyclopropyl, cyclobutyl, cyclopentyl, cyclohexyl, cyclobutenyl, cyclopentenyl, cyclohexenyl and cycloheptyl. Suitably cycloalkyl is selected from: cyclopropyl, cyclopentyl and cyclohexyl.

"Heterocyclyl" refers to a saturated or unsaturated non-aromatic ring containing 4 to 12 member atoms, of which 1 to 11 are carbon atoms and from 1 to 6 are heteroatoms. Heterocycloalkyl groups containing more than one heteroatom may contain different heteroatoms. Heterocycloalkyl groups are monocyclic ring systems or a monocyclic ring fused with an aryl ring or to a heteroaryl ring having from 3 to 6 member atoms. In certain embodiments, heterocyclyl is saturated. In other embodiments, heterocyclyl is unsaturated but not aromatic. Heterocyclyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7,tetrahydro-1H-benzimidazol, piperidinyl, 1,2,3,6-tetrahydro-pyridinyl and azetidinyl.

Suitably "Heterocyclyl" includes: pyrrolidinyl, oxazolidinyl, and morpholinyl,

"Heteroaryl" refers to a monocyclic aromatic 4 to 8 member ring containing from 1 to 7 carbon atoms and containing from 1 to 4 heteroatoms, provided that when the number of carbon atoms is 3, the aromatic ring contains at least two heteroatoms. Heteroaryl groups containing more than one heteroatom may contain different heteroatoms. Heteroaryl includes: pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl. Suitably, "heteroaryl" includes: pyrazolyl, pyrrolyl, isoxazolyl, pyridinyl, pyrimidinyl, pyridazinyl, and imidazolyl.

"Bicycloheteroaryl" refers to two fused rings, at least one of which is aromatic, containing from 1 to 6 heteroatoms as member atoms. Bicycloheteroaryl groups containing more than one heteroatom may contain different heteroatoms. Bicycloheteroaryl rings have from 6 to 11 member atoms. Bicycloheteroaryl includes: 1H-pyrrolo[3,2-c]pyridinyl, 1H-pyrazolo[4,3-c]pyridinyl, 1H-pyrazolo[3,4-d]pyrimidinyl, 1H-pyrrolo[2,3-d]pyrimidinyl, 7H-pyrrolo[2,3-d]pyrimidinyl, thieno[3,2-c]pyridinyl, thieno[2,3-d]pyrimidinyl, furo[2,3-c]pyridinyl, furo[2,3-d]pyrimidinyl, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzoxadiazole, imidazothiazole, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridinyl, furopyridinyl and napthyridinyl. Suitably "Bicycloheteroaryl" includes: benzoxadiazolyl and imidazothiazolyl.

"Heteroatom" refers to a nitrogen, sulphur or oxygen atom.

"Halogen" and "halo" refers to a fluorine, chlorine, bromine, or iodine atom.

As used herein, the term "mercapto" refers to the group —SH.

As used herein, the term "oxo" refers to the group =O.

As used herein, the term "hydroxy" refers to the group —OH.

As used herein, the term "amino" refers to the group —NH$_2$.

As used herein, the term "carboxy" refers to the group —C(O)OH.

As used herein, the term "cyano" refers to the group —CN.

As used herein, the term "nitro" refers to the group —NO$_2$.

Compound Preparation

The compounds according to Formula (I) are prepared using conventional organic synthetic methods. Suitable synthetic routes are depicted below in the following general reaction schemes. All of the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

As used in the Schemes, "Ar" and "r" groups represent corresponding groups on any of Formulas I to IV. The compounds of Formulas I to IV can be prepared generally as described in the Schemes using appropriate substitutions for starting materials.

Scheme 1

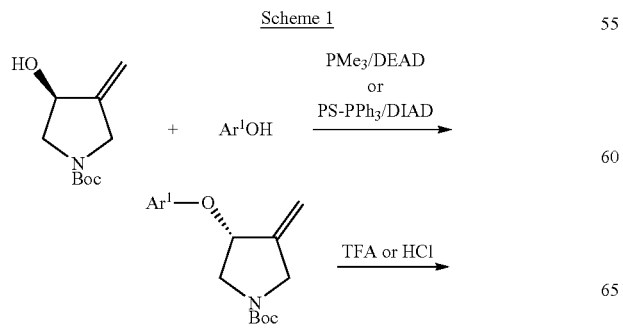

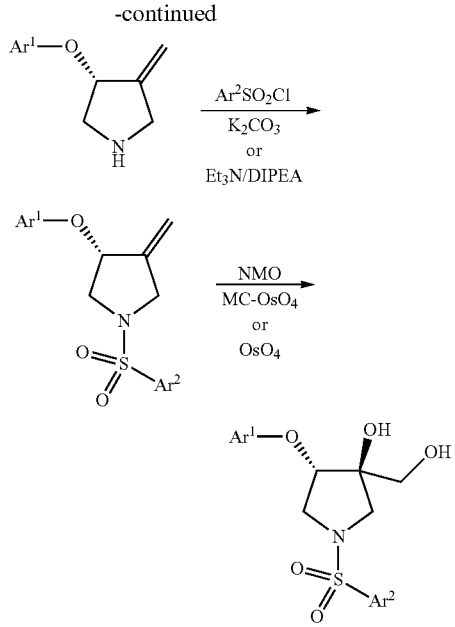

Compounds of Formula (I) can be prepared by the sequence in Scheme 1. The Boc protected hydroxyl pyrrolidine can be converted to the aryl ether with an appropriately substituted phenol using Mitsunobu conditions such as PMe$_3$/DEAD or PS—PPh$_3$/DIAD. The Boc protecting group can be removed with an acid such as TFA or HCl, and treatment of the unprotected pyrrolidine with an appropriately substituted arylsulfonyl chloride using a base such as K$_2$CO$_3$, Et$_3$N or DIPEA can give the sulfonamide. Dihydroxylation of the exocyclic olefin of the pyrrolidine ring with catalytic microencapsulated OsO$_4$ or OsO$_4$ using NMO as a cooxidant, provides compounds of Formula (I).

Scheme 2

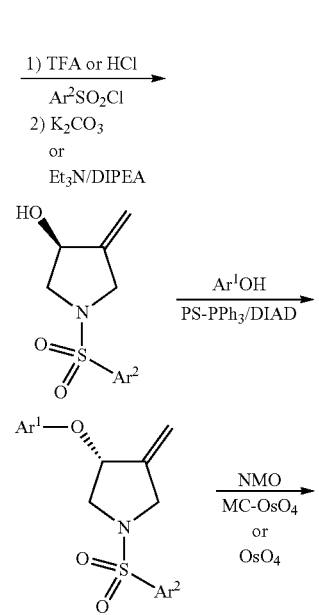

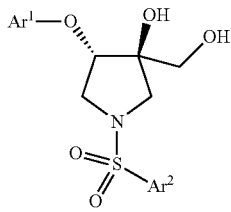

Alternatively, compounds of Formula (I) can be prepared as shown in Scheme 2.

The Boc protecting group can be removed with an acid such as TFA or HCl, and treatment of the unprotected pyrrolidine with an appropriately substituted arylsulfonyl chloride using a base such as $K_2CO_3$, $Et_3N$ or DIPEA can give the sulfonamide. Treating the sulfonamide with an appropriately substituted phenol using Mitsunobu conditions such as $PMe_3$/DEAD or PS—$PPh_3$/DIAD, provides the aryl ether. Dihydroxylation of the exocyclic olefin of the pyrrolidine ring with catalytic microencapsulated $OsO_4$ or $OsO_4$ using NMO as a cooxidant, provides compounds of Formula (I).

Scheme 3

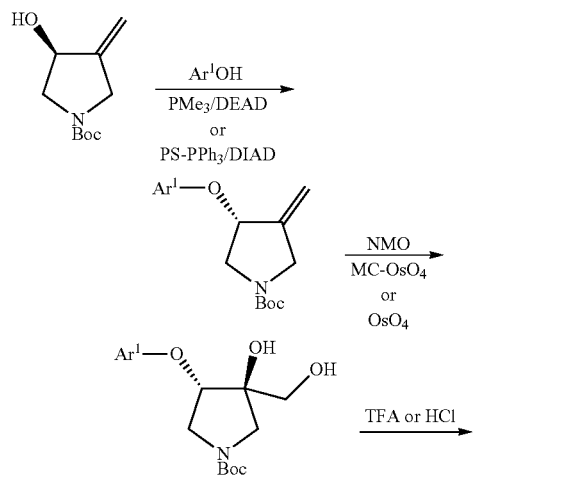

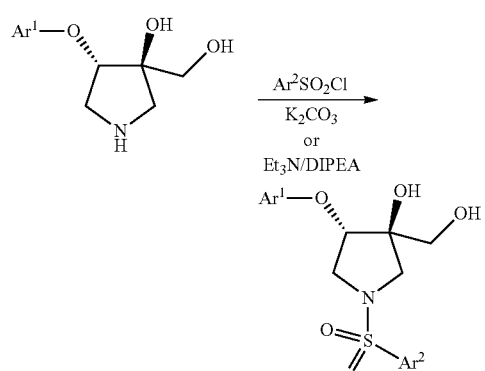

Alternatively, compounds of Formula (I) can be prepared as shown in Scheme 3. Treating Boc protected hydroxyl pyrrolidine with an appropriately substituted phenol using Mitsunobu conditions, $PMe_3$/DEAD or PS—$PPh_3$/DIAD, provides the aryl ether. Diol compounds can be prepared by dihydroxylation of the exocyclic olefin of the pyrrolidine ring with catalytic microencapsulated $OsO_4$ or $OsO_4$, using NMO as a cooxidant. Removal of the pyrrolidine Boc group with an acid such as TFA or HCl followed by treatment of the unprotected pyrrolidine with an appropriately substituted arylsulfonyl chloride using a base such as $K_2CO_3$, $Et_3N$ or DIPEA provides compounds of Formula (I).

Scheme 4

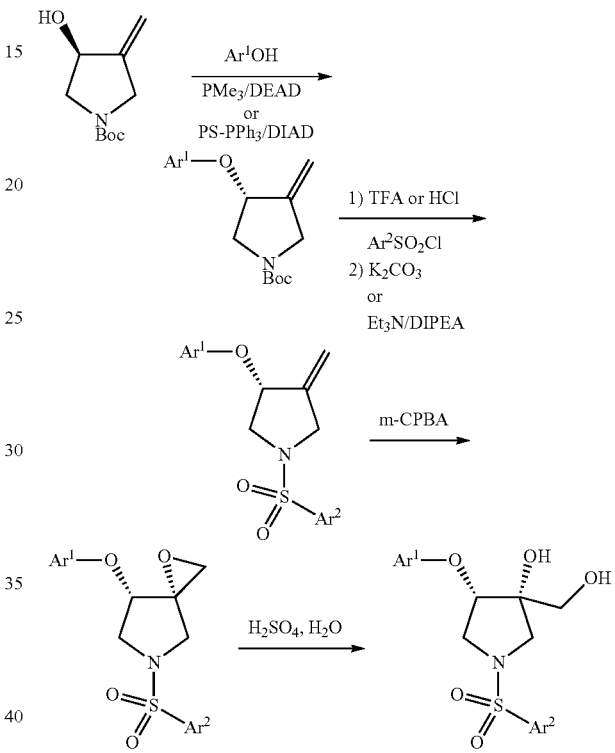

Alternatively, compounds of Formula (I) can be prepared as shown in Scheme 4. Treating Boc protected hydroxyl pyrrolidine with an appropriately substituted phenol using Mitsunobu conditions such as $PMe_3$/DEAD or PS—$PPh_3$/DIAD, provides the aryl ether. Removal of the Boc protecting group with an acid such as TFA or HCl followed by treatment of the unprotected pyrrolidine with an appropriately substituted arylsulfonyl chloride using a base such as $K_2CO_3$, $Et_3N$ or DIPEA provides the sulfonamide. Epoxidation of the exocylcic olefin on the pyrrolidine ring with m-CPBA provides the epoxide which upon treatment with $H_2SO_4$ and water can be hydrolyzed to provide compounds of Formula (I).

Scheme 5

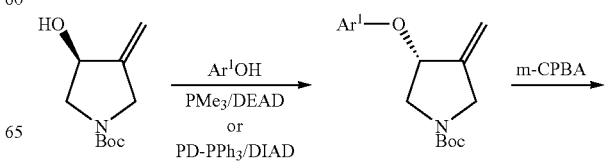

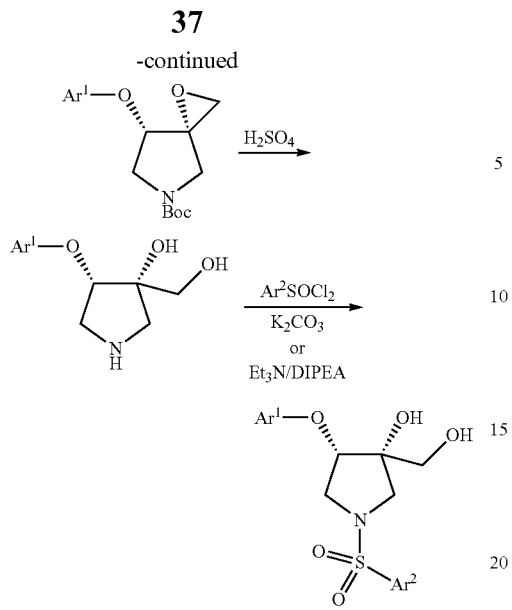

Alternatively, compounds of Formula (I) can be prepared as shown in Scheme 5. Treating Boc protected hydroxyl pyrrolidine with an appropriately substituted phenol using Mitsunobu conditions such as PMe$_3$/DEAD or PS—PPh$_3$/DIAD, provides the aryl ether. Epoxidation of the exocylcic olefin on the pyrrolidine ring with m-CPBA provides the epoxide. Hydrolysis of the epoxide and removal of the Boc group can be accomplished with H$_2$SO$_4$ and water to give the pyrrolidine diol. Treatment of the unprotected pyrrolidine with an appropriately substituted arylsulfonyl chloride using a base such as K$_2$CO$_3$, Et$_3$N or DIPEA provides compounds of Formula (I).

Scheme 6

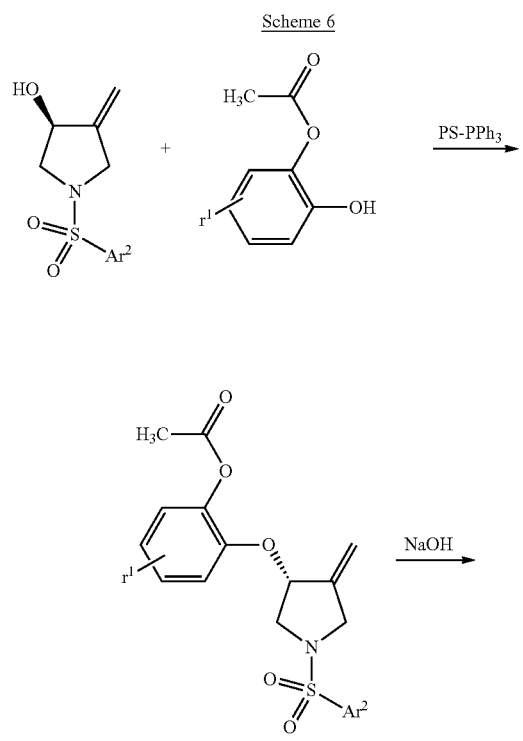

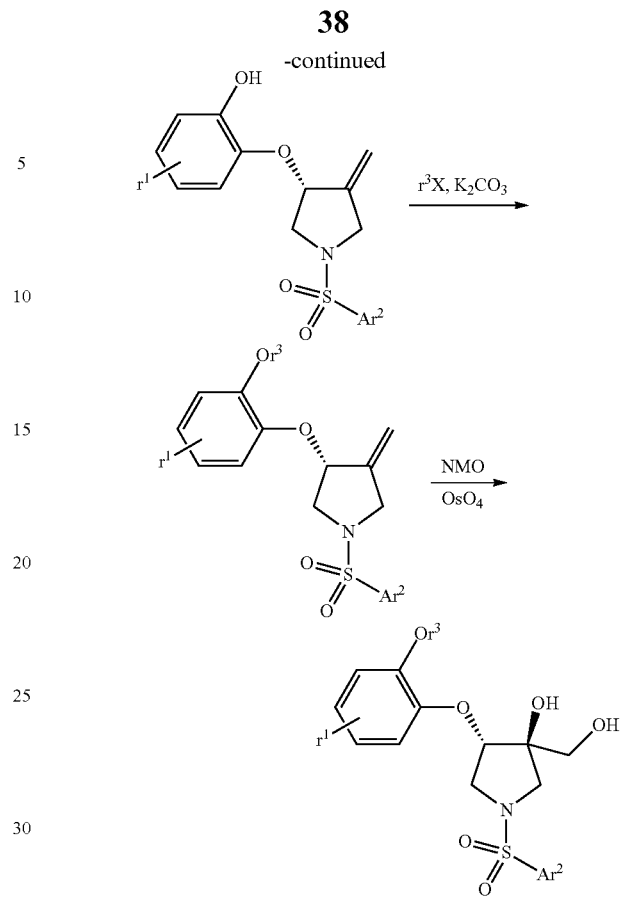

Alternatively, compounds of Formula (I) can be prepared as shown in Scheme 6. Treating the hydroxy pyrrolidine sulfonamide with an appropriately substituted phenol using Mitsunobu conditions such as PS—PPh$_3$/DIAD, provides the aryl ether. Hydrolysis of the ester with NaOH provides the phenol. The phenol can be converted to an aryl ether with an appropriate alkyl halide and base such as K$_2$CO$_3$. Dihydroxylation of the exocyclic olefin of the pyrrolidine ring with catalytic OsO$_4$ using NMO as a cooxidant, provides compounds of Formula (I).

Scheme 7

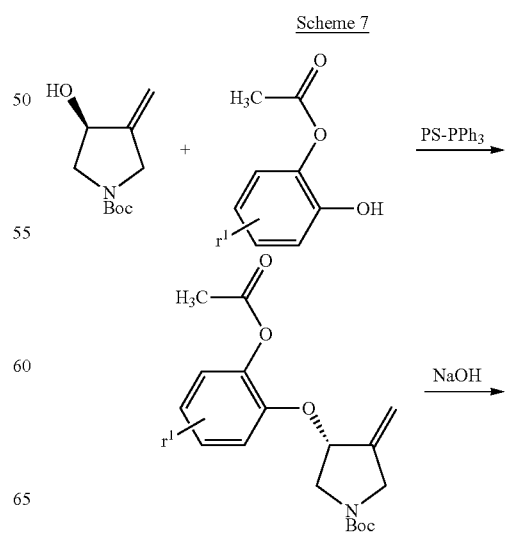

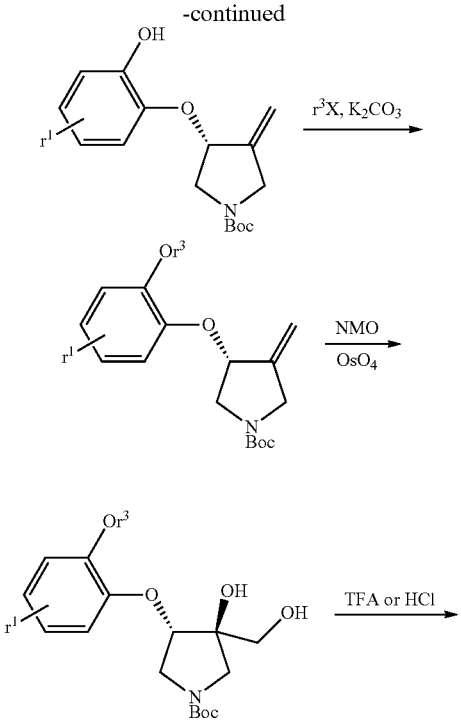

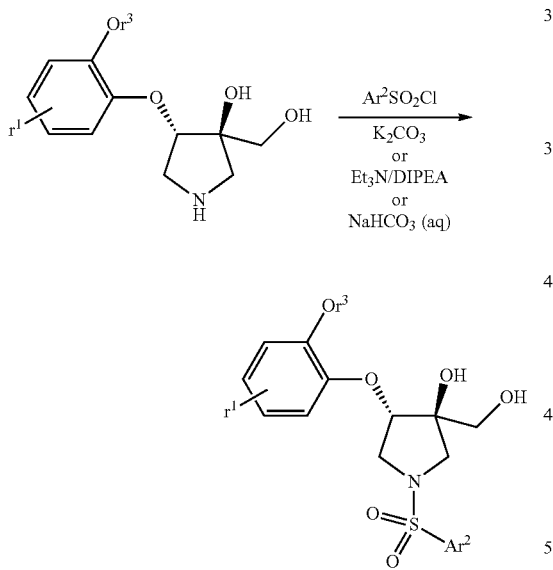

Alternatively, compounds of Formula (I) can be prepared as shown in Scheme 7. Treating Boc protected hydroxyl pyrrolidine with an appropriately substituted phenol using Mitsunobu conditions such as PS—PPh$_3$/DIAD, provides the aryl ether. Hydrolysis of the ester with NaOH can give the phenol. The phenol can be converted to an aryl ether with an appropriate alkyl halide and base such as K$_2$CO$_3$. Dihydroxylation of the exocyclic olefin of the pyrrolidine ring with catalytic OsO$_4$ using NMO as a cooxidant, provides the diol. Removal of the pyrrolidine Boc group with an acid such as TFA or HCl followed by treatment of the unprotected pyrrolidine with an appropriately substituted arylsulfonyl chloride using a base such as K$_2$CO$_3$, Et$_3$N or DIPEA, or NaHCO$_3$ provides compounds of Formula (I).

Scheme 8

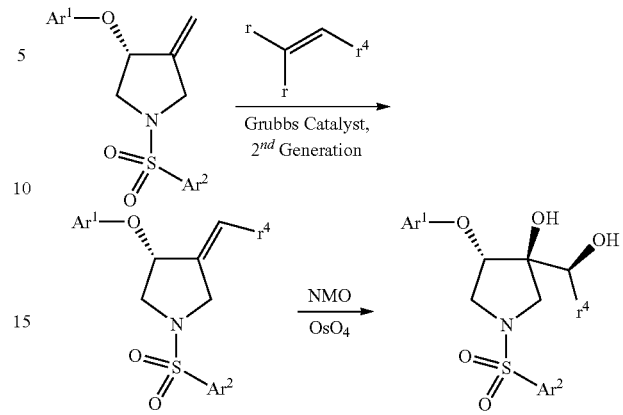

Alternatively compounds of Formula (I) can be prepared as shown in Scheme 8. Olefin metathesis of the exocyclic olefin of the substituted pyrrolidine with an appropriately substituted olefin using a catalyst such as Grubbs Catalyst, 2$^{nd}$ Generation, provides substituted exocyclic olefins. Dihydroxylation of the substituted exocyclic olefin with catalytic OsO$_4$ using NMO as a cooxidant, provides compounds of Formula (I).

Scheme 9

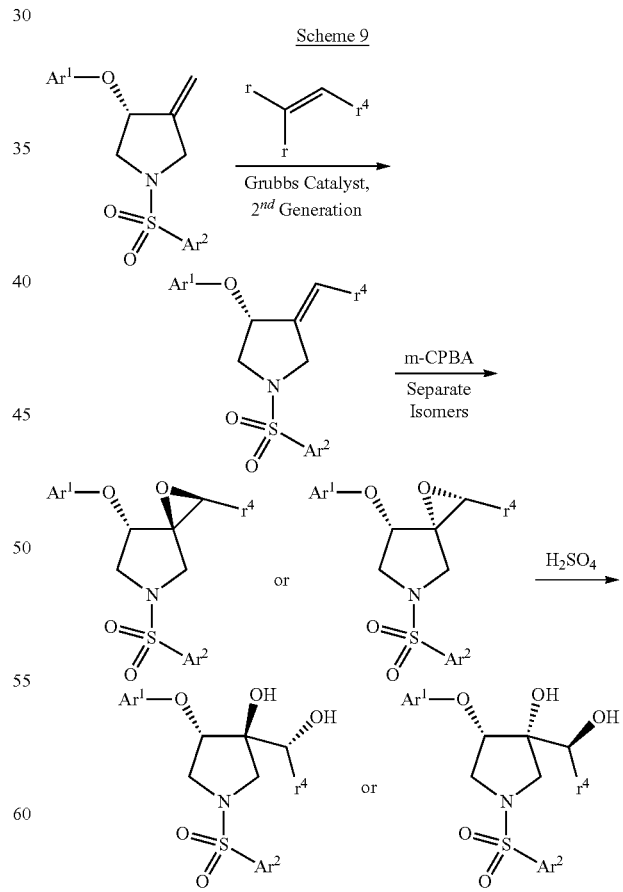

Alternatively, compounds of Formula (I) can be prepared as shown in Scheme 9. Olefin metathesis of the exocyclic olefin of the substituted pyrrolidine with an appropriately substituted olefin using Grubbs Catalyst, $2^{nd}$ Generation as a catalyst provides substituted exocyclic olefins. Epoxidation of the exocylcic olefin on the pyrrolidine ring with m-CPBA provides the epoxide as a mixture of diastereomers that can be separated by techniques such as silica gel column chromatography. Either of the individual diastereomeric epoxides can be hydrolyzed with $H_2SO_4$ to give compounds of Formula (I).

Scheme 10

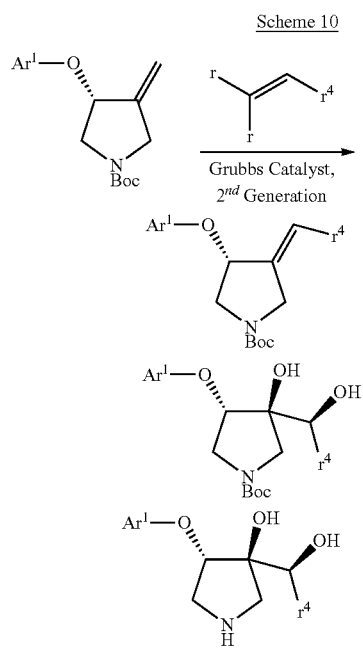

Alternatively, compounds of Formula (I) can be prepared as shown in Scheme 10. Olefin metathesis of the exocyclic olefin of the Boc protected pyrrolidine with an appropriately substituted olefin using a catalyst such as Grubbs Catalyst, $2^{nd}$ Generation, provides substituted exocyclic olefins. Dihydroxylation of the substituted exocyclic olefin of the pyrrolidine ring with catalytic $OsO_4$ using NMO as a cooxidant, provides the diol. Removal of the pyrrolidine Boc group with an acid such as HCl, followed by treatment of the unprotected pyrrolidine with an appropriately substituted arylsulfonyl chloride using a base such as $NaHCO_3$, provides compounds of Formula (I).

Scheme 11

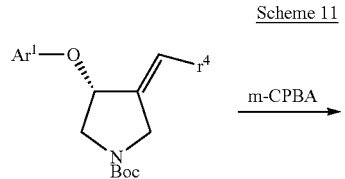

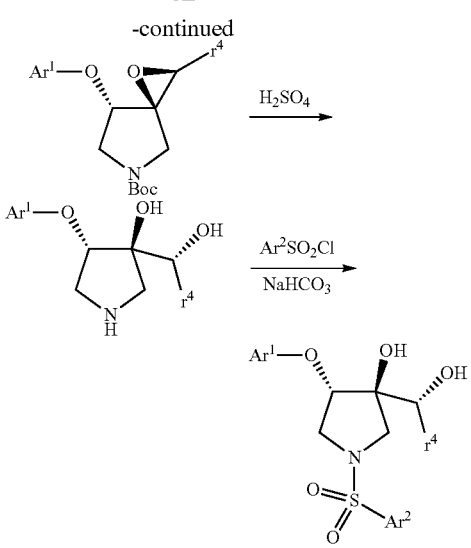

Alternatively, compounds of Formula (I) can be prepared as shown in Scheme 11. Epoxidation of the substituted exocyclic olefin of the Boc protected pyrrolidine with m-CPBA provides the epoxide. Hydrolysis of the epoxide with $H_2SO_4$ provides the dihydroxy compound and also removes the Boc group to give the pyrrolidine diol. Treatment of the unprotected pyrrolidine with an appropriately substituted arylsulfonyl chloride using a base such as $NaHCO_3$ provides compounds of Formula (I).

Scheme 12

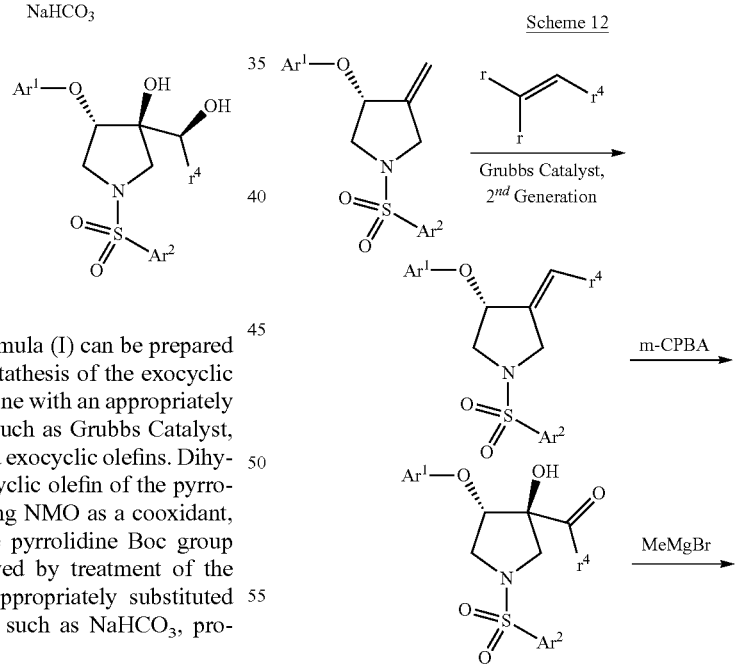

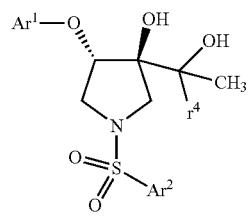

Alternatively, compounds of Formula (I) can be prepared as shown in Scheme 12. Olefin metathesis of the exocyclic olefin of the sulfonamide protected pyrrolidine with an appropriately substituted olefin using a catalyst such as Grubbs Catalyst, 2$^{nd}$ Generation, provides substituted exocyclic olefins. Oxidation of the new substituted olefin with m-CPBA provides the hydroxyl ketone. Treatment of the ketone with a Grignard reagent such as MeMgBr, provides the compounds of Formula (I).

Scheme 13

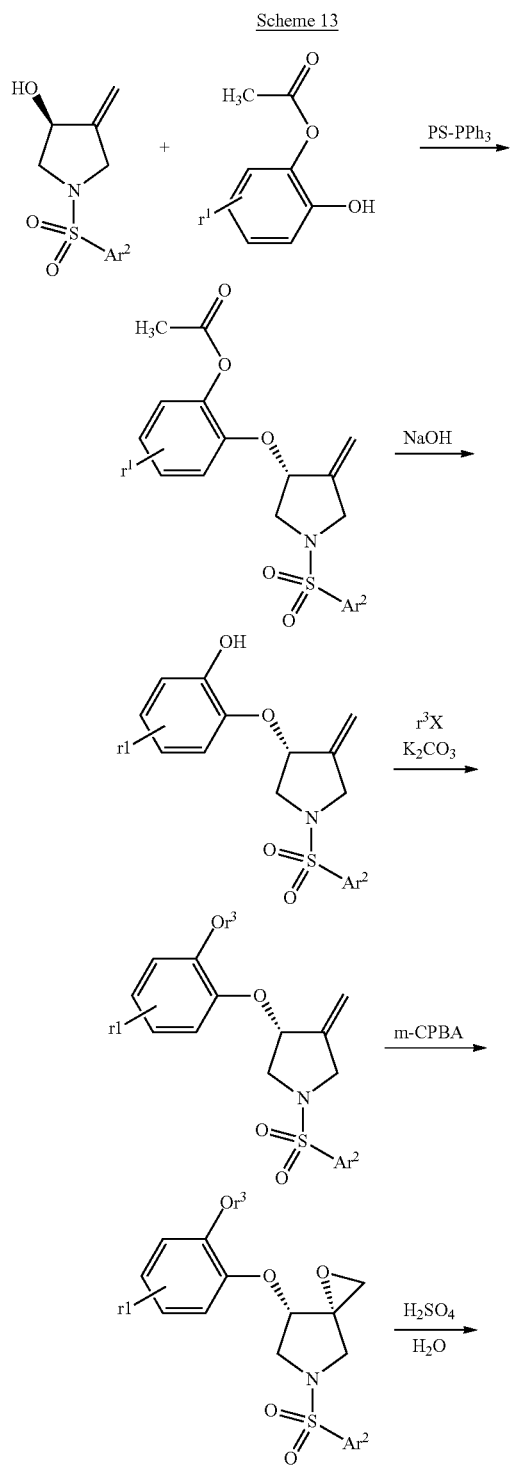

-continued

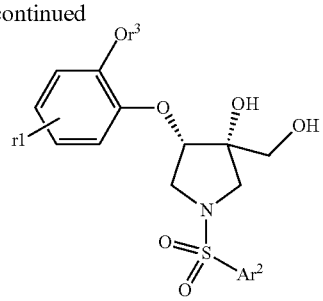

Alternatively, compounds of Formula (I) can be prepared as shown in Scheme 13. Treating the hydroxyl pyrrolidine sulfonamide with an appropriately substituted phenol using Mitsunobu conditions such as PS—PPh$_3$/DIAD, provides the aryl ether. Hydrolysis of the ester with NaOH provides the phenol. The phenol can be converted to an ether with an appropriate alkyl halide and base such as K$_2$CO$_3$. Epoxidation of the exocylcic olefin on the pyrrolidine ring can be accomplished with m-CPBA and the resulting epoxide can be hydrolyzed with H$_2$SO$_4$ and water to compounds of Formula (I).

Scheme 14

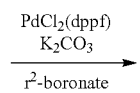

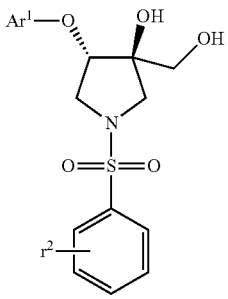

Compounds of Formula (I) can be prepared by the sequence in Scheme 14. An aryl bromide can be substituted by using the appropriate borate under Suzuki palladium catalyzed coupling conditions with a catalyst such as PdCl$_2$(dppf), to give substituted aryl compounds of Formula (I).

Scheme 15

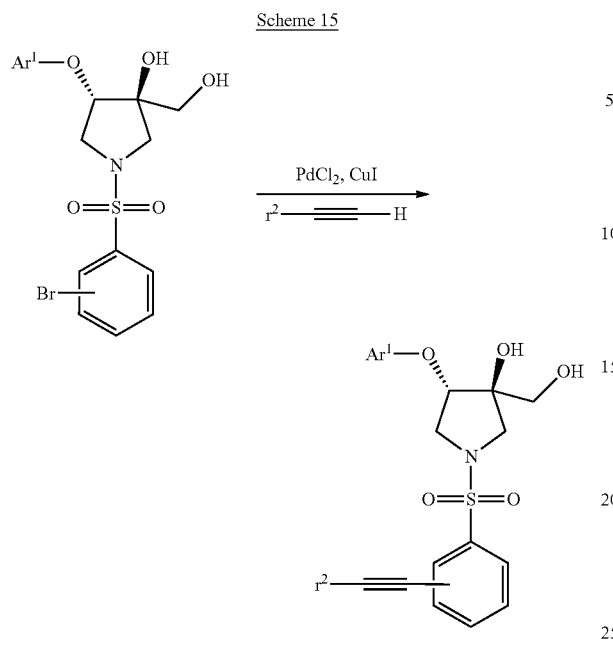

Alternatively, compounds of Formula (I) can be prepared as shown in Scheme 15. An aryl bromide can be substituted by an appropriate alkyne using palladium catalyzed coupling conditions with catalysts such as PdCl$_2$ and CuI, to give aryl alkyne compounds of Formula (I).

Scheme 16

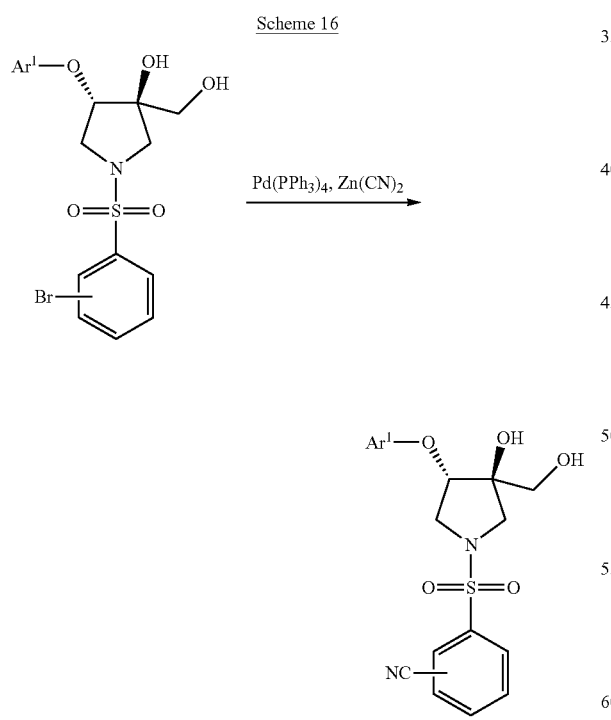

Alternatively, compounds of Formula (I) can be prepared as shown in Scheme 16. An aryl bromide can be cyanated by microwave irradiation using palladium catalyzed coupling conditions with catalysts such as Pd(PPh$_3$)$_4$ and zinc cyanide to give benzonitrile compounds of Formula (I).

Scheme 17

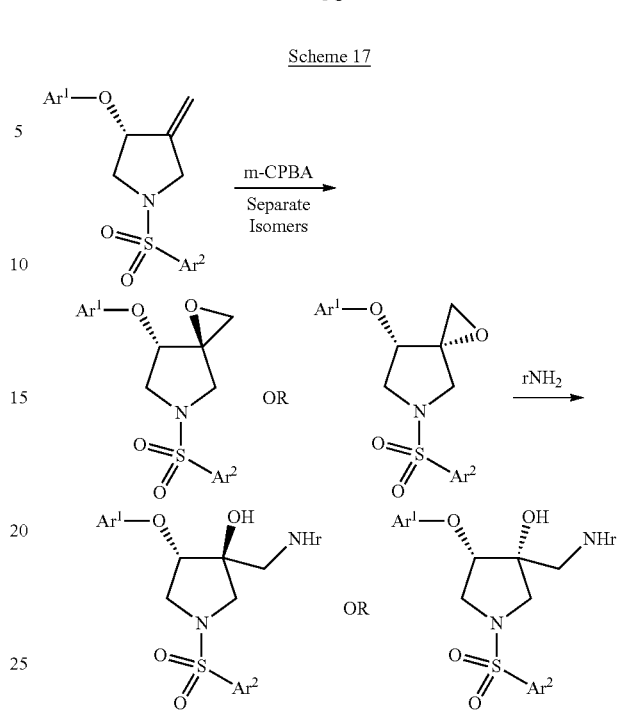

Compounds of Formula (I) can be prepared by the sequence in Scheme 17. Epoxidation of the exocylcic olefin on the pyrrolidine ring with m-CPBA can give the epoxide as a mixture of diastereomers that can be separated by techniques such as silica gel column chromatography. Either of the individual diastereomeric epoxides can be opened with an appropriately substituted amine to give amino alcohol compounds of Formula (I).

Scheme 18

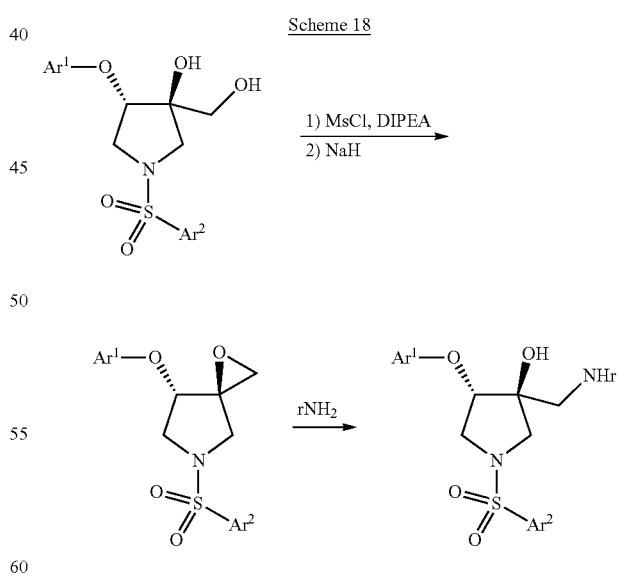

Alternatively, compounds of Formula (I) can be prepared as shown in Scheme 18. The primary alcohol can be mesylated with mesyl chloride using a base such as DIPEA and the epoxide can be formed by treatment with NaH. Opening of the epoxide with an appropriately substituted amine provides amino alcohol compounds of Formula (I).

Scheme 19

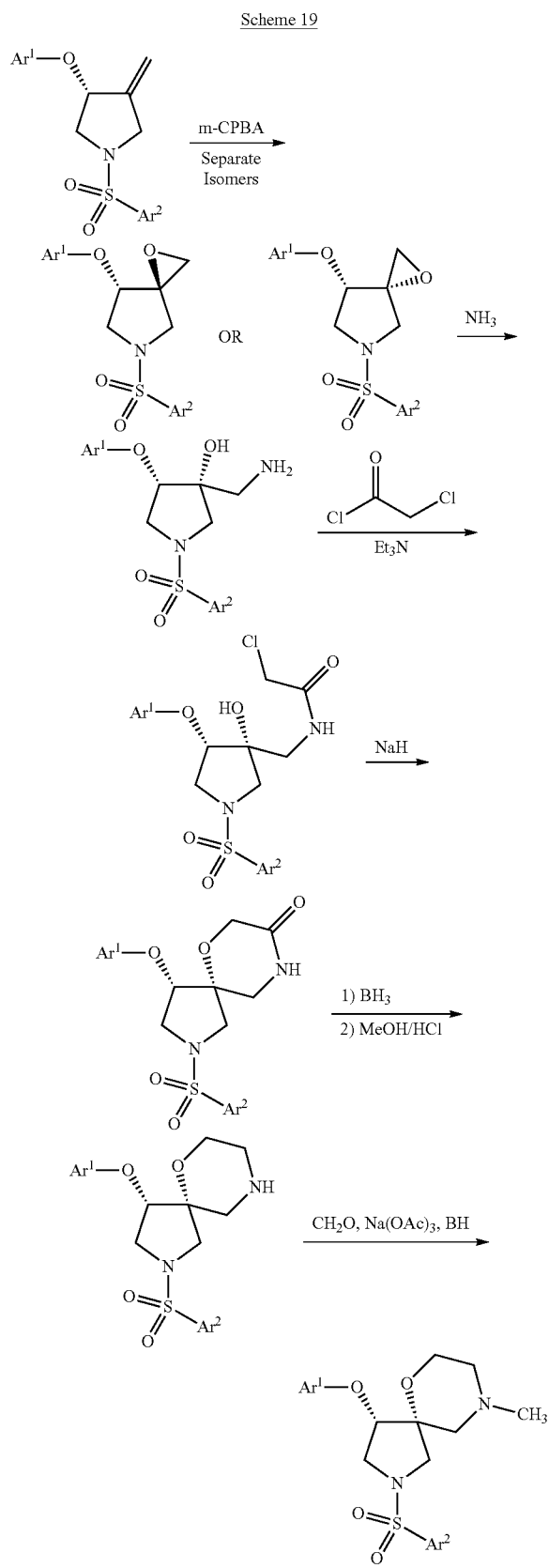

Compounds of Formula (I) can be prepared by the sequence in Scheme 19. Epoxidation of the exocylcic olefin on the pyrrolidine ring with m-CPBA can give the epoxide as a mixture of diastereomers that can be separated by techniques such as silica gel column chromatography. Either of the individual diastereomeric epoxides can be carried through the subsequent steps to give compounds of Formula (I). The epoxide can be opened with ammonia to give the amino alcohol. The chloroacetamide can be formed by acylation with 2-chloroacetyl chloride and a base such as $Et_3N$. Cyclization to the morpholin-3-one can be accomplished with a base such as NaH, and the carbonyl can be reduced with a reducing agent such as borane to give the morpholine. Reductive amination with an appropriate aldehyde or ketone such as formaldehyde in the presence of a reducing agent such as triacetoxyborohydride can give N-alkylated morpholine compounds of Formula (I).

Scheme 20

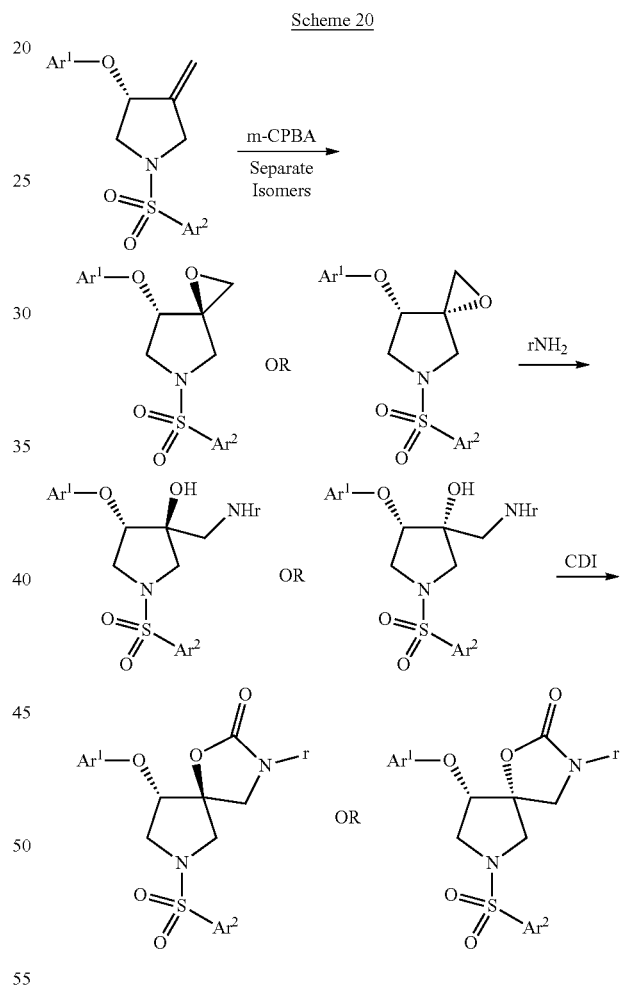

Compounds of Formula (I) can be prepared by the sequence in Scheme 20. Epoxidation of the exocylcic olefin on the pyrrolidine ring with m-CPBA provides the epoxide as a mixture of diastereomers that can be separated by techniques such as silica gel column chromatography. Either of the individual diastereomeric epoxides can be carried through the subsequent steps to give compounds of Formula (I). The epoxide can be opened with an appropriately substituted amine to give the amino alcohol. Cyclization of the amino alcohol with reagents such as CDI provides the oxazolidinone compounds of Formula (I).

Scheme 21

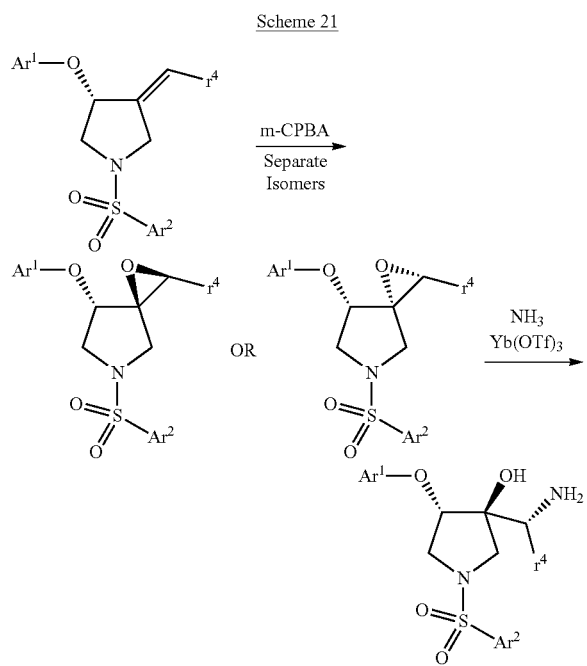

Compounds of Formula (I) can be prepared by the sequence in Scheme 21. Epoxidation of the exocylcic olefin on the pyrrolidine ring with m-CPBA provides the epoxide as a mixture of diastereomers that can be separated by techniques such as silica gel column chromatography. Either of the individual diastereomeric epoxides can be opened with an appropriately substituted amine, catalyzed with Yb(OTf)$_3$, to give amino alcohol compounds of Formula (I).

Scheme 22

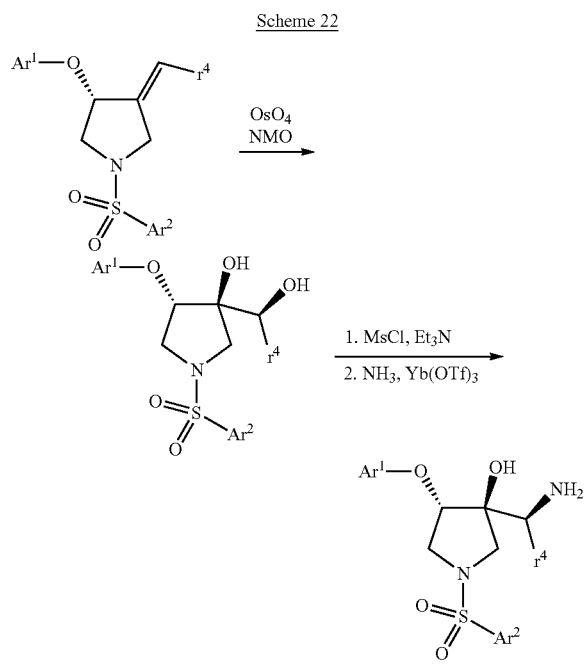

Alternatively, compounds of Formula (I) can be prepared as shown in Scheme 22. Dihydroxylation of the exocylcic substituted olefin on the pyrrolidine ring with catalytic OsO$_4$ using NMO as a cooxidant, provides the diol. The diol can be treated with mesyl chloride and a base such as Et$_3$N to form the epoxide which can be opened with an appropriately substituted amine, catalyzed with Yb(OTf)$_3$, to give amino alcohol compounds of Formula (I).

Biological Activity

As stated above, the compounds according to Formula I are TRPV4 antagonists. The biological activity of the compounds according to Formula I can be determined using any suitable assay for determining the activity of a candidate compound as a TRPV4 antagonist, as well as tissue and in vivo models. The biological activity of the compounds of Formula (I) are demonstrated by the following tests.

FLIPR Assay for hTRPV4 Expressed in BHK Cells:

TRPV4 channel activation results in an influx of divalent and monovalent cations including calcium. The resulting changes in intracellular calcium were monitored using a calcium specific fluorescent dye Fluo-4 (MDS Analytical Technologies). BHK/AC9 cells transduced with BacMam virus expressing the human TRPV4 gene at a MOI of 78 were plated in a 384 well poly-D lysine coated plate (15,000 cells/well in 50 µL culture medium containing DMEM/F12 with 15 mM HEPES, 10% FBS, 1% Penicillin-Streptomycin and 1% L-glutamine). Cells were incubated for 24 hours at 37° C. and 5% CO$_2$. Culture medium was then aspirated using a Tecan plate-washer and replaced with 20 µL/well of dye loading buffer: HBSS, 500 µM Brilliant Black (MDS Analytical Technologies), and 2 µM Fluo-4 AM. Dye loaded plates were then incubated in the dark at room temperature for 1-1.5 hours. 10 µL of test compounds diluted in HBSS (with 1.5 mM Calcium Chloride, 1.5 mM Magnesium Chloride and 10 mM HEPES, pH 7.4)+0.01% Chaps was added to each individual well of the plate, incubated for 10 min at room temperature in the dark and then 10 µL of agonist (N—((S)-1-(((R)-1-((2-cyanophenyl)sulfonyl)-3-oxoazepan-4-yl)amino)-4-methyl-1-oxopentan-2-yl)benzo[b]thiophene-2-carboxamide, (Thorneloe et al, *Sci. Transl. Med.* (2012), 4, 159ra148) (hereinafter: Agonist Compound) was added to have a final concentration equals to the agonist EC80. Calcium signals were measured using FLIPRTETRA (MDS Analytical Technologies) or FLIPR384 (MDS Analytical Technologies) and the inhibition of Agonist Compound-induced calcium signal by the test compound was determined.

All examples described herein possessed TRPV4 biological activity with IC$_{50}$ ranges from 0.1 nM-1 µM (see table below).

The compound of Example 6 was tested generally according to the above TRPV4 assay and in at least one set of experimental runs exhibited an average IC$_{50}$ (nM) value of 3.

The compound of Example 194 was tested generally according to the above TRPV4 assay and in at least one set of experimental runs exhibited an average IC$_{50}$ (nM) value of 40. EX #IC$_{50}$ EX #IC$_{50}$ EX #IC$_{50}$ EX #IC$_{50}$ EX #IC$_{50}$ EX #IC$_{50}$ 1+++44+++87++130++173+++216+++

| EX # | IC$_{50}$ |
|---|---|
| 1 | +++ |
| 2 | +++ |
| 3 | +++ |
| 4 | ++ |
| 5 | + |
| 6 | +++ |
| 7 | +++ |
| 8 | +++ |

| EX # | IC$_{50}$ |
|---|---|
| 9 | +++ |
| 10 | ++ |
| 11 | ++ |
| 12 | +++ |
| 13 | ++ |
| 14 | +++ |
| 15 | +++ |
| 16 | +++ |
| 17 | +++ |
| 18 | ++ |
| 19 | +++ |
| 20 | +++ |
| 21 | ++ |
| 22 | +++ |
| 23 | +++ |
| 24 | +++ |
| 25 | +++ |
| 26 | ++ |
| 27 | +++ |
| 28 | ++ |
| 29 | +++ |
| 30 | +++ |
| 31 | +++ |
| 32 | ++ |
| 33 | ++ |
| 34 | +++ |
| 35 | ++ |
| 36 | +++ |
| 37 | +++ |
| 38 | ++ |
| 39 | ++ |
| 40 | +++ |
| 41 | ++ |
| 42 | ++ |
| 43 | ++ |
| 44 | +++ |
| 45 | +++ |
| 46 | ++ |
| 47 | ++ |
| 48 | ++ |
| 49 | ++ |
| 50 | +++ |
| 51 | ++ |
| 52 | ++ |
| 53 | ++ |
| 54 | ++ |
| 55 | ++ |
| 56 | ++ |
| 57 | ++ |
| 58 | ++ |
| 59 | ++ |
| 60 | ++ |
| 61 | +++ |
| 62 | +++ |
| 63 | +++ |
| 64 | ++ |
| 65 | +++ |
| 66 | ++ |
| 67 | +++ |
| 68 | ++ |
| 69 | ++ |
| 70 | ++ |
| 71 | ++ |
| 72 | ++ |
| 73 | ++ |
| 74 | ++ |
| 75 | ++ |
| 76 | ++ |
| 77 | ++ |
| 78 | +++ |
| 79 | ++ |
| 80 | +++ |
| 81 | ++ |
| 82 | ++ |
| 83 | ++ |
| 84 | ++ |
| 85 | ++ |
| 86 | ++ |
| 87 | ++ |
| 88 | ++ |
| 89 | ++ |
| 90 | ++ |
| 91 | ++ |
| 92 | +++ |
| 93 | ++ |
| 94 | ++ |
| 95 | +++ |
| 96 | ++ |
| 97 | +++ |
| 98 | ++ |
| 99 | ++ |
| 100 | +++ |
| 101 | ++ |
| 102 | ++ |
| 103 | ++ |
| 104 | ++ |
| 105 | ++ |
| 106 | +++ |
| 107 | ++ |
| 108 | +++ |
| 109 | ++ |
| 110 | ++ |
| 111 | ++ |
| 112 | ++ |
| 113 | +++ |
| 114 | +++ |
| 115 | +++ |
| 116 | ++ |
| 117 | ++ |
| 118 | ++ |
| 119 | +++ |
| 120 | +++ |
| 121 | ++ |
| 122 | +++ |
| 123 | ++ |
| 124 | + |
| 125 | ++ |
| 126 | + |
| 127 | + |
| 128 | + |
| 129 | ++ |
| 130 | ++ |
| 131 | ++ |
| 132 | ++ |
| 133 | ++ |
| 134 | ++ |
| 135 | +++ |
| 136 | + |
| 137 | ++ |
| 138 | +++ |
| 139 | +++ |
| 140 | ++ |
| 141 | ++ |
| 142 | ++ |
| 143 | +++ |
| 144 | ++ |
| 145 | ++ |
| 146 | ++ |
| 147 | ++ |
| 148 | ++ |
| 149 | ++ |
| 150 | ++ |
| 151 | +++ |
| 152 | +++ |
| 153 | +++ |
| 154 | +++ |
| 155 | +++ |
| 156 | +++ |
| 157 | +++ |
| 158 | +++ |
| 159 | +++ |
| 160 | +++ |
| 161 | +++ |
| 162 | +++ |

| EX # | IC$_{50}$ |
|---|---|
| 163 | +++ |
| 164 | +++ |
| 165 | +++ |
| 166 | +++ |
| 167 | +++ |
| 168 | ++ |
| 169 | +++ |
| 170 | +++ |
| 171 | +++ |
| 172 | ++ |
| 173 | +++ |
| 174 | +++ |
| 175 | ++ |
| 176 | ++ |
| 177 | +++ |
| 178 | +++ |
| 179 | +++ |
| 180 | +++ |
| 181 | +++ |
| 182 | ++ |
| 183 | ++ |
| 184 | ++ |
| 185 | +++ |
| 186 | ++ |
| 187 | +++ |
| 188 | ++ |
| 189 | ++ |
| 190 | +++ |
| 191 | + |
| 192 | ++ |
| 193 | +++ |
| 194 | ++ |
| 195 | +++ |
| 196 | +++ |
| 197 | +++ |
| 198 | +++ |
| 199 | ++ |
| 200 | ++ |
| 201 | +++ |
| 202 | +++ |
| 203 | ++ |
| 204 | +++ |
| 205 | +++ |
| 206 | ++ |
| 207 | ++ |
| 208 | ++ |
| 209 | +++ |
| 210 | ++ |
| 211 | ++ |
| 212 | ++ |
| 213 | ++ |
| 214 | ++ |
| 215 | ++ |
| 216 | +++ |
| 217 | +++ |
| 218 | ++ |
| 219 | +++ |
| 220 | +++ |
| 221 | +++ |
| 222 | +++ |
| 223 | ++ |
| 224 | ++ |
| 225 | +++ |
| 226 | ++ |
| 227 | +++ |
| 228 | ++ |
| 229 | ++ |
| 230 | +++ |
| 231 | ++ |
| 232 | +++ |
| 233 | ++ |
| 234 | ++ |
| 235 | +++ |
| 236 | +++ |
| 237 | +++ |
| 238 | +++ |
| 239 | +++ |
| 240 | +++ |
| 241 | ++ |
| 242 | ++ |
| 243 | ++ |
| 244 | ++ |
| 245 | ++ |
| 246 | ++ |
| 247 | ++ |
| 248 | ++ |
| 249 | ++ |
| 250 | +++ |
| 251 | +++ |
| 252 | +++ |
| 253 | +++ |
| 254 | ++ |
| 255 | +++ |
| 256 | ++ |
| 257 | ++ |

IC$_{50}$ Ranges: 0.1-10 nM (+++), >10-100 nM (++), >100-1000 nM (+).

Methods of Use

In yet another aspect, this invention provides a compound of Formula (I) or a pharmaceutically acceptable salt thereof in the treatment of a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, renal dysfunction, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence, through the administration of a compound of Formula (I) or a pharmaceutically acceptable salt thereof. Suitably the compounds of the invention are used in the treatment of congestive heart failure. Suitably the compounds of the invention are used in the treatment of acute lung injury. Suitably the compounds of the invention are used in the treatment of cerebral edema. Suitably the compounds of the invention are used in the treatment of heart failure. Suitably the compounds of the invention are used in the treatment of cough; including acute cough, sub-acute cough and chronic cough. Suitably the compounds of the invention are used in the treatment of acute respiratory distress syndrome. Accordingly, in another aspect the invention is directed to methods of treating such conditions.

The compounds of Formula (I) are tested for their ability to treat cough in in vivo in pre-clinical models in which cough is induced, for example the guinea pig model cited in Bonvini S J, et al., J Allergy Clin Immunol. 2016 July;

138(1):249-261.e12. The efficacy of compounds of Formula (I) are tested for their ability to treat cough; including acute cough, sub-acute cough and chronic cough, in people using the objective cough monitoring and specific quality of life instruments as cited in Abdulqawi R, et al. *Lancet.* 2015 Mar. 28; 385(9974):1198-1205.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression.

The compounds of Formula (I) can be used in the prevention of a disease or condition disclosed herein. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" or "subject" refers to a human or other mammal.

In a further aspect, the invention provides for a compound of Formula (I) or a pharmaceutically acceptable salt thereof for use in the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, renal dysfunction, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for a compound of Formula (I) or a pharmaceutically acceptable salt thereof for use in the treatment of congestive heart failure. Suitably the invention provides for a compound of Formula (I) or a pharmaceutically acceptable salt thereof for use in the treatment of acute lung injury. Suitably the invention provides for a compound of Formula (I) or a pharmaceutically acceptable salt thereof for use in the treatment cerebral edema. Suitably the invention provides for a compound of Formula (I) or a pharmaceutically acceptable salt thereof for use in the treatment of heart failure. Suitably the invention provides for a compound of Formula (I) or a pharmaceutically acceptable salt thereof for use in the treatment of cough; including acute cough, sub-acute cough and chronic cough. Suitably the invention provides for a compound of Formula (I) or a pharmaceutically acceptable salt thereof for use in the treatment of acute respiratory distress syndrome.

In another aspect, the invention provides for the use of a compound of Formula (I) or a pharmaceutically acceptable salt thereof in the manufacture of a medicament for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder (COPD), ventilator induced lung injury, high altitude induced pulmonary edema, acute respiratory distress syndrome, acute lung injury, pulmonary fibrosis and other fibrosis-related disorders, sinusitis/rhinitis, asthma, cough; including acute cough, sub-acute cough and chronic cough, pulmonary hypertension, overactive bladder, cystitis, pain, motor neuron disorders, genetic gain of function disorders, amyotrophic lateral sclerosis, multiple sclerosis, cardiovascular disease, acute, chronic and polycystic kidney disease, stroke, hydrocephalus, glaucoma, retinopathy, endometriosis, pre-term labor, dermatitis, pruritus, pruritus in liver disease, ascites and complications of portal hypertension and liver cirrhosis, diabetes, metabolic disorder, obesity, migraine, Alzheimer's disease, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for the use of a compound of Formula (I) or a pharmaceutically acceptable salt thereof in the manufacture of a medicament for the treatment of congestive heart failure. Suitably the invention provides for the use of a compound of Formula (I) or a pharmaceutically acceptable salt thereof in the manufacture of a medicament for the treatment of acute lung injury. Suitably the invention provides for the use of a compound of Formula (I) or a pharmaceutically acceptable salt thereof in the manufacture of a medicament for the treatment of cerebral edema. Suitably the invention provides for a compound of Formula (I) or a pharmaceutically acceptable salt thereof in the manufacture of a medicament for the treatment of heart failure. Suitably the invention provides for a compound of Formula (I) or a pharmaceutically acceptable salt thereof in the manufacture of a medicament for the treatment of cough; including acute cough, sub-acute cough and chronic cough. Suitably the invention provides for a compound of Formula (I) or a pharmaceutically acceptable salt thereof in the manufacture of a medicament for the treatment of acute respiratory distress syndrome.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration. Suitably the administration is oral. Suitably the administration is intravenous. Suitably the administration is by inhalation.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 1-500 mg once daily or BID per person.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

The compounds of Formula (I) and pharmaceutically acceptable salts thereof may be used in combination with one or more other agents which may be useful in the prevention or treatment of respiratory disease for example; antigen immunotherapy, antihistamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast, pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

Suitably, for the treatment of asthma, COPD, compounds or pharmaceutical formulations of the invention may be administered together with an anti-inflammatory agent such as, for example, a corticosteroid, or a pharmaceutical formulation thereof. For example, a compound of the invention may be formulated together with an anti-inflammatory agent, such as a corticosteroid, in a single formulation, such as a dry powder formulation for inhalation. Alternatively, a pharmaceutical formulation comprising a compound of the invention may be administered in conjunction with a pharmaceutical formulation comprising an anti-inflammatory agent, such as a corticosteroid, either simultaneously or sequentially. In one embodiment, a pharmaceutical formulation comprising a compound of the invention and a pharmaceutical formulation comprising an anti-inflammatory agent, such as a corticosteroid, may each be held in device suitable for the simultaneous administration of both formulations via inhalation.

Suitable corticosteroids for administration together with a compound of the invention include, but are not limited to, fluticasone furoate, fluticasone propionate, beclomethasone diproprionate, budesonide, ciclesonide, mometasone furoate, triamcinolone, flunisolide and prednisilone. In one embodiment of the invention a corticosteroids for administration together with a compound of the invention via inhalation includes fluticasone furoate, fluticasone propionate, beclomethasone diproprionate, budesonide, ciclesonide, mometasone furoate, and, flunisolide.

Suitably, for the treatment of COPD, compounds or pharmaceutical formulations of the invention may be administered together with one or more bronchodilators, or pharmaceutical formulations thereof. For example, a compound of the invention may be formulated together with one or more bronchodilators in a single formulation, such as a dry powder formulation for inhalation. Alternatively, a pharmaceutical formulation comprising a compound of the invention may be administered in conjunction with a pharmaceutical formulation comprising one or more bronchodilators, either simultaneously or sequentially.

In a further alternative, a formulation comprising a compound of the invention and a bronchodilator may be administered in conjunction with a pharmaceutical formulation comprising a further bronchodilator. In one embodiment, a pharmaceutical formulation comprising a compound of the invention and a pharmaceutical formulation comprising one or more bronchodilators may each be held in device suitable for the simultaneous administration of both formulations via inhalation. In a further embodiment, a pharmaceutical formulation comprising a compound of the invention together with a bronchodilator and a pharmaceutical formulation comprising a further bronchodilator may each be held in one or more devices suitable for the simultaneous administration of both formulations via inhalation.

Suitable bronchodilators for administration together with a compound of the invention include, but are not limited to, $\beta_2$-adrenoreceptor agonists and anticholinergic agents. Examples of $\beta_2$-adrenoreceptor agonists, include, for example, vilanterol, salmeterol, salbutamol, formoterol, salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. Suitable anticholinergic agents include umeclidinium (for example, as the bromide), ipratropium (for example, as the bromide), oxitropium (for example, as the bromide) and tiotropium (for example, as the bromide). In one embodiment of the invention, a compound of the invention may be administered together with a 32-adrenoreceptor agonist, such as vilanterol, and an anticholinergic agent, such as, umeclidinium.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Reminqton's Pharmaceutical Sciences* $17^{th}$ ed. (Mack Publishing Company), *The Handbook of Pharmaceutical Additives* 1997 (Gower Publishing Limited), and *The Handbook of Pharmaceutical Excipients* $6^{th}$ ed. (the American Pharmaceutical Association and the Pharmaceutical Press).

The pharmaceutical compositions of the invention are prepared using techniques and methods known to those skilled in the art. Some of the methods commonly used in the art are described in *Reminqton's Pharmaceutical Sciences* 17th ed. (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g., as in Turbuhaler, see EP 69715, or in the devices described in U.S. Pat. No. 6,321,747). An example of a unit-dose device is Rotahaler (see GB 2064336). In one embodiment, the Diskus inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery. Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art. The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose. Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blockers, aldosterone antagonists, inotropes, NSAIDS, nitric oxide donors, calcium channel modulators, muscarinic antagonists, steroidal anti-inflammatory drugs, bronchodilators, antihistamines, leukotriene antagonists, HMG-CoA reductase inhibitors, dual non-selective βadrenoceptor and n1-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

LCMS data was generated using electrospray positive [ES+ve to give M+H$^+$ ion]equipped with a C18 column eluting with a gradient of 10%-100% acetonitrile/water containing either 0.05% or 0.1% TFA.

The naming program used is ACD Name Pro 6.02 or the naming functionality of Chem Draw Ultra 12.0.

The following abbreviations and terms have the indicated meanings throughout:

| Abbreviation | Meaning |
| --- | --- |
| aq | aqueous |
| BH$_3$ | borane |
| Boc | tert-butyloxycarbonyl |
| Boc$_2$O | di-tert-butyl dicarbonate |
| brine | saturated aqueous NaCl solution |
| t-BuOH | tert-butanol |
| Bz | benzoyl |
| CDI | carbonyldiimidazole |
| CH$_2$Cl$_2$ or DCM | methylene chloride |

-continued

| Abbreviation | Meaning |
| --- | --- |
| CH$_3$CN or MeCN | acetonitrile |
| Cs$_2$CO$_3$ | cesium carbonate |
| CuI | copper iodide |
| DCE | 1,2-dichloroethane |
| DEAD | diethylazodicarboxylate |
| DIAD | diisopropylazodicarboxylate |
| DME | dimethyl ether |
| DMF | N,N-dimethylformamide |
| DMSO | dimethylsulfoxide |
| dppf | 1,1'-bis(diphenylphosphino)ferrocene |
| ee | enantiomeric excess |
| ELSD | evaporative light scattering detector |
| Et$_3$N or TEA | triethylamine |
| EtOH | ethanol |
| Et$_2$O | diethyl ether |
| EtOAc | ethyl acetate |
| g | gram |
| Grubbs Catalyst, 2$^{nd}$ Generation | (1,3-Bis(2,4,6-trimethylphenyl)-2-imidazolidinylidene)dichloro(phenyl-methylene)(tricyclohexylphosphine)ruthenium |
| h, hr | hour |
| HCl | hydrochloric acid |
| H$_2$SO$_4$ | sulfuric acid |
| i-PrOH or IPA | isopropanol |
| i-Pr$_2$NEt or DIPEA or DIEA | diisopropylethylamine |
| K$_2$CO$_3$ | potassium carbonate |
| t-BuOK | potassium tert-butoxide |
| KOH | potassium hydroxide |
| L | liter |
| LCMS | liquid chromatography-mass spectroscopy |
| M | molar |
| MC-OsO$_4$ | microencapsulated osmium tetraoxide |
| m-CPBA | metachloroperbenzoic acid |
| Me | methyl |
| MeMgBr | methyl magnesium bromide |
| MeOH or CH$_3$OH | methanol |
| MgSO$_4$ | magnesium sulfate |
| min | minute |
| mL | milliliter |
| mm | millimeter |
| mmol | millimole |
| MS | mass spectrum |
| MsCl | methanesulfonyl chloride |
| MTBE | methyl tert-butyl ether |
| N | normal |
| NaCl | sodium chloride |
| Na$_2$CO$_3$ | sodium carbonate |
| Na$_2$S$_2$O$_3$ | sodium thiosulfate |
| NaHCO$_3$ | sodium bicarbonate |
| NaHSO$_3$ | sodium bisulfite |
| NaN$_3$ | sodium azide |
| NaOH | sodium hydroxide |
| Na$_2$SO$_3$ | sodium sulfite |
| Na$_2$SO$_4$ | sodium sulfate |
| NCS | N-chlorosuccinimide |
| NH$_3$ | ammonia |
| NH$_4$Cl | ammonium chloride |
| NH$_4$OH | ammonium hydroxide |
| NMO | N-methylmorpholine N-oxide |
| NMR | nuclear magnetic resonance spectroscopy |
| OsO$_4$ | osmium tetraoxide |
| Pd(Cl)$_2$ | palladium dichloride |
| Pd$_2$(dba)$_3$ | tris(dibenzylideneacetone)dipalladium (0) |
| Pd(PPh$_3$)$_4$ | tetrakis(triphenylphosphine)palladium(0) |
| PMe$_3$ | trimethyl phosphine |
| PPh$_3$ | triphenyl phosphine |
| PS-PPh$_3$ | polymer supported triphenyl phosphine |
| RT or rt | room temperature |
| Sat'd | saturated |
| SFC | supercritical fluid chromatography |
| SiO$_2$ | silica gel |

| Abbreviation | Meaning |
| --- | --- |
| SM | starting material |
| TBAF | tetra-n-butylammonium fluoride |
| TFA | trifluoroacetic acid |
| THF | tetrahydrofuran |
| TLC | thin layer chromatography |
| V | volume |
| Zn(CN)$_2$ | zinc cyanide |

Intermediate 1

(S)-tert-butyl 3-hydroxy-4-methylenepyrrolidine-1-carboxylate

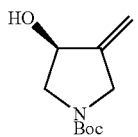

Step 1: tert-butyl 3-(benzoyloxy)-4-methylenepyrrolidine-1-carboxylate

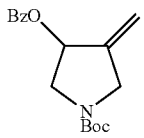

A 3 L reaction vessel equipped with an overhead stirrer was charged with tert-butyl 3-hydroxy-4-methylenepyrrolidine-1-carboxylate (158 g, 793 mmol, prepared in the manner of Alcaraz, L.; Cridland, A.; Kinchin, E. *Org. Lett.* 2001, 3, 4051) and Et$_3$N (170 mL, 1.19 mol) in 2-methyltetrahydrofuran (1500 mL). To the solution at 10° C. (internal temperature) was added benzoylchloride (110 mL, 952 mmol) such that the temperature remained at 10-12° C., followed by DMAP (19.4 g, 159 mmol) and then the mixture was warmed to rt and stirred overnight. The mixture was washed with water (1 L) and the organic layer was dried over MgSO$_4$, filtered and concentrated to give an amber oil. Flash column chromatography (SiO$_2$) eluting with a gradient of 10-25% EtOAc in heptane gave pure product fractions which were pooled and concentrated to give the title compound as a low-melting (56-58° C.) white solid (210 g, 671 mmol, 85% yield). $^1$H NMR (400 MHz, DMSO-d$_6$) δ: 7.91-8.07 (m, 2H), 7.62-7.71 (m, 1H), 7.47-7.59 (m, 2H), 5.73 (dd, J=4.4, 2.9 Hz, 1H), 5.42 (s, 1H), 5.35 (s, 1H), 4.05-4.16 (m, 1H), 3.92-4.02 (m, 1H), 3.73-3.85 (m, 1H), 3.50 (dd, J=12.4, 2.6 Hz, 1H), 1.41 (br s, 9H).

Step 2: Chiral Resolution: (R) and (S)-tert-butyl 3-(benzoyloxy)-4-methylenepyrrolidine-1-carboxylate

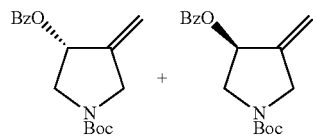

Racemic tert-butyl 3-hydroxy-4-methylenepyrrolidine-1-carboxylate (800 g) was resolved in 12.5 g batches at a 10 min cycle time via preparative HPLC (Chiralpak IC, 100× 250 mm) eluted with heptanes/IPA (75/25) at a flowrate of 500 mL/min. The respective enantiomer fractions were combined, concentrated under reduced pressure, and reconcentrated from Et$_2$O to give each enantiomer as a faint yellow liquid. R-isomer: 380 g, chiral HPLC: 96.2% ee, $^1$H NMR (400 MHz, CD$_3$OD) δ: 8.03 (d, J=7.3 Hz, 2H), 7.60-7.68 (m, 1H), 7.47-7.54 (m, 2H), 5.81 (br s, 1H), 5.50 (br s, 1H), 5.36 (br s, 1H), 4.17-4.25 (m, 1H), 4.01-4.10 (m, 1H), 3.83 (br s, 1H), 3.64 (dd, J=12.5, 1.8 Hz, 1H), 1.51 (br s, 9H). MS (m/z) 304 (M+H+). S-Isomer: 352 g, chiral HPLC: 98% ee, $^1$H NMR (400 MHz, CD$_3$OD) δ: 7.99-8.06 (m, 2H), 7.60-7.67 (m, 1H), 7.47-7.54 (m, 2H), 5.80 (br s, 1H), 5.49 (br s, 1H), 5.36 (br s, 1H), 4.16-4.25 (m, 1H), 4.01-4.09 (m, 1H), 3.83 (br s, 1H), 3.64 (dd, J=12.4, 2.1 Hz, 1H), 1.51 (s, 9H). MS (m/z) 303.9 (M+H+).

Step 3: (S)-tert-butyl 3-hydroxy-4-methylenepyrrolidine-1-carboxylate

KOH pellets (61.4 g, 1.09 mol) were added to MeOH (200 mL) at rt. The warm/hot solution was cooled in an ice bath to reduce the temperature to 25° C. While chilled in the ice bath, a solution of (S)-tert-butyl 3-(benzoyloxy)-4-methylenepyrrolidine-1-carboxylate (83 g, 274 mmol) in MeOH (100 mL) was added in one portion. The resulting solution was stirred at rt for 1 h. The suspension was filtered through celite and the cake rinsed with MeOH (60 mL) and MTBE (100 mL). The filtrate was concentrated under reduced pressure and the solid residue dissolved in water (250 mL). The aqueous phase was reconcentrated under reduced pressure to remove the last traces of MeOH and extracted with MTBE (3×330 mL). The combined organics were washed with brine (30 mL), dried over Na$_2$SO$_4$, filtered, and concentrated under reduced pressure to give the title compound as a light brownish oil (55.0 g, 95% yield). $^1$H NMR (400 MHz, CD$_3$OD) δ: 5.27 (br s, 1H), 5.14 (br s, 1H), 4.54-58 (m, 1H), 4.03-4.12 (m, 1H), 3.91-3.99 (br m, 1H), 3.58-3.68 (m, 1H), 3.21-3.28 (1H, partially hidden by solvent peak), 1.49 (s, 9H). MS (m/z) 199.9 (M+H+).

Inversion of Stereochemistry (S)-tert-butyl 3-(benzoyloxy)-4-methylenepyrrolidine-1-carboxylate

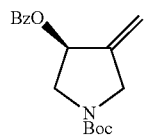

Step 1: (R)-tert-butyl 3-hydroxy-4-methylenepyrrolidine-1-carboxylate

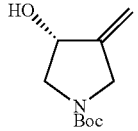

KOH pellets (66.0 g, 1.18 mol) were added to MeOH (250 mL) in a 1 L flask at rt. The warm/hot solution was cooled in an ice bath to reduce the temperature to 25° C. While chilled in the ice bath, a solution of (R)-tert-butyl 3-(benzoyloxy)-4-methylenepyrrolidine-1-carboxylate (102 g, 336 mmol) in MeOH (150 mL) was added in one portion. The resulting solution was stirred at rt for 1 h. The suspension was filtered through celite and the cake rinsed with MeOH (100 mL) and MTBE (150 mL). The filtrate was concentrated under reduced pressure and the solid residue dissolved in water (300 mL). The aqueous phase was reconcentrated under reduced pressure to remove the last traces of MeOH and extracted with MTBE (3×330 mL). The combined organics were washed with brine (30 mL), dried over $Na_2SO_4$, filtered, and concentrated under reduced pressure to give the title compound as a light brownish syrup (68.7 g, 103% yield). $^1$H NMR (400 MHz, $CD_3OD$) δ: 5.26 (br s, 1H), 5.15 (br s, 1H), 4.56 (br s, 1H), 4.01-4.14 (m, 1H), 3.97 (d, J=4.8 Hz, 1H) 3.64 (br s, 1H), 3.23-3.28 (1H, partially hidden by solvent peak), 1.49 (s, 9H). MS (m/z) 199.9 (M+H+).

Step 2: (S)-tert-butyl 3-(benzoyloxy)-4-methylenepyrrolidine-1-carboxylate

To a 2 L RB 3-neck flask fitted with a mechanical stirrer, thermometer and under nitrogen was added THF (700 mL) followed by (R)-tert-butyl 3-hydroxy-4-methylenepyrrolidine-1-carboxylate (37.0 g, 186 mmol), benzoic acid (27.2 g, 223 mmol) and PS—$PPh_3$ (3 mmol/g) (105 g, 316 mmol). Neat diisopropylazodicarboxylate (46.0 g, 223 mmol) was added dropwise and portionwise via an addition funnel over a 1 h period such that the internal temperature never rose above 10° C. After addition was completed, the mixture was stirred in the ice bath for 30 min. The ice bath was removed and the reaction allowed to warm for 2 h. To the mixture at rt was added 2.5 g DIAD and 10 g of the $PPh_3$-solid phase beads and the mixture was stirred at rt for an additional 20 h. The suspension was filtered, and the resins were washed with EtOAc (4×100 mL). The filtrate was concentrated under reduced pressure to give a crude brownish oil (108 g). The oil was taken up in MTBE (100 mL) to yield a suspension which was filtered to remove an off-white solid. The filtrate was concentrated and purified by flash column chromatography ($SiO_2$) eluting with a gradient of 0-50% EtOAc in hexanes. The product fractions were pooled and concentrated under reduced pressure to give the title compound as a clear pale yellowish oil (39.2 g, 70% yield). Chiral purity: 97.8% ee. $^1$H NMR (400 MHz, $CD_3OD$) δ: 8.02 (d, J=8.0 Hz, 2H), 7.59-7.66 (m, 1H), 7.46-7.53 (m, 2H), 5.80 (br s, 1H), 5.49 (br s, 1H), 5.35 (br s, 1H), 4.16-4.24 (m, 1H), 4.01-4.09 (m, 1H), 3.82 (br s, 1H), 3.64 (d, J=12.5 Hz, 1H), 1.50 (s, 9H). MS (m/z) 304.1 (M+H+). This compound can be hydrolyzed to give intermediate 1 as described above.

Intermediate 2

(S)-tert-butyl 3-methylene-4-((methylsulfonyl)oxy) pyrrolidine-1-carboxylate Boc

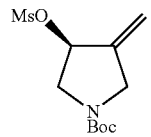

(S)-tert-butyl 3-methylene-4-((methylsulfonyl)oxy) pyrrolidine-1-carboxylate

To a cooled solution of (S)-tert-butyl 3-hydroxy-4-methylenepyrrolidine-1-carboxylate (20.4 g, 103 mmol) in DCM (200 mL) was added $Et_3N$ (21.4 mL, 154 mmol) at 0° C., followed by a dropwise addition of methanesulfonyl chloride (11.9 mL, 154 mmol) and the reaction mixture was stirred at rt for 30 min. The reaction mixture was diluted with DME, washed with $H_2O$, dried over $Na_2SO_4$, filtered and concentrated under reduced pressure to afford the title compound as a brown oil (28.8 g, 100% yield). The title compound was used as is in subsequent reactions.

Intermediate 3

(R)-tert-butyl 3-(4-cyano-3-fluorophenoxy)-4-methylenepyrrolidine-1-carboxylate

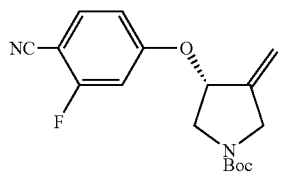

(R)-tert-butyl 3-(4-cyano-3-fluorophenoxy)-4-methylenepyrrolidine-1-carboxylate (S)-tert-butyl 3-hydroxy-4-methylenepyrrolidine-1-carboxylate (100 g, 500 mmol) was dissolved in THF (1200 mL) and treated with 2-fluoro-4-hydroxybenzonitrile (83 g, 600 mmol) and trimethylphosphine (1 M in THF, 600 mL, 600 mmol). The mixture was cooled to 0° C. and DEAD (40 wt % in toluene, 320 mL, 700 mmol) was added dropwise over a period of one hour maintaining the internal temperature below 8° C. The reaction mixture continued to stir at 0° C. for 30 minutes and then was allowed to warm to room temperature overnight. The reaction mixture was poured into 1 N NaOH (aq) (1 L) and stirred vigorously while a saturated solution of $Na_2S_2O_3$ (aq) (50 mL) was added. The mixture was poured into a 50/50 mixture of ethyl acetate/hexanes and the layers separated. The organic layer was separated, washed with 1 N NaOH (aq) (3×1 L), water (1×1 L), and brine (1×1 L), dried over $Na_2SO_4$, filtered and concentrated to an orange oil with a white solid (220 grams). The oil was triturated with hexanes:EtOAc, filtered to remove the white solid, and concentrated to give the title compound as an orange oil (152 g, 95% yield). $^1$H NMR (400 MHz, DMSO-d$_6$) δ: 7.86 (t, J=8.3 Hz, 1H), 7.31 (dd, J=11.8, 2.3 Hz, 1H), 7.07 (dd, J=8.8, 2.3 Hz, 1H), 5.47 (br s, 1H), 5.43 (br s, 1H), 5.34 (s, 1H), 4.03 (m, 1H, partially hidden by solvent peak), 3.89-3.99 (m, 1H), 3.68-3.80 (m, 1H), 3.46 (dd, J=12.3, 2.3 Hz, 1H), 1.41 (d, J=7.8 Hz, 9H). MS (m/z) 263.2 (M+H$^+$-t-Bu).

INTERMEDIATES 4-7 were prepared from (S)-tert-butyl 3-hydroxy-4-methylenepyrrolidine-1-carboxylate and the appropriate phenol by the method analogous to that described for intermediate 3.

| # | Name | Structure | MS (m/z) (M + H$^+$-t-Bu) |
|---|------|-----------|---------------------------|
| 4 | (R)-tert-butyl 3-(4-chlorophenoxy)-4-methylenepyrrolidine-1-carboxylate | 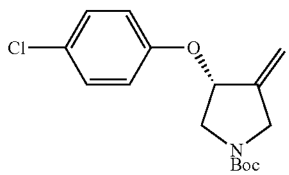 [SMILES: C=C1CN(C(=O)OC(C)(C)C)C[C@@H]1Oc1ccc(Cl)cc1] | 254.0 |
| 5 | (R)-tert-butyl 3-((6-cyanopyridin-3-yl)oxy)-4-methylenepyrrolidine-1-carboxylate | 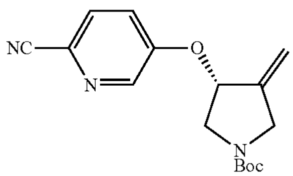 [SMILES: C=C1CN(C(=O)OC(C)(C)C)C[C@@H]1Oc1ccc(C#N)nc1] | 246.0 |
| 6 | (R)-tert-butyl 3-(3,4-difluorophenoxy)-4-methylenepyrrolidine-1-carboxylate | 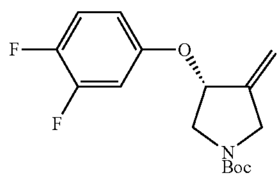 [SMILES: C=C1CN(C(=O)OC(C)(C)C)C[C@@H]1Oc1ccc(F)c(F)c1] | 255.9 |
| 7 | (R)-tert-butyl 3-(benzo[c][1,2,5]oxadiazol-5-yloxy)-4-methylenepyrrolidine-1-carboxylate | 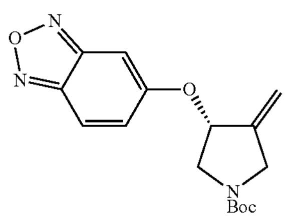 [SMILES: C=C1CN(C(=O)OC(C)(C)C)C[C@@H]1Oc1ccc2nonc2c1] | 261.9 |

Intermediate 8

(S)-2-((3-hydroxy-4-methylenepyrrolidin-1-yl)sulfonyl)-5-(trifluoromethyl)benzonitrile

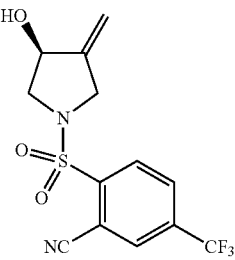

(S)-2-((3-hydroxy-4-methylenepyrrolidin-1-yl)sulfonyl)-5-(trifluoromethyl)benzonitrile To a solution of (S)-tert-butyl 3-hydroxy-4-methylenepyrrolidine-1-carboxylate (4.0 g, 20 mmol) in DCM (100 mL) was added TFA (7.7 mL, 100 mmol) and the resulting orange solution was stirred for 18 h. The reaction mixture was concentrated to dryness and reconcentrated with DCM (2×) to give the TFA salt of (S)-4-methylenepyrrolidin-3-ol as an orange oil. This material was dissolved in DCM (100 mL), cooled to 0° C., and 2-cyano-4-(trifluoromethyl)benzene-1-sulfonyl chloride (5.4 g, 20 mmol) was added followed by DIEA (14 mL, 80 mmol). Stirring was continued at 0° C. for 2 h and the temperature was allowed to warm to rt overnight. The reaction mixture was partitioned between water (100 mL) and DCM (100 mL) and the layers separated. The organic layer was removed, dried over Na$_2$SO$_4$, filtered and concentrated to a red oil. The crude product was purified by flash column chromatography (SiO$_2$) eluting with a gradient of 0-65% EtOAc in hexanes. The product fractions were pooled and concentrated to an orange solid. The solid was dissolved in DCM (35 mL) and diluted with hexane (65 mL) while stirring to form a solid which was removed by filtration, rinsed with hexane (5×5 mL) and collected as the title compound as a cream colored solid (3.94 g, 56% yield). $^1$H NMR (400 MHz, DMSO-d$_6$) δ: 8.68 (d, J=0.8 Hz, 1H), 8.29-8.35 (m, 1H), 8.21-8.27 (m, 1H), 5.50 (d, J=5.0 Hz, 1H), 5.16 (d, J=1.5 Hz, 1H), 5.10 (d, J=1.8 Hz, 1H), 4.45 (d, J=5.0 Hz, 1H), 3.94-4.08 (m, 2H), 3.62 (dd, J=10.0, 6.0 Hz, 1H), 3.14 (dd, J=10.0, 5.3 Hz, 1H). MS (m/z) 333.0 (M+H+).

INTERMEDIATES 9-13 were prepared from (S)-tert-butyl 3-hydroxy-4-methylenepyrrolidine-1-carboxylate and the appropriate arylsulfonylchloride by the method analogous to that described for intermediate 8.

| # | Name | Structure | MS (m/z) (M + H+) |
|---|---|---|---|
| 9 | (S)-5-chloro-2-((3-hydroxy-4-methylenepyrrolidin-1-yl)sulfonyl)benzonitrile | 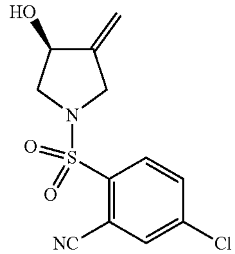 [SMILES: C=C1CN(S(=O)(=O)c2ccc(Cl)cc2C#N)C[C@H]1O] | 299.1 |
| 10 | (S)-1-((2,4-dichlorophenyl)sulfonyl)-4-methylenepyrrolidin-3-yl methanesulfonate | 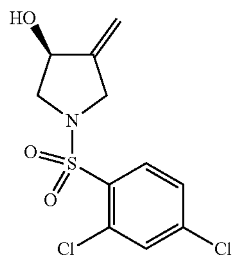 [SMILES: C=C1CN(S(=O)(=O)c2ccc(Cl)cc2Cl)C[C@H]1O] | 385.9 |
| 11 | (S)-2-((3-hydroxy-4-methylenepyrrolidin-1-yl)sulfonyl)benzonitrile | 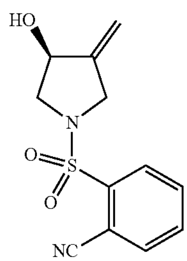 [SMILES: C=C1CN(S(=O)(=O)c2ccccc2C#N)C[C@H]1O] | 287.0 (M + Na+) |
| 12 | (S)-1-((2-chloro-4-(trifluoromethyl)phenyl)sulfonyl)-4-methylenepyrrolidin-3-ol | 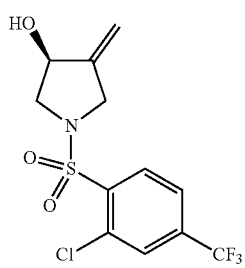 [SMILES: C=C1CN(S(=O)(=O)c2ccc(C(F)(F)F)cc2Cl)C[C@H]1O] | 342.0 |
| 13 | (S)-1-((5-chloropyridin-2-yl)sulfonyl)-4-methylenepyrrolidin-3-ol | 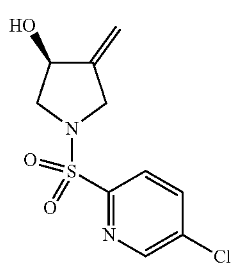 [SMILES: C=C1CN(S(=O)(=O)c2ccc(Cl)cn2)C[C@H]1O] | 275.1 |

Intermediate 14

(R)-4-((1-((2-cyano-4-(trifluoromethyl)phenyl)sulfonyl)-4-methylenepyrrolidin-3-yl)oxy)-2-fluorobenzonitrile

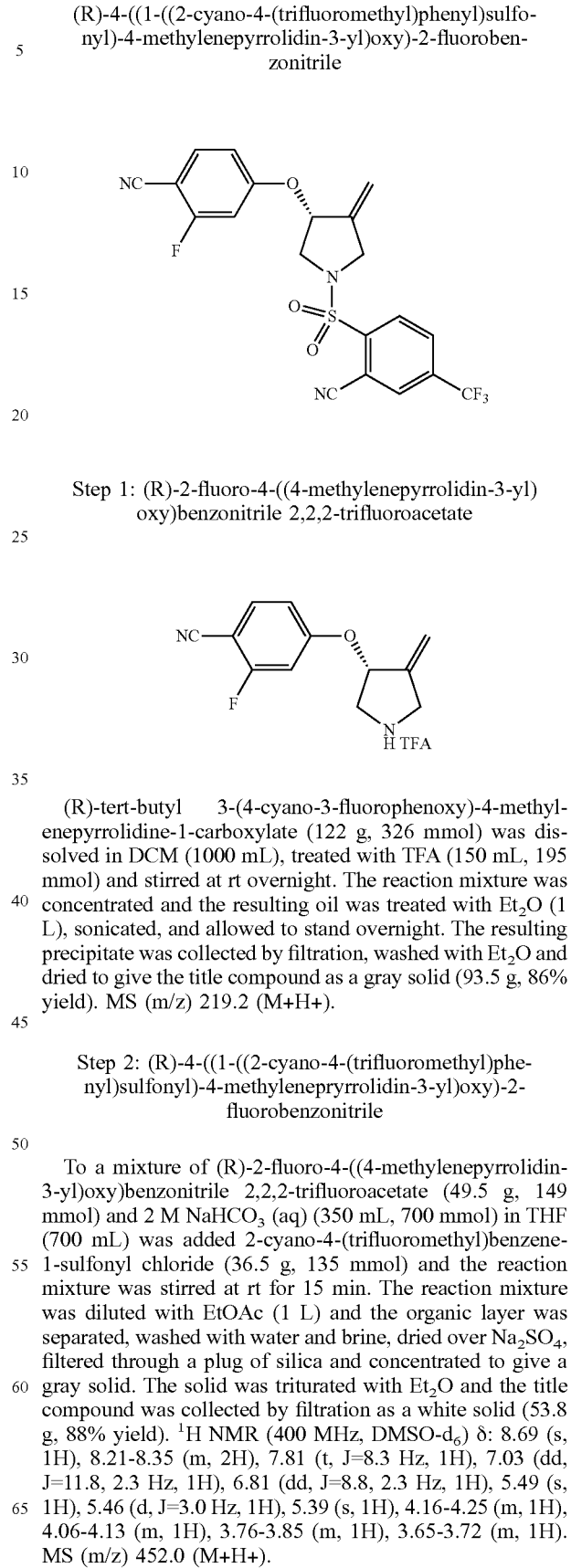

Step 1: (R)-2-fluoro-4-((4-methylenepyrrolidin-3-yl)oxy)benzonitrile 2,2,2-trifluoroacetate (R)-tert-butyl 3-(4-cyano-3-fluorophenoxy)-4-methylenepyrrolidine-1-carboxylate (122 g, 326 mmol) was dissolved in DCM (1000 mL), treated with TFA (150 mL, 195 mmol) and stirred at rt overnight. The reaction mixture was concentrated and the resulting oil was treated with Et$_2$O (1 L), sonicated, and allowed to stand overnight. The resulting precipitate was collected by filtration, washed with Et$_2$O and dried to give the title compound as a gray solid (93.5 g, 86% yield). MS (m/z) 219.2 (M+H+).

Step 2: (R)-4-((1-((2-cyano-4-(trifluoromethyl)phenyl)sulfonyl)-4-methylenepryrrolidin-3-yl)oxy)-2-fluorobenzonitrile To a mixture of (R)-2-fluoro-4-((4-methylenepyrrolidin-3-yl)oxy)benzonitrile 2,2,2-trifluoroacetate (49.5 g, 149 mmol) and 2 M NaHCO$_3$ (aq) (350 mL, 700 mmol) in THF (700 mL) was added 2-cyano-4-(trifluoromethyl)benzene-1-sulfonyl chloride (36.5 g, 135 mmol) and the reaction mixture was stirred at rt for 15 min. The reaction mixture was diluted with EtOAc (1 L) and the organic layer was separated, washed with water and brine, dried over Na$_2$SO$_4$, filtered through a plug of silica and concentrated to give a gray solid. The solid was triturated with Et$_2$O and the title compound was collected by filtration as a white solid (53.8 g, 88% yield). $^1$H NMR (400 MHz, DMSO-d$_6$) δ: 8.69 (s, 1H), 8.21-8.35 (m, 2H), 7.81 (t, J=8.3 Hz, 1H), 7.03 (dd, J=11.8, 2.3 Hz, 1H), 6.81 (dd, J=8.8, 2.3 Hz, 1H), 5.49 (s, 1H), 5.46 (d, J=3.0 Hz, 1H), 5.39 (s, 1H), 4.16-4.25 (m, 1H), 4.06-4.13 (m, 1H), 3.76-3.85 (m, 1H), 3.65-3.72 (m, 1H). MS (m/z) 452.0 (M+H+).

Intermediate 15

(R)-4-((1-((5-chloropyridin-2-yl)sulfonyl)-4-methyl-enepyrrolidin-3-yl)oxy)-2-fluorobenzonitrile

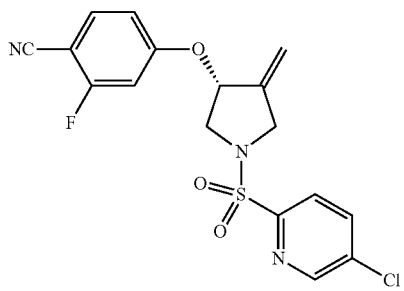 [SMILES: C=C1CN(S(=O)(=O)c2ccc(Cl)cn2)C[C@@H]1Oc1ccc(C#N)c(F)c1]

(R)-4-((1-((5-chloropyridin-2-yl)sulfonyl)-4-methyl-enepyrrolidin-3-yl)oxy)-2-fluorobenzonitrile To a mixture of (R)-2-fluoro-4-((4-methylenepyrrolidin-3-yl)oxy)benzonitrile 2,2,2-trifluoroacetate (93 g, 280 mmol) and sat'd $NaHCO_3$ (aq) (650 mL) in THF (800 mL) was added 5-chloropyridine-2-sulfonyl chloride (54 g, 255 mmol) and the reaction mixture was at rt overnight. The reaction mixture was diluted with EtOAc (1 L) and the organic layer was separated, washed with water and brine, dried over $Na_2SO_4$, filtered through a plug of silica and concentrated to give the title compound as an off white solid (84.6 g, 84% yield). $^1$H NMR (400 MHz, DMSO-$d_6$) δ: 8.79 (d, J=2.0 Hz, 1H), 8.23 (dd, J=8.3, 2.5 Hz, 1H), 7.96 (d, J=8.5 Hz, 1H), 7.83 (t, J=8.3 Hz, 1H), 7.07 (dd, J=11.8, 2.5 Hz, 1H), 6.82 (dd, J=8.7, 2.4 Hz, 1H), 5.44 (s, 1H), 5.40 (d, J=3.5 Hz, 1H), 5.34 (s, 1H), 4.18-4.26 (m, 1H), 4.03-4.11 (m, 1H), 3.81 (dd, J=12.3, 4.5 Hz, 1H), 3.60 (dd, J=12.3, 1.8 Hz, 1H). MS (m/z) 394.0 (M+H+).

Intermediate 16

(R,E)-tert-butyl 3-(4-cyano-3-fluorophenoxy)-4-ethylidenepyrrolidine-1-carboxylate

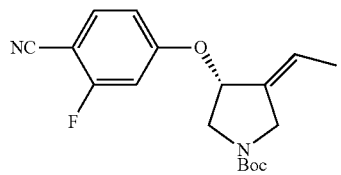

(R,E)-tert-butyl 3-(4-cyano-3-fluorophenoxy)-4-ethylidenepyrrolidine-1-carboxylate To a mixture of (R)-tert-butyl 3-(4-cyano-3-fluorophenoxy)-4-methylenepyrrolidine-1-carboxylate (3 g, 9.4 mmol) in 2-methyl-2-butene (50 mL, 472 mmol) was added Grubbs Catalyst, $2^{nd}$ Generation (350 mg, 0.41 mmol) followed by DCM (50 mL) and the reaction mixture was stirred at rt overnight. Additional Grubbs Catalyst, $2^{nd}$ Generation was added in increments (100 mg, 0.12 mmol) in order to drive the reaction to completion. The reaction mixture was concentrated and the residue purified by flash column chromatography ($SiO_2$) eluting with a gradient of 0-50% EtOAc in hexanes. The product fractions were pooled and concentrated to give the title compound as an oil (2.7 g, 86% yield). $^1$H NMR (400 MHz, DMSO-$d_6$) δ: 7.84 (t, J=8.3 Hz, 1H), 7.27 (dd, J=12.0, 2.0 Hz, 1H), 7.03 (dd, J=8.8, 2.0 Hz, 1H), 5.86-5.96 (m, 1H), 5.41 (br s, 1H), 3.97 (br s, 2H), 3.57-3.69 (m, 1H), 3.50 (d, J=14.8 Hz, 1H), 1.64 (d, J=6.8 Hz, 3H), 1.41 (d, J=14.1 Hz, 9H). MS (m/z) 355.2 (M+Na+).

Intermediate 17

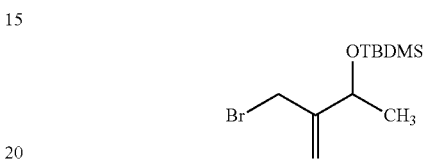

Intermediate 17 may be prepared according to procedures detailed in Maguire, R. J.; Mulzer, J.; Bats, J. W. *J. Org. Chem.* 1996, 61, 6936.

Intermediate 18

5-cyano-4-fluoro-2-hydroxyphenyl acetate

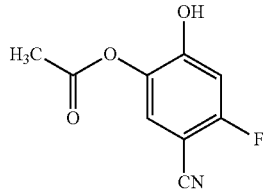

Step 1: 2-fluoro-4,5-dihydroxybenzonitrile

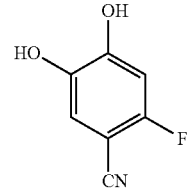 [SMILES: N#Cc1cc(O)c(O)cc1F]

A mixture of 2-fluoro-4,5-dimethoxybenzonitrile (1.5 g, 8.3 mmol) and pyridine hydrochloride (9.6 g, 83 mmol) (neat) was heated at 220° C. for 30 min. The reaction mixture was partitioned between EtOAc and water and the aqueous layer was extracted with additional EtOAc. The organic extracts were combined, dried over $Na_2SO_4$, filtered and concentrated to give the title compound as a white solid (1.0 g, 79% yield). MS (m/z) 153.9 (M+H+).

Step 2: 5-cyano-4-fluoro-2-hydroxyphenyl acetate

A mixture of 2-fluoro-4,5-dihydroxybenzonitrile (1 g, 6.53 mmol), acetic anhydride (0.62 mL, 6.5 mmol) and pyridine (5.3 mL, 65 mmol) in acetone (20 mL) was stirred at rt overnight. The reaction mixture was concentrated and the crude product was purified by flash column chromatography ($SiO_2$) eluting with a gradient of 0-100% EtOAc in hexanes.

The product fractions were pooled, and concentrated. The residue was dissolved in EtOAc and washed with water (x2), brine (x1), dried over Na$_2$SO$_4$, filtered and concentrated to give the title compound as a white solid (1.0 g, 78% yield). $^1$H NMR (400 MHz, DMSO-d$_6$) δ: 11.63 (br s, 1H), 7.70 (d, J=6.8 Hz, 1H), 6.95 (d, J=11.0 Hz, 1H), 2.27 (s, 3H). MS (m/z) 196.0 (M+H$^+$).

Intermediate 19

5-cyano-2-hydroxyphenyl acetate

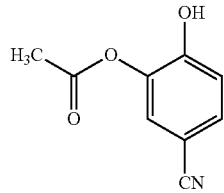

5-cyano-2-hydroxyphenyl acetate

A mixture of 3,4-dihydroxybenzonitrile (10 g, 74.0 mmol), acetic anhydride (7.0 mL, 74 mmol) and pyridine (60 mL, 740 mmol) in acetone (200 mL) was stirred at rt overnight.

The reaction mixture was concentrated, the residue dissolved in EtOAc and washed with water (x2) and brine (x1) and dried over Na$_2$SO$_4$, filtered and concentrated. The crude product was purified by flash column chromatography (SiO$_2$) eluting with a gradient of 0-100% EtOAc in hexanes. The product fractions were pooled and concentrated to give a solid which was triturated with Et$_2$O and filtered to give the title compound as a white solid (4.8 g, 31% yield). $^1$H NMR (400 MHz, DMSO-d$_6$) δ: 10.99 (br s, 1H), 7.51-7.66 (m, 2H), 7.06 (d, J=8.3 Hz, 1H), 2.27 (s, 3H). MS (m/z) 178.0 (M+H$^+$).

Intermediate 20

6-(difluoromethoxy)pyridine-3-sulfonyl chloride

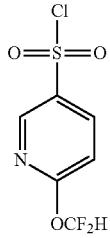

Step 1: 5-(benzylthio)-2-(difluoromethoxy)pyridine

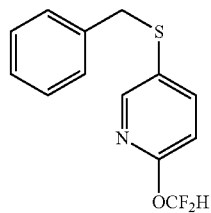

To a mixture of benzyl mercaptan (0.528 mL, 4.46 mmol), 5-bromo-2-(difluoromethoxy)pyridine (1 g, 4.46 mmol), xantphos (0.258 g, 0.446 mmol), and DIPEA (1.56 mL, 8.93 mmol) in toluene (25 mL) under nitrogen was added Pd$_2$(dba)$_3$ (0.204 g, 0.223 mmol) and the reaction mixture was heated at 110° C. overnight. The reaction mixture was cooled and water was added. The mixture was filtered and the filtrate was extracted with EtOAc. The organic layer was washed with sat'd NaHCO$_3$ (aq) and brine and dried over Na$_2$SO$_4$, filtered and concentrated. The residue was purified by flash column chromatography (SiO$_2$) eluting with a gradient of 0-100% EtOAc in hexanes. The product fractions were pooled and concentrated to give the title compound as a yellow oil (970 mg, 81% yield). MS (m/z) 268.2 (M+H$^+$).

Step 2: 6-(difluoromethoxy)pyridine-3-sulfonyl chloride

To a solution of 5-(benzylthio)-2-(difluoromethoxy)pyridine (860 mg, 3.2 mmol) in acetic acid (10 mL) and water (3.3 mL) was added NCS (1.7 g, 13 mmol) and the reaction mixture was stirred at rt for 1.5 hours. The reaction mixture was concentrated under reduced pressure, sat'd NaHCO$_3$ (aq) was added and the mixture was extracted with EtOAc. The organic layer was washed with brine, dried over Na$_2$SO$_4$, filtered and concentrated under reduced pressure. The residue was purified by flash column chromatography (SiO$_2$) eluting with a gradient of 0-100% EtOAc in hexanes. The product fractions were pooled and concentrated to give the title compound as a clear oil (900 mg, 80% yield). $^1$H NMR (400 MHz, DMSO-d$_6$) δ: 8.40 (d, J=1.8 Hz, 1H), 8.03 (dd, J=8.5, 2.3 Hz, 1H), 7.53-7.94 (m, 1H), 7.01-7.09 (m, 1H).

INTERMEDIATES 21-27 were prepared by the 2 step method analogous to that described for intermediate 20. The appropriate ArX used in the first step was commercially available as the bromide (X=Br) or chloride (X=Cl). Conversion of the thioether to the sulfonyl chloride in the second step can also be accomplished by bubbling Cl$_2$ gas into formic acid.

| # | Name | Structure | MS (m/z) (M + H$^+$) or $^1$H NMR |
|---|---|---|---|
| 21 | 5-(trifluoromethoxy)pyridine-2-sulfonyl chloride | 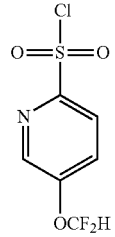 | 262.0 |

-continued

| # | Name | Structure | MS (m/z) (M + H⁺) or ¹H NMR |
|---|---|---|---|
| 22 | 6-(difluoromethyl)pyridine-3-sulfonyl chloride | 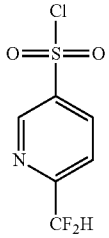 | 227.9 |
| 23 | 6-cyano-2-methylpyridine-3-sulfonyl chloride | 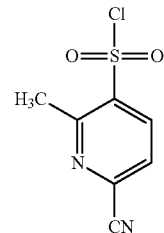 | 217.0 |
| 24 | 4-chloro-3-(trifluoromethoxy)benzene-1-sulfonyl chloride | 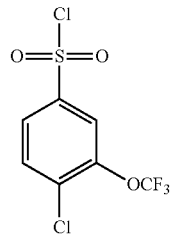 | Used as is, not characterized |
| 25 | 5-(difluoromethyl)pyridine-2-sulfonyl chloride | 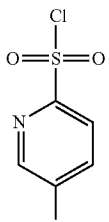 | 228.0 |
| 26 | 5-iodopyridine-2-sulfonyl chloride | 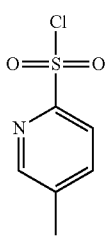 | Used as is, not characterized |
| 27 | 2-(difluoromethoxy)pyridine-3-sulfonyl chloride | 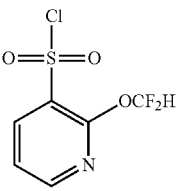 | 244.0 |

79

Intermediate 28

2-fluoro-4-(trifluoromethyl)benzene-1-sulfonyl chloride

2-fluoro-4-(trifluoromethyl)benzene-1-sulfonyl chloride 2-fluoro-4-(trifluoromethyl)aniline (1 g, 5.6 mmol) was added to a mixture of conc. HCl (4 mL) and acetic acid (3 mL). The mixture was cooled to 10° C. and a solution of sodium nitrite (0.42 g, 6.1 mmol) in a minimum amount of water was added dropwise and the mixture stirred at 10° C. for 45 min to form the diazonium salt. In a separate reaction flask, sulfur dioxide (0.36 g, 5.6 mmol) was bubbled into acetic acid (8 mL) until saturation. Copper(I) chloride (0.17 g, 1.7 mmol) was added and stirred until the mixture turned green. The flask was cooled in an ice bath, the diazonium salt mixture was added dropwise and the reaction mixture was allowed to warm to rt overnight with stirring. The reaction mixture was poured into ice, the resulting solid collected by filtration, washed well with water and dried to give the title compound (0.70 g, 48% yield). $^1$H NMR (400 MHz, CDCl$_3$) δ: 8.17 (t, J=7.4 Hz, 1H), 7.61-7.71 (m, 2H).

INTERMEDIATE 29-30 were prepared from the appropriate aniline by the one step method analogous to that described for intermediate 28.

| # | Name | Structure | $^1$H NMR |
|---|------|-----------|-----------|
| 29 | 4-cyano-2-(trifluoromethyl) benzene-1-sulfonyl chloride | ![structure] | $^1$H NMR (400 MHz, DMSO-d$_6$) δ: 8.23 (d, J = 8.0 Hz, 1H), 8.19 (s, 1H), 8.11 (d, J = 8.0 Hz, 1H) |
| 30 | 2-cyano-4-methoxybenzene-1-sulfonyl chloride | ![structure] | $^1$H NMR (400 MHz, CDCl$_3$) δ: 8.16 (d, J = 9.0 Hz, 1H), 7.44 (d, J = 2.5 Hz, 1H), 7.14-7.33 (m, 1H), 4.01 (s, 3H) |

80

Intermediate 31

4-cyano-2-(difluoromethyl)benzene-1-sulfonyl chloride

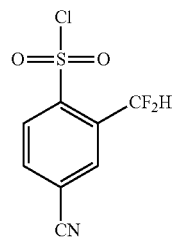 [SMILES: N#Cc1ccc(S(=O)(=O)Cl)c(C(F)F)c1]

Step 1: 4-bromo-3-(difluoromethyl)benzonitrile

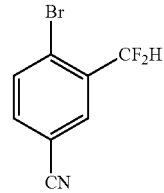 [SMILES: N#Cc1ccc(Br)c(C(F)F)c1]

4-Bromo-3-formylbenzonitrile (1.04 g, 4.94 mmol) was dissolved DCM (59.5 ml), treated with deoxofluor (2.7 ml, 14.8 mmol) and the reaction mixture was heated at 45° C. for 1.5 h. The reaction mixture was cooled in an ice/water bath and carefully quenched with sat'd NaHCO$_3$ (aq). The layers were separated, and the aqeuous phase was extracted with DCM. The organic layers were combined and concentrated under reduced pressure. The crude product was purified by flash column chromatography (SiO$_2$) eluting with a gradient of 0-75% MTBE in hexanes. The desired product fractions were pooled and concentrated under reduced pressure to give the title compound as a white solid (980 mg, 85% yield). MS (m/z) 231.9 (M+H$^+$).

Step 2: 4-(benzylthio)-3-(difluoromethyl)benzonitrile

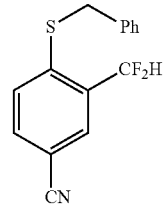 [SMILES: N#Cc1ccc(SCc2ccccc2)c(C(F)F)c1]

4-bromo-3-(difluoromethyl)benzonitrile (980 mg, 4.2 mmol), xantphos (82 mg, 0.14 mmol) and Pd$_2$(dba)$_3$ (97 mg, 0.11 mmol) were combined in 1,4-dioxane (30 mL). DIPEA (1.5 mL, 8.5 mmol) and benzyl mercaptan (600 μl, 5.1 mmol) were added and the reaction mixture was heated at 100° C. for 1 h. The mixture was concentrated and the crude product was purified by flash column chromatography (SiO$_2$) eluting with a gradient of 0-35% MTBE in hexanes.

The desired product fractions were pooled and concentrated under reduced pressure to give the title compound as an orange oil (1.1 g, 100% yield). MS (m/z) 276.1 (M+H$^+$).

Step 3:
4-cyano-2-(difluoromethyl)benzene-1-sulfonyl chloride 4-(benzylthio)-3-(difluoromethyl)benzonitrile (1.1 g, 4.2 mmol) was dissolved in THF (6 mL) and MeOH (6 mL), NCS (1.70 g, 13 mmol) was added and the reaction mixture was stirred at rt for 30 min. The mixture was concentrated under reduced pressure and purified by flash column chromatography (SiO$_2$) eluting with a gradient of 0-40% MTBE in hexanes. The desired product fractions were pooled and concentrated under reduced pressure to give the title compound as a white solid (540 mg, 51% yield). $^1$H NMR (400 MHz, CDCl$_3$) δ: 8.34 (d, J=8.3 Hz, 1H), 8.29 (s, 1H), 8.06 (d, J=8.3 Hz, 1H), 7.40-7.73 (m, 1H).

INTERMEDIATE 32 was prepared from the appropriate benzaldehyde by the 3 step method analogous to that described for intermediate 31.

| # | Name | Structure | MS (m/z) (M + H$^+$) |
|---|---|---|---|
| 32 | 4-cyano-2-(difluoromethyl)benzene-1-sulfonyl chloride | 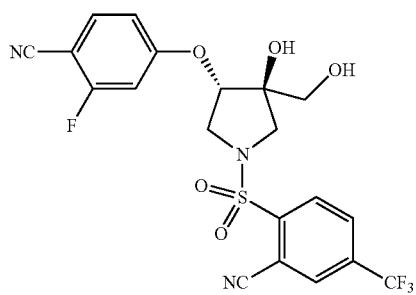 [SMILES: N#Cc1ccc(O[C@H]2CN(S(=O)(=O)c3ccc(C(F)(F)F)cc3C#N)C[C@@]2(O)CO)cc1F] | Used as is, not characterized |

Example 1

4-(((3S,4R)-1-((2-cyano-4-(trifluoromethyl)phenyl)sulfonyl)-4-hydroxy-4-(hydroxymethyl) pyrrolidin-3-yl)oxy)-2-fluorobenzonitrile Osmium tetroxide (2.5% in t-BuOH) (8.6 mL, 0.69 mmol) was added to a solution of (R)-4-((1-((2-cyano-4-(trifluoromethyl)phenyl)sulfonyl)-4-methylenepyrrolidin-3-yl)oxy)-2-fluorobenzonitrile (6.18 g, 13.7 mmol) and NMO (2.41 g, 20.5 mmol) in THF (150 mL) and the reaction mixture was stirred at rt. The reaction mixture was diluted with EtOAc, 10% Na$_2$S$_2$O$_3$ (aq) was carefully added, and the mixture stirred at rt for 1 h. The biphasic layers were separated and the organic layer was washed with 10% NaHCO$_3$ (aq), H$_2$O, and brine, dried over Na$_2$SO$_4$, filtered and evaporated under reduced pressure. The crude product was purified by flash column chromatography (SiO$_2$) eluting with a gradient of 0-100% EtOAc in hexanes. The product fractions were pooled and concentrated. The residue was triturated with Et$_2$O and filtered to give the title compound as a white solid (3.7 g, 53% yield). $^1$H NMR (400 MHz, DMSO-d$_6$) δ: 8.60 (s, 1H), 8.20-8.26 (m, 1H), 8.15-8.20 (m, 1H), 7.76 (t, J=8.4 Hz, 1H), 7.01 (dd, J=11.7, 2.4 Hz, 1H), 6.77 (dd, J=8.8, 2.3 Hz, 1H), 5.53 (s, 1H), 4.86 (t, J=5.6 Hz, 1H), 4.69 (d, J=2.8 Hz, 1H), 3.87 (dd, J=12.2, 3.1 Hz, 1H), 3.41-3.57 (m, 5H). MS (m/z) 486.1 (M+H$^+$).

The following compounds were prepared using procedures analogous to those described in Example 1 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 2 | 4-(((3S,4R)-1-((2,4-dichlorophenyl)sulfonyl)-4-hydroxy-4-(hydroxymethyl)pyrrolidin-3-yl)oxy)-2-fluorobenzonitrile | 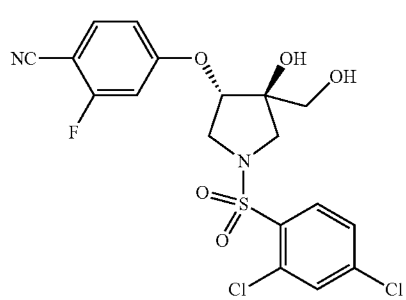 [SMILES: N#Cc1ccc(O[C@H]2CN(S(=O)(=O)c3ccc(Cl)cc3Cl)C[C@@]2(O)CO)cc1F] | 461.1 | $^1$H NMR (400 MHz, DMSO-d$_6$) δ: 7.92 (d, J = 8.5 Hz, 1H), 7.77-7.86 (m, 2H), 7.57 (dd, J = 8.7, 2.1 Hz, 1H), 7.11 (dd, J = 11.8, 2.3 Hz, 1H), 6.87 (dd, J = 8.7, 2.4 Hz, 1H), 5.54 (s, 1H), 4.86 (t, J = 5.6 Hz, 1H), 4.71 (d, J = 3.0 Hz, 1H), 3.86 (dd, J = 11.7, 3.1 Hz, 1H), 3.46-3.62 (m, 4H), 3.38 (1H, partially hidden by solvent peak) |

| Ex. | Name | Structure | MS (m/z) (M + H⁺) | ¹H NMR |
|---|---|---|---|---|
| 3 | 4-(((3S,4R)-1-((4-chloro-2-cyanophenyl)sulfonyl)-4-hydroxy-4-(hydroxymethyl)pyrrolidin-3-yl)oxy)-2-fluorobenzonitrile | 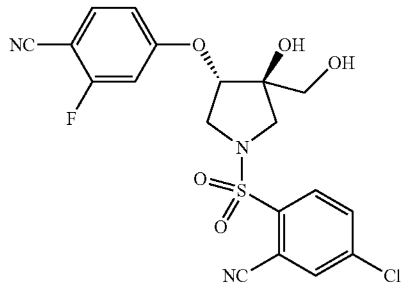 [SMILES: N#Cc1ccc(O[C@H]2CN(S(=O)(=O)c3ccc(Cl)cc3C#N)C[C@@]2(O)CO)cc1F] | 452.1 | ¹H NMR (400 MHz, DMSO-d₆) δ: 8.29 (d, J = 2.0 Hz, 1H), 7.89-7.98 (m, 2H), 7.76-7.83 (m, 1H), 7.04 (dd, J = 11.8, 2.3 Hz, 1H), 6.77 (dd, J = 8.8, 2.3 Hz, 1H), 5.51 (s, 1H), 4.85 (t, J = 5.6 Hz, 1H), 4.68 (d, J = 3.0 Hz, 1H), 3.83 (dd, J = 12.2, 3.1 Hz, 1H), 3.46-3.58 (m, 3H), 3.39-3.45 (m, 2H) |
| 4 | (3R,4S)-1-((2,4-dichlorophenyl)sulfonyl)-4-(3,4-difluorophenoxy)-3-(hydroxymethyl)pyrrolidin-3-ol | 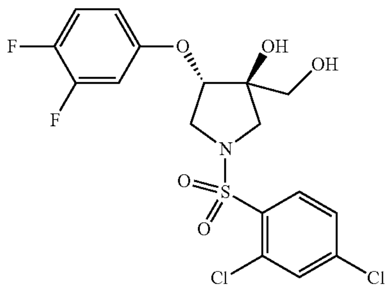 [SMILES: O=S(=O)(c1ccc(Cl)cc1Cl)N1C[C@H](Oc2ccc(F)c(F)c2)[C@](O)(CO)C1] | 454.0 | ¹H NMR (400 MHz, DMSO-d₆) δ: 7.93 (d, J = 8.5 Hz, 1H), 7.85 (d, J = 1.8 Hz, 1H), 7.55-7.61 (m, 1H), 7.31 (q, J = 9.6 Hz, 1H), 6.98 (m, 1H), 6.67 (d, J = 9.0 Hz, 1H), 5.42 (s, 1H), 4.80 (t, J = 5.5 Hz, 1H), 4.56 (d, J = 2.5 Hz, 1H), 3.81 (dd, J = 11.4, 2.9 Hz, 1H), 3.51-3.66 (m, 2H), 3.49 (d, J = 9.3 Hz, 2H), 3.36 (d, J = 10.3 Hz, 1H) |
| 5 | 2-fluoro-4-(((3S,4R)-4-hydroxy-4-(hydroxymethyl)-1-((6-(trifluoromethyl)pyridin-3-yl)sulfonyl)pyrrolidin-3-yl)oxy)benzonitrile | 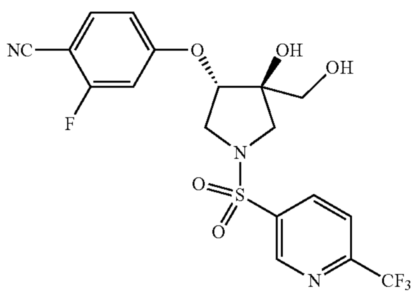 | 462.2 | ¹H NMR (400 MHz, DMSO-d₆) δ: 9.11 (d, J = 2.0 Hz, 1H), 8.44 (dd, J = 8.0, 2.0 Hz, 1H), 8.08 (d, J = 8.3 Hz, 1H), 7.75 (t, J = 8.3 Hz, 1H), 6.88 (dd, J = 11.8, 2.3 Hz, 1H), 6.66 (dd, J = 8.8, 2.3 Hz, 1H), 5.42 (s, 1H), 4.80 (t, J = 5.6 Hz, 1H), 4.62 (d, J = 3.0 Hz, 1H), 3.76 (dd, J = 12.3, 3.3 Hz, 1H), 3.37-3.54 (m, 5H) |

Example 6

2-(((3R,4S)-4-(4-chlorophenoxy)-3-hydroxy-3-(hydromethyl)pyrrolidin-1-yl)sulfonyl)-5-(trifluoromethyl)benzonitrile

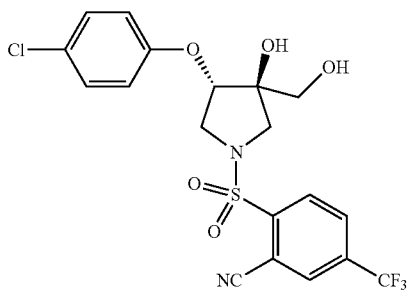 [SMILES: N#Cc1cc(C(F)(F)F)ccc1S(=O)(=O)N1C[C@H](Oc2ccc(Cl)cc2)[C@](O)(CO)C1]

Step 1: (R)-2-((3-(4-chlorophenoxy)-4-methylenepyrrolidin-1-yl)sulfonyl)-5-(trifluoromethyl)benzonitrile

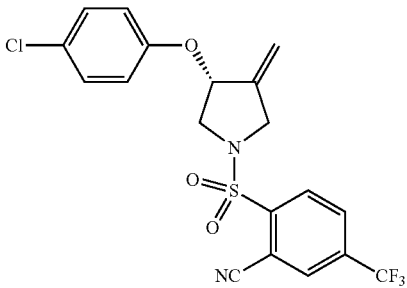 [SMILES: C=C1CN(S(=O)(=O)c2ccc(C(F)(F)F)cc2C#N)C[C@@H]1Oc1ccc(Cl)cc1]

To a mixture of 4-chlorophenol (58 mg, 0.45 mmol), PS—PPh₃ (3 mmol/g) (0.2 g, 0.6 mmol), and (S)-2-((3-hydroxy-4-methylenepyrrolidin-1-yl)sulfonyl)-5-(trifluoromethyl)benzonitrile (100 mg, 0.3 mmol) in DCM (5 mL) was added DIAD (0.088 mL, 0.45 mmol) dropwise and the reaction mixture was at rt for 17 h. The reaction mixture was filtered and the filtrate was concentrated to an orange oil. The crude product was purified by flash column chromatography (SiO$_2$) eluting with a gradient of 0-20% EtOAc in hexanes. The product fractions were pooled and concentrated to give the title compound as a colorless oil (103 mg, 73% yield). MS (m/z) 443.0 (M+H$^+$).

Step 2: 2-(((3R,4S)-4-(4-chlorophenoxy)-3-hydroxy-3-(hydroxymethyl)pyrrolidin-1-yl)sulfonyl)-5-(trifluoromethyl)benzonitrile To (R)-2-((3-(4-chlorophenoxy)-4-methylenepyrrolidin-1-yl)sulfonyl)-5-(trifluoromethyl)benzonitrile (0.098 g, 0.221 mmol) in THF (3.69 mL) was added NMO (0.039 g, 0.33 mmol) and OsO$_4$ (2.5% in t-BuOH, 0.14 mL, 0.011 mmol) and the reaction mixture was stirred at rt for 18 h. Sat'd NaHSO$_3$ (aq) (0.5 mL) was added to the reaction and stirred for 1 h. A red solid that formed was diluted with EtOAc (5 mL) and removed by filtration. The filtrate was concentrated, the resulting light yellow oil partitioned between EtOAc (20 mL) and water (10 mL) and the layers were separated. The organic layer was dried over Na$_2$SO$_4$, filtered, and concentrated. The resulting crude solid was stirred in DCM (2 mL) overnight and the title compound collected by filtration as a white solid (64 mg, 58% yield). $^1$H NMR (400 MHz, DMSO-d$_6$) δ: 8.58 (d, J=1.3 Hz, 1H), 8.16-8.25 (m, 2H), 7.21-7.29 (m, 2H), 6.72-6.79 (m, 2H), 5.43 (s, 1H), 4.83 (t, J=5.5 Hz, 1H), 4.54 (d, J=3.0 Hz, 1H), 3.81 (dd, J=11.5, 3.3 Hz, 1H), 3.47-3.59 (m, 4H), 3.40-3.45 (m, 1H). MS (m/z) 447.1 (M+H$^+$).

The following compounds were prepared using procedures analogous to those described in Example 6 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 7 | 2-(((3R,4S)-4-(benzo[c][1,2,5]oxadiazol-5-yloxy)-3-hydroxy-3-(hydroxymethyl)pyrrolidin-1-yl)sulfonyl)-5-(trifluoromethyl)benzonitrile | 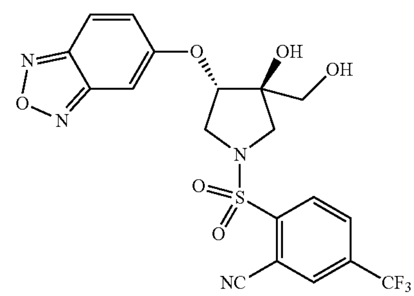 [SMILES: N#Cc1cc(C(F)(F)F)ccc1S(=O)(=O)N1C[C@H](Oc2ccc3nonc3c2)[C@](O)(CO)C1] | 484.8 | $^1$H NMR (400 MHz, DMSO-d$_6$) δ: 8.57 (s, 1H), 8.20 (s, 2H), 7.86 (d, J = 9.5 Hz, 1H), 7.34 (s, 1H), 6.87 (d, J = 9.8 Hz, 1H), 5.52 (br s, 1H), 4.86 (br s, 1H), 4.74 (d, J = 2.5 Hz, 1H), 3.93 (dd, J = 12.0, 2.8 Hz, 1H), 3.69 (d, J = 12.0 Hz, 1H), 3.44-3.64 (m, 4H) |
| 8 | 5-chloro-2-(((3R,4S)-4-(3,4-difluorophenoxy)-3-hydroxy-3-(hydroxymethyl)pyrrolidin-1-yl)sulfonyl)benzonitrile | 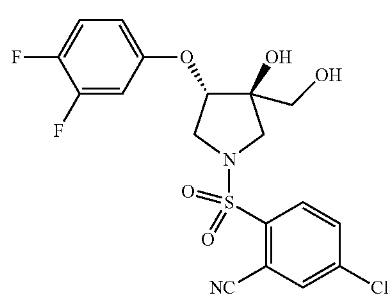 [SMILES: N#Cc1cc(Cl)ccc1S(=O)(=O)N1C[C@H](Oc2ccc(F)c(F)c2)[C@](O)(CO)C1] | 445.2 | $^1$H NMR (400 MHz, CD$_3$CN) δ: 7.96 (br s, 2H), 7.75 (d, J = 8.5 Hz, 1H), 7.11-7.24 (m, 1H), 6.67 (br m, 1H), 6.51 (br m, 1H), 4.50 (br s, 1H), 3.84 (d, J = 12.0 Hz, 1H), 3.73 (br m, 1H), 3.64 (br m, 3H), 3.44-3.55 (m, 2H), 3.11 (br s, 1H) |
| 9 | 2-(((3R,4S)-4-(4-cyano-2-fluorophenoxy)-3-hydroxy-3-(hydroxymethyl)pyrrolidin-1-yl)sulfonyl)-5-(trifluoromethyl)benzonitrile | 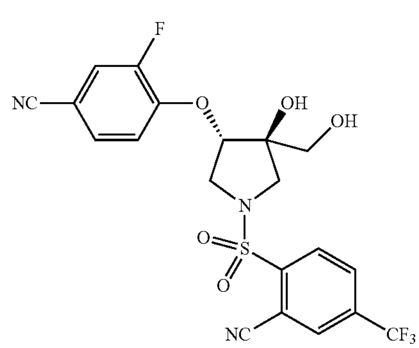 | 486.1 | $^1$H NMR (400 MHz, DMSO-d$_6$) δ: 8.57 (s, 1H), 8.14-8.25 (m, 2H), 7.59-7.74 (m, 2H), 7.39 (t, J = 8.7 Hz, 1H), 5.60 (s, 1H), 4.88 (t, J = 5.6 Hz, 1H), 4.72 (d, J = 2.8 Hz, 1H), 3.90 (dd, J = 12.4, 3.1 Hz, 1H), 3.62 (d, J = 12.3 Hz, 1H), 3.47-3.57 (m, 2H), 3.37-3.47 (m, 2H) |

-continued

| Ex. | Name | Structure | MS (m/z) (M + H⁺) | ¹H NMR |
|---|---|---|---|---|
| 10 | 2-(((3R,4S)-4-(4-cyano-2-methoxyphenoxy)-3-hydroxy-3-(hydroxymethyl)pyrrolidin-1-yl)sulfonyl)-5-(trifluoromethyl)benzonitrile | 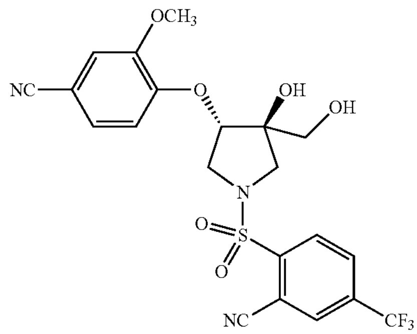 | 498.3 | ¹H NMR (400 MHz, DMSO-d₆) δ: 8.59 (s, 1H), 8.14-8.23 (m, 2H), 7.33-7.38 (m, 2H), 7.10 (d, J = 9.0 Hz, 1H), 5.49 (s, 1H), 4.80 (t, J = 5.5 Hz, 1H), 4.62 (d, J = 3.3 Hz, 1H), 3.86 (dd, J = 11.8, 3.3 Hz, 1H), 3.71 (s, 3H), 3.51-3.62 (m, 3H), 3.42-3.49 (m, 2H) |
| 11 | 4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethyl)benzonitrile | 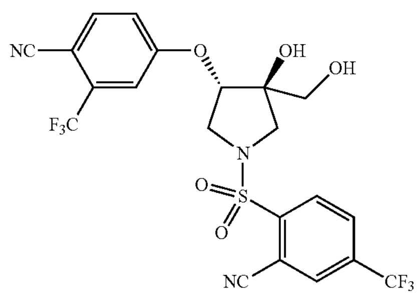 | 536.2 | ¹H NMR (400 MHz, DMSO-d₆) δ: 8.58 (s, 1H), 8.18-8.26 (m, 2H), 8.07 (d, J = 8.5 Hz, 1H), 7.36 (dd, J = 8.7, 2.4 Hz, 1H), 7.28 (d, J = 2.5 Hz, 1H), 4.82 (d, J = 3.0 Hz, 1H), 3.90 (dd, J = 12.0, 3.3 Hz, 1H), 3.43-3.66 (m, 5H, partially hidden by solvent peak) |
| 12 | 2-(((3R,4S)-4-(4-cyano-2-ethoxyphenoxy)-3-hydroxy-3-(hydroxymethyl)pyrrolidin-1-yl)sulfonyl)-5-(trifluoromethyl)benzonitrile | 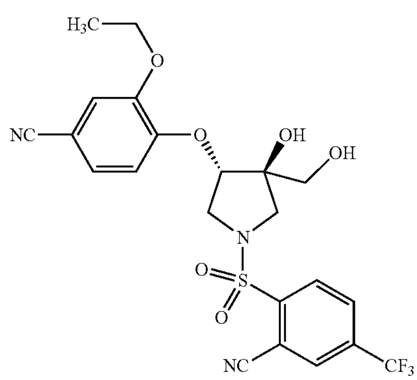 [SMILES: CCOc1cc(C#N)ccc1O[C@H]1CN(S(=O)(=O)c2ccc(C(F)(F)F)cc2C#N)C[C@@]1(O)CO] | 512.2 | ¹H NMR (400 MHz, DMSO-d₆) δ: 8.55 (s, 1H), 8.15 (d, J = 1.3 Hz, 2H), 7.34 (dd, J = 8.3, 2.0 Hz, 1H), 7.30 (d, J = 1.8 Hz, 1H), 7.07 (d, J = 8.5 Hz, 1H), 5.49 (s, 1H), 4.77 (t, J = 5.6 Hz, 1H), 4.58 (d, J = 3.0 Hz, 1H), 3.82-3.95 (m, 3H), 3.53-3.63 (m, 3H), 3.48 (q, J = 10.4 Hz, 2H), 1.26 (t, J = 6.9 Hz, 3H) |
| 13 | 5-(((3S,4R)-1-((2-cyano-4-(trifluoromethyl)phenyl)sulfonyl)-4-hydroxy-4-(hydroxymethyl)pyrrolidin-3-yl)oxy)pyrimidine-2-carbonitrile | 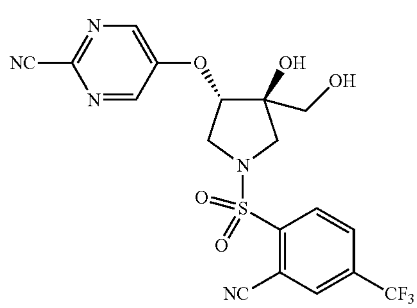 [SMILES: N#Cc1ncc(O[C@H]2CN(S(=O)(=O)c3ccc(C(F)(F)F)cc3C#N)C[C@@]2(O)CO)cn1] | 470.2 | ¹H NMR (400 MHz, DMSO-d₆) δ: 8.64 (s, 3H), 8.18-8.28 (m, 2H), 5.57 (s, 1H), 4.92 (d, J = 3.0 Hz, 1H), 4.87 (t, J = 5.6 Hz, 1H), 3.89 (dd, J = 12.3, 3.5 Hz, 1H), 3.67 (d, J = 11.8 Hz, 1H), 3.42-3.59 (m, 4H) |

| Ex. | Name | Structure | MS (m/z) (M + H+) | 1H NMR |
|---|---|---|---|---|
| 14 | 2-(((3R,4S)-4-(2-chloro-4-cyanophenoxy)-3-hydroxy-3-(hydroxymethyl)pyrrolidin-1-yl)sulfonyl)-5-(trifluoromethyl)benzonitrile | 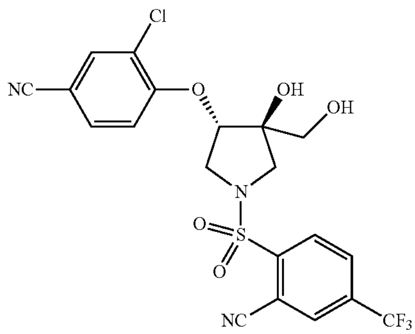 [SMILES: N#Cc1ccc(O[C@H]2CN(S(=O)(=O)c3ccc(C(F)(F)F)cc3C#N)C[C@@]2(O)CO)c(Cl)c1] | 502.3 | 1H NMR (400 MHz, DMSO-d6) δ: 8.56 (s, 1H), 8.13-8.19 (m, 2H), 7.89 (d, J = 2.0 Hz, 1H), 7.79 (dd, J = 8.5, 2.0 Hz, 1H), 7.36 (d, J = 8.8 Hz, 1H), 5.64 (s, 1H), 4.88 (t, J = 5.3 Hz, 1H), 4.75 (d, J = 2.5 Hz, 1H), 3.93 (dd, J = 12.4, 2.9 Hz, 1H), 3.45-3.67 (m, 4H), 3.39 (d, J = 10.5 Hz, 1H) |
| 15 | 4-(((3S,4R)-1-((2-cyano-4-(trifluoromethyl)phenyl)sulfonyl)-4-hydroxy-4-(hydroxymethyl)pyrrolidin-3-yl)oxy)-2,3-difluorobenzonitrile | 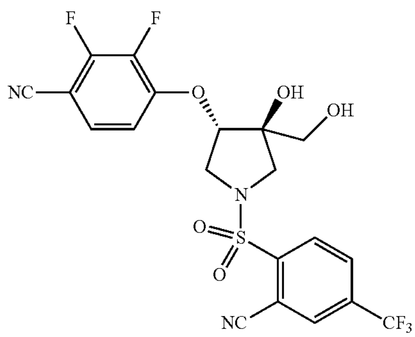 [SMILES: N#Cc1cc(C(F)(F)F)ccc1S(=O)(=O)N1C[C@H](Oc2ccc(C#N)c(F)c2F)[C@](O)(CO)C1] | 504.1 | 1H NMR (400 MHz, DMSO-d6) δ: 8.62 (d, J = 1.3 Hz, 1H), 8.14-8.26 (m, 2H), 7.70-7.78 (m, 1H), 7.29 (t, J = 7.7 Hz, 1H), 5.67 (br s, 1H), 4.89 (br s, 1H), 4.76 (d, J = 2.8 Hz, 1H), 3.92 (dd, J = 12.7, 2.9 Hz, 1H), 3.64 (d, J = 12.8 Hz, 1H), 3.43-3.56 (m, 4H, partially hidden by solvent peak) |
| 16 | 2-(((3R,4S)-4-(4-cyano-2-methylphenoxy)-3-hydroxy-3-(hydroxymethyl)pyrrolidin-1-yl)sulfonyl)-5-(trifluoromethyl)benzonitrile | 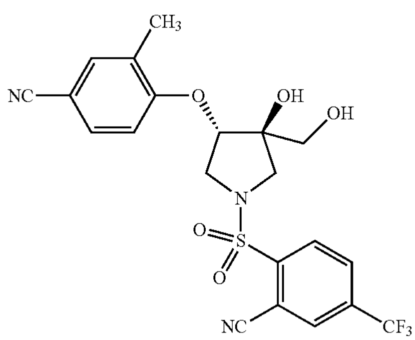 | 482.2 | 1H NMR (400 MHz, DMSO-d6) δ: 8.57 (s, 1H), 8.14-8.23 (m, 2H), 7.63 (dd, J = 8.5, 1.8 Hz, 1H), 7.52 (d, J = 1.5 Hz, 1H), 7.10 (d, J = 8.5 Hz, 1H), 5.55 (br s, 1H), 4.88 (br s, 1H), 4.66 (d, J = 2.8 Hz, 1H), 3.90 (dd, J = 12.2, 3.1 Hz, 1H), 3.42-3.63 (m, 5H), 1.77 (s, 3H) |
| 17 | 2-(((3R,4S)-4-(4-cyano-2-(trifluoromethyl)phenoxy)-3-hydroxy-3-(hydroxymethyl)pyrrolidin-1-yl)sulfonyl)-5-(trifluoromethyl)benzonitrile | 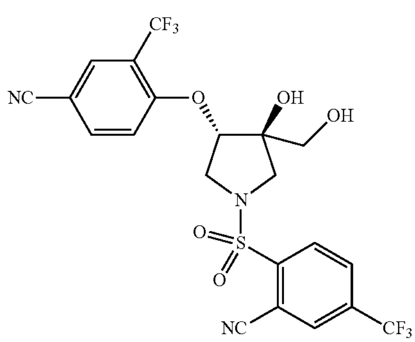 | 536.2 | 1H NMR (400 MHz, DMSO-d6) δ: 8.60 (s, 1H), 8.09-8.23 (m, 4H), 7.52 (d, J = 8.8 Hz, 1H), 5.66 (br s, 1H), 4.89 (d, J = 3.0 Hz, 2H), 3.96 (dd, J = 12.2, 3.1 Hz, 1H), 3.65 (d, J = 12.0 Hz, 1H), 3.45-3.57 (m, 3H), 3.24 (d, J = 10.3 Hz, 1H) |

-continued

| Ex. | Name | Structure | MS (m/z) (M + H⁺) | ¹H NMR |
|---|---|---|---|---|
| 18 | 6-(((3S,4R)-1-((2-cyano-4-(trifluoromethyl)phenyl)sulfonyl)-4-hydroxy-4-(hydroxymethyl)pyrrolidin-3-yl)oxy)-2-naphthonitrile | 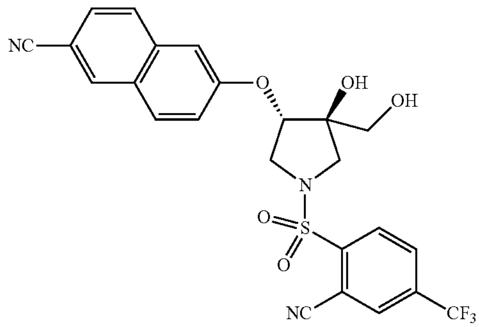 [SMILES: N#Cc1ccc2cc(O[C@H]3CN(S(=O)(=O)c4ccc(C(F)(F)F)cc4C#N)C[C@@]3(O)CO)ccc2c1] | 518.2 | ¹H NMR (400 MHz, DMSO-d₆) δ: 8.54 (s, 1H), 8.49 (s, 1H), 8.18 (d, J = 1.3 Hz, 2H), 7.92 (dd, J = 16.3, 8.8 Hz, 2H), 7.74 (dd, J = 8.5, 1.5 Hz, 1H), 7.43 (d, J = 2.3 Hz, 1H), 6.94 (dd, J = 8.9, 2.4 Hz, 1H), 5.53 (s, 1H), 4.87 (t, J = 5.5 Hz, 1H), 4.76 (d, J = 3.0 Hz, 1H), 3.93 (dd, J = 11.9, 3.1 Hz, 1H), 3.45-3.69 (m, 5H) |
| 19 | 4-(((3S,4R)-1-((2-cyano-4-(trifluoromethyl)phenyl)sulfonyl)-4-hydroxy-4-(hydroxymethyl)pyrrolidin-3-yl)oxy)-2,5-difluorobenzonitrile | 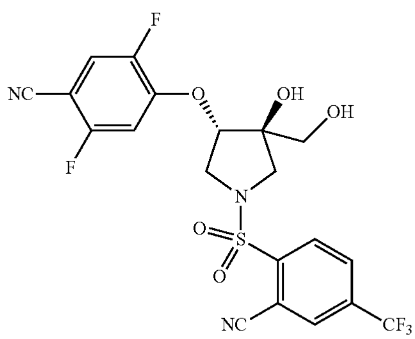 [SMILES: N#Cc1cc(F)c(O[C@H]2CN(S(=O)(=O)c3ccc(C(F)(F)F)cc3C#N)C[C@@]2(O)CO)cc1F] | 504.1 | ¹H NMR (400 MHz, DMSO-d₆) δ: 8.60 (s, 1H), 8.14-8.27 (m, 2H), 7.82 (dd, J = 10.5, 6.3 Hz, 1H), 7.60 (dd, J = 11.0, 7.0 Hz, 1H), 5.65 (s, 1H), 4.89 (t, J = 5.6 Hz, 1H), 4.72 (d, J = 2.8 Hz, 1H), 3.91 (dd, J = 12.8, 3.0 Hz, 1H), 3.67 (d, J = 12.5 Hz, 1H), 3.40-3.56 (m, 3H), 3.35 (1H, partially hidden by solvent peak) |
| 20 | 4-(((3S,4R)-1-((2-cyano-4-(trifluoromethyl)phenyl)sulfonyl)-4-hydroxy-4-(hydroxymethyl)pyrrolidin-3-yl)oxy)-2,6-difluorobenzonitrile | 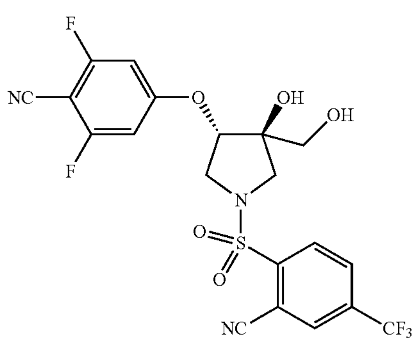 [SMILES: N#Cc1cc(C(F)(F)F)ccc1S(=O)(=O)N1C[C@H](Oc2cc(F)c(C#N)c(F)c2)[C@](O)(CO)C1] | 504.0 | ¹H NMR (400 MHz, DMSO-d₆) δ: 8.62 (d, J = 0.8 Hz, 1H), 8.13-8.28 (m, 2H), 6.92 (d, J = 10.0 Hz, 2H), 5.59 (s, 1H), 4.87 (t, J = 5.5 Hz, 1H), 4.69 (d, J = 2.8 Hz, 1H), 3.87 (dd, J = 12.4, 3.1 Hz, 1H), 3.45-3.61 (m, 3H), 3.39-3.44 (m, 2H) |
| 21 | 4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethoxy)benzonitrile | 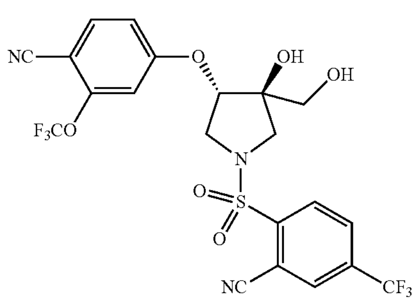 [SMILES: N#Cc1ccc(O[C@H]2CN(S(=O)(=O)c3ccc(C(F)(F)F)cc3C#N)C[C@@]2(O)CO)cc1OC(F)(F)F] | 552.2 | ¹H NMR (400 MHz, DMSO-d₆) δ: 8.59 (s, 1H), 8.16-8.27 (m, 2H), 7.93 (d, J = 9.0 Hz, 1H), 7.04-7.10 (m, 2H), 5.54 (s, 1H), 4.86 (t, J = 5.5 Hz, 1H), 4.76 (d, J = 3.0 Hz, 1H), 3.88 (dd, J = 12.0, 3.3 Hz, 1H), 3.40-3.60 (m, 5H) |

| Ex. | Name | Structure | MS (m/z) (M + H⁺) | ¹H NMR |
|---|---|---|---|---|
| 22 | 5-chloro-2-(((3R,4S)-3-hydroxy-3-(hydroxymethyl)-4-(3,4,5-trifluorophenoxy)pyrrolidin-1-yl)sulfonyl)benzonitrile | 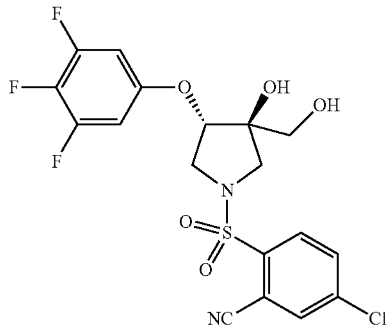 [SMILES: N#Cc1cc(Cl)ccc1S(=O)(=O)N1C[C@H](Oc2cc(F)c(F)c(F)c2)[C@](O)(CO)C1] | 463.1 | ¹H NMR (400 MHz, CD$_3$OD) δ: 7.94 (d, J = 8.3 Hz, 1H), 7.82 (s, 1H), 7.69 (d, J = 8.5 Hz, 1H), 6.38-6.47 (m, 2H), 4.45 (br s, 1H), 3.83 (d, J = 11.3 Hz, 1H), 3.73 (d, J = 11.5 Hz, 1H), 3.55-3.68 (m, 2H), 3.49 (s, 2H) |
| 23 | 5-chloro-2-(((3R,4S)-3-hydroxy-3-(hydroxymethyl)-4-(2,3,4-trifluorophenoxy)pyrrolidin-1-yl)sulfonyl)benzonitrile | 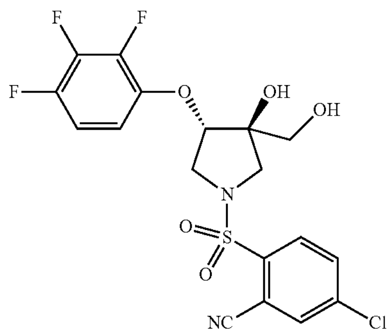 [SMILES: N#Cc1cc(Cl)ccc1S(=O)(=O)N1C[C@H](Oc2ccc(F)c(F)c2F)[C@](O)(CO)C1] | 463.0 | ¹H NMR (400 MHz, DMSO-d$_6$) δ: 8.28 (s, 1H), 7.89-7.99 (m, 2H), 7.18-7.29 (m, 1H), 7.04 (br s, 1H), 5.50 (s, 1H), 4.84 (t, J = 5.4 Hz, 1H), 4.59 (br s, 1H), 3.78-3.85 (m, 1H), 3.48-3.61 (m, 3H), 3.35-3.44 (m, 2H) |
| 24 | 5-chloro-2-(((3R,4S)-3-hydroxy-3-(hydroxymethyl)-4-(2,4,5-trifluorophenoxy)pyrrolidin-1-yl)sulfonyl)benzonitrile | 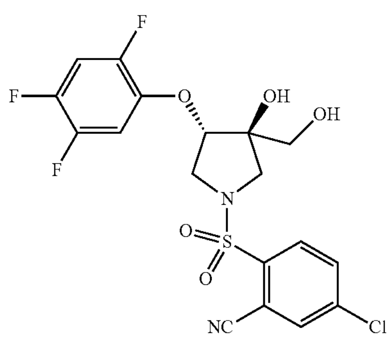 [SMILES: N#Cc1cc(Cl)ccc1S(=O)(=O)N1C[C@H](Oc2cc(F)c(F)cc2F)[C@](O)(CO)C1] | 463.0 | ¹H NMR (400 MHz, DMSO-d$_6$) δ: 8.26 (s, 1H), 7.94-7.99 (m, 1H), 7.88-7.94 (m, 1H), 7.42-7.56 (m, 2H), 5.49 (s, 1H), 4.83 (t, J = 5.4 Hz, 1H), 4.56 (br s, 1H), 3.81 (d, J = 9.5 Hz, 1H), 3.46-3.61 (m, 3H), 3.38 (q, J = 10.5 Hz, 2H) |
| 25 | 2-(((3R,4S)-4-(3,4-difluorophenoxy)-3-hydroxy-3-(hydroxymethyl)pyrrolidin-1-yl)sulfonyl)-5-(trifluoromethyl)benzonitrile | 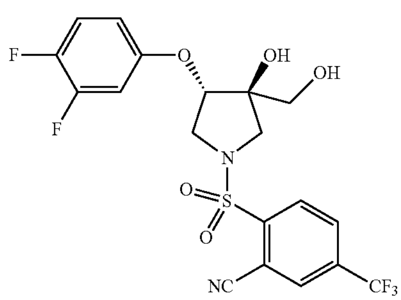 [SMILES: N#Cc1cc(C(F)(F)F)ccc1S(=O)(=O)N1C[C@H](Oc2ccc(F)c(F)c2)[C@](O)(CO)C1] | 479.1 | ¹H NMR (400 MHz, DMSO-d$_6$) δ: 8.58 (s, 1H), 8.15-8.29 (m, 2H), 7.21-7.34 (m, 1H), 6.86 (ddd, J = 12.5, 6.8, 3.0 Hz, 1H), 6.50-6.60 (m, 1H), 5.45 (s, 1H), 4.83 (t, J = 5.6 Hz, 1H), 4.52 (d, J = 3.0 Hz, 1H), 3.81 (dd, J = 11.9, 3.1 Hz, 1H), 3.39-3.59 (m, 5H) |

| Ex. | Name | Structure | MS (m/z) (M + H+) | 1H NMR |
|---|---|---|---|---|
| 26 | 2-(((3R,4S)-3-hydroxy-3-(hydroxymethyl)-4-(3,4,5-trifluorophenoxy)pyrrolidin-1-yl)sulfonyl)-5-(trifluoromethyl)benzonitrile | 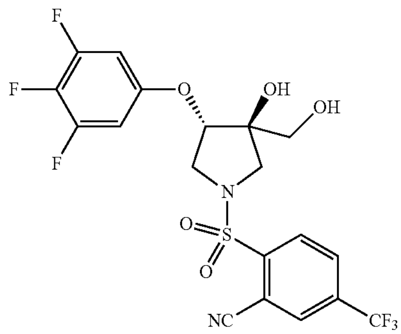 [SMILES: N#Cc1cc(C(F)(F)F)ccc1S(=O)(=O)N1C[C@H](Oc2cc(F)c(F)c(F)c2)[C@](O)(CO)C1] | 497.1 | 1H NMR (400 MHz, DMSO-d6) δ: 8.60 (s, 1H), 8.21-8.28 (m, 1H), 8.15-8.20 (m, 1H), 6.75 (dd, J = 9.8, 5.8 Hz, 2H), 5.50 (s, 1H), 4.83 (t, J = 5.5 Hz, 1H), 4.53 (d, J = 3.0 Hz, 1H), 3.82 (dd, J = 12.3, 3.0 Hz, 1H), 3.46-3.59 (m, 3H), 3.42 (s, 2H) |
| 27 | 2-(((3R,4S)-3-hydroxy-3-(hydroxymethyl)-4-(2,4,5-trifluorophenoxy)pyrrolidin-1-yl)sulfonyl)-5-(trifluoromethyl)benzonitrile | 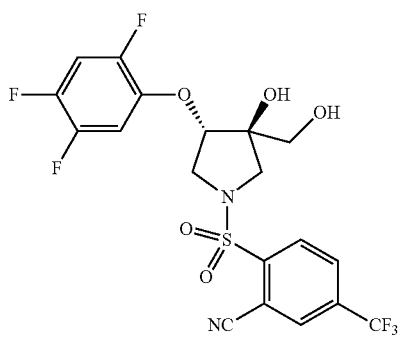 [SMILES: N#Cc1cc(C(F)(F)F)ccc1S(=O)(=O)N1C[C@H](Oc2cc(F)c(F)cc2F)[C@](O)(CO)C1] | 497.1 | 1H NMR (400 MHz, DMSO-d6) δ: 8.58 (s, 1H), 8.16-8.24 (m, 2H), 7.38-7.53 (m, 2H), 5.55 (s, 1H), 4.86 (t, J = 5.5 Hz, 1H), 4.56 (d, J = 2.8 Hz, 1H), 3.85 (dd, J = 12.3, 3.0 Hz, 1H), 3.63 (d, J = 12.3 Hz, 1H), 3.41-3.57 (m, 3H), 3.33-3.36 (m, 1H) |
| 28 | 2-(((3R,4S)-3-hydroxy-3-(hydroxymethyl)-4-(2,3,4-trifluorophenoxy)pyrrolidin-1-yl)sulfonyl)-5-(trifluoromethyl)benzonitrile | 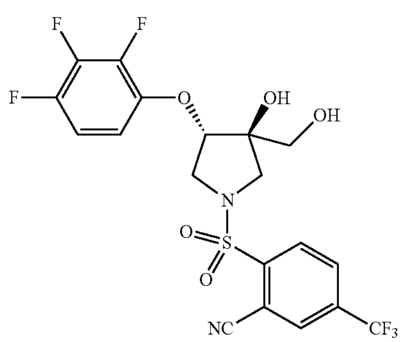 [SMILES: N#Cc1cc(C(F)(F)F)ccc1S(=O)(=O)N1C[C@H](Oc2ccc(F)c(F)c2F)[C@](O)(CO)C1] | 497.1 | 1H NMR (400 MHz, DMSO-d6) δ: 8.58 (d, J = 0.8 Hz, 1H), 8.14-8.25 (m, 2H), 7.18-7.29 (m, 1H), 7.05 (m, 1H), 5.57 (s, 1H), 4.88 (t, J = 5.6 Hz, 1H), 4.59 (d, J = 2.5 Hz, 1H), 3.86 (dd, J = 12.4, 2.9 Hz, 1H), 3.61 (d, J = 12.3 Hz, 1H), 3.37-3.58 (m, 4H) |
| 29 | 2-(((3R,4S)-4-(4-cyanophenoxy)-3-hydroxy-3-(hydroxymethyl)pyrrolidin-1-yl)sulfonyl)-5-(trifluoromethyl)benzonitrile | 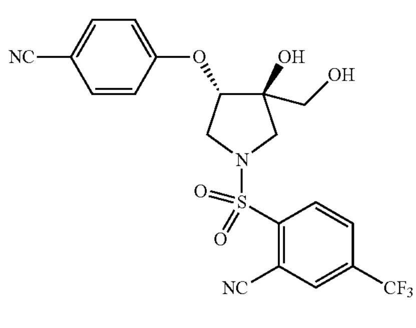 | 468.2 | 1H NMR (400 MHz, DMSO-d6) δ: 8.58 (s, 1H), 8.15-8.26 (m, 2H), 7.67-7.73 (m, 2H), 6.89-6.94 (m, 2H), 5.49 (s, 1H), 4.85 (t, J = 5.6 Hz, 1H), 4.68 (d, J = 3.0 Hz, 1H), 3.86 (dd, J = 11.9, 3.4 Hz, 1H), 3.41-3.59 (m, 5H) |

-continued

| Ex. | Name | Structure | MS (m/z) (M + H+) | 1H NMR |
|---|---|---|---|---|
| 30 | 2-(((3R,4S)-4-(4-chloro-3-fluorophenoxy)-3-hydroxy-3-(hydroxymethyl)pyrrolidin-1-yl)sulfonyl)-5-(trifluoromethyl)benzonitrile | 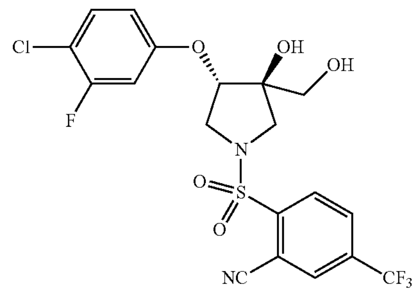 [SMILES: N#Cc1cc(C(F)(F)F)ccc1S(=O)(=O)N1C[C@H](Oc2ccc(Cl)c(F)c2)[C@](O)(CO)C1] | 495.1 | 1H NMR (400 MHz, DMSO-d6) δ: 8.58 (s, 1H), 8.15-8.28 (m, 2H), 7.39 (t, J = 8.8 Hz, 1H), 6.88 (dd, J = 11.3, 2.8 Hz, 1H), 6.61 (dt, J = 8.8, 1.5 Hz, 1H), 5.46 (s, 1H), 4.83 (t, J = 5.5 Hz, 1H), 4.57 (d, J = 3.0 Hz, 1H), 3.83 (dd, J = 11.9, 3.1 Hz, 1H), 3.38-3.60 (m, 5H) |
| 31 | 2-(((3R,4S)-4-(3-fluoro-4-(trifluoromethyl)phenoxy)-3-hydroxy-3-(hydroxymethyl)pyrrolidin-1-yl)sulfonyl)-5-(trifluoromethyl)benzonitrile | 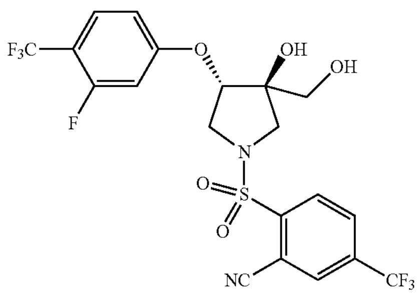 | 529.1 | 1H NMR (400 MHz, DMSO-d6) δ: 8.57 (s, 1H), 8.19 (s, 2H), 7.58 (t, J = 8.8 Hz, 1H), 6.97 (dd, J = 12.8, 2.0 Hz, 1H), 6.74 (dd, J = 8.8, 2.0 Hz, 1H), 5.52 (s, 1H), 4.86 (t, J = 5.5 Hz, 1H), 4.67 (d, J = 2.8 Hz, 1H), 3.86 (dd, J = 12.0, 3.3 Hz, 1H), 3.41-3.62 (m, 5H) |
| 32 | 2-(((3R,4S)-4-(4-(cyanomethyl)phenoxy)-3-hydroxy-3-(hydroxymethyl)pyrrolidin-1-yl)sulfonyl)-5-(trifluoromethyl)benzonitrile | 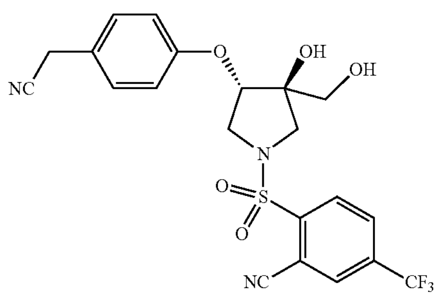 [SMILES: N#CCc1ccc(O[C@H]2CN(S(=O)(=O)c3ccc(C(F)(F)F)cc3C#N)C[C@@]2(O)CO)cc1] | 482.2 | 1H NMR (400 MHz, DMSO-d6) δ: 8.55 (s, 1H), 8.16-8.25 (m, 2H), 7.19 (d, J = 8.8 Hz, 2H), 6.72 (d, J = 8.5 Hz, 2H), 4.55 (d, J = 3.0 Hz, 1H), 3.94 (s, 2H), 3.81 (dd, J = 11.7, 3.1 Hz, 1H), 3.41-3.61 (m, 5H) |
| 33 | 2-(((3R,4S)-4-(3-(cyanomethyl)phenoxy)-3-hydroxy-3-(hydroxymethyl)pyrrolidin-1-yl)sulfonyl)-5-(trifluoromethyl)benzonitrile | 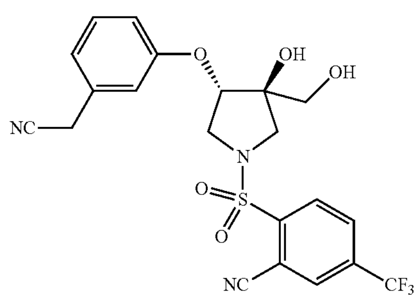 [SMILES: N#CCc1cccc(O[C@H]2CN(S(=O)(=O)c3ccc(C(F)(F)F)cc3C#N)C[C@@]2(O)CO)c1] | 482.2 | 1H NMR (400 MHz, DMSO-d6) δ: 8.59 (s, 1H), 8.16-8.27 (m, 2H), 7.25 (t, J = 8.0 Hz, 1H), 6.95 (d, J = 8.3 Hz, 1H), 6.76 (s, 1H), 6.69 (dd, J = 8.2, 2.1 Hz, 1H), 4.57 (d, J = 3.0 Hz, 1H), 3.97 (s, 2H), 3.82 (dd, J = 11.5, 3.3 Hz, 1H), 3.47-3.60 (m, 4H), 3.41-3.46 (m, 1H) |
| 34 | methyl 5-cyano-2-(((3S,4R)-1-((2-cyano-4-(trifluoromethyl)phenyl)sulfonyl)-4-hydroxy-4-(hydroxymethyl)pyrrolidin-3-yl)oxy)benzoate | 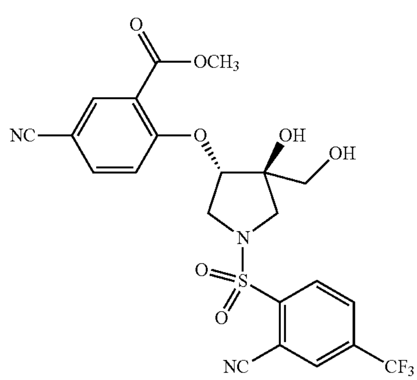 [SMILES: COC(=O)c1cc(C#N)ccc1O[C@H]1CN(S(=O)(=O)c2ccc(C(F)(F)F)cc2C#N)C[C@@]1(O)CO] | 526.1 | 1H NMR (400 MHz, DMSO-d6) δ: 8.49 (s, 1H), 8.06-8.13 (m, 2H), 7.97-8.03 (m, 2H), 7.35 (d, J = 8.5 Hz, 1H), 5.60 (s, 1H), 4.81 (t, J = 5.8 Hz, 1H), 4.75 (d, J = 2.8 Hz, 1H), 3.92 (dd, J = 12.3, 3.0 Hz, 1H), 3.72 (s, 3H), 3.53-3.66 (m, 3H), 3.40-3.49 (m, 2H) |

-continued

| Ex. | Name | Structure | MS (m/z) (M + H+) | 1H NMR |
|---|---|---|---|---|
| 35 | (3R,4S)-1-((2,4-dichlorophenyl)sulfonyl)-3-(hydroxymethyl)-4-((6-(trifluoromethyl)pyridin-3-yl)oxy)pyrrolidin-3-ol | 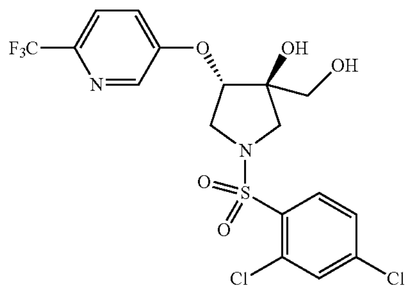 [SMILES: O=S(=O)(c1ccc(Cl)cc1Cl)N1C[C@H](Oc2ccc(C(F)(F)F)nc2)[C@](O)(CO)C1] | 486.9 | 1H NMR (400 MHz, DMSO-d6) δ: 8.32 (d, J = 2.8 Hz, 1H), 7.94 (d, J = 8.5 Hz, 1H), 7.78-7.86 (m, 2H), 7.54-7.62 (m, 2H), 5.55 (s, 1H), 4.87 (t, J = 5.6 Hz, 1H), 4.79 (d, J = 3.0 Hz, 1H), 3.87 (dd, J = 11.7, 3.4 Hz, 1H), 3.59-3.65 (m, 1H), 3.50-3.57 (m, 3H), 3.38 (d, J = 10.3 Hz, 1H) |
| 36 | 5-(((3S,4R)-1-((2,4-dichlorophenyl)sulfonyl)-4-hydroxy-4-(hydroxymethyl)pyrrolidin-3-yl)oxy)-3-fluoropicolinonitrile | 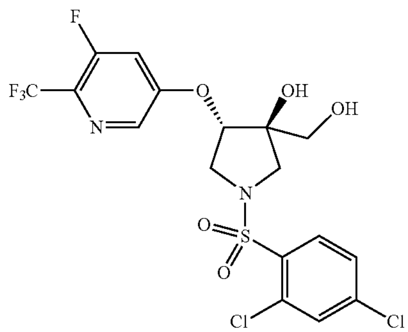 [SMILES: O=S(=O)(c1ccc(Cl)cc1Cl)N1C[C@H](Oc2cnc(C(F)(F)F)c(F)c2)[C@](O)(CO)C1] | 461.9 | 1H NMR (400 MHz, DMSO-d6) δ: 8.20-8.23 (m, 1H), 7.93 (d, J = 8.5 Hz, 1H), 7.81-7.87 (m, 2H), 7.59 (dd, J = 8.5, 2.3 Hz, 1H), 5.60 (s, 1H), 4.88 (t, J = 5.6 Hz, 1H), 4.80 (d, J = 3.0 Hz, 1H), 3.88 (dd, J = 12.0, 3.3 Hz, 1H), 3.45-3.63 (m, 4H), 3.38 (d, J = 10.3 Hz, 1H) |
| 37 | 2-(((3R,4S)-3-hydroxy-3-(hydroxymethyl)-4-(4-(trifluoromethyl)phenoxy)pyrrolidin-1-yl)sulfonyl)-5-(trifluoromethyl)benzonitrile | 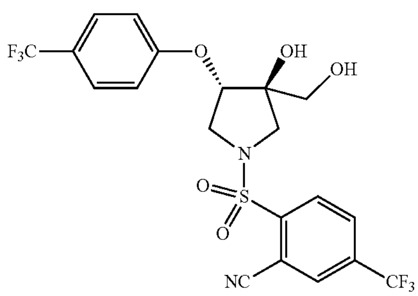 [SMILES: N#Cc1cc(C(F)(F)F)ccc1S(=O)(=O)N1C[C@H](Oc2ccc(C(F)(F)F)cc2)[C@](O)(CO)C1] | 511.1 | 1H NMR (400 MHz, DMSO-d6) δ: 8.55 (s, 1H), 8.18 (d, J = 1.3 Hz, 2H), 7.56 (d, J = 8.5 Hz, 2H), 6.91 (d, J = 8.5 Hz, 2H), 5.49 (s, 1H), 4.85 (t, J = 5.5 Hz, 1H), 4.66 (d, J = 3.0 Hz, 1H), 3.85 (dd, J = 11.9, 3.1 Hz, 1H), 3.41-3.62 (m, 5H) |
| 38 | 2-(((3R,4S)-4-(4-fluoro-3-(trifluoromethyl)phenoxy)-3-hydroxy-3-(hydroxymethyl)pyrrolidin-1-yl)sulfonyl)-5-(trifluoromethyl)benzonitrile | 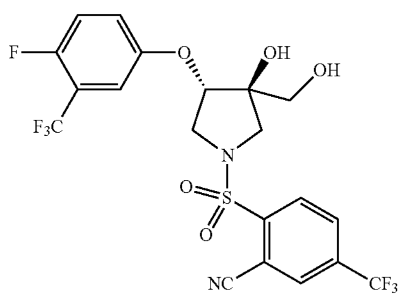 | 529.1 | 1H NMR (400 MHz, DMSO-d6) δ: 8.56 (s, 1H), 8.17-8.27 (m, 2H), 7.39 (t, J = 9.8 Hz, 1H), 7.14-7.20 (m, 1H), 7.04 (dd, J = 5.5, 3.0 Hz, 1H), 5.46 (s, 1H), 4.83 (t, J = 5.6 Hz, 1H), 4.63 (d, J = 3.0 Hz, 1H), 3.84 (dd, J = 11.8, 3.3 Hz, 1H), 3.40-3.62 (m, 5H) |
| 39 | 2-(((3R,4S)-4-(3,4-dichlorophenoxy)-3-hydroxy-3-(hydroxymethyl)pyrrolidin-1-yl)sulfonyl)-5-(trifluoromethyl)benzonitrile | 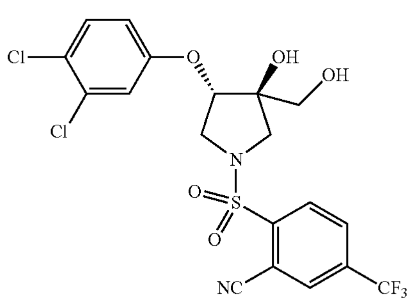 | 511.1 | 1H NMR (400 MHz, DMSO-d6) δ: 8.59 (d, J = 0.8 Hz, 1H), 8.17-8.27 (m, 2H), 7.45 (d, J = 8.8 Hz, 1H), 7.06 (d, J = 3.0 Hz, 1H), 6.78 (dd, J = 9.0, 2.8 Hz, 1H), 5.44 (s, 1H), 4.83 (t, J = 5.6 Hz, 1H), 4.60 (d, J = 3.0 Hz, 1H), 3.83 (dd, J = 11.9, 3.1 Hz, 1H), 3.39-3.57 (m, 5H) |

| Ex. | Name | Structure | MS (m/z) (M + H+) | 1H NMR |
|---|---|---|---|---|
| 40 | 2-(((3R,4S)-4-(3-fluoro-4-(trifluoromethoxy)phenoxy)-3-hydroxy-3-(hydroxymethyl)pyrrolidin-1-yl)sulfonyl)-5-(trifluoromethyl)benzonitrile | 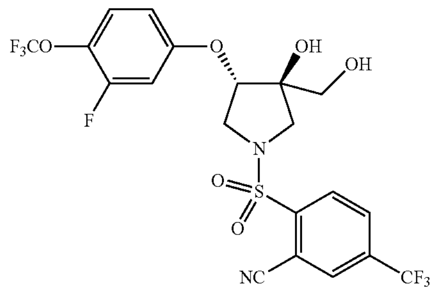 [SMILES: N#Cc1cc(C(F)(F)F)ccc1S(=O)(=O)N1C[C@H](Oc2ccc(OC(F)(F)F)c(F)c2)[C@](O)(CO)C1] | 545.1 | 1H NMR (400 MHz, DMSO-d6) δ: 8.53 (s, 1H), 8.20 (s, 2H), 7.38 (t, J = 8.9 Hz, 1H), 6.94 (dd, J = 12.2, 2.9 Hz, 1H), 6.64 (d, J = 9.0 Hz, 1H), 5.49 (s, 1H), 4.84 (t, J = 5.5 Hz, 1H), 4.58 (d, J = 2.8 Hz, 1H), 3.84 (dd, J = 11.9, 2.9 Hz, 1H), 3.40-3.59 (m, 5H) |
| 41 | 2-(((3R,4S)-4-(3-chloro-4-fluorophenoxy)-3-hydroxy-3-(hydroxymethyl)pyrrolidin-1-yl)sulfonyl)-5-(trifluoromethyl)benzonitrile | 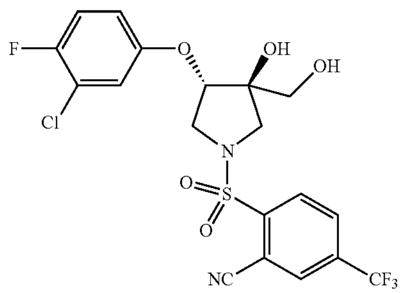 | 495.1 | 1H NMR (400 MHz, DMSO-d6) δ: 8.59 (d, J = 0.8 Hz, 1H), 8.17-8.28 (m, 2H), 7.26 (t, J = 9.0 Hz, 1H), 6.99 (dd, J = 6.3, 3.0 Hz, 1H), 6.74 (dt, J = 9.0, 3.5 Hz, 1H), 5.43 (s, 1H), 4.83 (t, J = 5.5 Hz, 1H), 4.55 (d, J = 2.8 Hz, 1H), 3.82 (dd, J = 11.8, 3.3 Hz, 1H), 3.39-3.57 (m, 5H) |
| 42 | 2-(((3R,4S)-3-hydroxy-3-(hydroxymethyl)-4-((6-(trifluoromethyl)pyridin-3-yl)oxy)pyrrolidin-1-yl)sulfonyl)-5-(trifluoromethyl)benzonitrile | 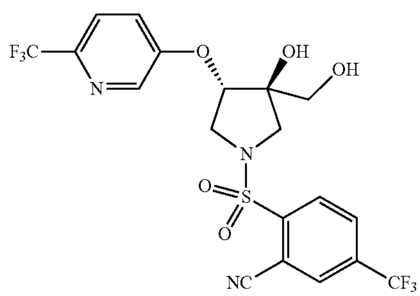 | 512.0 | 1H NMR (400 MHz, DMSO-d6) δ: 8.58 (s, 1H), 8.18-8.23 (m, 3H), 7.79 (d, J = 8.8 Hz, 1H), 7.55 (dd, J = 8.8, 2.8 Hz, 1H), 5.53 (s. 1H), 4.87 (t, J = 5.6 Hz, 1H), 4.77 (d, J = 2.8 Hz, 1H), 3.88 (dd, J = 12.0, 3.3 Hz, 1H), 3.42-3.62 (m, 5H) |
| 43 | 2-(((3R,4S)-4-(3-fluoro-4-methoxyphenoxy)-3-hydroxy-3-(hydroxymethyl)pyrrolidin-1-yl)sulfonyl)-5-(trifluoromethyl)benzonitrile | 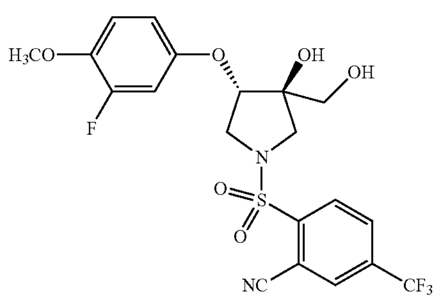 | 491.1 | 1H NMR (400 MHz, DMSO-d6) δ: 8.58 (d, J = 1.0 Hz, 1H), 8.14-8.27 (m, 2H), 6.98 (t, J = 9.5 Hz, 1H), 6.64 (dd, J = 12.9, 2.9 Hz, 1H), 6.45-6.52 (m, 1H), 5.40 (s, 1H), 4.82 (t, J = 5.5 Hz, 1H), 4.47 (d, J = 3.0 Hz, 1H), 3.74-3.82 (m, 4H), 3.39-3.58 (m, 5H) |
| 44 | 2-(((3R,4S)-4-(4-cyano-2-isopropoxy-phenoxy)-3-hydroxy-3-(hydroxymethyl)pyrrolidin-1-yl)sulfonyl)-5-(trifluoromethyl)benzonitrile | 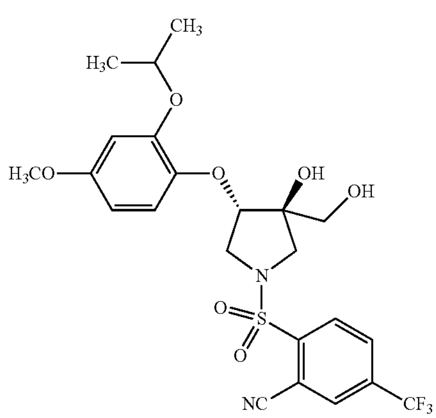 [SMILES: COc1ccc(O[C@H]2CN(S(=O)(=O)c3ccc(C(F)(F)F)cc3C#N)C[C@@]2(O)CO)c(OC(C)C)c1] | 526.2 | 1H NMR (400 MHz, DMSO-d6) δ: 8.55 (s, 1H), 8.14-8.21 (m, 2H), 7.34-7.39 (m, 2H), 7.10 (d, J = 8.8 Hz, 1H), 5.48 (s, 1H), 4.78 (t, J = 5.6 Hz, 1H), 4.60 (d, J = 3.0 Hz, 1H), 4.42 (dt, J = 12.0, 6.0 Hz, 1H), 3.84 (dd, J = 11.9, 3.1 Hz, 1H), 3.54-3.63 (m, 3H), 3.43-3.52 (m, 2H), 1.17 (dd, J = 14.4, 5.9 Hz, 6H) |

| Ex. | Name | Structure | MS (m/z) (M + H+) | 1H NMR |
|---|---|---|---|---|
| 45 | 2-(((3R,4S)-4-(4-cyano-2-cyclopropoxyphenoxy)-3-hydroxy-3-(hydroxymethyl)pyrrolidin-1-yl)sulfonyl)-5-(trifluoromethyl)benzonitrile | 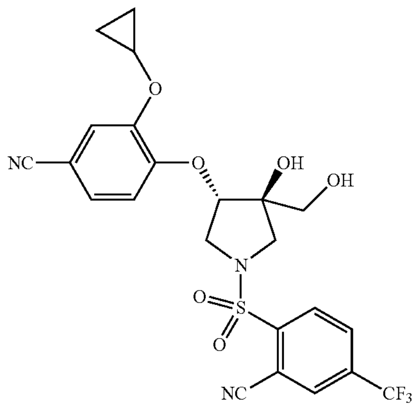 [SMILES: N#Cc1ccc(O[C@H]2CN(S(=O)(=O)c3ccc(C(F)(F)F)cc3C#N)C[C@@]2(O)CO)c(OC2CC2)c1] | 524.2 | 1H NMR (400 MHz, DMSO-d6) δ: 8.59 (s, 1H), 8.17-8.26 (m, 2H), 7.59 (d, J = 2.0 Hz, 1H), 7.39 (dd, J = 8.5, 2.0 Hz, 1H), 7.12 (d, J = 8.5 Hz, 1H), 5.44 (s, 1H), 4.75 (t, J = 5.5 Hz, 1H), 4.59 (d, J = 3.0 Hz, 1H), 3.80-3.91 (m, 2H), 3.57 (d, J = 11.8 Hz, 1H), 3.50-3.54 (m, 2H), 3.39-3.48 (m, 2H), 0.75-0.83 (m, 2H), 0.51-0.67 (m, 2H) |
| 46 | 2-(((3R,4S)-3-hydroxy-3-(hydroxymethyl)-4-phenoxypyrrolidin-1-yl)sulfonyl)-5-(trifluoromethyl)benzonitrile | 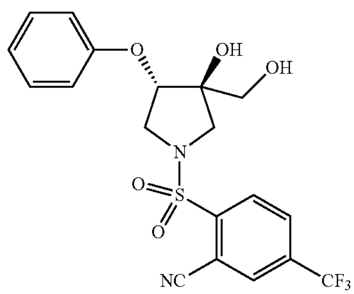 [SMILES: N#Cc1cc(C(F)(F)F)ccc1S(=O)(=O)N1C[C@H](Oc2ccccc2)[C@](O)(CO)C1] | 443.1 | 1H NMR (400 MHz, DMSO-d6) δ: 8.54 (s, 1H), 8.15-8.26 (m, 2H), 7.16-7.26 (m, 2H), 6.89-6.98 (m, 1H), 6.67 (d, J = 7.8 Hz, 2H), 5.41 (s, 1H), 4.82 (br s, 1H), 4.55 (d, J = 3.0 Hz, 1H), 3.81 (dd, J = 11.5, 3.3 Hz, 1H), 3.41-3.62 (m, 5H) |
| 47 | 2-(((3R,4S)-4-(4-fluorophenoxy)-3-hydroxy-3-(hydroxymethyl)pyrrolidin-1-yl)sulfonyl)-5-(trifluoromethyl)benzonitrile | 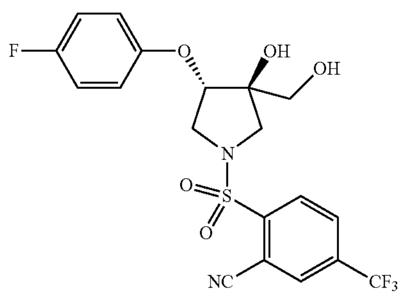 [SMILES: N#Cc1cc(C(F)(F)F)ccc1S(=O)(=O)N1C[C@H](Oc2ccc(F)cc2)[C@](O)(CO)C1] | 461.1 | 1H NMR (400 MHz, DMSO-d6) δ: 8.57 (s, 1H), 8.15-8.28 (m, 2H), 7.04 (t, J = 8.8 Hz, 2H), 6.68-6.75 (m, 2H), 5.41 (s, 1H), 4.83 (t, J = 5.6 Hz, 1H), 4.50 (d, J = 3.0 Hz, 1H), 3.79 (dd, J = 11.5, 3.3 Hz, 1H), 3.46-3.63 (m, 4H), 3.40-3.45 (m, 1H) |
| 48 | 2-(((3R,4S)-4-(4-chloro-2-methoxyphenoxy)-3-hydroxy-3-(hydroxymethyl)pyrrolidin-1-yl)sulfonyl)-5-(trifluoromethyl)benzonitrile | 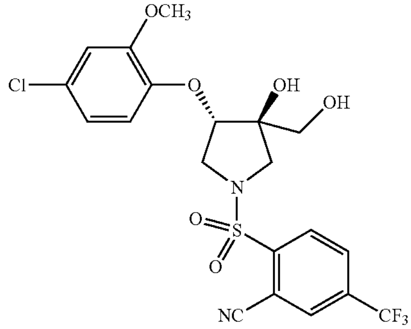 [SMILES: COc1cc(Cl)ccc1O[C@H]1CN(S(=O)(=O)c2ccc(C(F)(F)F)cc2C#N)C[C@@]1(O)CO] | 507.1 | 1H NMR (400 MHz, DMSO-d6) δ: 8.60 (s, 1H), 8.16-8.25 (m, 2H), 6.98 (d, J = 2.3 Hz, 1H), 6.84-6.94 (m, 2H), 5.39 (s, 1H), 4.76 (t, J = 5.5 Hz, 1H), 4.47 (d, J = 3.0 Hz, 1H), 3.74-3.82 (m, 1H), 3.69 (s, 3H), 3.53-3.59 (m, 3H), 3.40-3.52 (m, 2H) |

| Ex. | Name | Structure | MS (m/z) (M + H+) | 1H NMR |
|---|---|---|---|---|
| 49 | 4-(((3S,4R)-1-((2-chloro-4-(trifluoromethyl)phenyl)sulfonyl)-4-hydroxy-4-(hydroxymethyl)pyrrolidin-3-yl)oxy)benzonitrile | 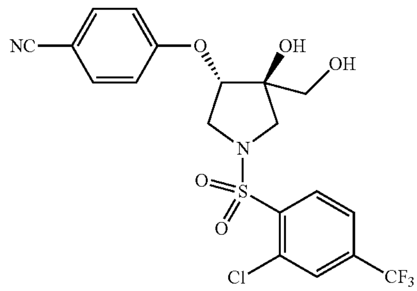 [SMILES: N#Cc1ccc(O[C@H]2CN(S(=O)(=O)c3ccc(C(F)(F)F)cc3Cl)C[C@@]2(O)CO)cc1] | 477.0 | 1H NMR (400 MHz, DMSO-d6) δ: 8.13 (d, J = 8.0 Hz, 1H), 8.09 (d, J = 1.0 Hz, 1H), 7.86 (dd, J = 8.3, 1.3 Hz, 1H), 7.69-7.75 (m, 2H), 6.98-7.05 (m, 2H), 5.56 (s, 1H), 4.88 (t, J = 5.4 Hz, 1H), 4.71 (d, J = 3.0 Hz, 1H), 3.89 (dd, J = 11.5, 3.3 Hz, 1H), 3.48-3.65 (m, 4H), 3.42 (d, J = 10.3 Hz, 1H) |
| 50 | 2-(((3R,4S)-3-hydroxy-3-(hydroxymethyl)-4-(4-(trifluoromethoxy)phenoxy)pyrrolidin-1-yl)sulfonyl)-5-(trifluoromethyl)benzonitrile | 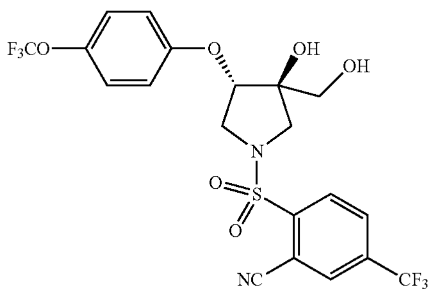 [SMILES: N#Cc1cc(C(F)(F)F)ccc1S(=O)(=O)N1C[C@H](Oc2ccc(OC(F)(F)F)cc2)[C@](O)(CO)C1] | 526.8 | 1H NMR (400 MHz, DMSO-d6) δ: 8.53 (s, 1H), 8.16-8.23 (m, 2H), 7.20 (d, J = 8.8 Hz, 2H), 6.81 (d, J = 9.0 Hz, 2H), 5.45 (s, 1H), 4.84 (t, J = 5.4 Hz, 1H), 4.56 (d, J = 2.5 Hz, 1H), 3.82 (dd, J = 11.7, 2.9 Hz, 1H), 3.48-3.61 (m, 4H), 3.42-3.47 (m, 1H) |
| 51 | 2-(((3R,4S)-3-hydroxy-3-(hydroxymethyl)-4-(p-tolyloxy)pyrrolidin-1-yl)sulfonyl)-5-(trifluoromethyl)benzonitrile | 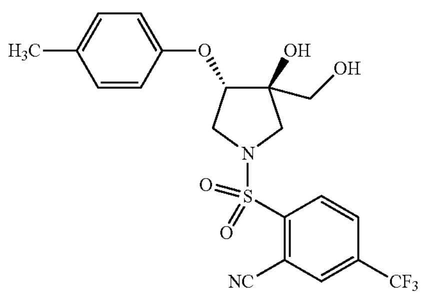 [SMILES: Cc1ccc(O[C@H]2CN(S(=O)(=O)c3ccc(C(F)(F)F)cc3C#N)C[C@@]2(O)CO)cc1] | 456.8 | 1H NMR (400 MHz, DMSO-d6) δ: 8.56 (s, 1H), 8.15-8.25 (m, 2H), 7.00 (d, J = 8.3 Hz, 2H), 6.56 (d, J = 8.5 Hz, 2H), 5.38 (s, 1H), 4.81 (t, J = 5.6 Hz, 1H), 4.49 (d, J = 3.0 Hz, 1H), 3.77 (dd, J = 11.5, 3.3 Hz, 1H), 3.46-3.60 (m, 4H), 3.40-3.45 (m, 1H), 2.22 (s, 3H) |
| 52 | 2-(((3R,4S)-3-hydroxy-3-(hydroxymethyl)-4-(4-methoxyphenoxy)pyrrolidin-1-yl)sulfonyl)-5-(trifluoromethyl)benzonitrile | 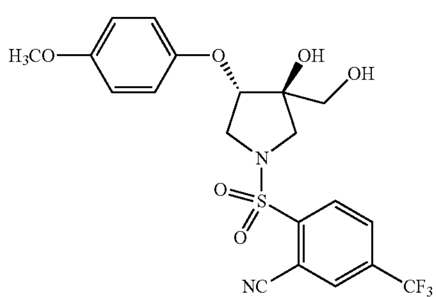 | 472.9 | 1H NMR (400 MHz, DMSO-d6) δ: 8.58 (d, J = 0.8 Hz, 1H), 8.15-8.27 (m, 2H), 6.74-6.80 (m, 2H), 6.60-6.66 (m, 2H), 5.37 (s, 1H), 4.81 (t, J = 5.5 Hz, 1H), 4.45 (d, J = 3.0 Hz, 1H), 3.72-3.78 (m, 1H), 3.69 (s, 3H), 3.36-3.60 (m, 5H) |
| 53 | 2-(((3R,4S)-4-(3-cyanophenoxy)-3-hydroxy-3-(hydroxymethyl)pyrrolidin-1-yl)sulfonyl)-5-(trifluoromethyl)benzonitrile | 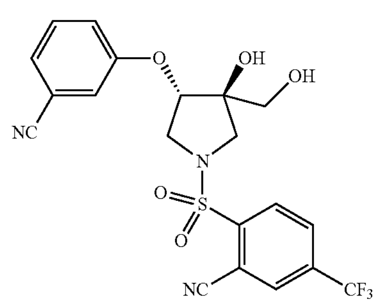 [SMILES: N#Cc1cccc(O[C@H]2CN(S(=O)(=O)c3ccc(C(F)(F)F)cc3C#N)C[C@@]2(O)CO)c1] | 467.8 | 1H NMR (400 MHz, DMSO-d6) δ: 8.56 (s, 1H), 8.15-8.25 (m, 2H), 7.37-7.45 (m, 2H), 7.30 (d, J = 1.3 Hz, 1H), 7.03 (dt, J = 7.0, 2.3 Hz, 1H), 5.46 (s, 1H), 4.83 (t, J = 5.5 Hz, 1H), 4.63 (d, J = 3.0 Hz, 1H), 3.85 (dd, J = 12.0, 3.0 Hz, 1H), 3.41-3.59 (m, 5H) |

-continued

| Ex. | Name | Structure | MS (m/z) (M + H⁺) | ¹H NMR |
|---|---|---|---|---|
| 54 | 2-(((3R,4S)-4-(5-cyano-2-methoxyphenoxy)-3-hydroxy-3-(hydroxymethyl)pyrrolidin-1-yl)sulfonyl)-5-(trifluoromethyl)benzonitrile | 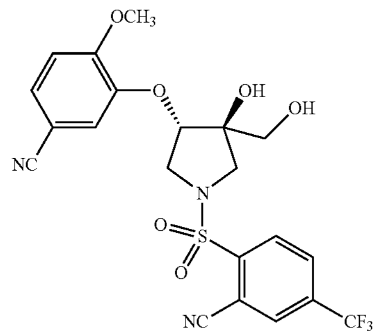 [SMILES: COc1ccc(C#N)cc1O[C@H]1CN(S(=O)(=O)c2ccc(C(F)(F)F)cc2C#N)C[C@@]1(O)CO] | 497.9 | ¹H NMR (400 MHz, DMSO-d$_6$) δ: 8.58 (s, 1H), 8.20 (m, 2H), 7.42-7.47 (m, 2H), 7.07 (d, J = 9.0 Hz, 1H), 5.43 (s, 1H), 4.78 (t, J = 5.6 Hz, 1H), 4.55 (d, J = 3.0 Hz, 1H), 3.84 (dd, J = 11.9, 3.4 Hz, 1H), 3.74 (s, 3H), 3.58-3.64 (m, 1H), 3.51-3.58 (m, 2H), 3.41-3.49 (m, 2H) |
| 55 | 2-(((3R,4S)-3-hydroxy-3-(hydroxymethyl)-4-((2-(trifluoromethyl)pyrimidin-5-yl)oxy)pyrrolidin-1-yl)sulfonyl)-5-(trifluoromethyl)benzonitrile | 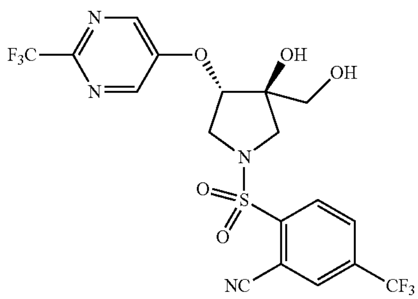 [SMILES: N#Cc1cc(C(F)(F)F)ccc1S(=O)(=O)N1C[C@H](Oc2cnc(C(F)(F)F)nc2)[C@](O)(CO)C1] | 513.1 | ¹H NMR (400 MHz, DMSO-d$_6$) δ: 8.66 (s, 2H), 8.62 (s, 1H), 8.23 (d, J = 1.0 Hz, 2H), 5.57 (s, 1H), 4.91 (d, J = 3.0 Hz, 1H), 4.87 (t, J = 5.6 Hz, 1H), 3.89 (dd, J = 12.2, 3.4 Hz, 1H), 3.68 (d, J = 12.0 Hz, 1H), 3.42-3.61 (m, 4H) |
| 56 | 2-(((3R,4S)-3-hydroxy-3-(hydroxymethyl)-4-(4-(trifluoromethyl)phenoxy)pyrrolidin-1-yl)sulfonyl)benzonitrile | 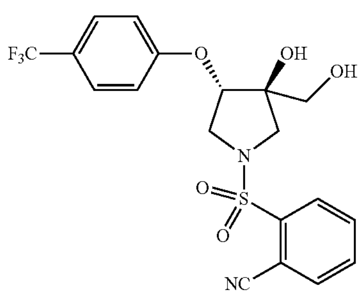 [SMILES: N#Cc1ccccc1S(=O)(=O)N1C[C@H](Oc2ccc(C(F)(F)F)cc2)[C@](O)(CO)C1] | 443.2 | ¹H NMR (400 MHz, DMSO-d$_6$) δ: 7.97-8.07 (m, 2H), 7.83-7.90 (m, 2H), 7.61 (d, J = 8.8 Hz, 2H), 6.92 (d, J = 8.5 Hz, 2H), 5.44 (s, 1H), 4.84 (t, J = 5.5 Hz, 1H), 4.68 (d, J = 3.0 Hz, 1H), 3.82 (dd, J = 11.5, 3.3 Hz, 1H), 3.46-3.60 (m, 3H), 3.42 (d, J = 5.5 Hz, 2H) |
| 57 | 4-(((3S,4R)-1-((5-chloropyridin-2-yl)sulfonyl)-4-hydroxy-4-(hydroxymethyl)pyrrolidin-3-yl)oxy)-1-naphthonitrile | 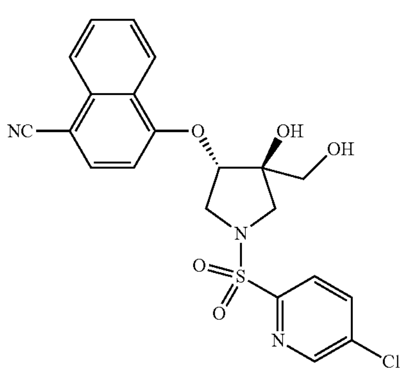 [SMILES: N#Cc1ccc(O[C@H]2CN(S(=O)(=O)c3ccc(Cl)cn3)C[C@@]2(O)CO)c2ccccc12] | 460.0 | ¹H NMR (400 MHz, DMSO-d$_6$) δ: 8.01-8.11 (m, 2H), 7.75-7.90 (m, 4H), 7.70 (d, J = 8.3 Hz, 1H), 7.55-7.63 (m, 1H), 7.08 (d, J = 8.3 Hz, 1H), 5.57 (s, 1H), 4.87 (t, J = 5.6 Hz, 1H), 4.80 (d, J = 2.8 Hz, 1H), 3.98 (dd, J = 12.3, 3.0 Hz, 1H), 3.82 (d, J = 12.0 Hz, 1H), 3.68-3.76 (m, 1H), 3.57-3.65 (m, 2H), 3.47 (d, J = 10.3 Hz, 1H) |

Example 58

4-(((3S,4R)-1-((5-chloropyridin-2-yl)sulfonyl)-4-hydroxy-4-(hydroxymethyl) pyrrolidin-3-yl)oxy)-2-fluorobenzonitrile

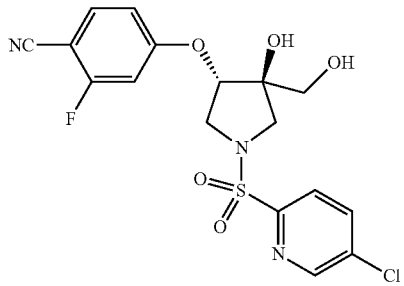 [SMILES: N#Cc1ccc(O[C@H]2CN(S(=O)(=O)c3ccc(Cl)cn3)C[C@@]2(O)CO)cc1F]

Step 1: (3R,4S)-tert-butyl 4-(4-cyano-3-fluorophenoxy)-3-hydroxy-3-(hydroxymethyl)pyrrolidine-1-carboxylate

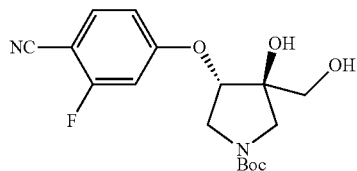 [SMILES: CC(C)(C)OC(=O)N1C[C@H](Oc2ccc(C#N)c(F)c2)[C@](O)(CO)C1]

(R)-tert-butyl 3-(4-cyano-3-fluorophenoxy)-4-methylenepyrrolidine-1-carboxylate (44.2 g, 139 mmol) was dissolved in THF (300 mL) and treated with NMO (24.4 g, 208 mmol) at rt under a nitrogen atmosphere. The reaction mixture was cooled to −78° C. and treated with OsO$_4$, (2.5% in t-BuOH, 87 mL, 6.9 mmol), stirred for 2 h at −78° C., then allowed to stand for 72 h in a −80° C. freezer. The cold mixture was allowed to warm to rt, stirred 2 h and was treated with sat'd Na$_2$S$_2$O$_3$ (aq) (500 mL) and EtOAc (500 mL). The organic layer was removed and washed with water (1 L), 1 N HCl (aq) (1 L), and brine (1 L), dried over Na$_2$SO$_4$, filtered, and concentrated to an orange oil. The crude product was purified by flash column chromatography (SiO$_2$) eluting with a gradient of 0-100% EtOAc in hexanes with a plateau at 50% EtOAc in hexanes. The product fractions were pooled and concentrated to give the title compound as a colorless oil (49.8 g, 97% yield). MS (m/z) 375.0 (M+Na$^+$).

Step 2: 2-fluoro-4-(((3S,4R)-4-hydroxy-4-(hydroxymethyl)pyrrolidin-3-yl)oxy)benzonitrile, Hydrochloride

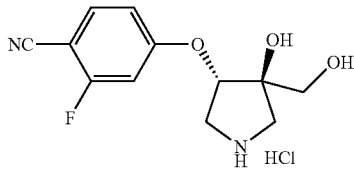

(3R,4S)-tert-butyl 4-(4-cyano-3-fluorophenoxy)-3-hydroxy-3-(hydroxymethyl)pyrrolidine-1-carboxylate (76 g, 216 mmol) was dissolved in 1,4-dioxane (300 mL), treated with 4 M HCl in dioxane (216 mL, 863 mmol) at rt under an atmosphere of nitrogen and the reaction mixture was stirred at rt for 100 min. The solvent was evaporated under reduced pressure and the residue was triturated in Et$_2$O (3 L) and allowed to stand overnight. The title compound was collected by filtration as a light tan solid (44 g, 63% yield). MS (m/z) 253.2 (M+H$^+$).

Step 3: 4-(((3S,4R)-1-((5-chloropyridin-2-yl)sulfonyl)-4-hydroxy-4-(hydroxymethyl) pyrrolidin-3-yl)oxy)-2-fluorobenzonitrile To a stirred suspension of 2-fluoro-4-(((3S,4R)-4-hydroxy-4-(hydroxymethyl)pyrrolidin-3-yl)oxy)benzonitrile, Hydrochloride (200 mg, 0.693 mmol) in DCM (10 mL) at 0° C. was added DIPEA (0.12 mL, 0.69 mmol) in one portion followed by 5-chloropyridine-2-sulfonyl chloride (160 mg, 0.76 mmol). The resultant solution was stirred for 30 min and then was diluted with DCM and treated with 10% Na$_2$CO$_3$ (aq). The layers were separated and the aqueous layer extracted with DCM (2×). The organic layers were combined, washed with brine, filtered and concentrated. The crude oil was purified by flash column chromatography (SiO$_2$) eluting with a gradient of 0-100% EtOAc in hexanes. The product fractions were pooled and concentrated to give the title compound as a white solid (160 mg, 51% yield). $^1$H NMR (400 MHz, DMSO-d$_6$) δ: 8.59 (d, J=2.0 Hz, 1H), 8.11 (dd, J=8.4, 2.4 Hz, 1H), 7.85 (d, J=8.5 Hz, 1H), 7.77 (t, J=8.3 Hz, 1H), 6.95 (dd, J=11.8, 2.0 Hz, 1H), 6.69 (dd, J=8.8, 2.0 Hz, 1H), 5.41 (s, 1H), 4.80 (t, J=5.6 Hz, 1H), 4.59 (d, J=2.5 Hz, 1H), 3.87 (dd, J=12.2, 2.9 Hz, 1H), 3.43-3.60 (m, 4H), 3.38 (d, J=10.5 Hz, 1H, partially hidden by solvent peak). MS (m/z) 428.0 (M+H$^+$).

The following compounds were prepared using procedures analogous to those described in Example 58 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 59 | 4-(((3S,4R)-1-((7-chlorobenzo[c][1,2,5]oxadiazol-4-yl)sulfonyl)-4-hydroxy-4-(hydroxymethyl)pyrrolidin-3-yl)oxy)-2-fluorobenzonitrile | 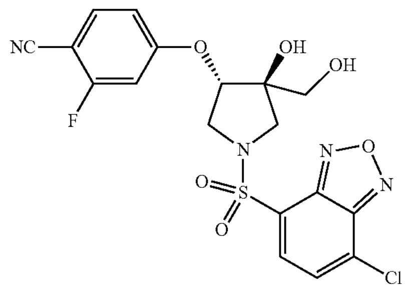 [SMILES: N#Cc1ccc(O[C@H]2CN(S(=O)(=O)c3ccc(Cl)c4nonc34)C[C@@]2(O)CO)cc1F] | 468.9 | ¹H NMR (400 MHz, DMSO-d₆) δ: 8.02 (d, J = 7.3 Hz, 1H), 7.88 (d, J = 7.5 Hz, 1H), 7.73 (t, J = 8.3 Hz, 1H), 6.79 (d, J = 11.8 Hz, 1H), 6.56 (d, J = 8.8 Hz, 1H), 5.35 (s, 1H), 4.74 (t, J = 5.3 Hz, 1H), 4.57 (br s, 1H), 3.95 (dd, J = 12.4, 2.6 Hz, 1H), 3.70 (d, J = 12.3 Hz, 1H), 3.36-3.51 (m, 4H) |
| 60 | 4-(((3S,4R)-1-(benzo[c][1,2,5]oxadiazol-5-ylsulfonyl)-4-hydroxy-4-(hydroxymethyl)pyrrolidin-3-yl)oxy)-2-fluorobenzonitrile | 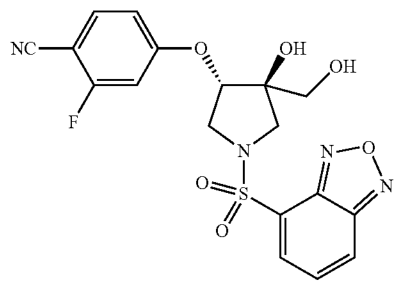 [SMILES: N#Cc1ccc(O[C@H]2CN(S(=O)(=O)c3cccc4nonc34)C[C@@]2(O)CO)cc1F] | 435.0 | ¹H NMR (400 MHz, DMSO-d₆) δ: 8.34 (d, J = 9.0 Hz, 1H), 8.07 (d, J = 6.8 Hz, 1H), 7.66-7.77 (m, 2H), 6.75 (d, J = 11.8 Hz, 1H), 6.48 (d, J = 8.8 Hz, 1H), 5.37 (s, 1H), 4.74 (br s, 1H), 4.58 (br s, 1H), 3.95 (dd, J = 12.4, 2.6 Hz, 1H), 3.75 (d, J = 12.3 Hz, 1H), 3.36-3.52 (m, 4H) |
| 61 | 4-(((3S,4R)-1-((2-cyanophenyl)sulfonyl)-4-hydroxy-4-(hydroxymethyl)pyrrolidin-3-yl)oxy)-2-fluorobenzonitrile | 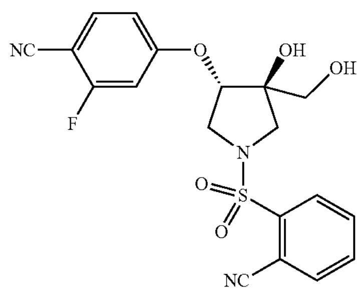 [SMILES: N#Cc1ccc(O[C@H]2CN(S(=O)(=O)c3ccccc3C#N)C[C@@]2(O)CO)cc1F] | 418.1 | ¹H NMR (400 MHz, DMSO-d₆) δ: 8.04-8.09 (m, 1H), 7.96-8.02 (m, 1H), 7.76-7.92 (m, 3H), 7.03 (dd, J = 11.8, 2.5 Hz, 1H), 6.73 (dd, J = 8.8, 2.3 Hz, 1H), 5.50 (s, 1H), 4.85 (t, J = 5.5 Hz, 1H), 4.70 (d, J = 2.8 Hz, 1H), 3.83 (dd, J = 12.0, 3.3 Hz, 1H), 3.44-3.59 (m, 3H), 3.39 (2H, partially hidden by solvent peak) |
| 62 | 3-(((3R,4S)-4-(4-cyano-3-fluorophenoxy)-3-hydroxy-3-(hydroxymethyl)pyrrolidin-1-yl)sulfonyl)picolinonitrile | 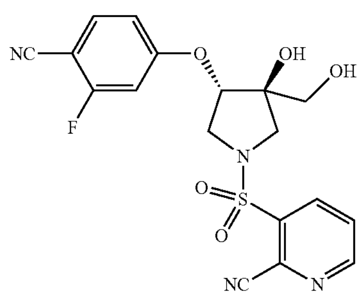 [SMILES: N#Cc1ccc(O[C@H]2CN(S(=O)(=O)c3cccnc3C#N)C[C@@]2(O)CO)cc1F] | 419.0 | ¹H NMR (400 MHz, DMSO-d₆) δ: 8.97 (dd, J = 4.8, 1.5 Hz, 1H), 8.43 (dd, J = 8.2, 1.4 Hz, 1H), 7.92 (dd, J = 8.0, 4.8 Hz, 1H), 7.80 (t, J = 8.3 Hz, 1H), 7.07 (dd, J = 11.8, 2.3 Hz, 1H), 6.76 (dd, J = 8.8, 2.0 Hz, 1H), 5.51 (s, 1H), 4.86 (br s, 1H), 4.72 (d, J = 3.0 Hz, 1H), 3.86 (dd, J = 11.9, 3.1 Hz, 1H), 3.42-3.61 (m, 5H) |
| 63 | 4-(((3S,4R)-1-((2-chloro-4-(trifluoromethyl)phenyl)sulfonyl)-4-hydroxy-4-(hydroxymethyl)pyrrolidin-3-yl)oxy)-2-fluorobenzonitrile | 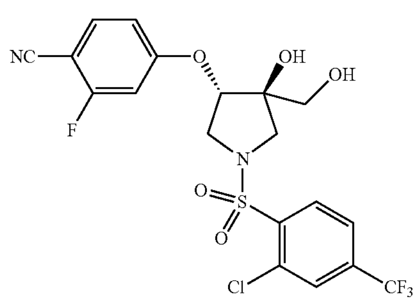 [SMILES: N#Cc1ccc(O[C@H]2CN(S(=O)(=O)c3ccc(C(F)(F)F)cc3Cl)C[C@@]2(O)CO)cc1F] | 495.0 | ¹H NMR (400 MHz, DMSO-d₆) δ: 8.14 (d, J = 8.3 Hz, 1H), 8.08 (s, 1H), 7.87 (d, J = 8.0 Hz, 1Hδ: 7.78 (t, J = 8.3 Hz, 1H), 7.08 (dd, J = 11.8, 2.0 Hz, 1H), 6.87 (dd, J = 8.8, 2.0 Hz, 1H), 5.58 (s, 1H), 4.88 (t, J = 5.6 Hz, 1H), 4.73 (d, J = 2.8 Hz, 1H), 3.90 (dd, J = 11.8, 3.0 Hz, 1H), 3.49-3.65 (m, 4H), 3.42 (d, J = 10.5 Hz, 1H) |

-continued

| Ex. | Name | Structure | MS (m/z) (M + H+) | 1H NMR |
|---|---|---|---|---|
| 64 | 4-(((3S,4R)-1-((2-bromo-4-methoxyphenyl)sulfonyl)-4-hydroxy-4-(hydroxymethyl)pyrrolidin-3-yl)oxy)-2-fluorobenzonitrile | 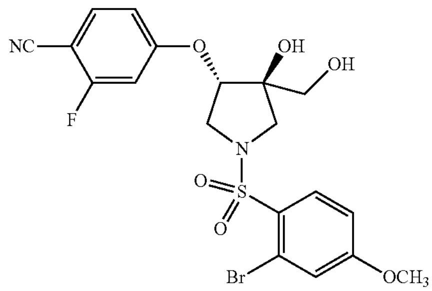 [SMILES: COc1ccc(S(=O)(=O)N2C[C@H](Oc3ccc(C#N)c(F)c3)[C@](O)(CO)C2)c(Br)c1] | 500.9 | 1H NMR (400 MHz, DMSO-d6) δ: 7.87 (d, J = 8.8 Hz, 1H), 7.80 (t, J = 8.3 Hz, 1H), 7.34 (d, J = 2.3 Hz, 1H), 7.01-7.13 (m, 2H), 6.88 (d, J = 8.8 Hz, 1H), 5.46 (s, 1H), 4.81 (t, J = 5.6 Hz, 1H), 4.72 (d, J = 2.3 Hz, 1H), 3.85 (s, 3H), 3.82 (d, J = 2.8 Hz, 1H), 3.57-3.64 (m, 1H), 3.43-3.56 (m, 3H), 3.35 (d, J = 10.0 Hz, 1H) |
| 65 | 4-(((3S,4R)-1-((2-bromo-4-(trifluoromethoxy)phenyl)sulfonyl)-4-hydroxy-4-(hydroxymethyl)pyrrolidin-3-yl)oxy)-2-fluorobenzonitrile | 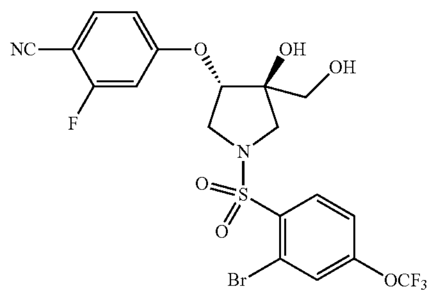 | 554.9 | 1H NMR (400 MHz, DMSO-d6) δ: 8.09 (d, J = 8.8 Hz, 1H), 7.90 (s, 1H), 7.80 (t, J = 8.3 Hz, 1H), 7.56 (d, J = 8.8 Hz, 1H), 7.12 (d, J = 11.8 Hz, 1H), 6.90 (d, J = 8.8 Hz, 1H), 5.53 (s, 1H), 4.84 (t, J = 5.5 Hz, 1H), 4.76 (d, J = 2.0 Hz, 1H), 3.89 (dd, J = 11.7, 2.9 Hz, 1H), 3.58-3.64 (m, 1H), 3.50-3.57 (m, 3H), 3.42 (d, J = 10.3 Hz, 1H) |
| 66 | 4-(((3S,4R)-1-((2-chloro-4-(trifluoromethoxy)phenyl)sulfonyl)-4-hydroxy-4-(hydroxymethyl)pyrrolidin-3-yl)oxy)-2-fluorobenzonitrile | 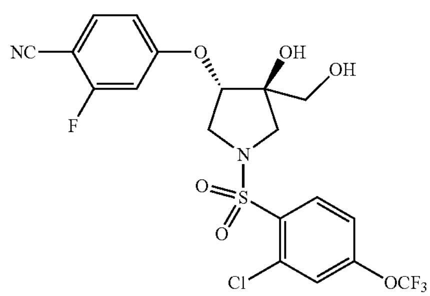 | 511.0 | 1H NMR (400 MHz, DMSO-d6) δ: 8.07 (d, J = 8.8 Hz, 1H), 7.76-7.84 (m, 2H), 7.49-7.55 (m, 1H), 7.11 (dd, J = 11.8, 2.5 Hz, 1H), 6.88 (dd, J = 8.8, 2.3 Hz, 1H), 5.55 (s, 1H), 4.86 (t, J = 5.6 Hz, 1H), 4.73 (d, J = 3.0 Hz, 1H), 3.87 (dd, J = 11.9, 3.1 Hz, 1H), 3.47-3.64 (m, 4H), 3.40 (d, J = 10.3 Hz, 1H) |
| 67 | 4-(((3S,4R)-1-((4-bromo-2-cyanophenyl)sulfonyl)-4-hydroxy-4-(hydroxymethyl)pyrrolidin-3-yl)oxy)-2-fluorobenzonitrile | 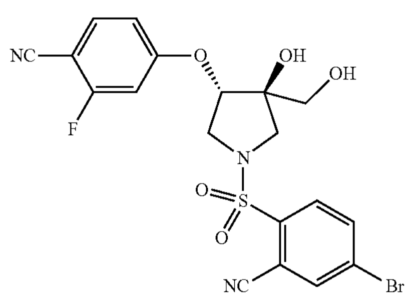 [SMILES: N#Cc1ccc(O[C@H]2CN(S(=O)(=O)c3ccc(Br)cc3C#N)C[C@@]2(O)CO)cc1F] | 496.0 | 1H NMR (400 MHz, DMSO-d6) δ: 8.38 (s, 1H), 8.05 (d, J = 8.5 Hz, 1H), 7.87 (d, J = 8.5 Hz, 1H), 7.79 (t, J = 8.3 Hz, 1H), 7.03 (d, J = 11.8 Hz, 1H), 6.77 (d, J = 8.8 Hz, 1H), 5.47 (s, 1H), 4.81 (t, J = 5.4 Hz, 1H), 4.69 (br s, 1H), 3.83 (dd, J = 12.0, 2.8 Hz, 1H), 3.46-3.59 (m, 3H), 3.36-3.45 (m, 2H) |
| 68 | 4-(((3S,4R)-1-((4-cyano-2-(trifluoromethyl)phenyl)sulfonyl)-4-hydroxy-4-(hydroxymethyl)pyrrolidin-3-yl)oxy)-2-fluorobenzonitrile | 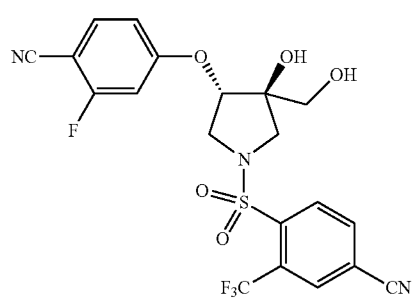 [SMILES: N#Cc1ccc(S(=O)(=O)N2C[C@H](Oc3ccc(C#N)c(F)c3)[C@](O)(CO)C2)c(C(F)(F)F)c1] | 486.0 | 1H NMR (400 MHz, DMSO-d6) δ: 8.54 (s, 1H), 8.37 (d, J = 8.3 Hz, 1H), 8.23 (d, J = 8.3 Hz, 1H), 7.84 (t, J = 8.3 Hz, 1H), 7.21 (d, J = 11.8 Hz, 1H), 6.97 (d, J = 8.8 Hz, 1H), 5.64 (br s, 1H), 4.87 (brs, 1H), 4.81 (d, J = 2.5 Hz, 1H), 3.88 (dd, J = 11.7, 2.9 Hz, 1H), 3.49-3.68 (m, 4H), 3.42-3.48 (m, 1H) |

-continued

| Ex. | Name | Structure | MS (m/z) (M + H⁺) | ¹H NMR |
|---|---|---|---|---|
| 69 | 5-(((3S,4R)-1-((2-cyano-4-(trifluoromethyl)phenyl)sulfonyl)-4-hydroxy-4-(hydroxymethyl)pyrrolidin-3-yl)oxy)picolinonitrile | 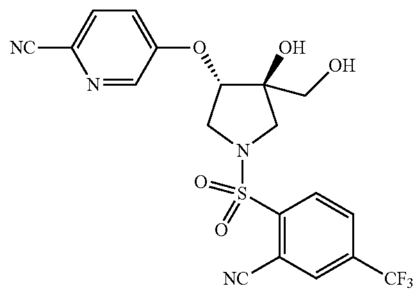 | 469.0 | ¹H NMR (400 MHz, DMSO-$d_6$) δ: 8.60 (s, 1H), 8.16-8.26 (m, 3H), 7.97 (d, J = 8.5 Hz, 1H), 7.55 (dd, J = 8.8, 3.0 Hz, 1H), 5.54 (s, 1H), 4.86 (t, J = 5.6 Hz, 1H), 4.78 (d, J = 3.0 Hz, 1H), 3.88 (dd, J = 12.0, 3.3 Hz, 1H), 3.40-3.62 (m, 5H) |
| 70 | 2-fluoro-4-(((3S,4R)-4-hydroxy-4-(hydroxymethyl)-1-((4-(trifluoromethyl)phenyl)sulfonyl)pyrrolidin-3-yl)oxy)benzonitrile | 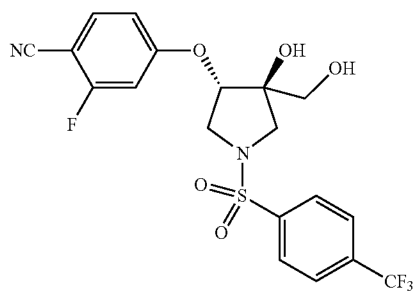 | 461.1 | ¹H NMR (400 MHz, DMSO-$d_6$) δ: 7.86-7.95 (m, 4H), 7.72 (t, J = 8.3 Hz, 1H), 6.82 (d, J = 11.8 Hz, 1H), 6.63 (d, J = 8.8 Hz, 1H), 4.60 (d, J = 2.5 Hz, 1H), 3.74 (dd, J = 12.3, 3.0 Hz, 1H), 3.31-3.53 (m, 5H, partially hidden by solvent peak) |
| 71 | 4-(((3S,4R)-1-((4-cyanophenyl)sulfonyl)-4-hydroxy-4-(hydroxymethyl)pyrrolidin-3-yl)oxy)-2-fluorobenzonitrile | 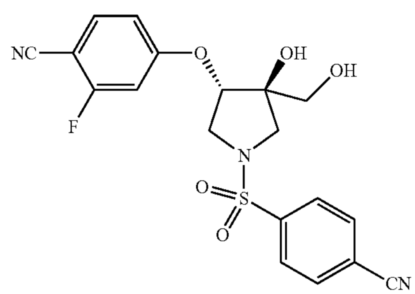 [SMILES: N#Cc1ccc(S(=O)(=O)N2C[C@H](Oc3ccc(C#N)c(F)c3)[C@](O)(CO)C2)cc1] | 418.1 | ¹H NMR (400 MHz, DMSO-$d_6$) δ: 8.00 (d, J = 8.3 Hz, 2H), 7.88 (d, J = 8.3 Hz, 2H), 7.76 (t, J = 8.4 Hz, 1H), 6.89 (d, J = 11.8 Hz, 1H), 6.68 (d, J = 8.8 Hz, 1H), 5.38 (s, 1H), 4.77 (t, J = 6.4 Hz, 1H), 4.61 (d, J = 2.5 Hz, 1H), 3.72 (dd, J = 12.0, 3.0 Hz, 1H), 3.42-3.56 (m, 2H), 3.33-3.39 (m, 3H, partially hidden by solvent peak) |
| 72 | 4-(((3S,4R)-1-((4-acetyl-2-cyanophenyl)sulfonyl)-4-hydroxy-4-(hydroxymethyl)pyrrolidin-3-yl)oxy)-2-fluorobenzonitrile | 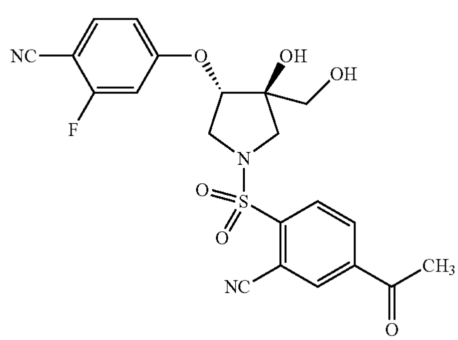 [SMILES: CC(=O)c1ccc(S(=O)(=O)N2C[C@H](Oc3ccc(C#N)c(F)c3)[C@](O)(CO)C2)c(C#N)c1] | 460.1 | ¹H NMR (400 MHz, DMSO-$d_6$) δ: 8.52 (s, 1H), 8.27 (d, J = 8.3 Hz, 1H), 8.10 (d, J = 8.3 Hz, 1H), 7.75 (t, J = 8.3 Hz, 1H), 7.00 (d, J = 11.8 Hz, 1H), 6.76 (dd, J = 8.8, 1.8 Hz, 1H), 5.50 (br s, 1H), 4.82 (br s, 1H), 4.69 (d, J = 2.3 Hz, 1H), 3.87 (dd, J = 12.2, 2.9 Hz, 1H), 3.40-3.60 (m, 5H, partially hidden by solvent peak), 2.69 (s, 3H) |
| 73 | 5-(((3S,4R)-1-((2,4-dichlorophenyl)sulfonyl)-4-hydroxy-4-(hydroxymethyl)pyrrolidin-3-yl)oxy)picolinonitrile | 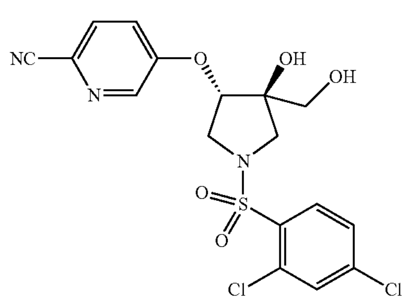 [SMILES: N#Cc1ccc(O[C@H]2CN(S(=O)(=O)c3ccc(Cl)cc3Cl)C[C@@]2(O)CO)cn1] | 444.0 | ¹H NMR (400 MHz, CDCl₃) δ: 8.35 (d, J = 2.3 Hz, 1H), 8.00 (d, J = 8.5 Hz, 1H), 7.67 (d, J = 8.5 Hz, 1H), 7.55 (s, 1H), 7.38 (d, J = 8.5 Hz, 1H), 7.30 (1H, partially hidden by solvent peak), 4.76 (d, J = 3.0 Hz, 1H), 3.95-4.07 (m, 2H), 3.77 (dd, J = 17.1, 11.3 Hz, 2H), 3.56-3.68 (m, 2H) |

| Ex. | Name | Structure | MS (m/z) (M + H⁺) | ¹H NMR |
|---|---|---|---|---|
| 74 | 5-(((3S,4R)-1-((2-chloro-4-(trifluoromethyl)phenyl)sulfonyl)-4-hydroxy-4-(hydroxymethyl)pyrrolidin-3-yl)oxy)picolinonitrile | 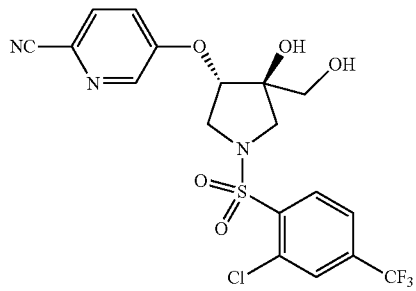 | 478.0 | ¹H NMR (400 MHz, DMSO-d₆) δ: 8.30 (br s, 1H), 8.15 (d, J = 8.0 Hz, 1H), 8.09 (s, 1H), 7.96 (d, J = 8.8 Hz, 1H), 7.88 (d, J = 8.3 Hz, 1H), 7.56-7.62 (m, 1H), 5.58 (s, 1H), 4.80-4.90 (m, 2H), 3.92 (d, J = 11.8 Hz, 1H), 3.51-3.66 (m, 4H), 3.42 (d, J = 10.3 Hz, 1H) |
| 75 | 5-(((3S,4R)-1-((2-chloro-4-methylphenyl)sulfonyl)-4-hydroxy-4-(hydroxymethyl)pyrrolidin-3-yl)oxy)picolinonitrile | 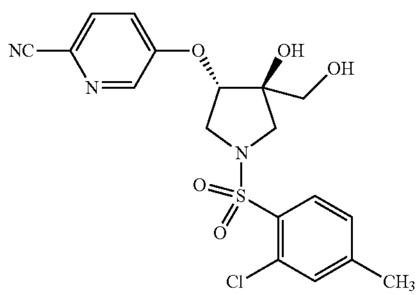 [SMILES: Cc1ccc(S(=O)(=O)N2C[C@H](Oc3ccc(C#N)nc3)[C@](O)(CO)C2)c(Cl)c1] | 423.9 | ¹H NMR (400 MHz, DMSO-d₆) δ: 8.24 (d, J = 2.0 Hz, 1H), 7.96 (s, 1H), 7.80 (d, J = 8.0 Hz, 1H), 7.55 (dd, J = 8.5, 2.0 Hz, 1H), 7.44 (s, 1H), 7.26 (d, J = 7.8 Hz, 1H), 5.49 (s, 1H), 4.81 (t, J = 5.4 Hz, 1H), 4.77 (br s, 1H), 3.80-3.88 (m, 1H), 3.57-3.65 (m, 1H), 3.45-3.56 (m, 3H), 3.36 (d, J = 10.3 Hz, 1H), 2.35 (s, 3H) |
| 76 | 5-(((3S,4R)-4-hydroxy-4-(hydroxymethyl)-1-((2,4,6-trichlorophenyl)sulfonyl)pyrrolidin-3yl)oxy)picolinonitrile | 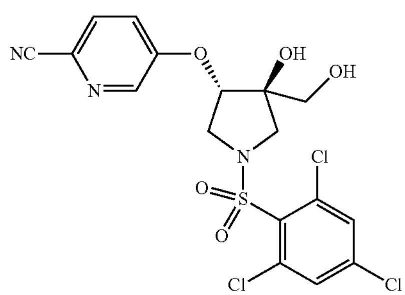 [SMILES: N#Cc1ccc(O[C@H]2CN(S(=O)(=O)c3c(Cl)cc(Cl)cc3Cl)C[C@@]2(O)CO)cn1] | 478.0 | ¹H NMR (400 MHz, DMSO-d₆) δ: 8.34 (d, J = 2.3 Hz, 1H), 7.98 (d, J = 8.8 Hz, 1H), 7.83 (s, 2H), 7.62 (dd, J = 8.8, 2.3 Hz, 1H), 5.52 (s, 1H), 4.81-4.89 (m, 2H), 3.91-3.96 (m, 1H), 3.52-3.70 (m, 4H), 3.43-3.48 (m, 1H) |
| 77 | 2-fluoro-4-(((3S,4R)-4-hydroxy-4-(hydroxymethyl)-1-((2,4,6-trichlorophenyl)sulfonyl)pyrrolidin-3-yl)oxy)benzonitrile | 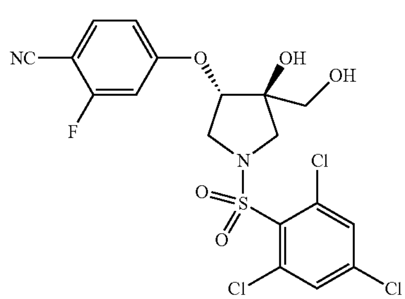 [SMILES: N#Cc1ccc(O[C@H]2CN(S(=O)(=O)c3c(Cl)cc(Cl)cc3Cl)C[C@@]2(O)CO)cc1F] | 494.9 | ¹H NMR (400 MHz, DMSO-d₆) δ: 7.85 (s, 2H), 7.77-7.84 (m, 1H), 7.16 (dd, J = 11.8, 2.3 Hz, 1H), 6.91 (dd, J = 8.7, 2.4 Hz, 1H), 5.53 (s, 1H), 4.87 (t, J = 5.6 Hz, 1H), 4.74 (d, J = 3.3 Hz, 1H), 3.92 (dd, J = 11.5, 3.3 Hz, 1H), 3.51-3.65 (m, 4H), 3.43 (d, J = 10.3 Hz, 1H) |
| 78 | 4-(((3S,4R)-1-((2-chloro-4-methylphenyl)sulfonyl)-4-hydroxy-4-(hydroxymethyl)pyrrolidin-3-yl)oxy)-2-fluorobenzonitrile | 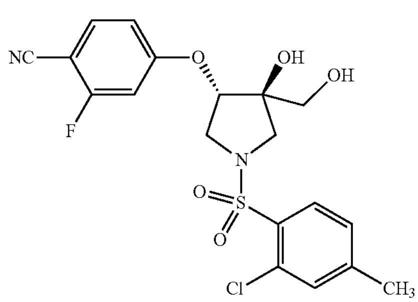 [SMILES: Cc1ccc(S(=O)(=O)N2C[C@H](Oc3ccc(C#N)c(F)c3)[C@](O)(CO)C2)c(Cl)c1] | 441.0 | ¹H NMR (400 MHz, DMSO-d₆) δ: 7.77-7.84 (m, 2H), 7.46 (d, J = 1.0 Hz, 1H), 7.27 (dd, J = 8.2, 0.9 Hz, 1H), 7.08 (dd, J = 11.8, 2.3 Hz, 1H), 6.84 (dd, J = 8.7, 2.4 Hz, 1H), 5.51 (s, 1H), 4.84 (t, J = 5.6 Hz, 1H), 4.70 (d, J = 2.8 Hz, 1H), 3.83 (dd, J = 11.8, 3.3 Hz, 1H), 3.42-3.61 (m, 4H), 3.31-3.37 (m, 1H, partially hidden by solvent peak), 2.35 (s, 3H) |

| Ex. | Name | Structure | MS (m/z) (M + H⁺) | ¹H NMR |
|---|---|---|---|---|
| 79 | 5-(((3R,4S)-4-(4-cyano-3-fluorophenoxy)-3-hydroxy-3-(hydroxymethyl)pyrrolidin-1-yl)sulfonyl)picolinonitrile | 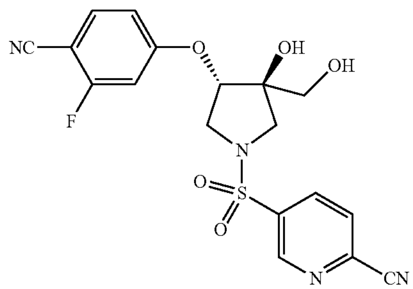 [SMILES: N#Cc1ccc(S(=O)(=O)N2C[C@H](Oc3ccc(C#N)c(F)c3)[C@](O)(CO)C2)cn1] | 419.0 | ¹H NMR (400 MHz, DMSO-d₆) δ: 9.06 (dd, J = 2.3, 0.8 Hz, 1H), 8.41 (dd, J = 8.3, 2.3 Hz, 1H), 8.23 (dd, J = 8.0, 0.8 Hz, 1H), 7.78 (t, J = 8.3 Hz, 1H), 6.95 (dd, J = 11.8, 2.3 Hz, 1H), 6.71 (dd, J = 8.8, 2.3 Hz, 1H), 5.41 (s, 1H), 4.81 (t, J = 5.6 Hz, 1H), 4.63 (d, J = 3.0 Hz, 1H), 3.75 (dd, J = 12.3, 3.3 Hz, 1H), 3.36-3.54 (m, 5H) |
| 80 | 4-(((3S,4R)-1-((4-cyano-2-methylphenyl)sulfonyl)-4-hydroxy-4-(hydroxymethyl)pyrrolidin-3-yl)oxy)-2-fluorobenzonitrile | 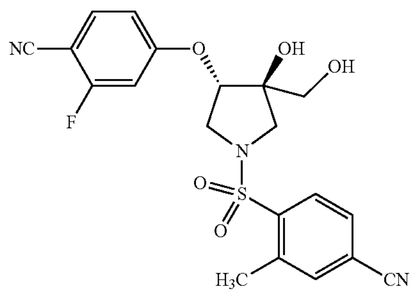 | 431.9 | ¹H NMR (400 MHz, DMSO-d₆) δ: 7.91-7.96 (m, 2H), 7.79-7.87 (m, 2H), 7.15 (d, J = 11.8 Hz, 1H), 6.90-6.97 (m, 1H), 4.76 (d, J = 2.5 Hz, 1H), 3.80 (dd, J = 11.4.2.9 Hz, 1H), 3.51-3.64 (m, 2H), 3.43 (d, J = 10.5 Hz, 2H), 3.31-3.37 (m, 1H), 2.57 (s, 3H), 2.09 (d, J = 5.3 Hz, 1H) |
| 81 | 2-fluoro-4-(((3S,4R)-4-hydroxy-4-(hydroxymethyl)-1-((2-methyl-4-(trifluoromethyl)phenyl)sulfonyl)pyrrolidin-3-yl)oxy)benzonitrile | 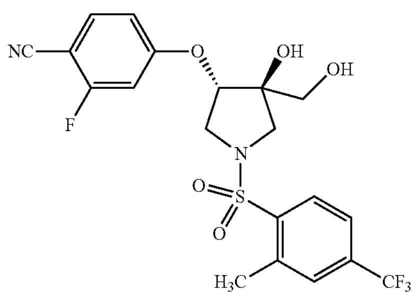 | 475.0 | ¹H NMR (400 MHz, DMSO-d₆) δ: 8.00 (d, J = 8.3 Hz, 1H), 7.77-7.85 (m, 2H), 7.72 (d, J = 8.0 Hz, 1H), 7.12 (d, J = 11.8 Hz, 1H), 6.91 (d, J = 8.5 Hz, 1H), 4.74 (d, J = 2.5 Hz, 1H), 3.80 (dd, J = 11.5, 3.0 Hz, 1H), 3.51-3.63 (m, 2H), 3.39-3.46 (m, 2H), 3.31-3.37 (m, 1H), 2.62 (s, 3H) |
| 82 | 5-(((3R,4S)-4-(4-cyano-2,5-difluorophenoxy)-3-hydroxy-3-(hydroxymethyl)pyrrolidin-1-yl)sulfonyl)picolinonitrile | 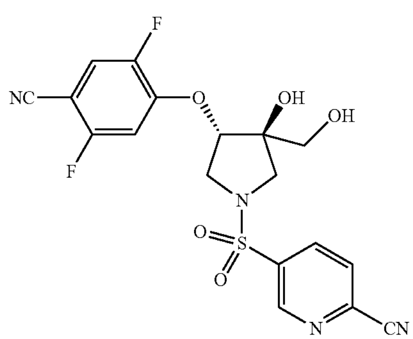 [SMILES: N#Cc1ccc(S(=O)(=O)N2C[C@H](Oc3cc(F)c(C#N)cc3F)[C@](O)(CO)C2)cn1] | 436.9 | ¹H NMR (400 MHz, DMSO-d₆) δ: 9.07 (d, J= 1.8 Hz, 1H), 8.41 (dd, J = 8.2, 1.9 Hz, 1H), 8.20 (d, J = 8.3 Hz, 1H), 7.88 (dd, J = 10.5, 6.3 Hz, 1H), 7.50 (dd, J = 11.0, 6.8 Hz, 1H), 5.53 (s, 1H), 4.84 (t, J = 5.6 Hz, 1H), 4.66 (d, J = 2.5 Hz, 1H), 3.79 (dd, J = 12.7, 2.9 Hz, 1H), 3.36-3.57 (m, 4H), 3.27 (d, J = 10.8 Hz, 1H) |
| 83 | 2-fluoro-4-(((3S,4R)-4-hydroxy-4-(hydroxymethyl)-1-((2-methyl-6-(trifluoromethyl)pyridin-3-yl)sulfonyl)pyrrolidin-3-yl)oxy)benzonitrile | 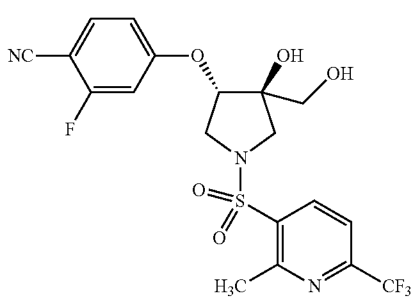 [SMILES: Cc1nc(C(F)(F)F)ccc1S(=O)(=O)N1C[C@H](Oc2ccc(C#N)c(F)c2)[C@](O)(CO)C1] | 475.8 | ¹H NMR (400 MHz, DMSO-d₆) δ: 8.43 (d, J = 8.3 Hz, 1H), 7.92 (d, J = 8.0 Hz, 1H), 7.78-7.84 (m, 1H), 7.15 (dd, J = 11.7,2.4 Hz, 1H), 6.92 (dd, J = 8.8, 2.3 Hz, 1H), 5.59 (s, 1H), 4.87 (t, J = 5.6 Hz, 1H), 4.76 (d, J = 3.3 Hz, 1H), 3.83 (dd, J = 11.7, 3.4 Hz, 1H), 3.50-3.63 (m, 2H), 3.44-3.50 (m, 2H), 3.36-3.41 (m, 1H), 2.81 (s, 3H) |

| Ex. | Name | Structure | MS (m/z) (M + H⁺) | ¹H NMR |
|---|---|---|---|---|
| 84 | 2-fluoro-4-(((3S,4R)-4-hydroxy-4-(hydroxymethyl)-1-((5-(trifluoromethyl)pyridin-2-yl)sulfonyl)pyrrolidin-3-yl)oxy)benzonitrile | 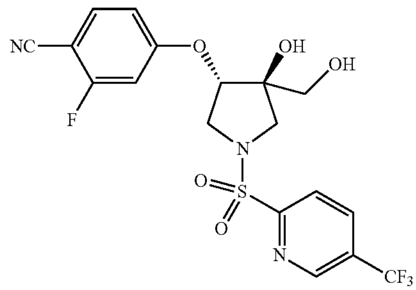 [SMILES: N#Cc1ccc(O[C@H]2CN(S(=O)(=O)c3ccc(C(F)(F)F)cn3)C[C@@]2(O)CO)cc1F] | 461.8 | ¹H NMR (400 MHz, DMSO-d₆) δ: 8.97 (s, 1H), 8.45 (d, J = 8.3 Hz, 1H), 8.05 (d, J = 8.3 Hz, 1H), 7.75 (t, J = 8.3 Hz, 1H), 6.91 (dd, J = 11.7, 1.9 Hz, 1H), 6.69 (dd, J = 8.8, 2.0 Hz, 1H), 5.42 (s, 1H), 4.80 (t, J = 5.6 Hz, 1H), 4.60 (d, J = 2.8 Hz, 1H), 3.90 (dd, J = 12.3, 3.0 Hz, 1H), 3.58 (d, J = 12.3 Hz, 1H), 3.37-3.53 (m, 4H) |
| 85 | 4-(((3S,4R)-1-((2-chlorophenyl)sulfonyl)-4-hydroxy-4-(hydroxymethyl)pyrrolidin-3-yl)oxy)-2-fluorobenzonitrile | 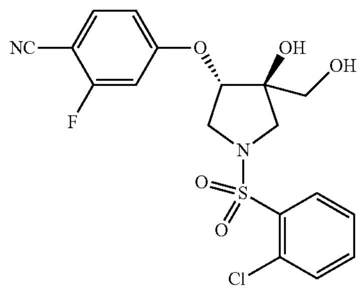 [SMILES: N#Cc1ccc(O[C@H]2CN(S(=O)(=O)c3ccccc3Cl)C[C@@]2(O)CO)cc1F] | 427.0 | ¹H NMR (400 MHz, CD₃OD) δ: 8.01-8.07 (m, 1H), 7.65 (dd, J = 8.8, 7.8 Hz, 1H), 7.55-7.60 (m, 2H), 7.41-7.49 (m, 1H), 6.89 (dd, J = 11.3, 2.3 Hz, 1H), 6.82 (dd, J = 8.5, 2.3 Hz, 1H), 4.76 (d, J = 3.3 Hz, 1H), 3.97 (dd, J = 11.5, 3.3 Hz, 1H), 3.78-3.82 (m, 1H), 3.71 (d, J = 11.8 Hz, 1H), 3.66 (d, J = 11.5 Hz, 1H), 3.57-3.62 (m, 1H), 3.48-3.53 (m, 1H) |
| 86 | 4-(((3S,4R)-1-((5-chlorothiophen-2-yl)sulfonyl)-4-hydroxy-4-(hydroxymethyl)pyrrolidin-3-yl)oxy)-2-fluorobenzonitrile | 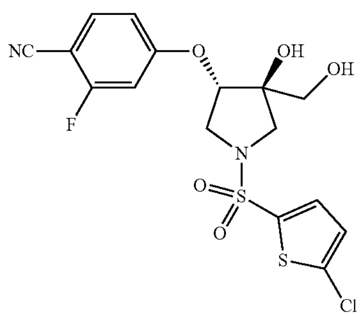 [SMILES: N#Cc1ccc(O[C@H]2CN(S(=O)(=O)c3ccc(Cl)s3)C[C@@]2(O)CO)cc1F] | 432.9 | ¹H NMR (400 MHz, DMSO-d₆) δ: 7.81 (t, J = 8.3 Hz, 1H), 7.50 (d, J = 4.0 Hz, 1H), 7.25 (d, J = 4.0 Hz, 1H), 6.99 (dd, J = 11.8, 2.0 Hz, 1H), 6.75 (dd, J = 8.8, 2.3 Hz, 1H), 5.52 (s, 1H), 4.86 (t, J = 5.4 Hz, 1H), 4.64 (d, J = 3.0 Hz, 1H), 3.78 (dd, J = 12.4, 3.1 Hz, 1H), 3.46-3.60 (m, 2H), 3.30-3.38 (3H, partially hidden by solvent peak) |
| 87 | 2-fluoro-4-(((3S,4R)-4-hydroxy-4-(hydroxymethyl)-1-((2-methyl-4-(trifluoromethyl)thiazol-5-yl)sulfonyl)pyrrolidin-3-yl)oxy)benzonitrile | 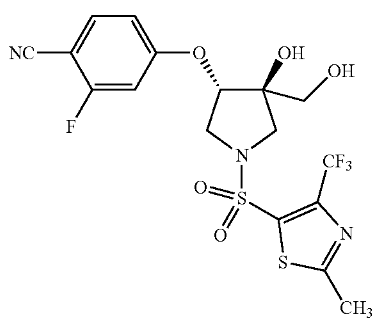 [SMILES: Cc1nc(C(F)(F)F)c(S(=O)(=O)N2C[C@H](Oc3ccc(C#N)c(F)c3)[C@](O)(CO)C2)s1] | 482.0 | ¹H NMR (400 MHz, DMSO-d₆) δ: 7.79-7.87 (m, 1H), 7.12 (dd, J = 11.8, 2.3 Hz, 1H), 6.82 (dd, J = 8.8, 2.3 Hz, 1H), 5.63 (s, 1H), 4.91 (t, J = 5.5Hz, 1H), 4.72 (d, J = 3.0 Hz, 1H), 3.87 (dd, J = 12.2, 3.1 Hz, 1H), 3.51-3.63 (m, 2H), 3.37-3.51 (m, 3H), 2.73 (s, 3H) |
| 88 | 4-(((3S,4R)-1-((2,4-dichlorothiazol-5-yl)sulfonyl)-4-hydroxy-4-(hydroxymethyl)pyrrolidin-3-yl)oxy)-2-fluorobenzonitrile | 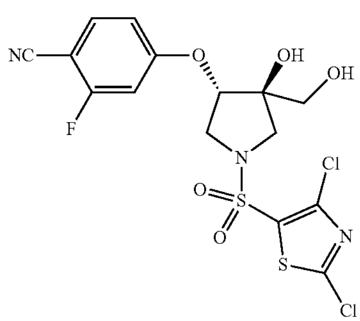 [SMILES: N#Cc1ccc(O[C@H]2CN(S(=O)(=O)c3sc(Cl)nc3Cl)C[C@@]2(O)CO)cc1F] | 467.9 | ¹H NMR (400 MHz, DMSO-d₆) δ: 7.84 (t, J = 8.3 Hz, 1H), 7.12 (dd, J = 11.8, 2.3 Hz, 1H), 6.86 (dd, J = 8.8, 2.3 Hz, 1H), 5.61 (s, 1H), 4.90 (t, J = 5.6 Hz, 1H), 4.73 (d, J = 2.8 Hz, 1H), 3.93 (dd, J = 12.3, 3.0 Hz, 1H), 3.51-3.64 (m, 4H), 3.43 (d, J = 10.8 Hz, 1H) |

-continued

| Ex. | Name | Structure | MS (m/z) (M + H⁺) | ¹H NMR |
|---|---|---|---|---|
| 89 | 4-(((3S,4R)-1-((4-chloro-1-methyl-1H-pyrazol-5-yl)sulfonyl)-4-hydroxy-4-(hydroxymethyl)pyrrolidin-3-yl)oxy)-2-fluorobenzonitrile | 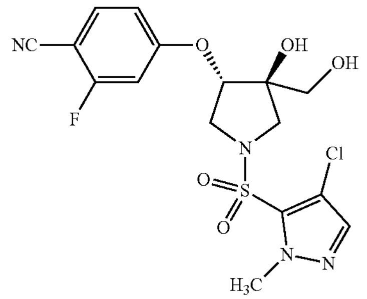 [SMILES: Cn1ncc(Cl)c1S(=O)(=O)N1C[C@H](Oc2ccc(C#N)c(F)c2)[C@](O)(CO)C1] | 431.0 | $^1$H NMR (400 MHz, DMSO-d$_6$) δ8: 7.80-7.87 (m, 1H), 7.75 (s, 1H), 7.12 (dd, J = 11.8, 2.3 Hz, 1H), 6.85 (dd, J = 8.8, 2.5 Hz, 1H), 5.55 (s, 1H), 4.88 (t, J = 5.6 Hz, 1H), 4.73 (d, J = 3.0 Hz, 1H), 4.01 (s, 3H), 3.85 (dd, J = 12.0, 3.3 Hz, 1H), 3.48-3.60 (m, 3H), 3.38-3.47 (m, 2H) |
| 90 | 4-(((3S,4R)-1-((6-chloroimidazo[2,1-b]thiazol-5-yl)sulfonyl)-4-hydroxy-4-(hydroxymethyl)pyrrolidin-3-yl)oxy)-2-fluorobenzonitrile | 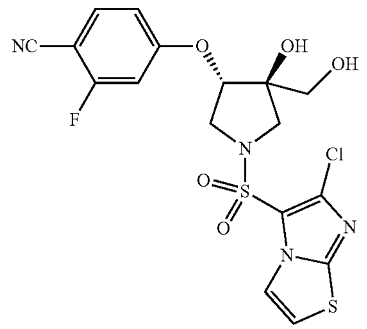 [SMILES: N#Cc1ccc(O[C@H]2CN(S(=O)(=O)c3c(Cl)nc4sccn34)C[C@@]2(O)CO)cc1F] | 472.9 | $^1$H NMR (400 MHz, DMSO-d$_6$) δ5: 7.94 (d, J = 4.5 Hz, 1H), 7.76 (t, J = 8.3 Hz, 1H), 7.48 (d, J = 4.5 Hz, 1H), 6.93 (dd, J = 11.8, 2.3 Hz, 1H), 6.67 (dd, J = 8.8, 2.3 Hz, 1H), 5.54 (s, 1H), 4.87 (t, J = 5.5 Hz, 1H), 4.66 (d, J = 3.0 Hz, 1H), 3.85 (dd, J = 12.4, 3.1 Hz, 1H), 3.42-3.56 (m, 4H), 3.37 (d, J = 10.8 Hz, 1H, partially hidden by solvent peak) |
| 91 | 4-(((3S,4R)-1-((6-chloropyridin-3-yl)sulfonyl)-4-hydroxy-4-(hydroxymethyl)pyrrolidin-3-yl)oxy)-2-fluorobenzonitrile | 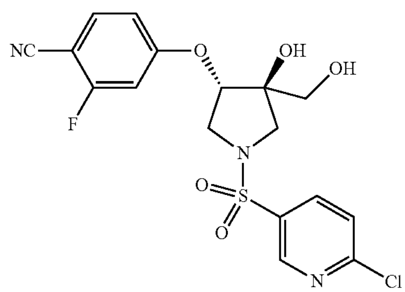 [SMILES: N#Cc1ccc(O[C@H]2CN(S(=O)(=O)c3ccc(Cl)nc3)C[C@@]2(O)CO)cc1F] | 428.3 | $^1$H NMR (400 MHz, DMSO-d$_6$) δ: 8.74 (d, J = 2.3 Hz, 1H), 8.18 (dd, J = 8.3, 2.5 Hz, 1H), 7.79 (t, J = 8.3Hz, 1H), 7.68 (d, J = 8.3 Hz, 1H), 6.95 (dd, J = 11.8, 2.3 Hz, 1H), 6.69 (dd, J =8.8, 2.3 Hz, 1H), 5.44 (s, 1H), 4.83 (t, J = 5.5 Hz, 1H), 4.62 (d, J = 3.0 Hz, 1H), 3.72 (dd, J = 12.3, 3.3 Hz, 1H), 3.43-3.55 (m, 2H), 3.32-3.41 (m, 3H, partially hidden by solvent peak) |
| 92 | 4-(((3S,4R)-1-((2,6-dichloropyridin-3-yl)sulfonyl)-4-hydroxy-4-(hydroxymethyl)pyrrolidin-3-yl)oxy)-2-fluorobenzonitrile | 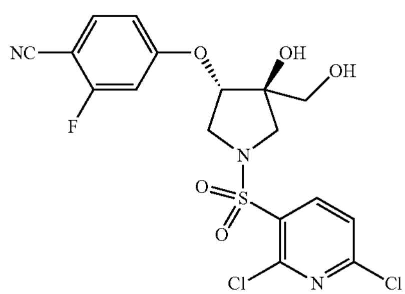 | 461.9 | $^1$H NMR (400 MHz, DMSO-d$_6$) δ: 8.35 (d, J = 8.0 Hz, 1H), 7.82 (t, J = 8.4 Hz, 1H), 7.73 (d, J = 8.3 Hz, 1H), 7.14 (dd, J = 11.8, 2.0 Hz, 1H), 6.89 (dd, J = 8.7, 2.1 Hz, 1H), 5.57 (s, 1H), 4.88 (t, J = 5.6 Hz, 1H), 4.74 (d, J = 2.8 Hz, 1H), 3.91 (dd, J = 11.8, 3.3 Hz, 1H), 3.49-3.63 (m, 4H), 3.41 (d, J = 10.3 Hz, 1H) |
| 93 | 4-(((3S,4R)-1-((2-ethynylphenyl)sulfonyl)-4-hydroxy-4-(hydroxymethyl)pyrrolidin-3-yl)oxy)-2-fluorobenzonitrile | 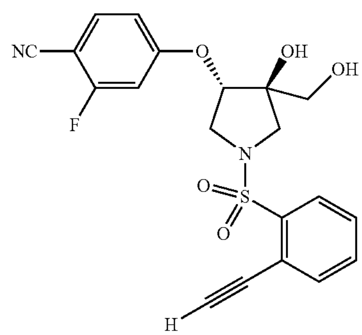 [SMILES: C#Cc1ccccc1S(=O)(=O)N1C[C@H](Oc2ccc(C#N)c(F)c2)[C@](O)(CO)C1] | 416.9 | $^1$H NMR (400 MHz, CD$_3$OD) δ: 7.93 (d, J = 7.8 Hz, 1H), 7.55-7.68 (m, 3H), 7.46-7.54 (m, 1H), 6.68-6.81 (m, 2H), 4.72 (br s, 1H), 3.92-3.99 (m, 1H), 3.88 (s, 1H), 3.73-3.84 (m, 2H), 3.47-3.68 (m, 3H) |

| Ex. | Name | Structure | MS (m/z) (M + H+) | 1H NMR |
|---|---|---|---|---|
| 94 | 4-(((3S,4R)-1-((2,3-dichlorophenyl)sulfonyl)-4-hydroxy-4-(hydroxymethyl)pyrrolidin-3-yl)oxy)-2-fluorobenzonitrile | 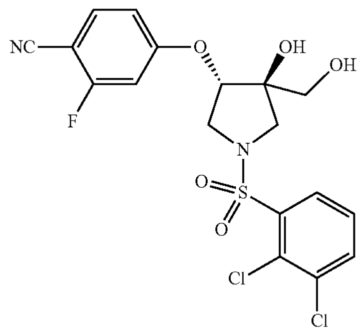 [SMILES: N#Cc1ccc(O[C@H]2CN(S(=O)(=O)c3cccc(Cl)c3Cl)C[C@@]2(O)CO)cc1F] | 460.9 | 1H NMR (400 MHz, DMSO-d6) δ: 7.93 (ddd, J = 12.5, 8.0, 1.5 Hz, 2H), 7.82 (t, J = 8.3 Hz, 1H), 7.53 (t, J = 8.0 Hz, 1H), 7.11 (dd, J = 11.8, 2.3 Hz, 1H), 6.88 (dd, J = 8.8, 2.3 Hz, 1H), 5.59 (s, 1H), 4.87 (t, J = 5.6 Hz, 1H), 4.74 (d, J = 3.0 Hz, 1H), 3.88 (dd, J = 11.8, 3.3 Hz, 1H), 3.46-3.64 (m, 4H), 3.40 (d, J = 10.3 Hz, 1H) |
| 95 | 4-(((3S,4R)-1-((3-chloro-2-cyanophenyl)sulfonyl)-4-hydroxy-4-(hydroxymethyl)pyrrolidin-3-yl)oxy)-2-fluorobenzonitrile | 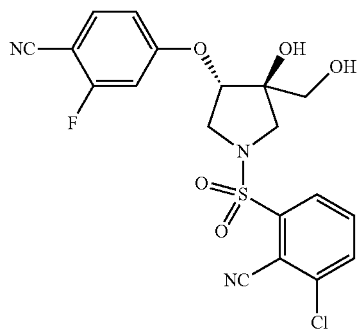 [SMILES: N#Cc1ccc(O[C@H]2CN(S(=O)(=O)c3cccc(Cl)c3C#N)C[C@@]2(O)CO)cc1F] | 452.0 | 1H NMR (400 MHz, DMSO-d6) δ: 8.05 (dd, J = 8.2, 1.1 Hz, 1H), 7.96-8.00 (m, 1H), 7.87-7.93 (m, 1H), 7.81 (t, J = 8.3 Hz, 1H), 7.03 (dd, J = 11.8, 2.3 Hz, 1H), 6.76 (dd, J = 8.8, 2.3 Hz, 1H), 5.58 (s, 1H), 4.88 (t, J = 5.5 Hz, 1H), 4.70 (d, J = 2.8 Hz, 1H), 3.86 (dd, J = 12.3, 3.0 Hz, 1H), 3.59 (d, J = 12.0 Hz, 1H), 3.46-3.56 (m, 2H), 3.37-3.44 (m, 2H) |
| 96 | 4-(((3S,4R)-1-((2,6-dichloro-4-(trifluoromethyl)phenyl)sulfonyl)-4-hydroxy-4-(hydroxymethyl)pyrrolidin-3-yl)oxy)-2-fluorobenzonitrile | 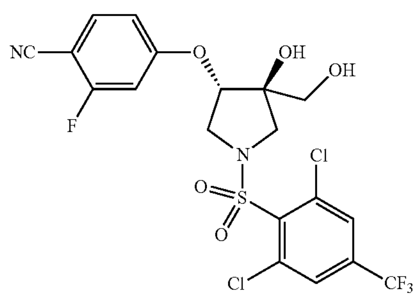 [SMILES: N#Cc1ccc(O[C@H]2CN(S(=O)(=O)c3c(Cl)cc(C(F)(F)F)cc3Cl)C[C@@]2(O)CO)cc1F] | 528.9 | 1H NMR (400 MHz, DMSO-d6) δ: 8.07 (s, 2H), 7.80 (t, J = 8.3 Hz, 1H), 7.14 (dd, J = 11.8, 2.3 Hz, 1H), 6.91 (dd, J = 8.7, 2.4 Hz, 1H), 5.56 (s, 1H), 4.88 (t, J = 5.6 Hz, 1H), 4.76 (d, J = 3.0 Hz, 1H), 3.96 (dd, J = 11.7, 3.1 Hz, 1H), 3.52-3.67 (m, 4H), 3.48 (d, J = 10.3 Hz, 1H) |
| 97 | 4-(((3S,4R)-1-((2-chloro-4-cyanophenyl)sulfonyl)-4-hydroxy-4-(hydroxymethyl)pyrrolidin-3-yl)oxy)-2-fluorobenzonitrile | 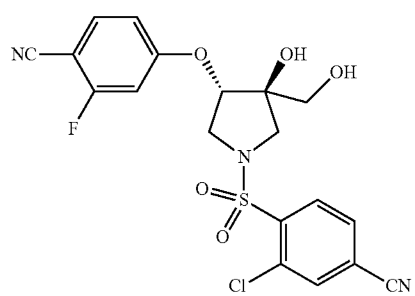 | 452.0 | 1H NMR (400 MHz, DMSO-d6) δ: 8.29 (d, J = 1.5 Hz, 1H), 8.05-8.11 (m, 1H), 7.96-8.01 (m, 1H), 7.78-7.87 (m, 1H), 7.14 (dd, J = 11.8, 2.3 Hz, 1H), 6.90 (dd, J = 8.7, 2.4 Hz, 1H), 5.59 (s, 1H), 4.88 (t, J = 5.5 Hz, 1H), 4.74 (d, J = 3.0 Hz, 1H), 3.90 (dd, J = 11.8, 3.3 Hz, 1H), 3.48-3.63 (m, 4H), 3.40 (d, J = 10.3 Hz, 1H) |
| 98 | 4-(((3S,4R)-1-((4-(difluoromethyl)phenyl)sulfonyl)-4-hydroxy-4-(hydroxymethyl)pyrrolidin-3-yl)oxy)-2-fluorobenzonitrile | 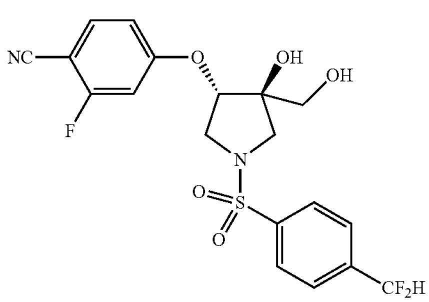 [SMILES: N#Cc1ccc(O[C@H]2CN(S(=O)(=O)c3ccc(C(F)F)cc3)C[C@@]2(O)CO)cc1F] | 443.1 | 1H NMR (400 MHz, DMSO-d6) δ: 7.85 (d, J = 8.3 Hz, 2H), 7.67-7.75 (m, 3H), 7.00-7.32 (m, 1H), 6.87 (dd, J = 11.8, 2.3 Hz, 1H), 6.58 (dd, J = 8.8, 2.3 Hz, 1H), 5.41 (s, 1H), 4.80 (t, J = 5.6 Hz, 1H), 4.60 (d, J = 3.0 Hz, 1H), 3.71 (dd, J = 12.2, 3.1 Hz, 1H), 3.40-3.53 (m, 2H), 3.24-3.33 (m, 3H, partially hidden by solvent peak) |

| Ex. | Name | Structure | MS (m/z) (M + H⁺) | ¹H NMR |
|---|---|---|---|---|
| 99 | 4-(((3S,4R)-1-((6-bromopyridin-3-yl)sulfonyl)-4-hydroxy-4-(hydroxymethyl)pyrrolidin-3-yl)oxy)-2-fluorobenzonitrile | 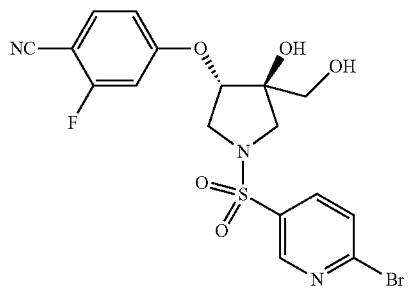 [SMILES: N#Cc1ccc(O[C@H]2CN(S(=O)(=O)c3ccc(Br)nc3)C[C@@]2(O)CO)cc1F] | 472.0 | $^1$H NMR (400 MHz, DMSO-$d_6$) δ: 8.71 (d, J = 2.0 Hz, 1H), 8.05 (dd, J = 8.4, 2.6 Hz, 1H), 7.72-7.84 (m, 2H), 6.95 (dd, J = 11.8, 2.3 Hz, 1H), 6.68 (dd, J = 8.7, 2.4 Hz, 1H), 5.42 (s, 1H), 4.81 (t, J = 5.6 Hz, 1H), 4.61 (d, J = 3.0 Hz, 1H), 3.72 (dd, J = 12.3, 3.3 Hz, 1H), 3.42-3.57 (m, 2H), 3.30-3.41 (m, 3H, partially hidden by solvent peak) |
| 100 | 4-(((3S,4R)-1-((2-chloro-6-(trifluoromethyl)pyridin-3-yl)sulfonyl)-4-hydroxy-4-(hydroxymethyl)pyrrolidin-3-yl)oxy)-2-fluorobenzonitrile | 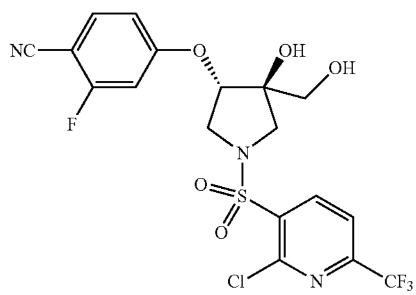 [SMILES: N#Cc1ccc(O[C@H]2CN(S(=O)(=O)c3ccc(C(F)(F)F)nc3Cl)C[C@@]2(O)CO)cc1F] | 496.1 | $^1$H NMR (400 MHz, DMSO-$d_6$) δ: 8.62 (d, J = 8.0 Hz, 1H), 8.12 (d, J = 8.0 Hz, 1H), 7.81 (t, J = 8.3 Hz, 1H), 7.14 (dd, J = 11.7, 2.1 Hz, 1H), 6.91 (dd, J = 8.8, 2.0 Hz, 1H), 5.59 (s, 1H), 4.88 (t, J = 5.5 Hz, 1H), 4.76 (d, J = 3.0 Hz, 1H), 3.96 (dd, J = 11.7, 3.1 Hz, 1H), 3.49-3.64 (m, 4H), 3.45 (d, J = 10.5 Hz, 1H) |
| 101 | 4-(((3S,4R)-1-((4-chlorophenyl)sulfonyl)-4-hydroxy-4-(hydroxymethyl)pyrrolidin-3-yl)oxy)-2-fluorobenzonitrile | 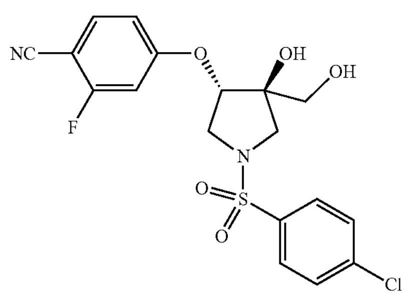 [SMILES: N#Cc1ccc(O[C@H]2CN(S(=O)(=O)c3ccc(Cl)cc3)C[C@@]2(O)CO)cc1F] | 427.1 | $^1$H NMR (400 MHz, DMSO-$d_6$) δ: 7.74-7.80 (m, 1H), 7.68-7.73 (m, 2H), 7.54-7.60 (m, 2H), 6.89 (dd, J = 11.7, 2.4 Hz, 1H), 6.65 (dd, J = 8.8, 2.3 Hz, 1H), 5.42 (s, 1H), 4.82 (t, J = 5.6 Hz, 1H), 4.59 (d, J = 3.0 Hz, 1H), 3.69 (dd, J = 12.2, 3.1 Hz, 1H), 3.41-3.54 (m, 2H), 3.29-3.35 (3H, partially hidden by solvent peak) |
| 102 | 4-(((3S,4R)-1-((4-bromophenyl)sulfonyl)-4-hydroxy-4-(hydroxymethyl)pyrrolidin-3-yl)oxy)-2-fluorobenzonitrile | 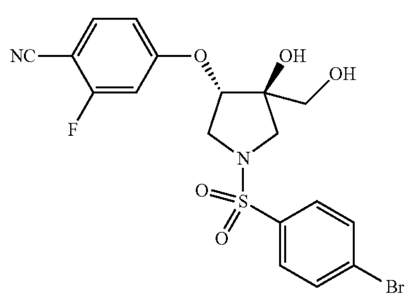 [SMILES: N#Cc1ccc(O[C@H]2CN(S(=O)(=O)c3ccc(Br)cc3)C[C@@]2(O)CO)cc1F] | 470.9 | $^1$H NMR (400 MHz, DMSO-$d_6$) δ: 7.73-7.80 (m, 1H), 7.68-7.73 (m, 2H), 7.60-7.64 (m, 2H), 6.89 (dd, J = 11.8, 2.3 Hz, 1H), 6.65 (dd, J = 8.8, 2.3 Hz, 1H), 5.43 (s, 1H), 4.82 (t, J = 5.6 Hz, 1H), 4.59 (d, J = 3.0 Hz, 1H), 3.69 (dd, J = 12.3, 3.3 Hz, 1H), 3.41-3.54 (m, 2H), 3.31-3.36 (m, 3H, partially hidden by solvent peak) |
| 103 | 2-fluoro-4-(((3S,4R)-4-hydroxy-4-(hydroxymethyl)-1-((4-iodophenyl)sulfonyl)pyrrolidin-3-yl)oxy)benzonitrile | 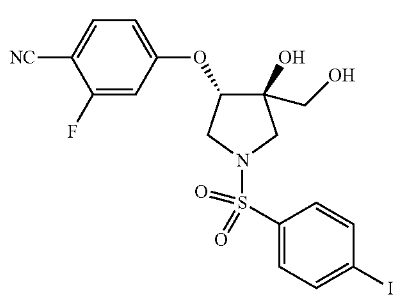 [SMILES: N#Cc1ccc(O[C@H]2CN(S(=O)(=O)c3ccc(I)cc3)C[C@@]2(O)CO)cc1F] | 518.9 | $^1$H NMR (400 MHz, DMSO-$d_6$) δ: 7.84-7.90 (m, 2H), 7.77 (t, J = 8.4 Hz, 1H), 7.42-7.47 (m, 2H), 6.87 (dd, J = 11.7, 2.4 Hz, 1H), 6.63 (dd, J = 8.8, 2.3 Hz, 1H), 5.43 (s, 1H), 4.81 (t, J = 5.6 Hz, 1H), 4.58 (d, J = 3.0 Hz, 1H), 3.68 (dd, J = 12.2, 3.1 Hz, 1H), 3.41-3.54 (m, 2H), 3.24-3.32 (m, 3H) |

| Ex. | Name | Structure | MS (m/z) (M + H⁺) | ¹H NMR |
|---|---|---|---|---|
| 104 | 4-(((3S,4R)-1-((4-cyano-2-methoxyphenyl)sulfonyl)-4-hydroxy-4-(hydroxymethyl)pyrrolidin-3-yl)oxy)-2-fluorobenzonitrile | 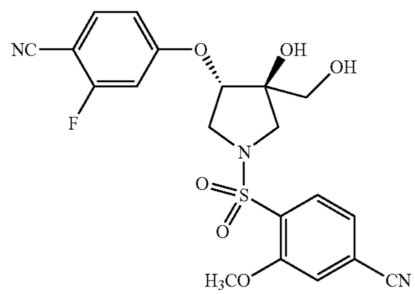 | 448.0 | ¹H NMR (400 MHz, DMSO-$d_6$) δ: 7.77-7.86 (m, 2H), 7.71 (d, J = 1.3 Hz, 1H), 7.49 (dd, J = 8.0, 1.5 Hz, 1H), 7.06 (dd, J = 11.8, 2.5 Hz, 1H), 6.83 (dd, J = 8.8, 2.3 Hz, 1H), 5.43 (s, 1H), 4.81 (t, J = 5.6 Hz, 1H), 4.64 (d, J = 3.0 Hz, 1H), 3.84 (dd, J = 11.9, 3.4 Hz, 1H), 3.73 (s, 3H), 3.45-3.59 (m, 3H), 3.37-3.42 (m, 1H), 3.28-3.33 (m, 1H) |
| 105 | 4-(((3S,4R)-1-((5-bromopyridin-2-yl)sulfonyl)-4-hydroxy-4-(hydroxymethyl)pyrrolidin-3-yl)oxy)-2-fluorobenzonitrile | 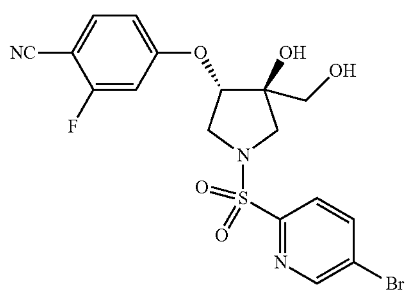 [SMILES: N#Cc1ccc(O[C@H]2CN(S(=O)(=O)c3ccc(Br)cn3)C[C@@]2(O)CO)cc1F] | 472.0 | ¹H NMR (400 MHz, DMSO-$d_6$) δ:8.67 (d, J = 2.0 Hz, 1H), 8.25 (dd, J = 8.3, 2.3 Hz, 1H), 7.74-7.81 (m, 2H), 6.95 (dd, J = 11.8, 2.0 Hz, 1H), 6.69 (dd, J = 8.8, 2.0 Hz, 1H), 5.41 (s, 1H), 4.79 (t, J = 5.5 Hz, 1H), 4.58 (d, J = 2.8 Hz, 1H), 3.86 (dd, J = 12.3, 3.0 Hz, 1H), 3.42-3.56 (m, 4H), 3.38 (1 H, partially hidden by solvent peak) |
| 106 | 3-chloro-4-(((3R,4S)-4-(4-chlorophenoxy)-3-hydroxy-3-(hydroxymethyl)pyrrolidin-1-yl)sulfonyl)benzonitrile | 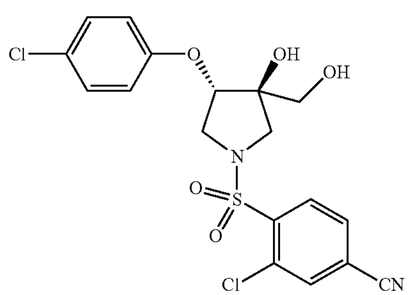 [SMILES: N#Cc1ccc(S(=O)(=O)N2C[C@H](Oc3ccc(Cl)cc3)[C@](O)(CO)C2)c(Cl)c1] | 443.0 | ¹H NMR (400 MHz, DMSO-$d_6$) δ: 8.60 (d, J = 2.5Hz, 1H), 8.11 (dd, J = 8.4, 2.4 Hz, 1H), 7.85 (d, J = 8.8 Hz, 1H), 7.21-7.30 (m, 2H), 6.64-6.73 (m, 2H), 4.44 (d, J = 3.0 Hz, 1H), 3.81 (dd, J = 11.8, 3.3 Hz, 1H), 3.43-3.56 (m, 4H), 3.36 (d, J = 10.5 Hz, 1H) |
| 107 | 2-(((3R,4S)-4-(4-chlorophenoxy)-3-hydroxy-3-(hydroxymethyl)pyrrolidin-1-yl)sulfonyl)benzonitrile | 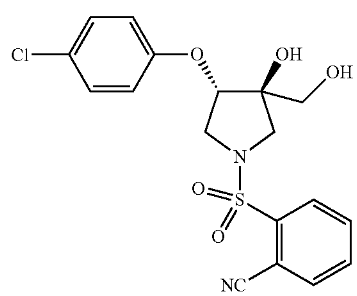 [SMILES: N#Cc1ccccc1S(=O)(=O)N1C[C@H](Oc2ccc(Cl)cc2)[C@](O)(CO)C1] | 409.1 | ¹H NMR (400 MHz, DMSO-$d_6$) δ: 8.04-8.08 (m, 1H), 7.97-8.02 (m, 1H), 7.86 (m, 2H), 7.25-7.33 (m, 2H), 6.72-6.80 (m, 2H), 5.39 (br s, 1H), 4.81 (br s, 1H), 4.55 (d, J = 3.0 Hz, 1H), 3.77 (dd, J = 11.7, 3.4 Hz, 1H), 3.57 (1H, partially hidden by solvent peak), 3.46-3.53 (m, 2H), 3.35-3.45 (m, 2H) |
| 108 | 3-bromo-4-(((3R,4S)-4-(4-chlorophenoxy)-3-hydroxy-3-(hydroxymethyl)pyrrolidin-1-yl)sulfonyl)benzonitrile | 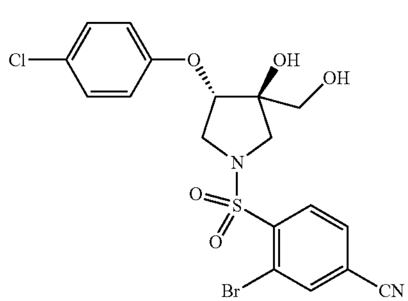 [SMILES: N#Cc1ccc(S(=O)(=O)N2C[C@H](Oc3ccc(Cl)cc3)[C@](O)(CO)C2)c(Br)c1] | 487.2 | ¹H NMR (400 MHz, DMSO-$d_6$) δ: 8.43 (d, J = 1.3 Hz, 1H), 8.06-8.10 (m, 1H), 7.99-8.04 (m, 1H), 7.28-7.35 (m, 2H), 6.85-6.95 (m, 2H), 5.52 (s, 1H), 4.86 (t, J = 5.5 Hz, 1H), 4.61 (d, J = 3.0 Hz, 1H), 3.85 (dd, J = 11.3, 3.3 Hz, 1H), 3.48-3.68 (m, 4H), 3.41 (d, J = 10.3 Hz, 1H) |

| Ex. | Name | Structure | MS (m/z) (M + H⁺) | ¹H NMR |
|---|---|---|---|---|
| 109 | 5-(((3R,4S)-4-(4-chlorophenoxy)-3-hydroxy-3-(hydroxymethyl)pyrrolidin-1-yl)sulfonyl)picolinonitrile | 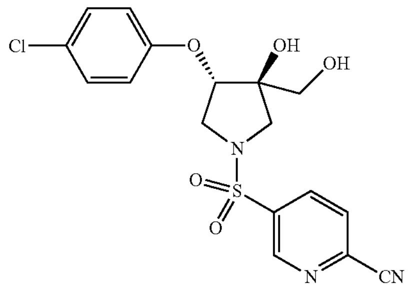 [SMILES: N#Cc1ccc(S(=O)(=O)N2C[C@H](Oc3ccc(Cl)cc3)[C@](O)(CO)C2)cn1] | 410.1 | ¹H NMR (400 MHz, DMSO-$d_6$) δ: 9.05 (dd, J = 2.3, 0.8 Hz, 1H), 8.41 (dd, J = 8.0, 2.3 Hz, 1H), 8.22 (dd, J = 8.0, 0.8 Hz, 1H), 7.27 (d, J = 9.0 Hz, 2H), 6.71 (d, J = 9.0 Hz, 2H), 5.30 (s, 1H), 4.78 (t, J = 5.5 Hz, 1H), 4.46 (d, J = 3.0 Hz, 1H), 3.70 (dd, J = 11.9, 3.4 Hz, 1H), 3.3 3.56 (m, 5H) |
| 110 | 3-(((3R,4S)-4-(4-chlorophenoxy)-3-hydroxy-3-(hydroxymethyl)pyrrolidin-1-yl)sulfonyl)picolinonitrile | 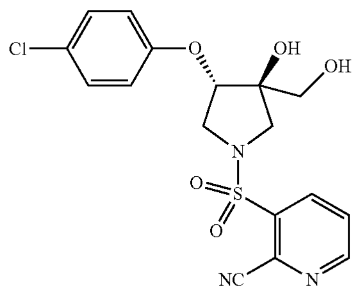 [SMILES: N#Cc1ncccc1S(=O)(=O)N1C[C@H](Oc2ccc(Cl)cc2)[C@](O)(CO)C1] | 410.1 | ¹H NMR (400 MHz, DMSO-$d_6$) δ: 8.97 (dd, J = 4.8, 1.3 Hz, 1H), 8.43 (dd, J = 8.2, 1.4 Hz, 1H), 7.92 (dd, J = 8.0, 4.8 Hz, 1H), 7.25-7.33 (m, 2H), 6.72-6.82 (m, 2H), 5.41 (s, 1H), 4.83 (t, J = 5.5 Hz, 1H), 4.56 (d, J = 3.0 Hz, 1H), 3.80 (dd, J = 11.7, 3.4 Hz, 1H), 3.40-3.60 (m, 5H) |
| 111 | 2-fluoro-4-(((3S,4R)-4-hydroxy-4-(hydroxymethyl)-1-((4-(2,2,2-trifluoroethyl)phenyl)sulfonyl)pyrrolidin-3-yl)oxy)benzonitrile | 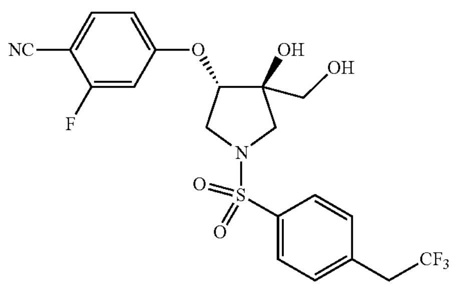 [SMILES: N#Cc1ccc(O[C@H]2CN(S(=O)(=O)c3ccc(CC(F)(F)F)cc3)C[C@@]2(O)CO)cc1F] | 475.0 | ¹H NMR (400 MHz, DMSO-$d_6$) δ: 7.69-7.79 (m, 3H), 7.52 (d, J = 7.8 Hz, 2H), 6.91 (dd, J = 11.8, 2.0 Hz, 1H), 6.57 (dd, J = 8.8, 2.0 Hz, 1H), 5.41 (s, 1H), 4.81 (t, J = 5.5 Hz, 1H), 4.61 (d, J = 2.8 Hz, 1H), 3.67-3.87 (m, 3H), 3.40-3.52 (m, 2H), 3.24-3.33 (m, 3H, partially hidden by solvent peak) |
| 112 | 2-fluoro-4-(((3S,4R)-4-hydroxy-4-(hydroxymethyl)-1-((5-(trifluoromethyl)thiophen-2-yl)sulfonyl)pyrrolidin-3-yl)oxy)benzonitrile | 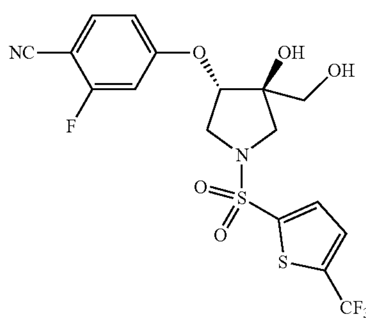 [SMILES: N#Cc1ccc(O[C@H]2CN(S(=O)(=O)c3ccc(C(F)(F)F)s3)C[C@@]2(O)CO)cc1F] | 467.1 | ¹H NMR (400 MHz, DMSO-$d_6$) δ: 7.71-7.84 (m, 3H), 6.93 (dd, J = 11.5, 1.8 Hz, 1H), 6.74 (dd, J = 8.8, 2.0 Hz, 1H), 5.52 (s, 1H), 4.85 (t, J = 5.6 Hz, 1H), 4.65 (d, J = 2.5 Hz, 1H), 3.82 (dd, J = 12.4, 2.9 Hz, 1H), 3.53 (qd, J = 11.5, 5.5 Hz, 2H), 3.37-3.44 (m, 3H, partially hidden by solvent peak) |
| 113 | 4-(((3S,4R)-1-((4-cyano-2-fluorophenyl)sulfonyl)-4-hydroxy-4-(hydroxymethyl)pyrrolidin-3-yl)oxy)-2-fluorobenzonitrile | 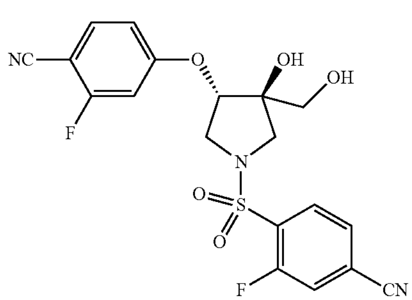 [SMILES: N#Cc1ccc(S(=O)(=O)N2C[C@H](Oc3ccc(C#N)c(F)c3)[C@](O)(CO)C2)c(F)c1] | 436.0 | ¹H NMR (400 MHz, DMSO-$d_6$) δ: 8.11 (dd, J = 10.3, 1.3 Hz, 1H), 7.89-7.95 (m, 1H), 7.75-7.86 (m, 2H), 7.05 (dd, J = 11.8, 2.3 Hz, 1H), 6.82 (dd, J = 8.8, 2.3 Hz, 1H), 5.49 (s, 1H), 4.84 (t, J = 5.5 Hz, 1H), 4.67 (d, J = 3.0 Hz, 1H), 3.83 (dd, J = 12.2, 2.9 Hz, 1H), 3.35-3.57 (m, 5H) |

| Ex. | Name | Structure | MS (m/z) (M + H+) | 1H NMR |
|---|---|---|---|---|
| 114 | 4-(((3S,4R)-1-((2-cyano-4-iodophenyl)sulfonyl)-4-hydroxy-4-(hydroxymethyl)pyrrolidin-3-yl)oxy)-2-fluorobenzonitrile | 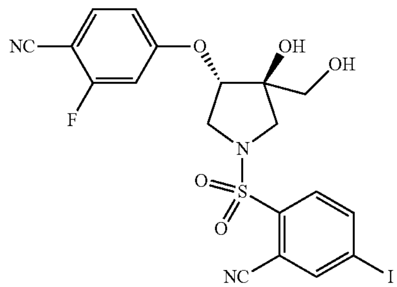 [SMILES: N#Cc1ccc(O[C@H]2CN(S(=O)(=O)c3ccc(I)cc3C#N)C[C@@]2(O)CO)cc1F] | 543.9 | 1H NMR (400 MHz, DMSO-d6) δ: 8.46 (d, J = 1.8 Hz, 1H), 8.20 (dd, J = 8.3, 1.8 Hz, 1H), 7.79 (t, J = 8.3 Hz, 1H), 7.66 (d, J = 8.3 Hz, 1H), 7.02 (dd, J = 11.8, 2.3 Hz, 1H), 6.75 (dd, J = 8.8, 2.3 Hz, 1H), 5.54 (s, 1H), 4.87 (t, J = 5.5 Hz, 1H), 4.67 (d, J = 2.8 Hz, 1H), 3.81 (dd, J = 12.2, 3.1 Hz, 1H), 3.45-3.58 (m, 3H), 3.36-3.44 (m, 2H) |
| 115 | 4-(((3S,4R)-1-((2-chloro-4-iodophenyl)sulfonyl)-4-hydroxy-4-(hydroxymethyl)pyrrolidin-3-yl)oxy)-2-fluorobenzonitrile | 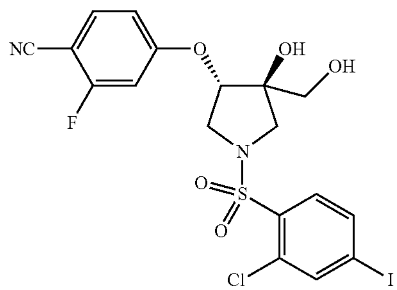 [SMILES: N#Cc1ccc(O[C@H]2CN(S(=O)(=O)c3ccc(I)cc3Cl)C[C@@]2(O)CO)cc1F] | 552.9 | 1H NMR (400 MHz, DMSO-d6) δ: 8.04 (d, J = 1.5 Hz, 1H), 7.76-7.90 (m, 2H), 7.63 (d, J = 8.3 Hz, 1H), 7.09 (dd, J = 11.8, 2.3 Hz, 1H), 6.86 (dd, J = 8.8, 2.3 Hz, 1H), 5.54 (s, 1H), 4.86 (t, J = 5.5 Hz, 1H), 4.70 (d, J = 2.8 Hz, 1H), 3.84 (dd, J = 11.8, 3.0 Hz, 1H), 3.43-3.64 (m, 4H), 3.38 (1H, partially hidden by solvent peak) |
| 116 | 2-fluoro-4-(((3S,4R)-1-((3-fluoro-4-(trifluoromethyl)phenyl)sulfonyl)-4-hydroxy-4-(hydroxymethyl)pyrrolidin-3-yl)oxy)benzonitrile | 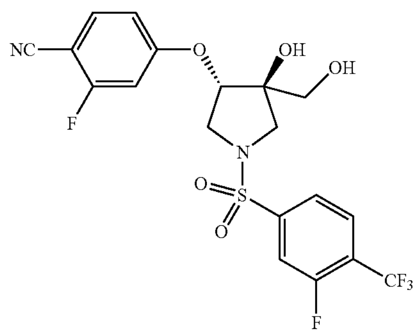 [SMILES: N#Cc1ccc(O[C@H]2CN(S(=O)(=O)c3ccc(C(F)(F)F)c(F)c3)C[C@@]2(O)CO)cc1F] | 479.0 | 1H NMR (400 MHz, DMSO-d6) δ: 7.95 (t, J = 7.5 Hz, 1H), 7.89 (d, J = 10.0 Hz, 1H), 7.71-7.79 (m, 2H), 6.89 (dd, J = 11.8, 2.3 Hz, 1H), 6.67 (dd, J = 8.7, 2.4 Hz, 1H), 5.45 (s, 1H), 4.81 (t, J = 5.5 Hz, 1H), 4.61 (d, J = 3.0 Hz, 1H), 3.75 (dd, J = 12.2, 3.1 Hz, 1H), 3.40-3.57 (m, 3H), 3.35 (m, 2H, partially hidden by solvent peak) |
| 117 | 4-(((3S,4R)-1-((2-bromophenyl)sulfonyl)-4-hydroxy-4-(hydroxymethyl)pyrrolidin-3-yl)oxy)-2-fluorobenzonitrile | 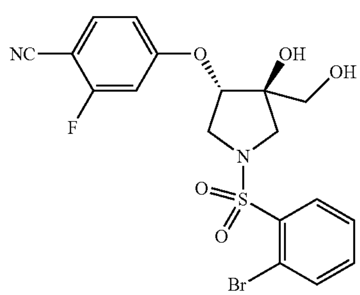 | 470.9 | 1H NMR (400 MHz, DMSO-d6) δ: 7.94-7.99 (m, 1H), 7.78-7.85 (m, 2H), 7.49-7.59 (m, 2H), 7.15 (dd, J = 11.8, 2.3 Hz, 1H), 6.90 (dd, J = 8.8, 2.3 Hz, 1H), 5.55 (s, 1H), 4.86 (t, J = 5.6 Hz, 1H), 4.76 (d, J = 3.0 Hz, 1H), 3.88 (dd, J = 11.7, 3.4 Hz, 1H), 3.45-3.64 (m, 4H), 3.37-3.41 (m, 1H) |
| 118 | 2-fluoro-4-(((3S,4R)-1-((3-fluoro-4-methylphenyl)sulfonyl)-4-hydroxy-4-(hydroxymethyl)pyrrolidin-3-yl)oxy)benzonitrile | 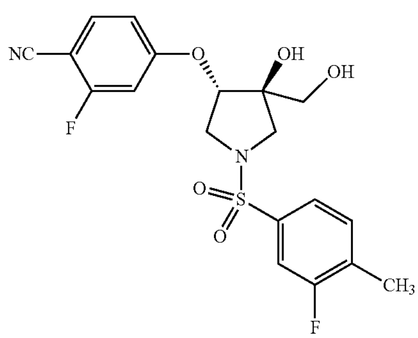 [SMILES: Cc1ccc(S(=O)(=O)N2C[C@H](Oc3ccc(C#N)c(F)c3)[C@](O)(CO)C2)cc1F] | 425.0 | 1H NMR (400 MHz, DMSO-d6) δ: 7.79 (t, J = 8.3 Hz, 1H), 7.38-7.47 (m, 3H), 6.85 (dd, J = 11.8, 2.3 Hz, 1H), 6.62 (dd, J = 8.8, 2.3 Hz, 1H), 5.43 (s, 1H), 4.81 (t, J = 5.6 Hz, 1H), 4.58 (d, J = 3.0 Hz, 1H), 3.70 (dd, J = 12.2, 3.1 Hz, 1H), 3.42-3.54 (m, 2H), 3.32-3.39 (1H, partially hidden by solvent peak), 3.25-3.31 (m, 2H), 2.30 (d, J = 1.8 Hz, 3H) |

| Ex. | Name | Structure | MS (m/z) (M + H⁺) | ¹H NMR |
|---|---|---|---|---|
| 119 | 2-fluoro-4-(((3S,4R)-4-hydroxy-4-(hydroxymethyl)-1-((2-iodophenyl)sulfonyl)pyrrolidin-3-yl)oxy)benzonitrile | 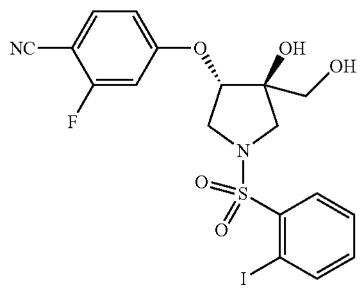 | 518.9 | ¹H NMR (400 MHz, DMSO-d$_6$) δ: 8.12 (dd, J = 7.8, 1.0 Hz, 1H), 7.94 (dd, J =8.0, 1.5 Hz, 1H), 7.82 (t, J = 8.4 Hz, 1H), 7.56 (m, 1H), 7.30 (m, 1H), 7.15 (dd, J = 11.8, 2.3 Hz, 1H), 6.90 (dd, J = 8.8, 2.3 Hz, 1H), 5.56 (s, 1H), 4.87 (t, J = 5.6 Hz, 1H), 4.77 (d, J = 3.0 Hz, 1H), 3.87 (dd, J = 11.5, 3.3 Hz, 1H), 3.58-3.64 (m, 1H), 3.50-3.57 (m, 2H), 3.43-3.48 (m, 1H), 3.37 (d, J = 10.3 Hz, 1H) |
| 120 | 4-(((3S,4R)-1-((2-bromo-4-chlorophenyl)sulfonyl)-4-hydroxy-4-(hydroxymethyl)pyrrolidin-3-yl)oxy)-2-fluorobenzonitrile | 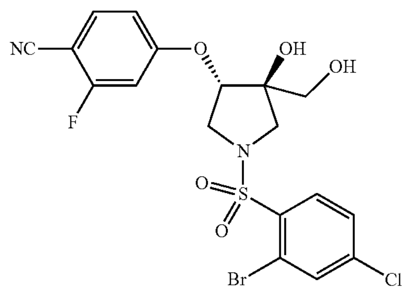 | 504.9 | ¹H NMR (400 MHz, DMSO-d$_6$) δ: 7.99 (d, J = 2.0 Hz, 1H), 7.93 (d, J = 8.5 Hz, 1H), 7.81 (t, J = 8.3 Hz, 1H), 7.62 (dd, J = 8.5, 2.0 Hz, 1H), 7.13 (dd, J = 11.8, 2.3 Hz, 1H), 6.89 (dd, J = 8.8, 2.3 Hz, 1H), 5.57 (s, 1H), 4.87 (t, J = 5.5 Hz, 1H), 4.74 (d, J = 3.0 Hz, 1H), 3.87 (dd, J = 11.7, 3.1 Hz, 1H), 3.57-3.63 (m, 1H), 3.48-3.56 (m, 3H), 3.39 (d, J = 10.3 Hz, 1H) |
| 121 | 4-(((3S,4R)-1-((4-bromo-2-(trifluoromethyl)phenyl)sulfonyl)-4-hydroxy-4-(hydroxymethyl)pyrrolidin-3-yl)oxy)-2-fluorobenzonitrile | 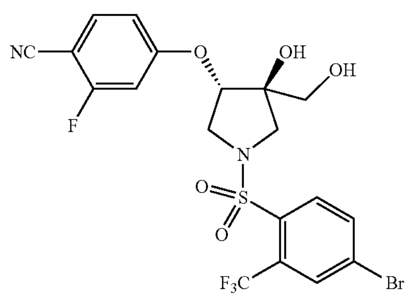 [SMILES: N#Cc1ccc(O[C@H]2CN(S(=O)(=O)c3ccc(Br)cc3C(F)(F)F)C[C@@]2(O)CO)cc1F] | 538.9 | ¹H NMR (400 MHz, DMSO-d$_6$) δ: 8.16 (br s, 1H), 8.09 (d, J = 7.8 Hz, 1H), 7.98 (d, J = 8.3 Hz, 1H), 7.84 (t, J = 8.3 Hz, 1H), 7.19 (d, J = 11.8 Hz, 1H), 6.95 (d, J = 7.0 Hz, 1H), 5.63 (s, 1H), 4.87-4.93 (m, 1H), 4.77 (br s, 1H), 3.83 (d, J = 11.5 Hz, 1H), 3.38-3.63 (m, 5H) |
| 122 | 4-(((3S,4R)-1-((2-(difluoromethoxy)pyridin-3-yl)sulfonyl)-4-hydroxy-4-(hydroxymethyl)pyrrolidin-3-yl)oxy)-2-fluorobenzonitrile | 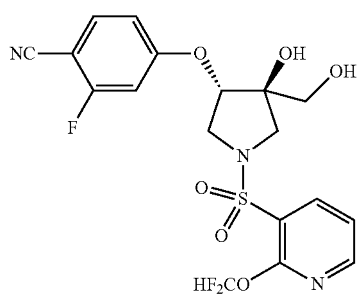 | 460.0 | ¹H NMR (400 MHz, DMSO-d$_6$) δ: 8.45 (dd, J = 5.0, 1.8 Hz, 1H), 8.26 (dd, J = 7.5, 1.8 Hz, 1H), 7.72-7.82 (m, 2H), 7.38 (dd, J = 7.8, 5.0 Hz, 1H), 7.04 (dd, J = 11.8, 2.3 Hz, 1H), 6.77 (dd, J = 8.8, 2.3 Hz, 1H), 5.47 (s, 1H), 4.85 (t, J = 5.5 Hz, 1H), 4.69 (d, J = 3.0 Hz, 1H), 3.86 (dd, J = 12.0, 3.3 Hz, 1H), 3.44-3.61 (m, 4H), 3.39 (d, J= 10.5 Hz, 1H) |
| 123 | 4-(((3S,4R)-1-((4-bromo-1-methyl-1H-pyrazol-5-yl)sulfonyl)-4-hydroxy-4-(hydroxymethyl)pyrrolidin-3-yl)oxy)-2-fluorobenzonitrile | 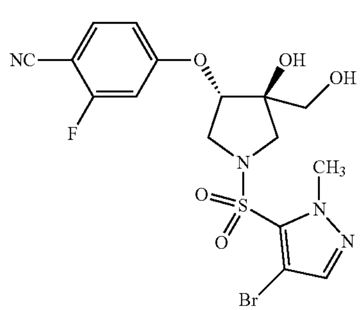 [SMILES: Cn1ncc(Br)c1S(=O)(=O)N1C[C@H](Oc2ccc(C#N)c(F)c2)[C@](O)(CO)C1] | 475.0 | ¹H NMR (400 MHz, DMSO-d$_6$) δ: 7.83 (t, J = 8.3 Hz, 1H), 7.74 (s, 1H), 7.12 (dd, J = 11.8, 2.3 Hz, 1H), 6.84 (dd, J = 8.8, 2.3 Hz, 1H), 5.57 (s, 1H), 4.89 (t, J = 5.5 Hz, 1H), 4.74 (d, J = 3.0 Hz, 1H), 4.03 (s, 3H), 3.86 (dd, J = 12.0, 3.3 Hz, 1H), 3.49-3.60 (m, 3H), 3.39-3.47 (m, 2H) |

-continued

| Ex. | Name | Structure | MS (m/z) (M + H⁺) | ¹H NMR |
|---|---|---|---|---|
| 124 | 4-(((3S,4R)-1-((4-chloro-1,3-dimethyl-1H-pyrazol-5-yl)sulfonyl)-4-hydroxy-4-(hydroxymethyl)pyrrolidin-3-yl)oxy)-2-fluorobenzonitrile | 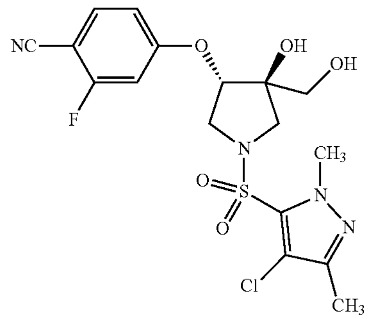 [SMILES: Cc1nn(C)c(S(=O)(=O)N2C[C@H](Oc3ccc(C#N)c(F)c3)[C@](O)(CO)C2)c1Cl] | 445.0 | $^1$H NMR (400 MHz, DMSO-$d_6$) δ: 7.84 (t, J = 8.4 Hz, 1H), 7.08 (dd, J = 11.8, 2.3 Hz, 1H), 6.81 (dd, J = 8.7, 2.4 Hz, 1H), 5.59 (s, 1H), 4.88 (t, J = 5.6 Hz, 1H), 4.71 (d, J = 2.8 Hz, 1H), 3.96 (s, 3H), 3.84 (dd, J = 12.2, 3.1 Hz, 1H), 3.49-3.62 (m, 3H), 3.37-3.46 (m, 2H), 2.08 (s, 3H) |
| 125 | (3R,4S)-4-(benzo[c][1,2,5]oxadiazol-5-yloxy)-1-((2-fluoro-4-(trifluoromethyl)phenyl)sulfonyl)-3-(hydroxymethyl)pyrrolidin-3-ol | 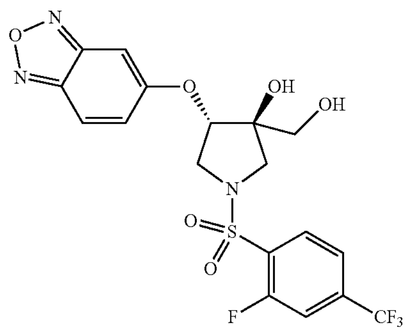 [SMILES: O=S(=O)(c1ccc(C(F)(F)F)cc1F)N1C[C@H](Oc2ccc3nonc3c2)[C@](O)(CO)C1] | 477.9 | $^1$H NMR (400 MHz, DMSO-$d_6$) δ: 7.90-8.09 (m, 2H), 7.86 (d, J = 9.5 Hz, 1H), 7.69 (d, J = 8.3 Hz, 1H), 7.31 (s, 1H), 6.90 (d, J = 9.5 Hz, 1H), 4.71 (br s, 1H), 3.84-3.95 (m, 1H), 3.52-3.65 (m, 3H), 3.38-3.50 (m, 2H) |
| 126 | 4-(((3S,4R)-1-((6-(difluoromethoxy)pyridin-3-yl)sulfonyl)-4-hydroxy-4-(hydroxymethyl)pyrrolidin-3-yl)oxy)-2-fluorobenzonitrile | 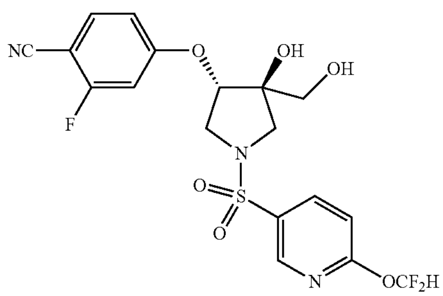 | 460.3 | $^1$H NMR (400 MHz, DMSO-$d_6$) δ: 8.61 (s, 1H), 8.23 (d, J = 8.5 Hz, 1H), 7.55-7.98 (m, 2H), 7.21 (d, J = 8.5 Hz, 1H), 6.94 (d, J = 11.8 Hz, 1H), 6.69 (d, J = 8.5 Hz, 1H), 5.42 (s, 1H), 4.81 (br s, 1H), 4.61 (br s, 1H), 3.72 (d, J = 11.0 Hz, 1H), 3.33-3.58 (5H, partially hidden by solvent peak) |
| 127 | 2-fluoro-4-(((3S,4R)-4-hydroxy-4-(hydroxymethyl)-1-((5-(trifluoromethoxy)pyridin-2-yl)sulfonyl)pyrrolidin-3-yl)oxy)benzonitrile | 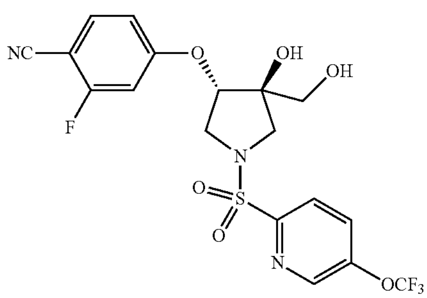 | 478.0 | $^1$H NMR (400 MHz, DMSO-$d_6$) δ: 8.67 (d, J = 2.0 Hz, 1H), 8.05-8.12 (m, 1H), 7.97-8.02 (m, 1H), 7.77 (t, J = 8.3 Hz, 1H), 6.96 (dd, J = 11.8, 2.0 Hz, 1H), 6.68-6.77 (m, 1H), 5.40 (br s, 1H), 4.81 (br s, 1H), 4.61 (d, J = 2.8 Hz, 1H), 3.89 (dd, J = 12.3, 3.3 Hz, 1H), 3.43-3.58 (m, 4H), 3.37-3.42 (1H, partially hidden by solvent peak) |
| 128 | 2-fluoro-4-(((3S,4R)-4-hydroxy-4-(hydroxymethyl)-1-((2-(trifluoromethyl)pyrimidin-5-yl)sulfonyl)pyrrolidin-3-yl)oxy)benzonitrile | 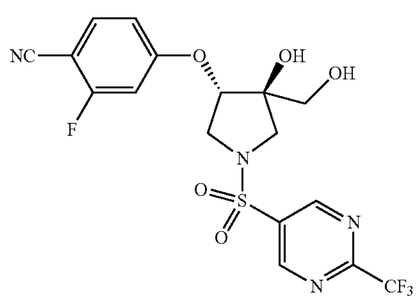 [SMILES: N#Cc1ccc(O[C@H]2CN(S(=O)(=O)c3cnc(C(F)(F)F)nc3)C[C@@]2(O)CO)cc1F] | 463.0 | $^1$H NMR (400 MHz, DMSO-$d_6$) δ:9.47 (s, 2H), 7.78 (t, J = 8.3 Hz, 1H), 6.97 (dd, J = 11.8, 2.3 Hz, 1H), 6.73 (dd, J =8.8, 2.3 Hz, 1H), 5.40 (s, 1H), 4.81 (t, J = 5.5 Hz, 1H), 4.67 (d, J = 3.3 Hz, 1H), 3.82 (dd, J = 12.4, 3.4 Hz, 1H), 3.39-3.58 (m, 5H) |

| Ex. | Name | Structure | MS (m/z) (M + H⁺) | ¹H NMR |
|---|---|---|---|---|
| 129 | 4-(((3S,4R)-1-((4-chloro-3-(trifluoromethoxy)phenyl)sulfonyl)-4-hydroxy-4-(hydroxymethyl)pyrrolidin-3-yl)oxy)-2-fluorobenzonitrile | 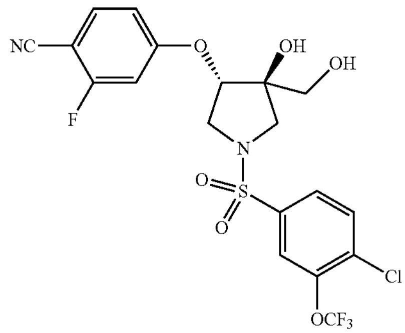 [SMILES: N#Cc1ccc(O[C@H]2CN(S(=O)(=O)c3ccc(Cl)c(OC(F)(F)F)c3)C[C@@]2(O)CO)cc1F] | 511.0 | ¹H NMR (400 MHz, CD₃OD) δ: 7.76 (q, J = 8.4 Hz, 3H), 7.62 (t, J = 8.2 Hz, 1H), 6.71 (d, J = 11.3 Hz, 1H), 6.63 (d, J = 8.8 Hz, 1H), 4.65 (br s, 1H), 3.86 (dd, J = 12.2, 2.9 Hz, 1H), 3.69-3.76 (m, 1H), 3.58-3.66 (m, 1H), 3.36-3.54 (m, 3H) |
| 130 | 2-fluoro-4-(((3S,4R)-4-hydroxy-4-(hydroxymethyl)-1-((5-iodopyridin-2-yl)sulfonyl)pyrrolidin-3-yl)oxy)benzonitrile | 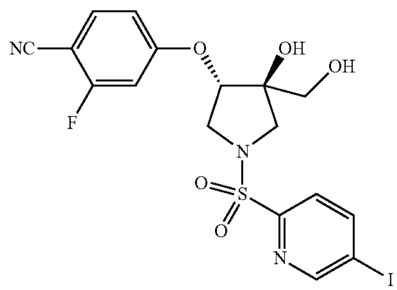 [SMILES: N#Cc1ccc(O[C@H]2CN(S(=O)(=O)c3ccc(I)cn3)C[C@@]2(O)CO)cc1F] | 519.9 | ¹H NMR (400 MHz, DMSO-d₆) δ: 8.74 (d, J = 1.5 Hz, 1H), 8.38 (dd, J = 8.3, 2.0 Hz, 1H), 7.78 (t, J = 8.4 Hz, 1H), 7.62 (d, J = 8.3 Hz, 1H), 6.92 (dd, J = 11.8, 2.3 Hz, 1H), 6.67 (dd, J = 8.7, 2.1 Hz, 1H), 5.40 (s, 1H), 4.78 (t, J = 5.6 Hz, 1H), 4.57 (d, J = 2.8 Hz, 1H), 3.85 (dd, J = 12.3, 3.3 Hz, 1H), 3.40-3.60 (m, 4H), 3.32-3.39 (m, 1H, partially hidden by solvent peak) |
| 131 | 5-(((3R,4S)-4-(4-cyano-3-fluorophenoxy)-3-hydroxy-3-(hydroxymethyl)pyrrolidin-1-yl)sulfonyl)-6-methylpicolinonitrile | 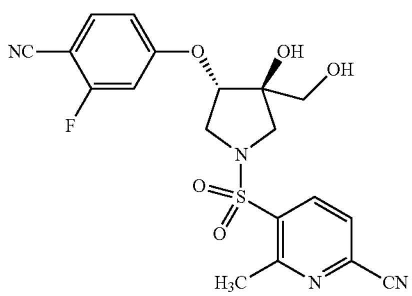 [SMILES: Cc1nc(C#N)ccc1S(=O)(=O)N1C[C@H](Oc2ccc(C#N)c(F)c2)[C@](O)(CO)C1] | 433.0 | ¹H NMR (400 MHz, DMSO-d₆) δ: 8.37 (d, J = 8.0 Hz, 1H), 8.08 (d, J = 8.0 Hz, 1H), 7.84 (t, J = 8.3 Hz, 1H), 7.18 (dd, J = 11.8, 2.3 Hz, 1H), 6.95 (dd, J = 8.8, 2.3 Hz, 1H), 5.61 (s, 1H), 4.88 (t, J =5.5 Hz, 1H), 4.76 (d, J = 3.0 Hz, 1H), 3.83 (dd, J = 11.7, 3.4 Hz, 1H), 3.50-3.63 (m, 2H), 3.47 (d, J = 11.0 Hz, 2H), 3.36-3.41 (m, 1H, partially hidden by solvent peak), 2.77 (s, 3H) |
| 132 | 2-fluoro-4-(((3S,4R)-4-hydroxy-4-(hydroxymethyl)-1-((6-(trifluoromethoxy)pyridin-2-yl)sulfonyl)pyrrolidin-3-yl)oxy)benzonitrile | 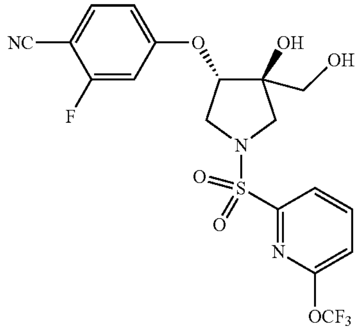 [SMILES: N#Cc1ccc(O[C@H]2CN(S(=O)(=O)c3cccc(OC(F)(F)F)n3)C[C@@]2(O)CO)cc1F] | 478.0 | ¹H NMR (400 MHz, DMSO-d₆) δ: 8.22 (t, J = 7.9 Hz, 1H), 7.86 (d, J = 7.3 Hz, 1H), 7.76 (t, J = 8.4 Hz, 1H), 7.54 (d, J = 8.3 Hz, 1H), 6.93 (dd, J = 11.8, 2.3 Hz, 1H), 6.59 (dd, J = 8.8, 2.3 Hz, 1H), 5.44 (s, 1H), 4.81 (t, J = 5.6 Hz, 1H), 4.62 (d, J = 2.8 Hz, 1H), 3.90 (dd, J = 12.3, 3.3 Hz, 1H), 3.42-3.55 (m, 4H), 3.38 (d, J = 10.5 Hz, 1H) |

| Ex. | Name | Structure | MS (m/z) (M + H+) | 1H NMR |
|---|---|---|---|---|
| 133 | 2-fluoro-4-(((3S,4R)-4-hydroxy-4-(hydroxymethyl)-1-((6-(2,2,2-trifluoroethoxy)pyridazin-3-yl)sulfonyl)pyrrolidin-3-yl)oxy)benzonitrile | 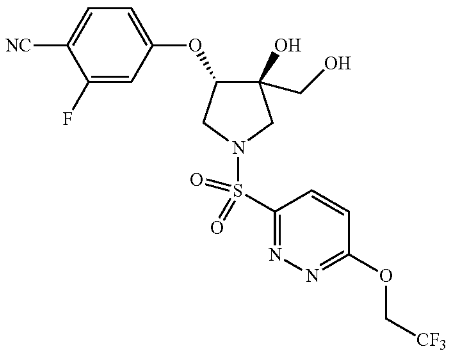 [SMILES: N#Cc1ccc(O[C@H]2CN(S(=O)(=O)c3ccc(OCC(F)(F)F)nn3)C[C@@]2(O)CO)cc1F] | 493.1 | 1H NMR (400 MHz, DMSO-d6) δ: 7.75-7.84 (m, 2H), 7.05-7.16 (m, 2H), 6.79 (dd, J = 8.8, 2.3 Hz, 1H), 5.48 (s, 1H), 4.88-5.09 (m, 2H), 4.85 (t, J = 5.6 Hz, 1H), 4.69 (d, J = 3.3 Hz, 1H), 3.90 (dd, J = 12.2, 3.4 Hz, 1H), 3.52-3.61 (m, 1H), 3.42-3.52 (m, 3H), 3.36-3.41 (m, 1H) |
| 134 | 4-(((3S,4R)-1-((6-(difluoromethoxy)pyridin-2-yl)sulfonyl)-4-hydroxy-4-(hydroxymethyl)pyrrolidin-3-yl)oxy)-2-fluorobenzonitrile | 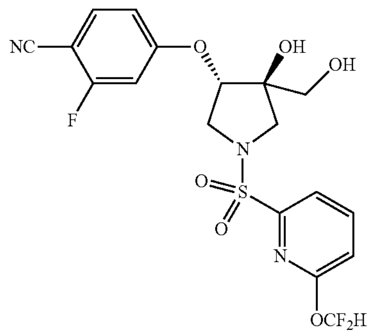 | 460.1 | 1H NMR (400 MHz, DMSO-d6) δ: 8.08-8.16 (m, 1H), 7.78 (t, J = 8.3 Hz, 1H), 7.71 (d, J = 7.3 Hz, 1H), 7.30-7.69 (m, 2H), 6.97 (dd, J = 11.8, 2.3 Hz, 1H), 6.68 (dd, J = 8.8, 2.3 Hz, 1H), 5.43 (s, 1H), 4.82 (t, J = 5.6 Hz, 1H), 4.64 (d, J = 3.0 Hz, 1H), 3.91 (dd, J = 12.2, 3.4 Hz, 1H), 3.43-3.62 (m, 4H), 3.38 (d, J = 10.5 Hz, 1H) |

Example 135

4-(((3S,4S)-1-((2-cyano-4-(trifluoromethyl)phenyl)-4-hydroxy-4-(hydroxymethyl) pyrrolidin-3-yl)oxy)-2-fluorobenzonitrile

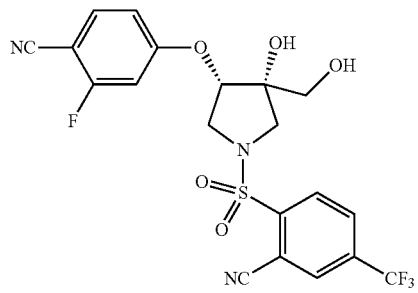 [SMILES: N#Cc1ccc(O[C@H]2CN(S(=O)(=O)c3ccc(C(F)(F)F)cc3C#N)C[C@]2(O)CO)cc1F]

Step 1: 4-(((3S,7S)-5-((2-cyano-4-(trifluoromethyl)phenyl)sulfonyl)-1-oxa-5-azaspiro[2.4]heptan-7-yl)oxy)-2-fluorobenzonitrile

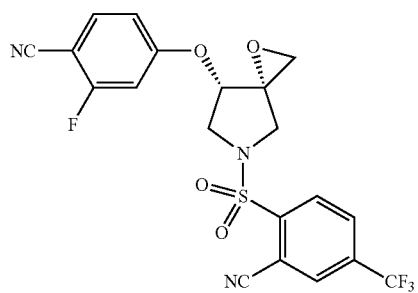 [SMILES: N#Cc1ccc(O[C@H]2CN(S(=O)(=O)c3ccc(C(F)(F)F)cc3C#N)C[C@]23CO3)cc1F]

To a solution of (R)-4-((1-((2-cyano-4-(trifluoromethyl)phenyl)sulfonyl)-4-methylenepyrrolidin-3-yl)oxy)-2-fluorobenzonitrile (13.4 g, 29.7 mmol) in DCE (200 mL) was added m-CPBA (16.6 g, 74.2 mmol) and the reaction mixture was stirred at 40° C. for 77 h. The reaction was quenched with sat'd NaHSO3 (aq) and sat'd NaHCO3 (aq). The organic layer was separated, washed with 1 N NaOH (aq) (2×) and brine, dried over Na2SO4, filtered and concentrated. The crude residue was purified by flash column chromatography (SiO2) eluting with a gradient of 0-100% EtOAc in hexanes. The product fractions were pooled and concentrated to give the title compound as a white solid (6.2 g, 45% yield). MS (m/z) 468.0 (M+H+).

Step 2: 4-(((3S,4S)-1-((2-cyano-4-(trifluoromethyl)phenyl)sulfonyl)-4-hydroxy-4-(hydroxymethyl)pyrrolidin-3-yl)oxy)-2-fluorobenzonitrile To a solution of 4-(((3S,7S)-5-((2-cyano-4-(trifluoromethyl)phenyl)sulfonyl)-1-oxa-5-azaspiro[2.4]heptan-7-yl)oxy)-2-fluorobenzonitrile (6.2 g, 13 mmol) in THF (100 mL) was added 2 M H2SO4 (aq) (15 mL, 30 mmol) and the reaction mixture was stirred at 40° C. overnight. The reaction mixture was concentrated and the residue diluted with EtOAc and neutralized with 2 M NaOH (aq) (15 mL) and then sat'd NaHCO3 (aq). The organic layer was separated, dried over Na2SO4, filtered and concentrated. The residue was purified by flash column chromatography (SiO2) eluting with a gradient of 0-100% EtOAc in hexanes.

The product fractions were pooled, concentrated and the residue was recrystallized from toluene to give the title compound as a whitish solid (5.5 g, 85% yield). 1H NMR (400 MHz, DMSO-d6) δ: 8.71 (s, 1H), 8.29-8.35 (m, 1H), 8.22-8.28 (m, 1H), 7.75-7.85 (m, 1H), 7.11 (dd, J=11.8, 2.5 Hz, 1H), 6.91 (dd, J=8.8, 2.3 Hz, 1H), 5.36 (s, 1H), 5.19 (t, J=5.6 Hz, 1H), 4.93 (t, J=5.4 Hz, 1H), 3.94 (dd, J=10.5, 5.8 Hz, 1H), 3.54 (d, J=10.3 Hz, 1H), 3.44 (dd, J=10.7, 4.9 Hz, 1H), 3.36 (d, J=5.5 Hz, 2H, partially hidden by solvent peak), 3.30 (d, J=10.3 Hz, 1H). MS (m/z) 486.0 (M+H⁺).

Example 136

4-(((3S,4S)-1-((5-chloropyridin-2-yl)sulfonyl)-4-hydroxy-4-(hydroxymethyl) pyrrolidin-3-yl)oxy)-2-fluorobenzonitrile

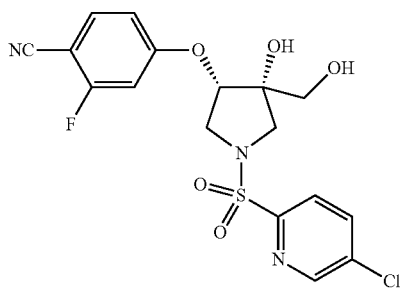 [SMILES: N#Cc1ccc(O[C@H]2CN(S(=O)(=O)c3ccc(Cl)cn3)C[C@]2(O)CO)cc1F]

Step 1: (3S,7S)-tert-butyl 7-(4-cyano-3-fluorophenoxy)-1-oxa-5-azaspiro[2.4]heptane-5-carboxylate

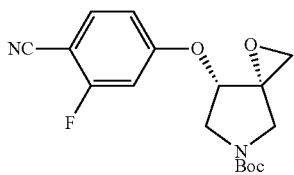 [SMILES: CC(C)(C)OC(=O)N1C[C@H](Oc2ccc(C#N)c(F)c2)[C@@]2(CO2)C1]

To a solution of (R)-tert-butyl 3-(4-cyano-3-fluorophenoxy)-4-methylenepyrrolidine-1-carboxylate (30 g, 94 mmol) in DCE (750 mL) was added m-CPBA (53 g, 240 mmol) and the mixture was stirred at rt for 72 h. The reaction was quenched with sat'd NaHSO₃ (aq) followed by sat'd NaHCO₃ (aq) and stirred 1 h. The organic layer was separated, dried over Na₂SO₄, filtered and concentrated to give a crude mixture of the cis and trans isomers. Separation of the individual isomers was accomplished by flash column chromatography (SiO₂) eluting with a gradient of 0-100% EtOAc in hexanes. The separated isomer fractions were each pooled and concentrated to give the individual cis and trans isomers of the title compound. Cis-isomer: (2ⁿᵈ elutant, 13.8 g, 44% yield), ¹H NMR (400 MHz, DMSO-d₆) δ: 7.84 (t, J=8.4 Hz, 1H), 7.23 (dd, J=11.9, 2.4 Hz, 1H), 7.01 (dd, J=8.8, 2.3 Hz, 1H), 5.01 (d, J=3.0 Hz, 1H), 3.71-3.83 (m, 1H), 3.44-3.58 (m, 3H), 3.17 (d, J=5.3 Hz, 1H), 3.08 (d, J=5.3 Hz, 1H), 1.41 (br s, 9H). MS (m/z) 357.2 (M+H⁺). Trans-isomer: (1ˢᵗ elutant), ¹H NMR (400 MHz, DMSO-d₆) δ: 7.87 (t, J=8.4 Hz, 1H), 7.29 (dd, J=11.8, 2.3 Hz, 1H), 7.05 (dd, J=8.8, 2.5 Hz, 1H), 4.87 (br s, 1H), 3.86 (d, J=12.5 Hz, 2H), 3.48 (dd, J=12.5, 2.0 Hz, 1H), 3.23 (d, J=12.0 Hz, 1H), 3.16-3.18 (m, 1H), 3.12-3.15 (m, 1H), 1.32-1.52 (m, 9H). MS (m/z) 357.2 (M+H⁺).

Step 2: 2-fluoro-4-(((3S,4S)-4-hydroxy-4-(hydroxymethyl)pyrrolidin-3-yl)oxy)benzonitrile

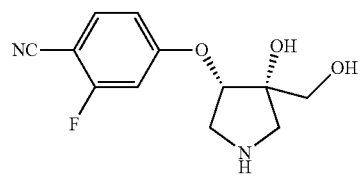 [SMILES: N#Cc1ccc(O[C@H]2CNC[C@]2(O)CO)cc1F]

To a solution of (3S,7S)-tert-butyl 7-(4-cyano-3-fluorophenoxy)-1-oxa-5-azaspiro[2.4]heptane-5-carboxylate (13.8 g, 37.1 mmol) in THF (75 mL) was added 2 M H₂SO₄ (aq) (24 mL, 48 mmol) and the reaction mixture was stirred at 45° C. overnight. The reaction mixture was cooled, diluted with THF (32 mL) and stored as a 0.28 M solution of the sulfate salt of the title compound. MS (m/z) 253.2 (M+H⁺).

Step 3: 4-(((3S,4S)-1-((5-chloropyridin-2-yl)sulfonyl)-4-hydroxy-4-(hydroxymethyl) pyrrolidin-3-yl)oxy)-2-fluorobenzonitrile To the previously prepared 0.28 M solution of 2-fluoro-4-(((3S,4S)-4-hydroxy-4-(hydroxymethyl)pyrrolidin-3-yl)oxy)benzonitrile sulfate (2.5 mL, 0.70 mmol) was added THF (5 mL) followed by 2 M NaHCO₃ (aq) to adjust the pH to 8. 5-chloropyridine-2-sulfonyl chloride (445 mg, 2.10 mmol) was added and the reaction mixture was stirred at rt for 30 min. The reaction mixture was partitioned between EtOAc and water. The organic layer was removed, washed with brine, dried over Na₂SO₄, filtered and concentrated. The crude product was purified by flash column chromatography (SiO₂) eluting with a gradient of 0-100% EtOAc in hexanes. The product fractions were pooled and concentrated to give the title compound as a white solid (202 mg, 66% yield). ¹H NMR (400 MHz, DMSO-d₆) δ: 8.80 (d, J=2.3 Hz, 1H), 8.25 (dd, J=8.4, 2.4 Hz, 1H), 7.96 (d, J=8.5 Hz, 1H), 7.77-7.87 (m, 1H), 7.08 (dd, J=11.8, 2.3 Hz, 1H), 6.90 (dd, J=8.8, 2.3 Hz, 1H), 5.26 (s, 1H), 5.11 (t, J=5.8 Hz, 1H), 4.81 (t, J=5.1 Hz, 1H), 3.93 (dd, J=11.0, 5.8 Hz, 1H), 3.43-3.52 (m, 2H), 3.23-3.32 (m, 3H). MS (m/z) 428.0 (M+H⁺).

The following compounds were prepared using procedures analogous to those described in Example 136 using appropriately substituted starting materials. As is appreciated by those skilled in the art, these analogous examples may involve variations in general reaction conditions.

| Ex. Name | Structure | MS (m/z) (M + H⁺) | ¹H NMR |
|---|---|---|---|
| 137 4-(((3S,4S)-1-((2-cyanophenyl)sulfonyl)-4-hydroxy-4-(hydroxymethyl)pyrrolidin-3-yl)oxy)-2-fluorobenzonitrile | | 418.2 | ¹H NMR (400 MHz, DMSO-d₆) δ: 8.17 (dd, J = 7.2, 1.9 Hz, 1H), 8.03-8.09 (m, 1H), 7.88-7.99 (m, 2H), 7.77-7.84 (m, 1H), 7.13 (dd, J = 11.8, 2.3 Hz, 1H), 6.90 (dd, J = 8.8, 2.3 Hz, 1H), 5.33 (s, 1H), 5.18 (t, J = 5.6 Hz, 1H), 4.91 (t, J = 5.3 Hz, 1H), 3.90 (dd, J = 10.7, 5.6 Hz, 1H), 3.50 (d, J = 10.0 Hz, 1H), 3.38-3.45 (m, 1H), 3.32-3.35 (2H, partially hidden by solvent peak), 3.24 (d, J = 10.3 Hz, 1H) |
| 138 4-(((3S,4S)-1-((2-cyano-4-fluorophenyl)sulfonyl)-4-hydroxy-4-(hydroxymethyl)pyrrolidin-3-yl)oxy)-2-fluorobenzonitrile | | 436.1 | ¹H NMR (400 MHz, DMSO-d₆) δ: 8.25 (dd, J = 8.7, 2.6 Hz, 1H), 8.12 (dd, J = 8.8, 5.3 Hz, 1H), 7.78-7.87 (m, 2H), 7.15 (dd, J = 11.9, 2.4 Hz, 1H), 6.93 (dd, J = 8.8, 2.3 Hz, 1H), 5.34 (s, 1H), 5.18 (t, J = 5.6 Hz, 1H), 4.91 (t, J = 5.3 Hz, 1H), 3.89 (dd, J = 10.7, 5.6 Hz, 1H), 3.50 (d, J = 10.3 Hz, 1H), 3.37-3.44 (m, 2H), 3.33-3.35 (1H, partially hidden by solvent peak), 3.25 (d, J = 10.3 Hz, 1H) |
| 139 4-(((3S,4S)-1-((4-chloro-2-cyanophenyl)sulfonyl)-4-hydroxy-4-(hydroxymethyl)pyrrolidin-3-yl)oxy)-2-fluorobenzonitrile | | 452.0 | ¹H NMR (400 MHz, DMSO-d₆) δ: 8.41 (S, 1H), 7.98-8.07 (m, 2H), 7.82 (t, J = 8.3 Hz, 1H), 7.14 (dd, J = 11.8, 2.0 Hz, 1H), 6.93 (dd, J = 8.8, 2.0 Hz, 1H), 5.34 (s, 1H), 5.18 (t, J = 5.5 Hz, 1H), 4.91 (t, J = 5.3 Hz, 1H), 3.90 (dd, J = 10.7,5.6 Hz, 1H), 3.50 (d, J = 10.3 Hz, 1H), 3.37-3.43 (m, 2H), 3.35 (br s, 1H, partially hidden by solvent peak), 3.25 (d, J = 10.3 Hz, 1H) |
| 140 3-(((3S,4S)-4-(4-cyano-3-fluorophenoxy)-3-hydroxy-3-(hydroxymethyl)pyrrolidin-1-yl)sulfonyl)picolinonitrile | | 419.1 | ¹H NMR (400 MHz, DMSO-d₆) δ: 9.03 (d, J = 4.8 Hz, 1H), 8.49 (d, J = 8.0 Hz, 1H), 7.99 (dd, J = 8.3, 4.8 Hz, 1H), 7.82 (t, J = 8.4 Hz, 1H), 7.15 (dd, J = 11.9, 2.1 Hz, 1H), 6.91 (dd, J = 8.8, 2.3 Hz, 1H), 5.35 (s, 1H), 5.19 (t, J = 5.5 Hz, 1H), 4.94 (t, J = 5.5 Hz, 1H), 3.95 (dd, J = 10.5, 5.8 Hz, 1H), 3.55 (d, J = 10.5 Hz, 1H), 3.43 (dd, J = 10.5, 5.0 Hz, 1H), 3.33-3.37 (2H, partially hidden by solvent peak), 3.31 (d, J = 10.5 Hz, 1H) |
| 141 4-(((3S,4S)-1-((2-chloro-4-cyanophenyl)sulfonyl)-4-hydroxy-4-(hydroxymethyl)pyrrolidin-3-yl)oxy)-2-fluorobenzonitrile | | 452.0 | ¹H NMR (400 MHz, DMSO-d₆) δ: 8.37 (d, J = 1.5 Hz, 1H), 8.13-8.17 (m, 1H), 8.03-8.09 (m, 1H), 7.83 (t, J = 8.3 Hz, 1H), 7.21 (dd, J = 11.8, 2.3 Hz, 1H), 7.01 (dd, J = 8.8, 2.3 Hz, 1H), 5.43 (s, 1H), 5.21 (t, J = 5.5 Hz, 1H), 4.98 (t, J = 5.5 Hz, 1H), 3.95 (dd, J = 10.3, 6.0 Hz, 1H), 3.54 (d, J = 10.3 Hz, 1H), 3.47 (dd, J = 10.3, 5.3 Hz, 1H), 3.39 (d, J = 5.5 Hz, 2H), 3.31 (d, J = 10.0 Hz, 1H) |

| Ex. | Name | Structure | MS (m/z) (M + H⁺) | ¹H NMR |
|---|---|---|---|---|
| 142 | 4-(((3S,4S)-1-((2,4-dichlorophenyl)sulfonyl)-4-hydroxy-4-(hydroxymethyl)pyrrolidin-3-yl)oxy)-2-fluorobenzonitrile | 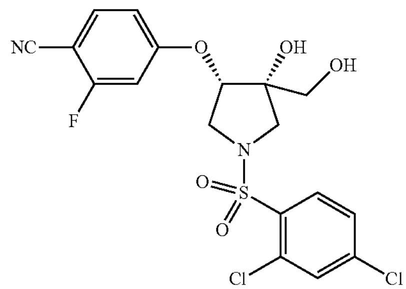 [SMILES: N#Cc1ccc(O[C@H]2CN(S(=O)(=O)c3ccc(Cl)cc3C#N)C[C@]2(O)CO)cc1F] | 461.1 | ¹H NMR (400 MHz, DMSO-d₆) δ: 7.99 (d, J = 8.8 Hz, 1H), 7.94 (d, J = 2.0 Hz, 1H), 7.82 (t, J = 8.3 Hz, 1H), 7.66 (dd, J = 8.5, 2.3 Hz, 1H), 7.20 (dd, J = 11.9, 2.4 Hz, 1H), 7.00 (dd, J = 8.8, 2.3 Hz, 1H), 5.39 (s, 1H), 5.20 (t, J = 5.5 Hz, 1H), 4.95 (t, J = 5.3 Hz, 1H), 3.90 (dd, J = 10.4, 5.9 Hz, 1H), 3.50 (d, J = 10.0 Hz, 1H), 3.44 (dd, J = 10.4, 4.9 Hz, 1H), 3.38 (d, J = 5.5 Hz, 2H), 3.27 (d, J = 9.8 Hz, 1H) |
| 143 | 4-(((3S,4S)-1-((4-bromo-2-cyanophenyl)sulfonyl)-4-hydroxy-4-(hydroxymethyl)pyrrolidin-3-yl)oxy)-2-fluorobenzonitrile | 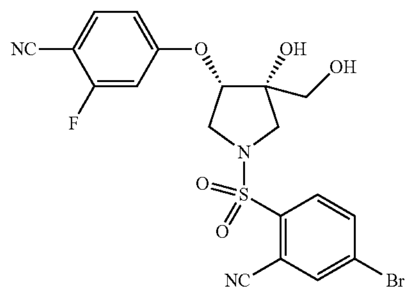 [SMILES: N#Cc1ccc(O[C@H]2CN(S(=O)(=O)c3ccc(Br)cc3C#N)C[C@]2(O)CO)cc1F] | 496.0 | ¹H NMR (400 MHz, DMSO-d₆) δ: 8.51 (d, J = 2.0 Hz, 1H), 8.15 (dd, J = 8.5, 2.0 Hz, 1H), 7.94 (d, 8.5 Hz, 1H), 7.82 (t, J = 8.4 Hz, 1H), 7.13 (dd, J = 11.9, 2.4 Hz, 1H), 6.93 (dd, J = 8.8, 2.3 Hz, 1H), 5.36 (s, 1H), 5.21 (t, J = 5.5 Hz, 1H), 4.91 (t, J = 5.3 Hz, 1H), 3.90 (dd, J = 10.8, 5.8 Hz, 1H), 3.50 (d, J = 10.3 Hz, 1H), 3.36-3.42 (m, 2H), 3.35 (1H, partially hidden by solvent peak), 3.25 (d, J = 10.3 Hz, 1H) |
| 144 | 4-(((3S,4S)-1-((2-bromo-4-fluorophenyl)sulfonyl)-4-hydroxy-4-(hydroxymethyl)pyrrolidin-3-yl)oxy)-2-fluorobenzonitrile | 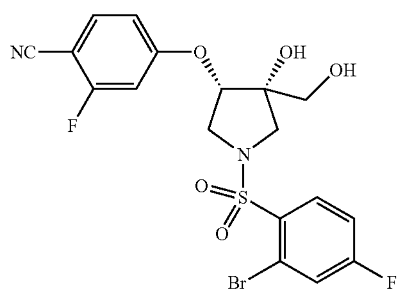 [SMILES: N#Cc1ccc(O[C@H]2CN(S(=O)(=O)c3ccc(F)cc3Br)C[C@]2(O)CO)cc1F] | 489.0 | ¹H NMR (400 MHz, DMSO-d₆) δ: 8.09 (dd, J = 8.9, 5.9 Hz, 1H), 7.92 (dd, J = 8.5, 2.5 Hz, 1H), 7.83 (t, J = 8.4 Hz, 1H), 7.49 (m, 1H), 7.22 (dd, J = 11.8, 2.3 Hz, 1H), 7.02 (dd, J = 8.8, 2.5 Hz, 1H), 5.40 (s, 1H), 5.21 (t, J = 5.6 Hz, 1H), 4.97 (t, J = 5.4 Hz, 1H), 3.92 (dd, J = 10.3, 6.0 Hz, 1H), 3.44-3.53 (m, 2H), 3.39 (d, J = 5.8 Hz, 2H), 3.27 (d, J = 10.0 Hz, 1H) |
| 145 | 4-(((3S,4S)-1-((2-cyano-4-methoxyphenyl)sulfonyl)-4-hydroxy-4-(hydroxymethyl)pyrrolidin-3-yl)oxy)-2-fluorobenzonitrile | 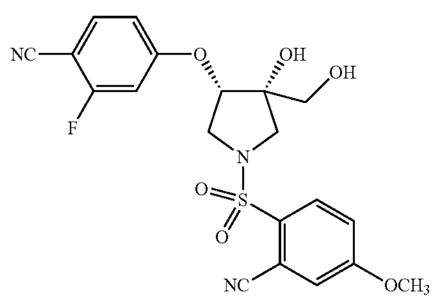 [SMILES: COc1ccc(S(=O)(=O)N2C[C@H](Oc3ccc(C#N)c(F)c3)[C@@](O)(CO)C2)c(C#N)c1] | 448.1 | ¹H NMR (400 MHz, DMSO-d₆) δ: 7.95 (d, J = 9.0 Hz, 1H), 7.81 (t, J = 8.3Hz, 1H), 7.74 (d, J = 2.5 Hz, 1H), 7.42 (dd, J = 8.9, 2.6 Hz, 1H), 7.12 (dd, J = 11.9, 1.9 Hz, 1H), 6.91 (dd, J = 8.8, 2.0 Hz, 1H), 5.31 (s, 1H), 5.17 (t, J = 5.5 Hz, 1H), 4.88 (t, J = 5.0 Hz, 1H), 3.93 (s, 3H), 3.85 (dd, J = 10.8, 5.5 Hz, 1H), 3.46 (d, J = 10.0 Hz, 1H), 3.31-3.39 (m, 3H, partially hidden by solvent peak), 3.20 (d, J = 10.0 Hz, 1H) |
| 146 | 2-(((3S,4S)-4-(4-chlorophenoxy)-3-hydroxy-3-(hydroxymethyl)pyrrolidin-1-yl)sulfonyl)-5-(trifluoromethyl)benzonitrile | 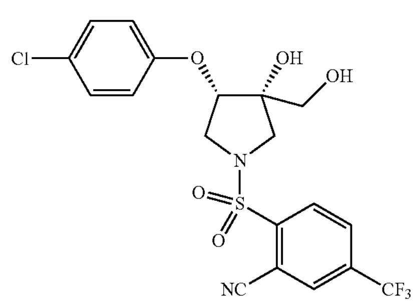 [SMILES: N#Cc1cc(C(F)(F)F)ccc1S(=O)(=O)N1C[C@H](Oc2ccc(Cl)cc2)[C@@](O)(CO)C1] | 477.0 | ¹H NMR (400 MHz, CD₃OD) δ: 8.39 (s, 1H), 8.29 (d, J = 8.3 Hz, 1H), 8.17 (dd, J = 8.3, 1.3 Hz, 1H), 7.20-7.28 (m, 2H), 6.87-6.96 (m, 2H), 4.79 (t, J = 5.5 Hz, 1H), 4.00 (dd, J = 10.5, 5.8 Hz, 1H), 3.66 (d, J = 10.5 Hz, 1H), 3.52-3.61 (m, 3H), 3.47 (d, J = 10.5 Hz, 1H) |

-continued

| Ex. | Name | Structure | MS (m/z) (M + H+) | 1H NMR |
|---|---|---|---|---|
| 147 | 2-(((3S,4S)-4-(4-chlorophenoxy)-3-hydroxy-3-(hydroxymethyl)pyrrolidin-1-yl)sulfonyl)-5-fluorobenzonitrile | 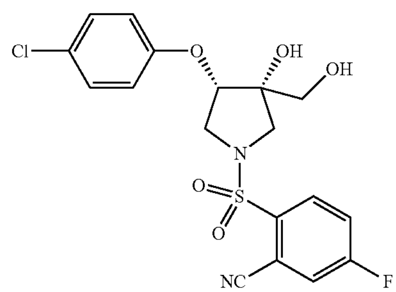 [SMILES: N#Cc1cc(F)ccc1S(=O)(=O)N1C[C@H](Oc2ccc(Cl)cc2)[C@@](O)(CO)C1] | 427.1 | 1H NMR (400 MHz, DMSO-d6) δ: 8.23 (dd, J = 8.5, 2.8 Hz, 1H), 8.12 (dd, J = 8.8, 5.3 Hz, 1H), 7.81 (m, 1H), 7.27-7.35 (m, 2H), 6.94-7.00 (m, 2H), 5.19 (s, 1H), 5.09 (t, J = 5.5 Hz, 1H), 4.72 (t, J = 5.9 Hz, 1H), 3.87 (dd, J = 10.3, 6.0 Hz, 1H), 3.50 (d, J = 10.3 Hz, 1H), 3.30-3.38 (m, 3H, partially hidden by solvent peak), 3.25 (d, J = 10.3 Hz, 1H) |
| 148 | 2-(((3S,4S)-3-hydroxy-3-(hydroxymethyl)-4-(4-(trifluoromethyl)phenoxy)pyrrolidin-1-yl)sulfonyl)-5-(trifluoromethyl)benzonitrile | 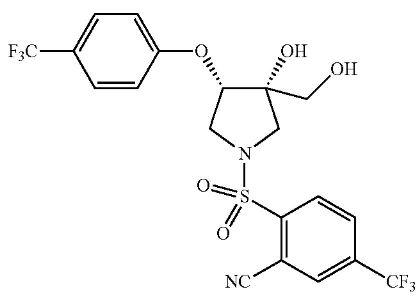 [SMILES: N#Cc1cc(C(F)(F)F)ccc1S(=O)(=O)N1C[C@H](Oc2ccc(C(F)(F)F)cc2)[C@@](O)(CO)C1] | 511.1 | 1H NMR (400 MHz, DMSO-d6) δ: 8.69 (s, 1H), 8.22-8.32 (m, 2H), 7.61 (d, J = 8.8 Hz, 2H), 7.10 (d, J = 8.8 Hz, 2H), 5.29 (s, 1H), 5.15 (t, J = 5.5 Hz, 1H), 4.88 (t, J = 5.6 Hz, 1H), 3.96 (dd, J = 10.3, 6.0 Hz, 1H), 3.56 (d, J = 10.3 Hz, 1H), 3.30-3.44 (m, 4H, partially hidden by solvent peak) |
| 149 | 5-fluoro-2-(((3S,4S)-3-hydroxy-3-(hydroxymethyl)-4-(4-(trifluoromethyl)phenoxy)pyrrolidin-1-yl)sulfonyl)benzonitrile | 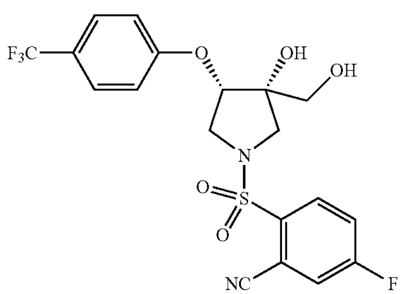 [SMILES: N#Cc1cc(F)ccc1S(=O)(=O)N1C[C@H](Oc2ccc(C(F)(F)F)cc2)[C@@](O)(CO)C1] | 461.1 | 1H NMR (400 MHz, DMSO-d6) δ: 8.23 (dd, J = 8.5, 2.8 Hz, 1H), 8.13 (dd, J = 9.0, 5.3 Hz, 1H), 7.81 (m, 1H), 7.63 (d, J = 8.8 Hz, 2H), 7.13 (d, J = 8.8 Hz, 2H), 5.26 (s, 1H), 5.13 (t, J = 5.6 Hz, 1H), 4.86 (t, J = 5.8 Hz, 1H), 3.91 (dd, J = 10.3, 6.0 Hz, 1H), 3.52 (d, J = 10.3 Hz, 1H), 3.32-3.42 (m, 3H, partially hidden by solvent peak), 3.28 (d, J = 10.3 Hz, 1H) |
| 150 | 3-chloro-4-(((3R,4S)-3-hydroxy-3-(hydroxymethyl)-4-(4-(trifluoromethyl)phenoxy)pyrrolidin-1-yl)sulfonyl)benzonitrile | 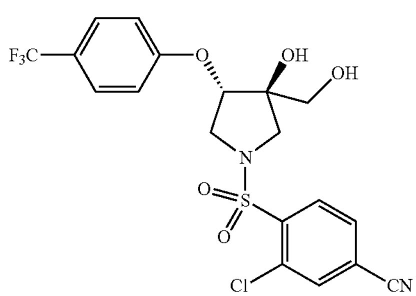 [SMILES: N#Cc1ccc(S(=O)(=O)N2C[C@H](Oc3ccc(C(F)(F)F)cc3)[C@](O)(CO)C2)c(Cl)c1] | 477.1 | 1H NMR (400 MHz, DMSO-d6) δ: 8.28 (d, J = 1.5 Hz, 1H), 8.08 (d, J = 8.3 Hz, 1H), 7.95 (dd, J = 8.3, 1.5 Hz, 1H), 7.62 (d, J = 8.8 Hz, 2H), 7.04 (d, J = 8.5 Hz, 2H), 5.55 (s, 1H), 4.87 (t, J = 5.6 Hz, 1H), 4.71 (d, J = 3.0 Hz, 1H), 3.88 (dd, J = 11.4, 3.1 Hz, 1H), 3.48-3.67 (m, 4H), 3.41 (d, J = 10.5 Hz, 1H) |
| 151 | 5-chloro-2-(((3S,4S)-4-(4-chlorophenoxy)-3-hydroxy-3-(hydroxymethyl)pyrrolidin-1-yl)sulfonyl)benzonitrile | 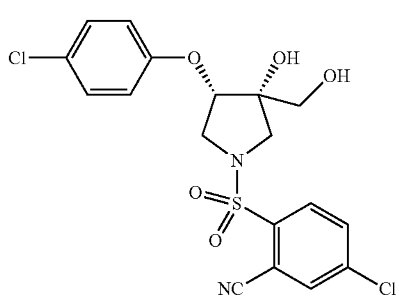 [SMILES: N#Cc1cc(Cl)ccc1S(=O)(=O)N1C[C@H](Oc2ccc(Cl)cc2)[C@@](O)(CO)C1] | 443.0 | 1H NMR (400 MHz, DMSO-d6) δ: 8.39 (d, J = 2.0 Hz, 1H), 7.97-8.07 (m, 2H), 7.31 (d, J = 9.0 Hz, 2H), 6.96 (d, J = 9.0 Hz, 2H), 5.20 (s, 1H), 5.11 (t, J = 5.5 Hz, 1H), 4.72 (t, J = 5.9 Hz, 1H), 3.87 (dd, J = 10.3, 6.0 Hz, 1H), 3.50 (d, J = 10.5 Hz, 1H), 3.29-3.36 (m, 3H, partially hidden by solvent peak), 3.26 (d, J = 10.5 Hz, 1H) |

-continued

| Ex. Name | Structure | MS (m/z) (M + H⁺) | ¹H NMR |
|---|---|---|---|
| 152 5-chloro-2-(((3S,4S)-3-hydroxy-3-(hydroxymethyl)-4-(4-(trifluoromethyl)phenoxy)pyrrolidin-1-yl)sulfonyl)benzonitrile | | 477.0 | ¹H NMR (400 MHz, DMSO-$d_6$) δ: 8.39 (d, J = 2.0 Hz, 1H), 8.02-8.07 (m, 1H), 7.97-8.02 (m, 1H), 7.63 (d, J = 8.8 Hz, 2H), 7.12 (d, J = 8.8 Hz, 2H), 5.28 (s, 1H), 5.15 (t, J = 5.5 Hz, 1H), 4.86 (t, J = 5.8 Hz, 1H), 3.91 (dd, J = 10.3, 5.8 Hz, 1H), 3.52 (d, J = 10.3 Hz, 1H), 3.33-3.40 (m, 3H, partially hidden by solvent peak), 3.28 (d, J = 10.3 Hz, 1H) |
| 153 5-fluoro-2-(((3R,4S)-3-hydroxy-3-(hydroxymethyl)-4-(4-(trifluoromethyl)phenoxy)pyrrolidin-1-yl)sulfonyl)benzonitrile | | 461.1 | ¹H NMR (400 MHz, DMSO-$d_6$) δ: 8.10 (dd, J = 8.5, 2.5 Hz, 1H), 8.05 (dd, J = 8.9, 5.1 Hz, 1H), 7.70 (m, 1H), 7.61 (d, J = 8.8 Hz, 2H), 6.97 (d, J = 8.8 Hz, 2H), 5.46 (S, 1H), 4.85 (t, J = 5.5 Hz, 1H), 4.67 (d, J = 3.3 Hz, 1H), 3.82 (dd, J = 11.7, 3.4 Hz, 1H), 3.54-3.62 (m, 1H), 3.45-3.54 (m, 3H), 3.38-3.43 (m, 1H) |
| 154 5-chloro-2-(((3R,4S)-4-(4-chlorophenoxy)-3-hydroxy-3-(hydroxymethyl)pyrrolidin-1-yl)sulfonyl)benzonitrile | | 442.9 | ¹H NMR (400 MHz, DMSO-$d_6$) δ: 8.26 (d, J = 1.8 Hz, 1H), 7.87-7.98 (m, 2H), 7.28 (d, J = 8.8 Hz, 2H), 6.76 (d, J = 8.8 Hz, 2H), 5.41 (s, 1H), 4.82 (t, J = 5.4 Hz, 1H), 4.53 (br s, 1H), 3.73-3.80 (m, 1H), 3.36-3.60 (m, 5H, partially hidden by solvent peak) |
| 155 2-(((3R,4S)-4-(4-chlorophenoxy)-3-hydroxy-3-(hydroxymethyl)pyrrolidin-1-yl)sulfonyl)-5-fluorobenzonitrile | | 427.1 | ¹H NMR (400 MHz, DMSO-$d_6$) δ: 8.12 (dd, J = 8.5, 2.8 Hz, 1H), 8.05 (dd, J = 9.0, 5.3 Hz, 1H), 7.73 (m, 1H), 7.25-7.32 (m, 2H), 6.79 (d, J = 9.0 Hz, 2H), 5.40 (s, 1H), 4.82 (t, J = 5.5 Hz, 1H), 4.54 (d, J = 3.0 Hz, 1H), 3.77 (dd, J = 11.5, 3.3 Hz, 1H), 3.42-3.59 (m, 4H), 3.35-3.41 (m, 1H) |
| 156 5-chloro-2-(((3R,4S)-3-hydroxy-3-(hydroxymethyl)-4-(4-(trifluoromethyl)phenoxy)pyrrolidin-1-yl)sulfonyl)benzonitrile | | 477.0 | ¹H NMR (400 MHz, DMSO-$d_6$) δ: 8.24 (d, J = 2.3 Hz, 1H), 7.93-7.98 (m, 1H), 7.85-7.91 (m, 1H), 7.60 (d, J = 8.5 Hz, 2H), 6.94 (d, J = 8.5 Hz, 2H), 5.47 (s, 1H), 4.85 (t, J = 5.5 Hz, 1H), 4.65 (d, J = 3.0 Hz, 1H), 3.81 (dd, J = 11.8, 3.3 Hz, 1H), 3.45-3.62 (m, 4H), 3.38-3.43 (m, 1H) |

Example 157

4-(((3S,4R)-1-((2-cyano-4-(trifluoromethyl)phenyl)sulfonyl)-4-hydroxy-4-(hydroxymethyl) pyrrolidin-3-yl)oxy)-2-fluoro-5-(2,2,2-trifluoroethoxy)benzonitrile

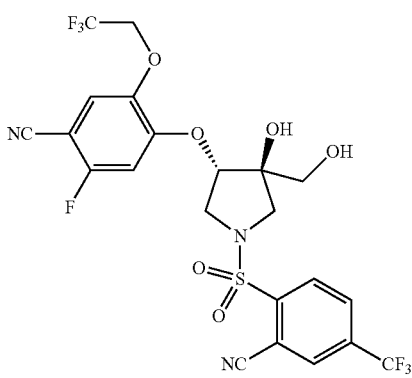 [SMILES: N#Cc1cc(OCC(F)(F)F)c(O[C@H]2CN(S(=O)(=O)c3ccc(C(F)(F)F)cc3C#N)C[C@@]2(O)CO)cc1F]

Step 1: (R)-5-cyano-2-((1-((2-cyano-4-(trifluoromethyl)phenyl)sulfonyl)-4-methylenepyrrolidin-3-yl)oxy)-4-fluorophenylacetate

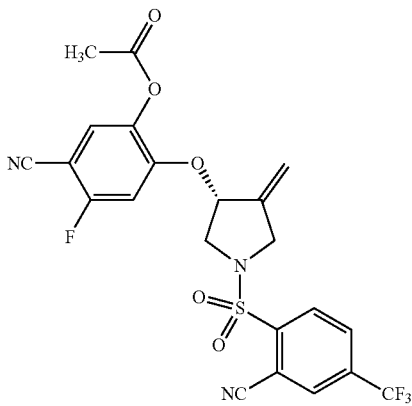 [SMILES: C=C1CN(S(=O)(=O)c2ccc(C(F)(F)F)cc2C#N)C[C@@H]1Oc1cc(F)c(C#N)cc1OC(C)=O]

To a solution of (S)-2-((3-hydroxy-4-methylenepyrrolidin-1-yl)sulfonyl)-5-(trifluoromethyl)benzonitrile (1.4 g, 4.2 mmol), 5-cyano-4-fluoro-2-hydroxyphenyl acetate (0.97 g, 4.2 mmol) and PS—PPh$_3$ (3 mmol/g) (2.1 mL, 6.3 mmol) in DCM (50 mL) was added DIAD (1.0 mL, 5.27 mmol) and the reaction mixture was stirred at rt overnight. The reaction mixture was filtered and the filtrate flash chromatographed (SiO$_2$) eluting with a gradient of 0-80% EtOAc in hexanes. The product fractions were pooled and concentrated to give the title compound as a light yellow solid (1.78 g, 83% yield). MS (m/z) 509.9 (M+H$^+$).

Step 2: (R)-4-((1-((2-cyano-4-(trifluoromethyl)phenyl)sulfonyl)-4-methylenepyrrolidin-3-yl)oxy)-2-fluoro-5-hydroxybenzonitrile

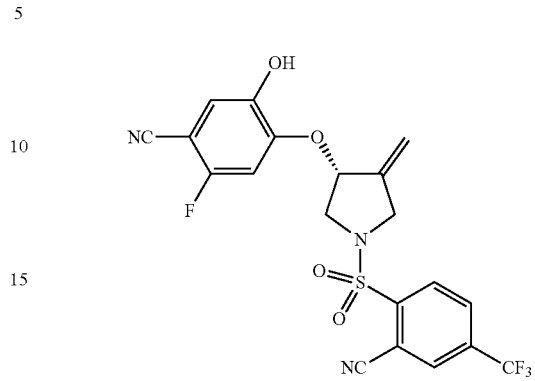

To a solution of (R)-5-cyano-2-((1-((2-cyano-4-(trifluoromethyl)phenyl)sulfonyl)-4-methylenepyrrolidin-3-yl)oxy)-4-fluorophenyl acetate (1.78 g, 3.49 mmol) in THF (50 mL) was added 1 N NaOH (aq) (50 mL, 50.0 mmol) and the reaction mixture was stirred at rt for 30 min. The reaction mixture was diluted with EtOAc and the aqueous layer was brought to neutral pH with the addition of 1 N HCl (aq) (50 mL). The organic layer was separated, washed with brine, dried over Na$_2$SO$_4$, filtered and concentrated. The resulting residue was triturated with Et$_2$O and the title compound was collected by filtration as a white powder (1.2 g, 74% yield). MS (m/z) 467.9 (M+H$^+$).

Step 3: (R)-4-((1-((2-cyano-4-(trifluoromethyl)phenyl)sulfonyl)-4-methylenepyrrolidin-3-yl)oxy)-2-fluoro-5-(2,2,2-trifluoroethoxy)benzonitrile

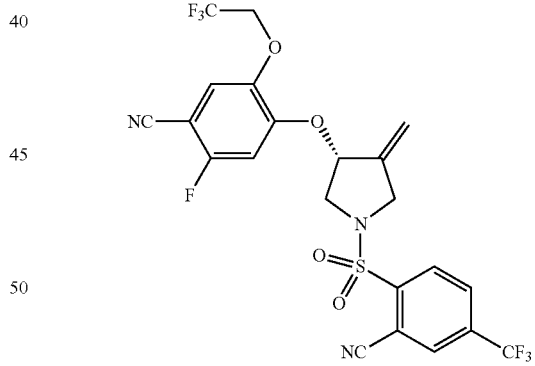

To a solution of (R)-4-((1-((2-cyano-4-(trifluoromethyl)phenyl)sulfonyl)-4-methylenepyrrolidin-3-yl)oxy)-2-fluoro-5-hydroxybenzonitrile (200 mg, 0.43 mmol) in DMF (3 mL) was added 1,1,1-trifluoro-2-iodoethane (0.17 mL, 1.7 mmol) and the reaction mixture was stirred at rt overnight. The reaction mixture was partitioned between EtOAc and water. The organic layer was separated, washed with water and brine, dried over Na$_2$SO$_4$, filtered and concentrated. The crude residue was purified by flash column chromatography (SiO$_2$) eluting with a gradient of 0-100% EtOAc in hexanes. The product fractions were pooled and concentrated to give the title compound (183 mg, 78% yield). MS (m/z) 549.8 (M+H$^+$).

Step 4: 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-(2,2,2-trifluoroethoxy)benzonitrile To a solution of (R)-4-((1-((2-cyano-4-(trifluoromethyl)phenyl)sulfonyl)-4-methylenepyrrolidin-3-yl)oxy)-2-fluoro-5-(2,2,2-trifluoroethoxy)benzonitrile (206 mg, 0.375 mmol) and NMO (66 mg, 0.56 mmol) in THF (5 mL) was added $OsO_4$ (2.5% in t-BuOH, 0.24 mL, 0.02 mmol) and the reaction mixture was stirred at rt overnight. The reaction was quenched with $NaHSO_3$ (aq), the THF was removed by concentrating under a stream of nitrogen and DCM (5 mL) was added to the aqueous phase. The organic layer was separated, dried over $Na_2SO_4$, filtered and concentrated. The crude residue was purified by reverse phase HPLC (C18 Sunfire 30×150 mm preparatory column, eluting with a gradient of 10-90% $CH_3CN/H_2O$ (0.1% TFA)). The product fractions were concentrated to give the title compound as a white solid (66 mg, 30% yield). $^1H$ NMR (400 MHz, DMSO-$d_6$) δ: 8.56 (s, 1H), 8.14-8.21 (m, 2H), 7.59 (d, J=6.5 Hz, 1H), 7.45 (d, J=11.3 Hz, 1H), 5.58 (s, 1H), 4.83 (t, J=5.6 Hz, 1H), 4.68 (d, J=2.8 Hz, 1H), 4.49-4.64 (m, 2H), 3.90 (dd, J=12.4, 3.1 Hz, 1H), 3.67 (d, J=12.3 Hz, 1H), 3.48-3.59 (m, 2H), 3.45 (d, J=10.5 Hz, 1H), 3.31 (d, J=10.5 Hz, 1H). MS (m/z) 583.8 (M+H$^+$).

The following compounds were prepared using procedures analogous to those described in Example 157 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 158 | 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-methoxybenzonitrile | 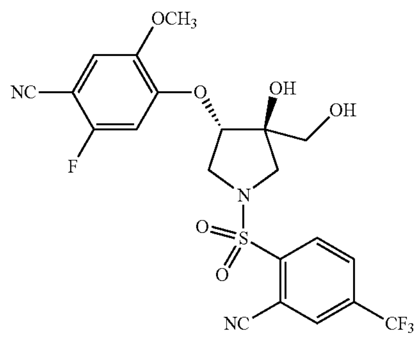 [SMILES: COc1cc(C#N)c(F)cc1O[C@H]1CN(S(=O)(=O)c2ccc(C(F)(F)F)cc2C#N)C[C@@]1(O)CO] | 516.1 | $^1$H NMR (400 MHz, DMSO-$d_6$) δ: 8.60 (s, 1H), 8.15-8.24 (m, 2H), 7.37 (d, J = 6.5 Hz, 1H), 7.31 (d, J = 11.3 Hz, 1H), 5.54 (s, 1H), 4.82 (t, J = 5.5 Hz, 1H), 4.64 (d, J = 3.0 Hz, 1H), 3.87 (dd, J = 12.3, 3.3 Hz, 1H), 3.67 (s, 3H), 3.62 (d, J = 12.0 Hz, 1H), 3.48-3.57 (m, 2H), 3.38-3.47 (m, 2H) |
| 159 | 4-(((3S,4R)-1-((2-cyano-4-(trifluoromethyl)phenyl)sulfonyl)-4-hydroxy-4-(hydroxymethyl)pyrrolidin-3-yl)oxy)-5-ethoxy-2-fluorobenzonitrile | 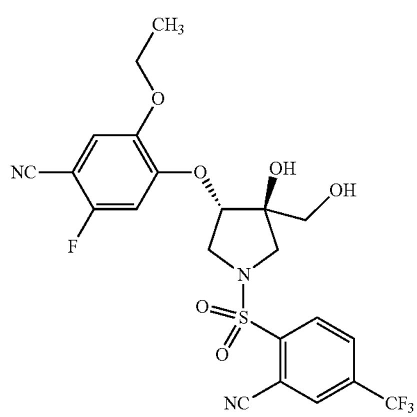 [SMILES: CCOc1cc(C#N)c(F)cc1O[C@H]1CN(S(=O)(=O)c2ccc(C(F)(F)F)cc2C#N)C[C@@]1(O)CO] | 529.8 | $^1$H NMR (400 MHz, DMSO-$d_6$) δ: 8.57 (s, 1H), 8.14-8.23 (m, 2H), 7.25-7.35 (m, 2H), 5.56 (s, 1H), 4.79 (t, J = 5.6 Hz, 1H), 4.61 (d, J = 2.8 Hz, 1H), 3.80-3.91 (m, 3H), 3.63 (d, J = 12.3 Hz, 1H), 3.55 (tt, J = 11.0, 5.6 Hz, 2H), 3.40-3.49 (m, 2H), 1.17-1.25 (m, 3H) |

| Ex. | Name | Structure | MS (m/z) (M + H⁺) | ¹H NMR |
|---|---|---|---|---|
| 160 | 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-propoxybenzonitrile | 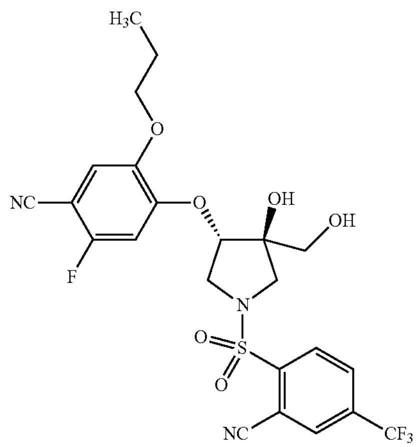 [SMILES: CCCOc1cc(C#N)c(F)cc1O[C@H]1CN(S(=O)(=O)c2ccc(C(F)(F)F)cc2C#N)C[C@@]1(O)CO] | 543.8 | ¹H NMR (400 MHz, DMSO-d₆) δ: 8.56 (s, 1H), 8.16 (s, 2H), 7.25-7.36 (m, 2H), 5.56 (s, 1H), 4.80 (t, J = 5.6 Hz, 1H), 4.62 (d, J = 2.8 Hz, 1H), 3.87 (dd, J = 12.3, 3.0 Hz, 1H), 3.72-3.82 (m, 2H), 3.64 (d, J = 12.3 Hz, 1H), 3.50-3.61 (m, 2H), 3.44 (q, J = 10.3 Hz, 2H), 1.54-1.70 (m, 2H), 0.91 (t, J = 7.4 Hz, 3H) |
| 161 | 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-isopropoxybenzonitrile | 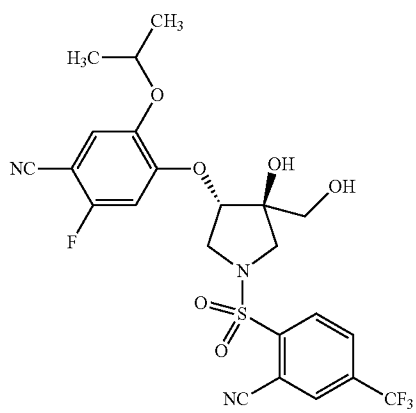 [SMILES: CC(C)Oc1cc(C#N)c(F)cc1O[C@H]1CN(S(=O)(=O)c2ccc(C(F)(F)F)cc2C#N)C[C@@]1(O)CO] | 543.8 | ¹H NMR (400 MHz, DMSO-d₆) δ: 8.56 (s, 1H), 8.14-8.22 (m, 2H), 7.39 (d, J = 6.5 Hz, 1H), 7.31 (d, J = 11.3 Hz, 1H), 5.55 (s, 1H), 4.82 (t, J = 5.6 Hz, 1H), 4.64 (d, J = 2.8 Hz, 1H), 4.28 (dt, J = 12.1, 6.1 Hz, 1H), 3.87 (dd, J = 12.2, 3.1 Hz, 1H), 3.52-3.63 (m, 3H), 3.40-3.49 (m, 2H), 1.13 (dd, J = 14.7, 5.9 Hz, 6H) |
| 162 | 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-hydroxybenzonitrile | 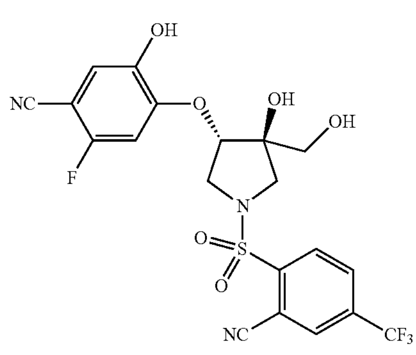 [SMILES: N#Cc1cc(O)c(O[C@H]2CN(S(=O)(=O)c3ccc(C(F)(F)F)cc3C#N)C[C@@]2(O)CO)cc1F] | 501.9 | ¹H NMR (400 MHz, CD₃OD) δ: 8.30 (s, 1H), 8.24 (d, J = 8.3 Hz, 1H), 8.09 (d, J = 8.3 Hz, 1H), 6.94-7.03 (m, 2H), 4.70 (d, J = 2.8 Hz, 1H), 3.98 (dd, J = 12.3, 3.3 Hz, 1H), 3.77-3.87 (m, 2H), 3.69 (dd, J = 11.0, 2.3 Hz, 2H), 3.53-3.61 (m, 1H) |

| Ex. | Name | Structure | MS (m/z) (M + H⁺) | ¹H NMR |
|---|---|---|---|---|
| 163 | 5-(benzyloxy)-4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile | 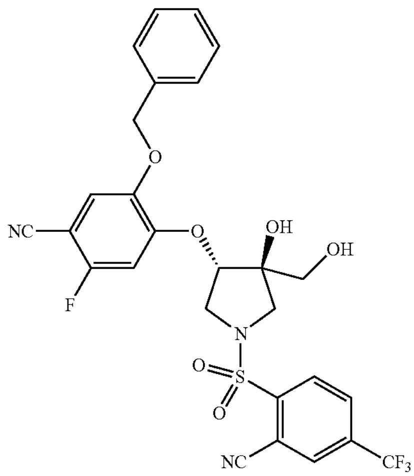 [SMILES: N#Cc1cc(OCc2ccccc2)c(O[C@H]2CN(S(=O)(=O)c3ccc(C(F)(F)F)cc3C#N)C[C@@]2(O)CO)cc1F] | 592.2 | ¹H NMR (400 MHz, DMSO-d₆) δ: 8.47 (d, J = 1.3 Hz, 1H), 8.15-8.20 (m, 1H), 8.09-8.14 (m, 1H), 7.51 (d, J = 6.3 Hz, 1H), 7.29-7.43 (m, 6H), 5.55 (s, 1H), 4.96-5.06 (m, 2H), 4.84 (t, J = 5.6 Hz, 1H), 4.69 (d, J = 3.0 Hz, 1H), 3.88 (dd, J = 12.0, 3.0 Hz, 1H), 3.66 (d, J = 12.3 Hz, 1H), 3.56 (qd, J = 11.0, 5.6 Hz, 2H), 3.45-3.49 (m, 1H), 3.40-3.44 (m, 1H) |
| 164 | 5-butoxy-4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile | 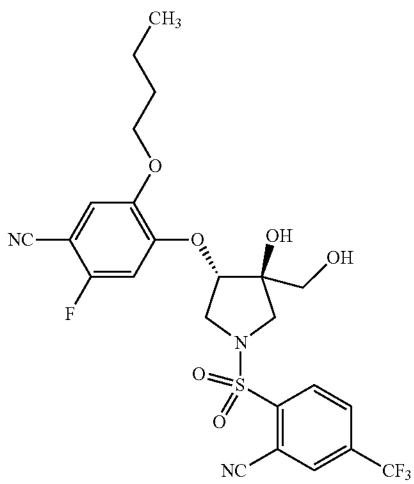 [SMILES: CCCCOc1cc(C#N)c(F)cc1O[C@H]1CN(S(=O)(=O)c2ccc(C(F)(F)F)cc2C#N)C[C@@]1(O)CO] | 558.2 | ¹H NMR (400 MHz, DMSO-d₆) δ: 8.56 (s, 1H), 8.16 (d, J = 1.0 Hz, 2H), 7.24-7.38 (m, 2H), 5.55 (s, 1H), 4.79 (t, J = 5.6 Hz, 1H), 4.62 (d, J = 2.8 Hz, 1H), 3.77-3.91 (m, 3H), 3.63 (d, J = 12.3 Hz, 1H), 3.50-3.60 (m, 2H), 3.38-3.50 (m, 2H), 1.59 (m, 2H), 1.29-1.43 (m, 2H), 0.90 (t, J = 7.4 Hz, 3H) |
| 165 | 4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-isobutoxybenzonitrile | 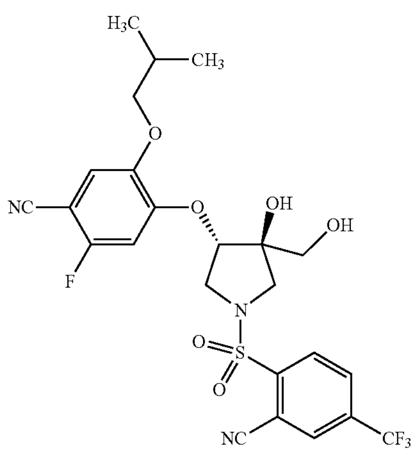 [SMILES: CC(C)COc1cc(C#N)c(F)cc1O[C@H]1CN(S(=O)(=O)c2ccc(C(F)(F)F)cc2C#N)C[C@@]1(O)CO] | 558.3 | ¹H NMR (400 MHz, DMSO-d₆) δ: 8.56 (s, 1H), 8.16 (d, J = 1.0 Hz, 2H), 7.26-7.35 (m, 2H), 5.56 (s, 1H), 4.82 (t, J = 5.6 Hz, 1H), 4.63 (d, J = 2.8 Hz, 1H), 3.88 (dd, J = 12.2, 2.9 Hz, 1H), 3.51-3.68 (m, 5H), 3.44-3.50 (m, 1H), 3.36-3.42 (m, 1H), 1.89 (dt, J = 13.1, 6.6 Hz, 1H), 0.91 (d, J = 6.8 Hz, 6H) |

| Ex. | Name | Structure | MS (m/z) (M + H⁺) | ¹H NMR |
|---|---|---|---|---|
| 166 | 2-(((3R,4S)-4-(4-cyano-2-propoxyphenoxy)-3-hydroxy-3-(hydroxymethyl)pyrrolidin-1-yl)sulfonyl)-5-(trifluoromethyl)benzonitrile | 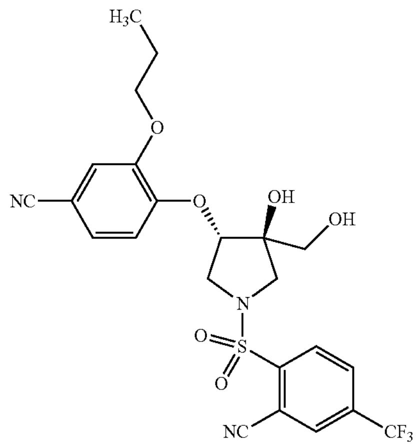 [SMILES: CCCOc1cc(C#N)ccc1O[C@H]1CN(S(=O)(=O)c2ccc(C(F)(F)F)cc2C#N)C[C@@]1(O)CO] | 526.2 | $^1$H NMR (400 MHz, DMSO-$d_6$) δ: 8.55 (s, 1H), 8.14 (d, J = 1.0 Hz, 2H), 7.27-7.37 (m, 2H), 7.07 (d, J = 8.3 Hz, 1H), 5.50 (s, 1H), 4.78 (t, J = 5.6 Hz, 1H), 4.59 (d, J = 3.0 Hz, 1H), 3.79-3.88 (m, 3H), 3.54-3.64 (m, 3H), 3.44-3.51 (m, 2H), 1.61-1.71 (m, 2H), 0.94 (t, J = 7.4 Hz, 3H) |
| 167 | 2-(((3R,4S)-4-(4-cyano-2-(2,2,2-trifluoroethoxy)phenoxy)-3-hydroxy-3-(hydroxymethyl)pyrrolidin-1-yl)sulfonyl)-5-(trifluoromethyl)benzonitrile | 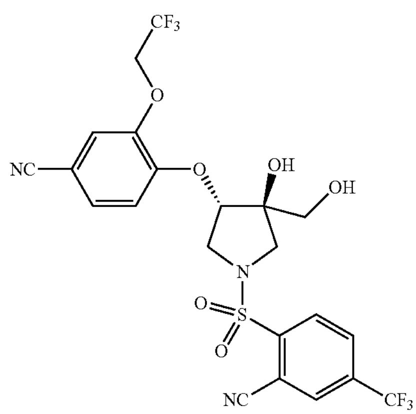 [SMILES: N#Cc1ccc(O[C@H]2CN(S(=O)(=O)c3ccc(C(F)(F)F)cc3C#N)C[C@@]2(O)CO)c(OCC(F)(F)F)c1] | 566.2 | $^1$H NMR (400 MHz, DMSO-$d_6$) δ: 8.55 (s, 1H), 8.13-8.20 (m, 2H), 7.48-7.57 (m, 2H), 7.22 (d, J = 8.5 Hz, 1H), 5.52 (s, 1H), 4.81 (t, J = 5.6 Hz, 1H), 4.54-4.73 (m, 3H), 3.89 (dd, J = 12.0, 3.0 Hz, 1H), 3.63 (d, J = 11.8 Hz, 1H), 3.50-3.59 (m, 2H), 3.42-3.48 (m, 1H), 3.35-3.40 (m, 1H) |
| 168 | 2-(((3R,4S)-4-(4-cyano-2-hydroxyphenoxy)-3-hydroxy-3-(hydroxymethyl)pyrrolidin-1-yl)sulfonyl)-5-(trifluoromethyl)benzonitrile | 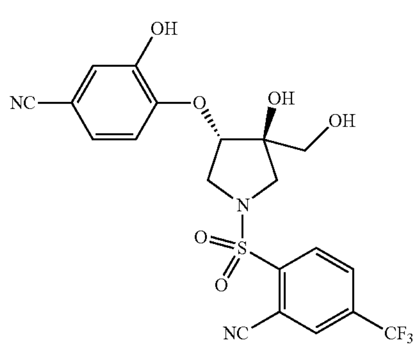 [SMILES: N#Cc1ccc(O[C@H]2CN(S(=O)(=O)c3ccc(C(F)(F)F)cc3C#N)C[C@@]2(O)CO)c(O)c1] | 483.8 | $^1$H NMR (400 MHz, DMSO-$d_6$) δ: 9.37 (br s, 1H), 8.52 (s, 1H), 8.09-8.18 (m, 2H), 7.20 (dd, J = 8.3, 2.0 Hz, 1H), 7.01-7.08 (m, 2H), 5.43 (s, 1H), 4.82 (br s, 1H), 4.62 (d, J = 2.8 Hz, 1H), 3.83 (dd, J = 11.8, 3.0 Hz, 1H), 3.63-3.70 (m, 2H), 3.50-3.61 (m, 2H), 3.40 (d, J = 10.3 Hz, 1H) |

-continued

| Ex. | Name | Structure | MS (m/z) (M + H⁺) | ¹H NMR |
|---|---|---|---|---|
| 169 | 2-(((3R,4S)-4-(2-butoxy-4-cyanophenoxy)-3-hydroxy-3-(hydroxymethyl)pyrrolidin-1-yl)sulfonyl)-5-(trifluoromethyl)benzonitrile | 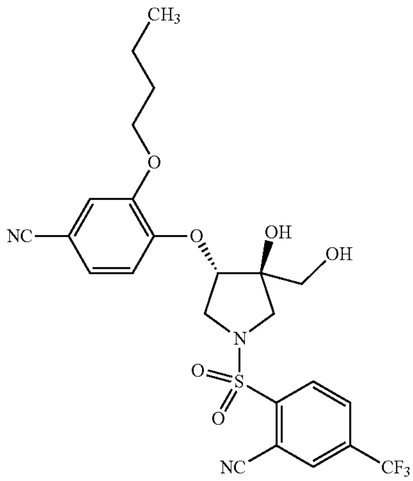 [SMILES: CCCCOc1cc(C#N)ccc1O[C@H]1CN(S(=O)(=O)c2ccc(C(F)(F)F)cc2C#N)C[C@@]1(O)CO] | 540.2 | $^{1}$H NMR (400 MHz, DMSO-$d_6$) δ: 8.54 (s, 1H), 8.15 (s, 2H), 7.28-7.36 (m, 2H), 7.07 (d, J = 8.3 Hz, 1H), 5.49 (s, 1H), 4.77 (t, J = 5.6 Hz, 1H), 4.59 (d, J = 2.8 Hz, 1H), 3.82-3.90 (m, 3H), 3.53-3.65 (m, 3H), 3.43-3.50 (m, 2H), 1.63 (m, 2H), 1.33-1.45 (m, 2H), 0.92 (t, J = 7.4 Hz, 3H) |
| 170 | 2-(((3R,4S)-4-(4-cyano-2-isobutoxyphenoxy)-3-hydroxy-3-(hydroxymethyl)pyrrolidin-1-yl)sulfonyl)-5-(trifluoromethyl)benzonitrile | 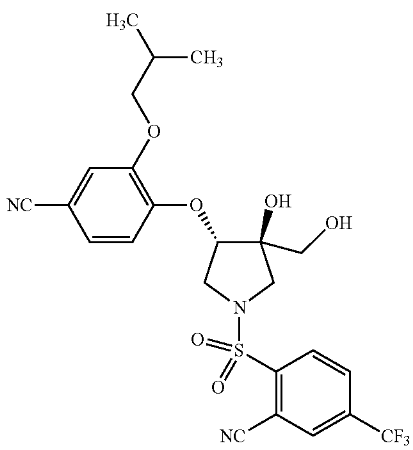 [SMILES: CC(C)COc1cc(C#N)ccc1O[C@H]1CN(S(=O)(=O)c2ccc(C(F)(F)F)cc2C#N)C[C@@]1(O)CO] | 540.2 | $^{1}$H NMR (400 MHz, DMSO-$d_6$) δ: 8.55 (s, 1H), 8.14 (d, J = 1.0 Hz, 2H), 7.27-7.37 (m, 2H), 7.08 (d, J = 8.3 Hz, 1H), 5.50 (s, 1H), 4.79 (t, J = 5.6 Hz, 1H), 4.61 (d, J = 2.8 Hz, 1H), 3.86 (dd, J = 11.9, 3.1 Hz, 1H), 3.54-3.69 (m, 5H), 3.46 (s, 2H), 1.89-2.00 (m, 1H), 0.93 (d, J = 6.8 Hz, 6H) |
| 171 | 2-(((3R,4S)-4-(2-(benzyloxy)-4-cyanophenoxy)-3-hydroxy-3-(hydroxymethyl)pyrrolidin-1-yl)sulfonyl)-5-(trifluoromethyl)benzonitrile | 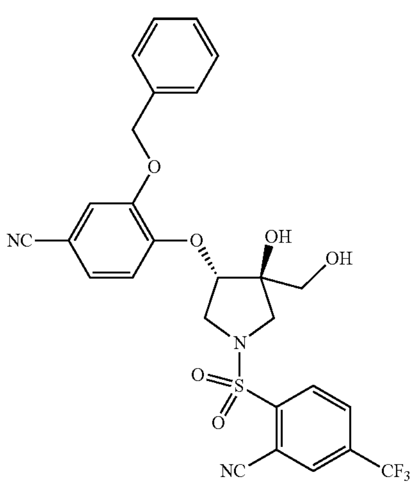 [SMILES: N#Cc1ccc(O[C@H]2CN(S(=O)(=O)c3ccc(C(F)(F)F)cc3C#N)C[C@@]2(O)CO)c(OCc2ccccc2)c1] | 574.2 | $^{1}$H NMR (400 MHz, DMSO-$d_6$) δ: 8.48 (s, 1H), 8.08-8.18 (m, 2H), 7.48 (d, J = 1.8 Hz, 1H), 7.31-7.43 (m, 6H), 7.16 (d, J = 8.5 Hz, 1H), 5.49 (s, 1H), 5.02-5.12 (m, 2H), 4.82 (t, J = 5.6 Hz, 1H), 4.67 (d, J = 3.0 Hz, 1H), 3.86 (dd, J = 11.8, 3.3 Hz, 1H), 3.53-3.65 (m, 3H), 3.47 (s, 2H) |

Example 172

4-(((3S,4R)-1-((4-cyanophenyl)sulfonyl)-4-hydroxy-4-(hydroxymethyl)pyrrolidin-3-yl)oxy)-3-(2,2,2-trifluoroethoxy)benzonitrile

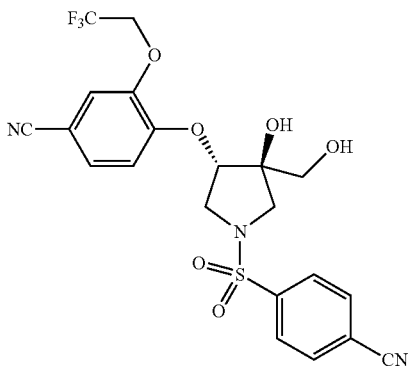 [SMILES: N#Cc1ccc(S(=O)(=O)N2C[C@H](Oc3ccc(C#N)cc3OCC(F)(F)F)[C@](O)(CO)C2)cc1]

Step 1: (R)-tert-butyl 3-(2-acetoxy-4-cyanophenoxy)-4-methylenepyrrolidine-1-carboxylate

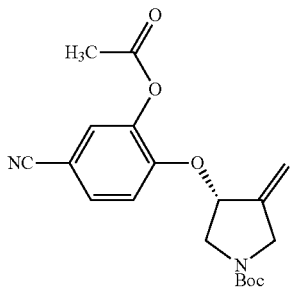 [SMILES: C=C1CN(C(=O)OC(C)(C)C)C[C@@H]1Oc1ccc(C#N)cc1OC(C)=O]

DIAD (3.05 mL, 15.7 mmol) was slowly added to a mixture of 5-cyano-2-hydroxyphenyl acetate (2.9 g, 14 mmol), PS—PPh₃ (3 mmol/g) (6.3 g, 19 mmol) and (S)-tert-butyl 3-hydroxy-4-methylenepyrrolidine-1-carboxylate (2.5 g, 13 mmol) in DCM (125 mL) and the reaction mixture was at rt for 15 h. The reaction mixture was filtered and concentrated and the resulting orange oil purified by flash column chromatography (SiO₂) eluting with a gradient of 0-50% EtOAc in hexanes. The product fractions were pooled and concentrated to a white solid. The solid was triturated with 20% Et₂O in hexanes (75 mL) and filtered and the filtrate concentrated to give the title compound as a colorless oil (1.26 g, 22% yield). MS (m/z) 381.0 (M+H⁺-t-Bu).

Step 2: (R)-tert-butyl 3-(4-cyano-2-hydroxyphenoxy)-4-methylenepyrrolidine-1-carboxylate

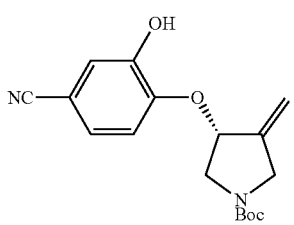 [SMILES: C=C1CN(C(=O)OC(C)(C)C)C[C@@H]1Oc1ccc(C#N)cc1O]

To a solution of (R)-tert-butyl 3-(2-acetoxy-4-cyanophenoxy)-4-methylenepyrrolidine-1-carboxylate (1.25 g, 3.49 mmol) in THF (26 mL) was added water (9 mL) and 2 M NaOH (aq) (8.7 mL, 17 mmol) and the reaction mixture was stirred at rt for 1 h. 1 N HCl (aq) was added to the reaction to adjust the pH=5, and the mixture was extracted with EtOAc (2×35 mL). The combined organic layers were washed with brine (2×15 mL), dried over MgSO₄, filtered and concentrated. The resulting crude oil was purified by flash column chromatography (SiO₂) eluting with a gradient of 0-45% EtOAc in hexanes. The product fractions were pooled and concentrated to give the title compound as a colorless oil (913 mg, 70% yield). MS (m/z) 261.0 (M+H⁺-t-Bu).

Step 3: (R)-tert-butyl 3-(4-cyano-2-(2,2,2-trifluoroethoxy)phenoxy)-4-methylenepyrrolidine-1-carboxylate

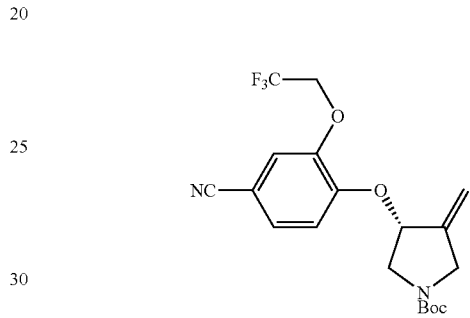

To a solution of (R)-tert-butyl 3-(4-cyano-2-hydroxyphenoxy)-4-methylenepyrrolidine-1-carboxylate (0.908 g, 2.87 mmol) in DMF (20 mL) was added K₂CO₃ (0.80 g, 5.7 mmol) and 2,2,2-trifluoroethyltrifluoromethanesulfonate (0.52 mL, 3.6 mmol) and the reaction mixture was at rt for 1 h. Water (50 mL) was added over 5 min and the mixture extracted with Et₂O:EtOAc (2:1) (2×30 mL). The combined organic extracts were washed with water (3×20 mL), dried over Na₂SO₄, filtered, and concentrated. The crude yellow oil was purified by flash column chromatography (SiO₂) eluting with a gradient of 0-45% EtOAc in hexanes. The product fractions were pooled and concentrated to give the title compound as a colorless oil (808 mg, 67% yield). MS (m/z) 343.0 (M+H⁺-t-Bu).

Step 4: (3R,4S)-tert-butyl 4-(4-cyano-2-(2,2,2-trifluoroethoxy)phenoxy)-3-hydroxy-3-(hydroxymethyl)pyrrolidine-1-carboxylate

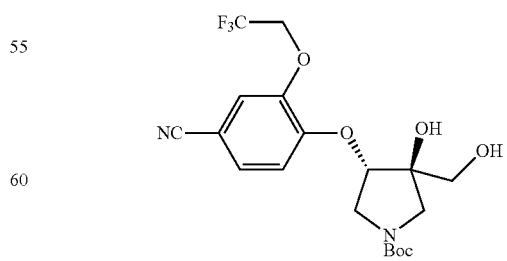

To a solution of (R)-tert-butyl 3-(4-cyano-2-(2,2,2-trifluoroethoxy)phenoxy)-4-methylenepyrrolidine-1-carboxylate (0.80 g, 2.0 mmol) in THF (25 mL) was added NMO (0.353 g, 3.01 mmol). The mixture was cooled to −78° C., OsO₄ (2.5% in t-BuOH, 1.0 mL, 0.08 mmol) was added over 5 min and the reaction mixture was allowed to warm to rt overnight. The reaction mixture was treated with sat'd NaHSO₃ (aq) (4 mL), stirred for 1 h, and then EtOAc (5 mL) was added and the biphasic mixture filtered through celite followed by rinsing with EtOAc (4×5 mL). The filtrate was diluted with EtOAc (10 mL), washed with water (20 mL) and brine (2×10 mL), dried over MgSO₄, filtered and concentrated. The crude orange oil was purified by flash column chromatography (SiO₂) eluting with a gradient of 0-80% EtOAc in hexanes. The product fractions were pooled and concentrated to give the title compound as a colorless oil (710 mg, 78% yield). MS (m/z) 333.0 (M+H$^{+-}$Boc).

Step 5: 4-(((3S,4R)-4-hydroxy-4-(hydroxymethyl)pyrrolidin-3-yl)oxy)-3-(2,2,2-trifluoroethoxy)benzonitrile, Hydrochloride

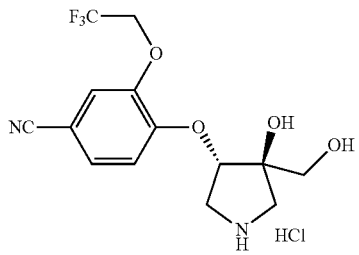 [SMILES: N#Cc1ccc(O[C@H]2CNC[C@@]2(O)CO)c(OCC(F)(F)F)c1 ; Cl]

4 N HCl in dioxane (2.04 mL, 8.15 mmol) was added to a solution of (3R,4S)-tert-butyl 4-(4-cyano-2-(2,2,2-trifluoroethoxy)phenoxy)-3-hydroxy-3-(hydroxymethyl)pyrrolidine-1-carboxylate (0.705 g, 1.63 mmol) in 1,4-dioxane (16 mL) and the reaction mixture was stirred at rt for 90 min. Additional 4 M HCl in dioxane (3×2 mL, 8.2 mmol) was added to the reaction with stirring a total of 26 h in order to drive the reaction to completion. The reaction mixture was concentrated under reduced pressure. The resulting solid was triturated with Et₂O and the title compound was collected by filtration as a pale orange solid (555 mg, 88% yield). MS (m/z) 333.0 (M+H⁺).

Step 6: 4-(((3S,4R)-1-((4-cyanophenyl)sulfonyl)-4-hydroxy-4-(hydroxymethyl)pyrrolidin-3-yl)oxy)-3-(2,2,2-trifluoroethoxy)benzonitrile To a biphasic mixture of 4-(((3S,4R)-4-hydroxy-4-(hydroxymethyl)pyrrolidin-3-yl)oxy)-3-(2,2,2-trifluoroethoxy)benzonitrile, Hydrochloride (50 mg, 0.14 mmol) in THF (1.36 ml) and sat'd NaHCO₃ (aq) (0.75 mL) was added 4-cyanobenzene-1-sulfonyl chloride (33 mg, 0.16 mmol) and the mixture was stirred at rt overnight. The reaction mixture was treated with water (5 mL) and extracted with EtOAc (2×10 mL). The organic layers were combined and washed with brine (5 mL), dried over MgSO₄, filtered, and concentrated. The resulting crude white solid was purified by flash column chromatography (SiO₂) eluting with a gradient of 5-70% EtOAc in hexanes. The product fractions were pooled and concentrated to give the title compound as a white solid (55 mg, 76% yield). ¹H NMR (400 MHz, DMSO-d₆) δ: 7.94 (d, J=8.3 Hz, 2H), 7.84 (d, J=8.3 Hz, 2H), 7.57 (s, 1H), 7.49 (d, J=8.3 Hz, 1H), 7.14 (d, J=8.5 Hz, 1H), 5.34 (s, 1H), 4.59-4.76 (m, 3H), 4.56 (d, J=2.5 Hz, 1H), 3.74 (dd, J=11.9, 2.9 Hz, 1H), 3.46-3.60 (m, 2H), 3.43 (d, J=12.0 Hz, 1H), 3.33-3.38 (m, 1H), 3.24 (d, J=10.3 Hz, 1H). MS (m/z) 498.1 (M+H⁺).

The following compounds were prepared using procedures analogous to those described in Example 172 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 173 | 4-(((3S,4R)-1-((2-cyanophenyl)sulfonyl)-4-hydroxy-4-(hydroxymethyl)pyrrolidin-3-yl)oxy)-2-fluoro-5-(2,2,2-trifluoroethoxy)benzonitrile | 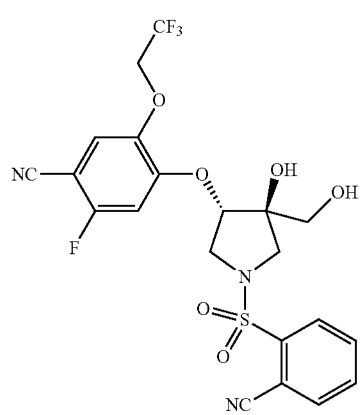 [SMILES: N#Cc1cc(OCC(F)(F)F)c(O[C@H]2CN(S(=O)(=O)c3ccccc3C#N)C[C@@]2(O)CO)cc1F] | 516.0 | ¹H NMR (400 MHz, DMSO-d₆) δ: 7.98-8.02 (m, 1H), 7.92-7.96 (m, 1H), 7.77-7.82 (m, 2H), 7.55 (d, J = 6.3 Hz, 1H), 7.42 (d, J = 11.0 Hz, 1H), 5.54 (s, 1H), 4.81 (t, J = 5.6 Hz, 1H), 4.65 (d, J = 3.0 Hz, 1H), 4.54-4.64 (m, 2H), 3.85 (dd, J = 12.3, 3.0 Hz, 1H), 3.63 (d, J = 12.0 Hz, 1H), 3.47-3.59 (m, 2H), 3.41 (d, J = 10.3 Hz, 1H), 3.29 (d, J = 10.5 Hz, 1H) |

-continued

| Ex. | Name | Structure | MS (m/z) (M + H⁺) | ¹H NMR |
|---|---|---|---|---|
| 174 | 5-(((3R,4S)-4-(4-cyano-5-fluoro-2-(2,2,2-trifluoroethoxy)phenoxy)-3-hydroxy-3-(hydroxymethyl)pyrrolidin-1-yl)sulfonyl)picolinonitrile | 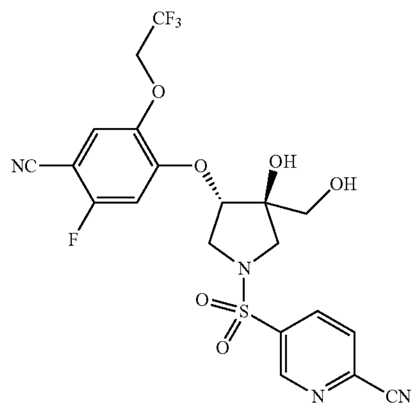 [SMILES: N#Cc1ccc(S(=O)(=O)N2C[C@H](Oc3cc(F)c(C#N)cc3OCC(F)(F)F)[C@](O)(CO)C2)cn1] | 517.0 | ¹H NMR (400 MHz, DMSO-d₆) δ: 9.02 (d, J = 2.3 Hz, 1H), 8.38 (dd, J = 8.3, 2.3 Hz, 1H), 8.18 (d, J = 8.0 Hz, 1H), 7.64 (d, J = 6.3 Hz, 1H), 7.36 (d, J = 11.3 Hz, 1H), 5.45 (s, 1H), 4.79 (t, J = 5.6 Hz, 1H), 4.54-4.69 (m, 3H), 3.78 (dd, J = 12.5, 3.3 Hz, 1H), 3.44-3.58 (m, 3H), 3.40 (d, J = 10.8 Hz, 1H), 3.21 (d, J = 10.8 Hz, 1H) |
| 175 | 2-fluoro-4-(((3S,4R)-4-hydroxy-4-(hydroxymethyl)-1-((6-(trifluoromethyl)pyridin-3-yl)sulfonyl)pyrrolidin-3-yl)oxy)-5-(2,2,2-trifluoroethoxy)benzonitrile | 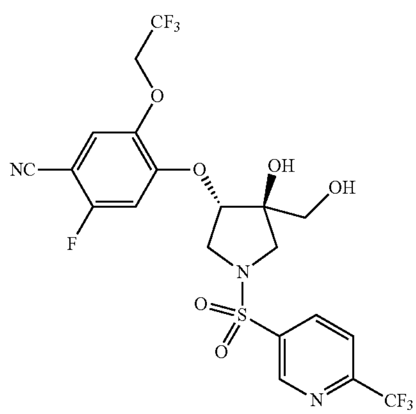 [SMILES: N#Cc1cc(OCC(F)(F)F)c(O[C@H]2CN(S(=O)(=O)c3ccc(C(F)(F)F)nc3)C[C@@]2(O)CO)cc1F] | 560.0 | ¹H NMR (400 MHz, DMSO-d₆) δ: 9.06 (d, J = 2.0 Hz, 1H), 8.43 (dd, J = 8.2, 1.9 Hz, 1H), 8.04 (d, J = 8.0 Hz, 1H), 7.59 (d, J = 6.5 Hz, 1H), 7.36 (d, J = 11.3 Hz, 1H), 5.46 (s, 1H), 4.80 (t, J = 5.6 Hz, 1H), 4.47-4.65 (m, 3H), 3.78 (dd, J = 12.3, 3.3 Hz, 1H), 3.45-3.56 (m, 3H), 3.42 (d, J = 10.5 Hz, 1H), 3.26 (d, J = 10.8 Hz, 1H) |
| 176 | 2-fluoro-4-(((3S,4R)-4-hydroxy-4-(hydroxymethyl)-1-(phenylsulfonyl)pyrrolidin-3-yl)oxy)-5-(2,2,2-trifluoroethoxy)benzonitrile | 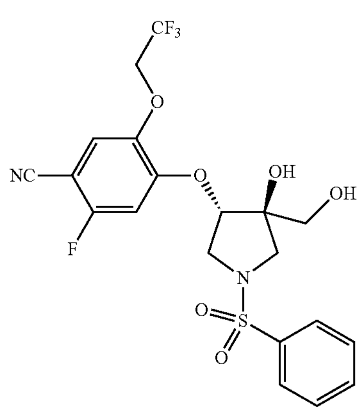 [SMILES: N#Cc1cc(OCC(F)(F)F)c(O[C@H]2CN(S(=O)(=O)c3ccccc3)C[C@@]2(O)CO)cc1F] | 491.0 | ¹H NMR (400 MHz, DMSO-d₆) δ: 7.59-7.70 (m, 3H), 7.54 (d, J = 6.3 Hz, 1H), 7.43-7.50 (m, 2H), 7.32 (d, J = 11.0 Hz, 1H), 5.37 (s, 1H), 4.74 (t, J = 5.8 Hz, 1H), 4.52-4.67 (m, 3H), 3.70 (dd, J = 12.2, 3.4 Hz, 1H), 3.45-3.57 (m, 2H), 3.41 (d, J = 12.0 Hz, 1H), 3.31 (d, J = 10.3 Hz, 1H), 3.19-3.24 (m, 1H) |

| Ex. | Name | Structure | MS (m/z) (M + H⁺) | ¹H NMR |
|---|---|---|---|---|
| 177 | 4-(((3S,4R)-1-((2,4-dichlorophenyl)sulfonyl)-4-hydroxy-4-(hydroxymethyl)pyrrolidin-3-yl)oxy)-2-fluoro-5-(2,2,2-trifluoroethoxy)benzonitrile | 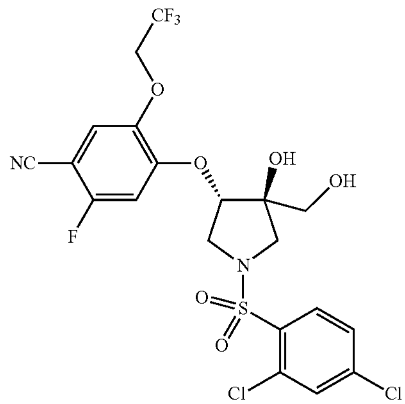 [SMILES: N#Cc1cc(OCC(F)(F)F)c(O[C@H]2CN(S(=O)(=O)c3ccc(Cl)cc3Cl)C[C@@]2(O)CO)cc1F] | 558.9 | ¹H NMR (400 MHz, DMSO-d₆) δ: 7.90 (d, J = 8.5 Hz, 1H), 7.80 (d, J = 2.3 Hz, 1H), 7.64 (d, J = 6.5 Hz, 1H), 7.53 (dd, J = 8.5, 2.3 Hz, 1H), 7.42 (d, J = 11.3 Hz, 1H), 5.58 (s, 1H), 4.83 (t, J = 5.8 Hz, 1H), 4.61-4.73 (m, 3H), 3.88 (dd, J = 11.9, 3.1 Hz, 1H), 3.50-3.64 (m, 3H), 3.37-3.41 (m, 1H), 3.36 (m, 1H, partially hidden by solvent peak) |
| 178 | 4-(((3S,4R)-1-((4-cyanophenyl)sulfonyl)-4-hydroxy-4-(hydroxymethyl)pyrrolidin-3-yl)oxy)-2-fluoro-5-(2,2,2-trifluoroethoxy)benzonitrile | 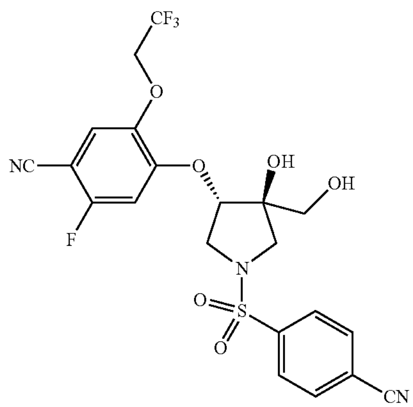 | 515.9 | ¹H NMR (400 MHz, DMSO-d₆) δ: 7.94 (d, J = 8.3 Hz, 2H), 7.82-7.87 (m, 2H), 7.61 (d, J = 6.3 Hz, 1H), 7.34 (d, J = 11.0 Hz, 1H), 5.45 (s, 1H), 4.77 (t, J = 5.8 Hz, 1H), 4.52-4.66 (m, 3H), 3.75 (dd, J = 12.4, 3.1 Hz, 1H), 3.43-3.55 (m, 3H), 3.35 (d, 1H, obscured by solvent peak), 3.17 (d, J = 10.5 Hz, 1H) |
| 179 | 4-(((3S,4R)-1-((2-cyanophenyl)sulfonyl)-4-hydroxy-4-(hydroxymethyl)pyrrolidin-3-yl)oxy)-2-fluoro-5-isobutoxybenzonitrile | 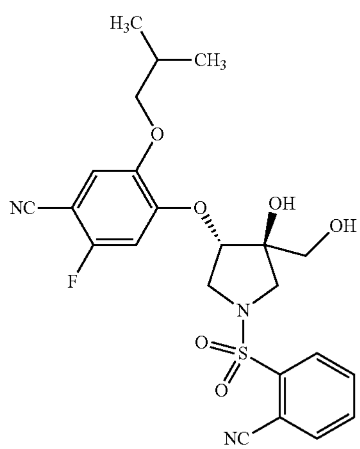 [SMILES: CC(C)COc1cc(C#N)c(F)cc1O[C@H]1CN(S(=O)(=O)c2ccccc2C#N)C[C@@]1(O)CO] | 489.9 | ¹H NMR (400 MHz, DMSO-d₆) δ: 7.97-8.02 (m, 1H), 7.90-7.96 (m, 1H), 7.75-7.82 (m, 2H), 7.25-7.35 (m, 2H), 5.52 (s, 1H), 4.79 (t, J = 5.5 Hz, 1H), 4.62 (d, J = 2.8 Hz, 1H), 3.84 (dd, J = 12.2, 3.1 Hz, 1H), 3.50-3.69 (m, 5H), 3.37-3.45 (m, 2H), 1.86-1.94 (m, 1H), 0.92 (dd, J = 6.5, 5.8 Hz, 6H) |

| Ex. | Name | Structure | MS (m/z) (M + H+) | 1H NMR |
|---|---|---|---|---|
| 180 | 4-(((3S,4R)-1-((4-cyanophenyl)sulfonyl)-4-hydroxy-4-(hydroxymethyl)pyrrolidin-3-yl)oxy)-2-fluoro-5-isobutoxybenzonitrile | 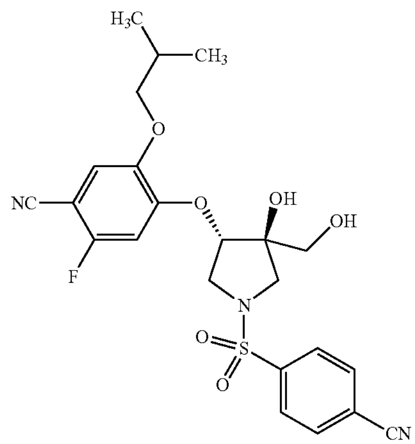 [SMILES: CC(C)COc1cc(C#N)c(F)cc1O[C@H]1CN(S(=O)(=O)c2ccc(C#N)cc2)C[C@@]1(O)CO] | 490.4 | 1H NMR (400 MHz, DMSO-d6) δ: 7.91 (d, J = 8.0 Hz, 2H), 7.78-7.86 (m, 2H), 7.33 (d, J = 6.0 Hz, 1H), 7.20 (d, J = 11.0 Hz, 1H), 5.45 (s, 1H), 4.74 (t, J = 5.5 Hz, 1H), 4.51 (br s, 1H), 3.76 (d, J = 10.5 Hz, 1H), 3.63-3.70 (m, 1H), 3.45-3.62 (m, 4H), 3.37 (1H, partially hidden by solvent peak), 3.15 (d, J = 10.3 Hz, 1H), 1.80-1.96 (m, 1H), 0.92 (t, J = 7.8 Hz, 6H) |
| 181 | 5-(((3R,4S)-4-(4-cyano-5-fluoro-2-isobutoxyphenoxy)-3-hydroxy-3-(hydroxymethyl)pyrrolidin-1-yl)sulfonyl)picolinonitrile | 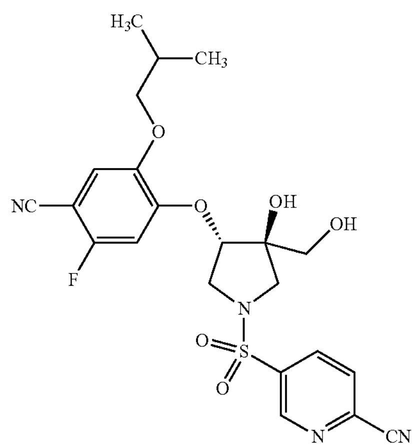 [SMILES: CC(C)COc1cc(C#N)c(F)cc1O[C@H]1CN(S(=O)(=O)c2ccc(C#N)nc2)C[C@@]1(O)CO] | 491.0 | 1H NMR (400 MHz, DMSO-d6) δ: 9.01 (s, 1H), 8.34 (dd, J = 8.2, 2.1 Hz, 1H), 8.12 (d, J = 8.0 Hz, 1H), 7.35 (d, J = 6.3 Hz, 1H), 7.22 (d, J = 11.0 Hz, 1H), 5.47 (s, 1H), 4.76 (t, J = 5.6 Hz, 1H), 4.54 (d, J = 2.8 Hz, 1H), 3.79 (d, J = 9.5 Hz, 1H), 3.70 (dd, J = 9.0, 5.8 Hz, 1H), 3.47-3.63 (m, 4H), 3.40 (d, J = 10.8 Hz, 1H), 3.20 (d, J = 10.8 Hz, 1H), 1.92 (dt, J = 12.8, 6.7 Hz, 1H), 0.93 (dd, J = 9.2, 6.9 Hz, 6H) |
| 182 | 2-fluoro-4-(((3S,4R)-4-hydroxy-4-(hydroxymethyl)-1-((4-(trifluoromethyl)phenyl)sulfonyl)pyrrolidin-3-yl)oxy)-5-isobutoxybenzonitrile | 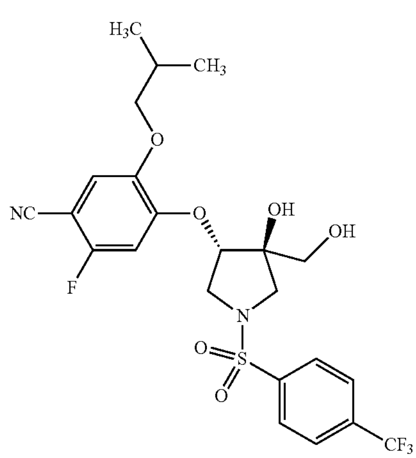 [SMILES: CC(C)COc1cc(C#N)c(F)cc1O[C@H]1CN(S(=O)(=O)c2ccc(C(F)(F)F)cc2)C[C@@]1(O)CO] | 532.8 | 1H NMR (400 MHz, DMSO-d6) δ: 7.87-7.92 (m, 2H), 7.81-7.86 (m, 2H), 7.29 (d, J = 6.3 Hz, 1H), 7.20 (d, J = 11.3 Hz, 1H), 5.42 (s, 1H), 4.74 (t, J = 5.6 Hz, 1H), 4.54 (s, 1H), 3.74 (d, J = 8.8 Hz, 1H), 3.43-3.62 (m, 5H), 3.35-3.40 (m, 1H, partially hidden by solvent peak), 3.24 (d, J = 10.0 Hz, 1H), 1.83-1.94 (m, 1H), 0.91 (d, J = 6.5 Hz, 6H) |

| Ex. | Name | Structure | MS (m/z) (M + H+) | 1H NMR |
|---|---|---|---|---|
| 183 | 2-fluoro-4-(((3S,4R)-4-hydroxy-4-(hydroxymethyl)-1-((6-(trifluoromethyl)pyridin-3-yl)sulfonyl)pyrrolidin-3-yl)oxy)-5-isobutoxybenzonitrile | 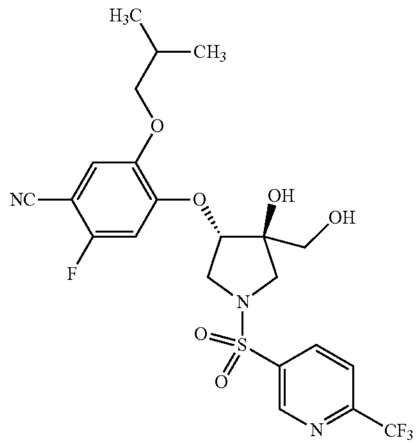 [SMILES: CC(C)COc1cc(C#N)c(F)cc1O[C@H]1CN(S(=O)(=O)c2ccc(C(F)(F)F)nc2)C[C@@]1(O)CO] | 533.8 | 1H NMR (400 MHz, DMSO-d6) δ: 9.06 (s, 1H), 8.42 (d, J = 8.0 Hz, 1H), 8.03 (d, J = 8.3 Hz, 1H), 7.32 (d, J = 6.3 Hz, 1H), 7.23 (d, J = 11.0 Hz, 1H), 5.43 (s, 1H), 4.76 (t, J = 5.5 Hz, 1H), 4.58 (s, 1H), 3.77 (dd, J = 12.5, 3.0 Hz, 1H), 3.61 (d, J = 6.3 Hz, 2H), 3.49-3.58 (m, 3H), 3.43 (d, J = 10.8 Hz, 1H), 3.29 (d, J = 10.8 Hz, 1H), 1.91 (dt, J = 12.9, 6.6 Hz, 1H), 0.92 (d, J = 6.5 Hz, 6H) |
| 184 | 5-(((3R,4S)-4-(4-cyano-2-(2,2,2-trifluoroethoxy)phenoxy)-3-hydroxy-3-(hydroxymethyl)pyrrolidin-1-yl)sulfonyl)picolinonitrile | 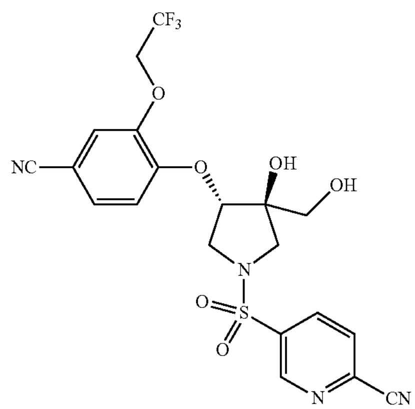 [SMILES: N#Cc1ccc(O[C@H]2CN(S(=O)(=O)c3ccc(C#N)nc3)C[C@@]2(O)CO)c(OCC(F)(F)F)c1] | 499.1 | 1H NMR (400 MHz, DMSO-d6) δ: 9.00 (s, 1H), 8.33-8.39 (m, 1H), 8.18 (d, J = 8.0 Hz, 1H), 7.59 (s, 1H), 7.51 (d, J = 8.3 Hz, 1H), 7.17 (d, J = 8.3 Hz, 1H), 5.35 (s, 1H), 4.56-4.76 (m, 4H), 3.77 (dd, J = 12.0, 2.8 Hz, 1H), 3.46-3.59 (m, 3H), 3.40 (d, J = 10.8 Hz, 1H), 3.25-3.30 (m, 1H) |
| 185 | 4-(((3S,4R)-1-((2-cyanophenyl)sulfonyl)-4-hydroxy-4-(hydroxymethyl)pyrrolidin-3-yl)oxy)-3-(2,2,2-trifluoroethoxy)benzonitrile | 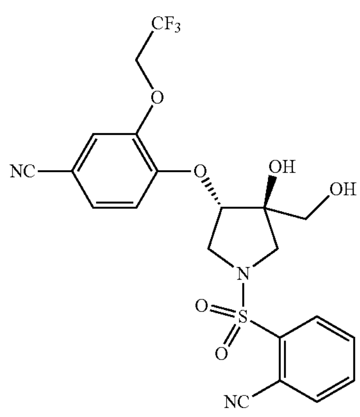 [SMILES: N#Cc1ccc(O[C@H]2CN(S(=O)(=O)c3ccccc3C#N)C[C@@]2(O)CO)c(OCC(F)(F)F)c1] | 498.2 | 1H NMR (400 MHz, DMSO-d6) δ: 7.97-8.01 (m, 1H), 7.90-7.95 (m, 1H), 7.78 (m, 2H), 7.46-7.53 (m, 2H), 7.19 (d, J = 8.5 Hz, 1H), 5.48 (br s, 1H), 4.56-4.83 (m, 4H), 3.84 (dd, J = 12.0, 3.3 Hz, 1H), 3.60 (1H, partially hidden under solvent peak), 3.49-3.55 (m, 1H), 3.32-3.44 (m, 2H) |

-continued

| Ex. | Name | Structure | MS (m/z) (M + H⁺) | ¹H NMR |
|---|---|---|---|---|
| 186 | 4-(((3S,4R)-1-((5-chloropyridin-2-yl)sulfonyl)-4-hydroxy-4-(hydroxymethyl)pyrrolidin-3-yl)oxy)-3-(2,2,2-trifluoroethoxy)benzonitrile | 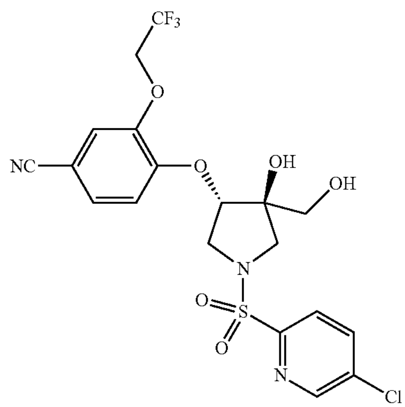 [SMILES: N#Cc1ccc(O[C@H]2CN(S(=O)(=O)c3ccc(Cl)cn3)C[C@@]2(O)CO)c(OCC(F)(F)F)c1] | 508.0 | $^1$H NMR (400 MHz, DMSO-d$_6$) δ: 8.36 (d, J = 2.3 Hz, 1H), 8.08 (dd, J = 8.4, 2.4 Hz, 1H), 7.83 (d, J = 8.5 Hz, 1H), 7.58 (s, 1H), 7.51 (d, J = 8.5 Hz, 1H), 7.15 (d, J = 8.5 Hz, 1H), 5.39 (s, 1H), 4.59-4.75 (m, 3H), 4.53 (d, J = 2.8 Hz, 1H), 3.89 (dd, J = 12.3, 3.0 Hz, 1H), 3.69 (d, J = 12.0 Hz, 1H), 3.46-3.58 (m, 2H), 3.35-3.40 (m, 1H, partially hidden by solvent peak), 3.24-3.31 (m, 1H) |
| 187 | 4-(((3S,4R)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile | 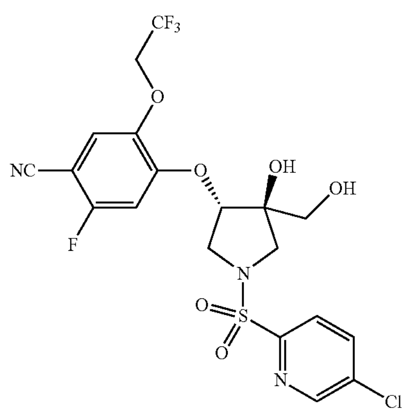 [SMILES: N#Cc1cc(OCC(F)(F)F)c(O[C@H]2CN(S(=O)(=O)c3ccc(Cl)cn3)C[C@@]2(O)CO)cc1F] | 526.0 | $^1$H NMR (400 MHz, DMSO-d$_6$) δ: 8.41 (d, J = 2.3 Hz, 1H), 8.09 (dd, J = 8.4, 2.4 Hz, 1H), 7.84 (d, J = 8.5 Hz, 1H), 7.63 (d, J = 6.3 Hz, 1H), 7.36 (d, J = 11.0 Hz, 1H), 5.45 (s, 1H), 4.75 (t, J = 5.8 Hz, 1H), 4.52-4.68 (m, 3H), 3.89 (dd, J = 12.5, 3.0 Hz, 1H), 3.71 (d, J = 12.5 Hz, 1H), 3.44-3.55 (m, 2H), 3.35-3.39 (m, 1H, partially hidden by solvent peak), 3.24 (d, J = 10.3 Hz, 1H) |
| 188 | 2-fluoro-4-(((3S,4R)-4-hydroxy-4-(hydroxymethyl)-1-((6-methylpyridazin-3-yl)sulfonyl)pyrrolidin-3-yl)oxy)-5-isobutoxybenzonitrile | 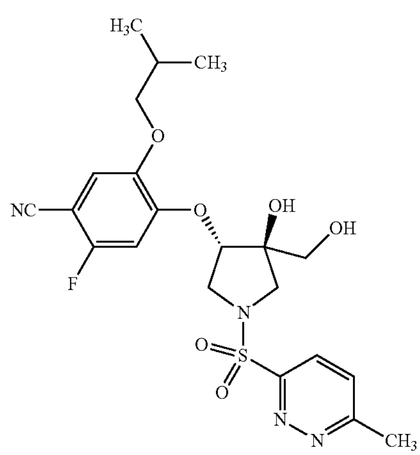 [SMILES: Cc1ccc(S(=O)(=O)N2C[C@H](Oc3cc(F)c(C#N)cc3OCC(C)C)[C@](O)(CO)C2)nn1] | 481.1 | $^1$H NMR (400 MHz, DMSO-d$_6$) δ: 7.97 (d, J = 8.8 Hz, 1H), 7.75 (d, J = 8.5 Hz, 1H), 7.38 (d, J = 6.3 Hz, 1H), 7.24 (d, J = 11.0 Hz, 1H), 5.41 (s, 1H), 4.74 (t, J = 5.6 Hz, 1H), 4.55 (d, J = 2.8 Hz, 1H), 3.91 (dd, J = 12.3, 3.3 Hz, 1H), 3.73 (d, J = 12.3 Hz, 1H), 3.48-3.68 (m, 4H), 3.39-3.44 (m, 1H), 3.29-3.34 (m, 1H, partially hidden by solvent peak), 2.66 (s, 3H), 1.85-1.95 (m, 1H), 0.91 (dd, J = 6.8, 2.3 Hz, 6H) |

Example 189

4-(((3S,4R)-1-((5-chloropyridin-2-yl)sulfonyl)-4-hydroxy-4-((S)-1-hydroxybutyl)pyrrolidin-3-yl)oxy)-2-fluorobenzonitrile

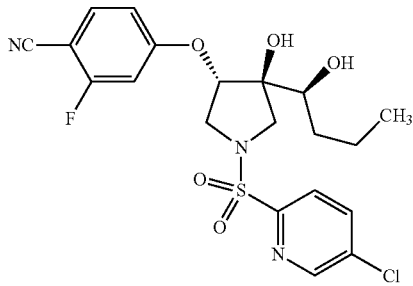 [SMILES: CCC[C@H](O)[C@]1(O)CN(S(=O)(=O)c2ccc(Cl)cn2)C[C@@H]1Oc1ccc(C#N)c(F)c1]

Step 1: (R,E)-4-((4-butylidene-1-((5-chloropyridin-2-yl)sulfonyl)pyrrolidin-3-yl)oxy)-2-fluorobenzonitrile

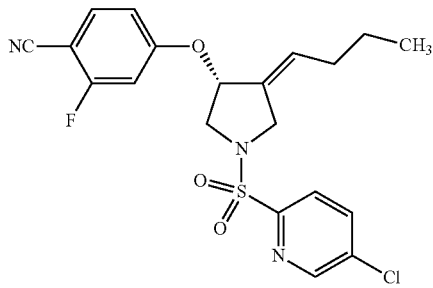 [SMILES: CCC/C=C1\CN(S(=O)(=O)c2ccc(Cl)cn2)C[C@@H]1Oc1ccc(C#N)c(F)c1]

To a mixture of (R)-4-((1-((5-chloropyridin-2-yl)sulfonyl)-4-methylenepyrrolidin-3-yl)oxy)-2-fluorobenzonitrile (330 mg, 0.838 mmol) in pent-1-ene (10 g, 14 mmol) was added Grubbs Catalyst, $2^{nd}$ Generation (50 mg, 0.059 mmol) followed by DCM (6 mL) and the reaction mixture was stirred at rt overnight in a sealed vial. Two additional portions of Grubbs Catalyst, $2^{nd}$ Generation (50 mg, 0.059 mmol) were added to the reaction with stirring for 24 h after each addition. The reaction mixture was concentrated and purified by flash column chromatography ($SiO_2$) eluting with a gradient of 0-50% EtOAc in hexanes. The product fractions were pooled and concentrated to give the title compound (162 mg, 44% yield). MS (m/z) 458.0 (M+Na$^+$).

Step 2: 4-(((3S,4R)-1-((5-chloropyridin-2-yl)sulfonyl)-4-hydroxy-4-((S)-1-hydroxybutyl)pyrrolidin-3-yl)oxy)-2-fluorobenzonitrile To a solution of (R,E)-4-((4-butylidene-1-((5-chloropyridin-2-yl)sulfonyl)pyrrolidin-3-yl)oxy)-2 fluorobenzonitrile (50 mg, 0.12 mmol) and NMO (30 mg, 0.26 mmol) in water (1.0 mL), $CH_3CN$ (1.0 mL) and acetone (1.0 mL) was added mMC-$OsO_4$ (10% wt, 0.031 mL, 9.8 μmol) and the reaction mixture was stirred at rt overnight. The reaction mixture was filtered, rinsed with additional acetone and the filtrate was concentrated under reduced pressure. The crude residue was purified by flash column chromatography ($SiO_2$) eluting with a gradient of 0-100% EtOAc in hexanes. The product fractions were pooled and concentrated to give the title compound (22 mg, 41% yield). $^1$H NMR (400 MHz, DMSO-$d_6$) δ: 8.57 (d, J=2.0 Hz, 1H), 8.11 (dd, J=8.4, 2.4 Hz, 1H), 7.85 (d, J=8.5 Hz, 1H), 7.77 (t, J=8.3 Hz, 1H), 6.92 (dd, J=11.8, 2.3 Hz, 1H), 6.65 (dd, J=8.8, 2.3 Hz, 1H), 5.13 (s, 1H), 4.51-4.60 (m, 2H), 3.83 (dd, J=12.3, 2.8 Hz, 1H), 3.60 (t, J=7.5 Hz, 1H), 3.52 (d, J=12.3 Hz, 1H), 3.35-3.41 (m, 1H), 3.26-3.32 (m, 1H), 1.41-1.54 (m, 2H), 1.04-1.29 (m, 2H), 0.85-0.91 (m, 3H). MS (m/z) 470.0 (M+H$^+$).

The following compounds were prepared using procedures analogous to those described in Example 189 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 190 | 4-(((3S,4R)-1-((2-cyano-4-(trifluoromethyl)phenyl)sulfonyl)-4-hydroxy-4-(1-hydroxyethyl)pyrrolidin-3-yl)oxy)-2-fluorobenzonitrile | 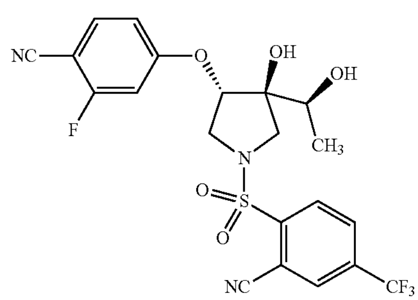 [SMILES: C[C@H](O)[C@]1(O)CN(S(=O)(=O)c2ccc(C(F)(F)F)cc2C#N)C[C@@H]1Oc1ccc(C#N)c(F)c1] | 500.3 | $^1$H NMR (400 MHz, DMSO-$d_6$) δ: 8.58 (s, 1H), 8.14-8.27 (m, 2H), 7.75 (t, J = 8.3 Hz, 1H), 6.97 (dd, J = 11.8, 2.3 Hz, 1H), 6.74 (dd, J = 8.8, 2.3 Hz, 1H), 5.23 (s, 1H), 4.65-4.72 (m, 2H), 3.80-3.89 (m, 2H), 3.56 (d, J = 12.3 Hz, 1H), 3.35-3.43 (m, 2H, partially hidden by solvent peak), 1.02 (d, J = 6.5 Hz, 3H) |

| Ex. | Name | Structure | MS (m/z) (M + H⁺) | ¹H NMR |
|---|---|---|---|---|
| 191 | 4-(((3S,4R)-1-((5-chloropyridin-2-yl)sulfonyl)-4-hydroxy-4-(1-hydroxyethyl)pyrrolidin-3-yl)oxy)-2-fluorobenzonitrile | 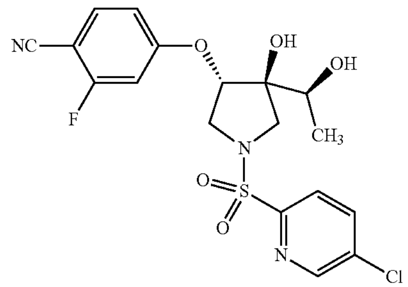 [SMILES: C[C@H](O)[C@]1(O)CN(S(=O)(=O)c2ccc(Cl)cn2)C[C@@H]1Oc1ccc(C#N)c(F)c1] | 442.2 | $^1$H NMR (400 MHz, DMSO-d$_6$) δ: 8.57 (d, J = 1.8 Hz, 1H), 8.07-8.15 (m, 1H), 7.85 (d, J = 8.3 Hz, 1H), 7.73-7.80 (m, 1H), 6.92 (dd, J = 11.8, 2.3 Hz, 1H), 6.65 (dd, J = 8.8, 2.3 Hz, 1H), 5.13 (s, 1H), 4.63 (d, J = 6.0 Hz, 1H), 4.57 (d, J = 2.8 Hz, 1H), 3.79-3.89 (m, 2H), 3.53 (d, J = 12.3 Hz, 1H), 3.38 (1H, partially hidden by solvent peak), 3.25 (d, J = 10.3 Hz, 1H), 1.01 (d, J = 6.3 Hz, 3H) |
| 192 | 4-(((3S,4R)-1-((5-chloropyridin-2-yl)sulfonyl)-4-hydroxy-4-((S)-1-hydroxy-3-methylbutyl)pyrrolidin-3-yl)oxy)-2-fluorobenzonitrile | 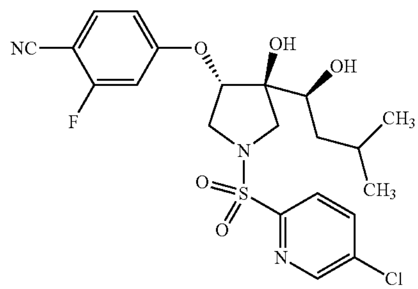 [SMILES: CC(C)C[C@H](O)[C@]1(O)CN(S(=O)(=O)c2ccc(Cl)cn2)C[C@@H]1Oc1ccc(C#N)c(F)c1] | 484.3 | $^1$H NMR (400 MHz, DMSO-d$_6$) δ: 8.59 (s, 1H), 8.07-8.14 (m, 1H), 7.85 (d, J = 8.3 Hz, 1H), 7.77 (t, J = 8.2 Hz, 1H), 6.95 (d, J = 12.0 Hz, 1H), 6.68 (d, J = 7.0 Hz, 1H), 5.12 (s, 1H), 4.59 (s, 1H), 4.53 (d, J = 7.5 Hz, 1H), 3.83 (d, J = 10.5 Hz, 1H), 3.69 (m, 1H), 3.51 (d, J = 12.0 Hz, 1H), 3.31-3.38 (1H, hidden by solvent peak), 3.23-3.31 (m, 1H), 1.73 (br m, 1H), 1.50-1.57 (m, 1H), 0.87 (dd, J = 16.8, 6.5 Hz, 6H), 0.73-0.83 (m, 1H) |

Example 193

4-(((3S,4R)-1-((2-cyano-4-(trifluoromethyl)phenyl)sulfonyl)-4-hydroxy-4-((R)-1-hydroxyethyl)pyrrolidin-3-yl)oxy)-2-fluorobenzonitrile

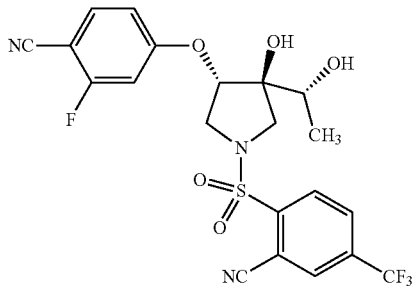 [SMILES: C[C@@H](O)[C@]1(O)CN(S(=O)(=O)c2ccc(C(F)(F)F)cc2C#N)C[C@@H]1Oc1ccc(C#N)c(F)c1]

Step 1: (R,E)-4-((1-((2-cyano-4-(trifluoromethyl)phenyl)sulfonyl)-4-ethylidenepyrrolidin-3-yl)oxy)-2-fluorobenzonitrile

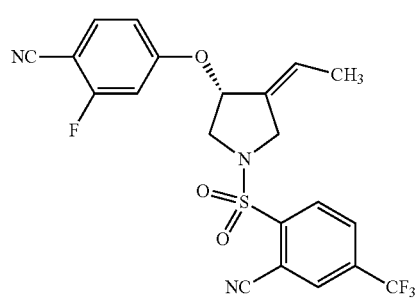 [SMILES: C/C=C1\CN(S(=O)(=O)c2ccc(C(F)(F)F)cc2C#N)C[C@@H]1Oc1ccc(C#N)c(F)c1]

To a mixture of (R)-4-((1-((2-cyano-4-(trifluoromethyl)phenyl)sulfonyl)-4-methylenepyrrolidin-3-yl)oxy)-2-fluorobenzonitrile (1.00 g, 2.22 mmol) in 2-methyl-2-butene (17 mL, 160 mmol) was added Grubbs Catalyst, 2$^{nd}$ Generation (100 mg, 0.118 mmol) followed by DCM (12 mL) and the reaction was stirred at 45° C. for 72 h in a sealed vial. Three additional portions of Grubbs Catalyst, 2$^{nd}$ Generation (75 mg, 0.089 mmol each) were added to the reaction with stirring at 45° C. for 24 h after each addition in order to drive the reaction toward completion. The reaction mixture was concentrated and the residue purified by flash column chromatography (SiO$_2$) eluting with a gradient of 0-100% EtOAc in hexanes. The product fractions were pooled and concentrated to give the title compound (500 mg, 48% yield). MS (m/z) 488.0 (M+Na⁺).

Step 2: 4-(((2S,3R,7S)-5-((2-cyano-4-(trifluoromethyl)phenyl)sulfonyl)-2-methyl-1-oxa-5-azaspiro[2.4]heptan-7-yl)oxy)-2-fluorobenzonitrile OR 4-(((2R,3S,7S)-5-((2-cyano-4-(trifluoromethyl)phenyl)sulfonyl)-2-methyl-1-oxa-5-azaspiro[2.4]heptan-7-yl)oxy)-2-fluorobenzonitrile

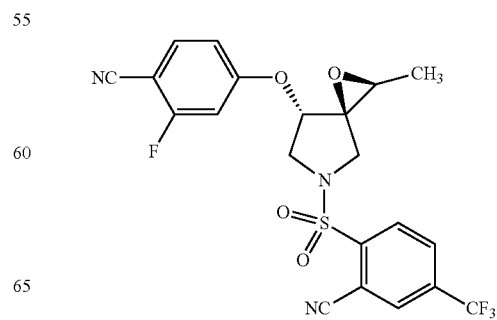

OR

-continued

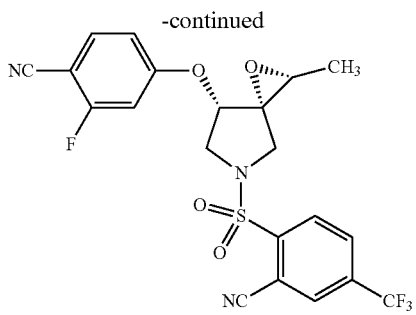

To a solution of (R,E)-4-((1-((2-cyano-4-(trifluoromethyl)phenyl)sulfonyl)-4-ethylidenepyrrolidin-3-yl)oxy)-2-fluorobenzonitrile (400 mg, 0.859 mmol) in DCM (10 mL) was added m-CPBA (580 mg, 2.6 mmol) and the reaction mixture was stirred at 40° C. for 48 h. The reaction was quenched with sat'd $NaHSO_3$ (aq) followed by sat'd $NaHCO_3$ (aq) and stirred 1 h. The organic layer was separated, dried over $Na_2SO_4$, filtered and concentrated. Separation of the individual diasteromers was accomplished by flash column chromatography ($SiO_2$) eluting with a gradient of 0-100% EtOAc in hexanes. The separated isomer fractions were each pooled and concentrated to give the individual trans and cis isomers of the title compound. Trans-isomer: (1$^{st}$ elutant, 140 mg as a white solid, 34% yield) $^1$H NMR (400 MHz, DMSO-$d_6$) δ: 8.66 (s, 1H), 8.22-8.31 (m, 2H), 7.80 (t, J=8.3 Hz, 1H), 7.05 (dd, J=11.8, 2.3 Hz, 1H), 6.81 (dd, J=8.8, 2.3 Hz, 1H), 4.79 (d, J=2.5 Hz, 1H), 3.88-4.02 (m, 2H), 3.66 (d, J=12.3 Hz, 1H), 3.41-3.51 (m, 2H), 1.23-1.30 (m, 3H). MS (m/z) 482.0 (M+H$^+$). Cis-isomer: (2$^{nd}$ elutant, 160 mg as a clear film, 39% yield) $^1$H NMR (400 MHz, DMSO-$d_6$) δ: 8.71 (s, 1H), 8.26-8.34 (m, 2H), 7.77 (t, J=8.3 Hz, 1H), 6.95 (d, J=11.3 Hz, 1H), 6.74 (d, J=8.5 Hz, 1H), 4.96 (br s, 1H), 3.87 (dd, J=12.7, 3.4 Hz, 1H), 3.71-3.79 (m, 1H), 3.58 (s, 2H), 3.45 (d, J=5.3 Hz, 1H), 1.23 (d, J=5.3 Hz, 3H). MS (m/z) 482.0 (M+H$^+$).

Step 3: 4-(((3S,4R)-1-((2-cyano-4-(trifluoromethyl)phenyl)sulfonyl)-4-hydroxy-4-((R)-1-hydroxyethyl)pyrrolidin-3-yl)oxy)-2-fluorobenzonitrile To a solution of 4-(((2S,3R,7S)-5-((2-cyano-4-(trifluoromethyl)phenyl)sulfonyl)-2-methyl-1-oxa-5-azaspiro[2.4]heptan-7-yl)oxy)-2-fluorobenzonitrile (140 mg, 0.29 mmol) in THF (8 mL) was added 2 M $H_2SO_4$ (aq) (2 mL, 4 mmol) and the reaction mixture was stirred at 40° C. overnight. The reaction mixture was concentrated and the residue was purified by flash column chromatography ($SiO_2$) eluting with a gradient of 0-100% EtOAc in hexanes. The product fractions were pooled and concentrated to give the title compound (40 mg, 28% yield). $^1$H NMR (400 MHz, DMSO-$d_6$) δ: 8.58 (s, 1H), 8.13-8.25 (m, 2H), 7.77 (t, J=8.3 Hz, 1H), 7.03 (d, J=9.8 Hz, 1H), 6.77 (d, J=8.5 Hz, 1H), 5.43 (s, 1H), 4.82 (d, J=5.8 Hz, 1H), 4.58 (d, J=2.5 Hz, 1H), 3.83-3.93 (m, 2H), 3.51-3.63 (m, 3H), 0.93 (d, J=6.3 Hz, 3H). MS (m/z) 500.0 (M+H$^+$).

Example 194

4-(((3S,4S)-1-((2-cyano-4-(trifluoromethyl)phenyl)sulfonyl)-4-hydroxy-4-((S)-1-hydroxyethyl) pyrrolidin-3-yl)oxy)-2-fluorobenzonitrile

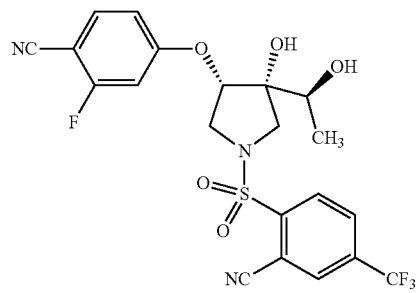 [SMILES: C[C@H](O)[C@@]1(O)CN(S(=O)(=O)c2ccc(C(F)(F)F)cc2C#N)C[C@@H]1Oc1ccc(C#N)c(F)c1]

To a solution of 4-(((2R,3S,7S)-5-((2-cyano-4-(trifluoromethyl)phenyl)sulfonyl)-2-methyl-1-oxa-5-azaspiro[2.4]heptan-7-yl)oxy)-2-fluorobenzonitrile (160 mg, 0.33 mmol) in THF (8 mL) was added 2 M $H_2SO_4$ (aq) (2 mL, 4 mmol) and the reaction mixture was stirred at 40° C. overnight. The reaction mixture was concentrated and the residue was purified by flash column chromatography ($SiO_2$) eluting with a gradient of 0-100% EtOAc in hexanes. The product fractions were pooled and concentrated to give the title compound (90 mg, 54% yield). $^1$H NMR (400 MHz, DMSO-$d_6$) δ: 8.72 (s, 1H), 8.23-8.34 (m, 2H), 7.78-7.86 (m, 1H), 7.23 (dd, J=11.9, 2.4 Hz, 1H), 7.01 (dd, J=8.8, 2.3 Hz, 1H), 5.21 (s, 1H), 5.15 (d, J=5.5 Hz, 1H), 5.07 (t, J=7.2 Hz, 1H), 4.03 (m, 1H, partially hidden by solvent peak), 3.51-3.60 (m, 2H), 3.26-3.33 (m, 2H, partially hidden by solvent peak), 1.07 (d, J=6.3 Hz, 3H). MS (m/z) 500.0 (M+H$^+$).

The following compounds were prepared using procedures analogous to those described in Examples 193-194 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 195 | 4-(((3S,4R)-1-((5-chloropyridin-2-yl)sulfonyl)-4-hydroxy-4-((R)-1-methoxyethyl)pyrrolidin-3-yl)oxy)-2-fluorobenzonitrile | 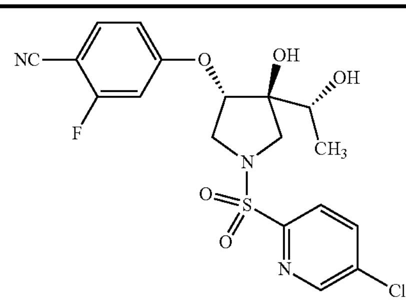 | 442.3 | $^1$H NMR (400 MHz, DMSO-$d_6$) δ: 8.57 (d, J = 2.0 Hz, 1H), 8.10 (dd, J = 8.5, 2.3 Hz, 1H), 7.84 (d, J = 8.3 Hz, 1H), 7.78 (t, J = 8.3 Hz, 1H), 6.96 (d, J = 11.5 Hz, 1H), 6.68 (d, J = 9.0 Hz, 1H), 5.30 (s, 1H), 4.75 (br s, 1H), 4.46 (d, J = 2.5 Hz, 1H), 3.88 (dd, J = 12.7, 2.6 Hz, 2H), 3.49-3.64 (m, 3H), 0.91 (d, J = 6.3 Hz, 3H) |

-continued

| Ex. | Name | Structure | MS (m/z) (M + H+) | 1H NMR |
|---|---|---|---|---|
| 196 | 4-(((3S,4R)-1-((5-chloropyridin-2-yl)sulfonyl)-4-hydroxy-4-((R)-1-hydroxypropyl)pyrrolidin-3-yl)oxy)-2-fluorobenzonitrile | 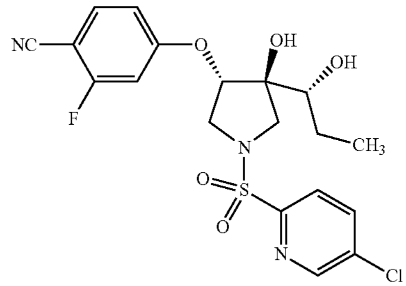 [SMILES: CC[C@@H](O)[C@]1(O)CN(S(=O)(=O)c2ccc(Cl)cn2)C[C@@H]1Oc1ccc(C#N)c(F)c1] | 456.4 | 1H NMR (400 MHz, DMSO-d6) δ: 8.58 (d, J = 2.3 Hz, 1H), 8.11 (dd, J = 8.4, 2.4 Hz, 1H), 7.84 (d, J = 8.3 Hz, 1H), 7.78 (t, J = 8.3 Hz, 1H), 6.96 (dd, J = 11.7, 2.1 Hz, 1H), 6.68 (dd, J = 8.7, 2.1 Hz, 1H), 5.29 (s, 1H), 4.70 (d, J = 7.0 Hz, 1H), 4.52 (d, J = 2.8 Hz, 1H), 3.85-3.93 (m, 1H), 3.46-3.65 (m, 4H), 1.32-1.45 (m, 1H), 1.04-1.17 (m, 1H), 0.76 (t, J = 7.3 Hz, 3H) |
| 197 | 4-(((3S,4R)-1-((5-chloropyridin-2-yl)sulfonyl)-4-hydroxy-4-((R)-1-hydroxy-3-methylbutyl)pyrrolidin-3-yl)oxy)-2-fluorobenzonitrile | 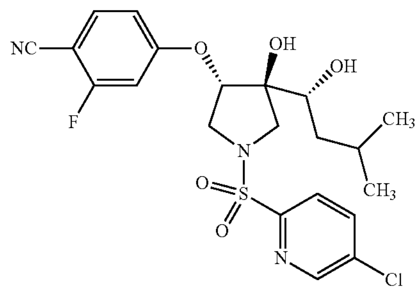 [SMILES: CC(C)C[C@@H](O)[C@]1(O)CN(S(=O)(=O)c2ccc(Cl)cn2)C[C@@H]1Oc1ccc(C#N)c(F)c1] | 484.2 | 1H NMR (400 MHz, DMSO-d6) δ: 8.57 (d, J = 2.5 Hz, 1H), 8.11 (dd, J = 8.5, 2.5 Hz, 1H), 7.73-7.88 (m, 2H), 6.96 (dd, J = 11.8, 2.3 Hz, 1H), 6.65 (dd, J = 8.8, 2.3 Hz, 1H), 5.29 (s, 1H), 4.65 (br s, 1H), 4.49 (d, J = 2.8 Hz, 1H), 3.89 (dd, J = 12.5, 3.0 Hz, 1H), 3.70 (d, J = 10.0 Hz, 1H), 3.50-3.64 (m, 3H), 1.60-1.71 (m, 1H), 1.40-1.51 (m, 1H), 0.76 (d, J = 6.8 Hz, 3H), 0.67-0.73 (m, 1H), 0.62 (d, J = 6.5 Hz, 3H) |
| 198 | 4-(((3S,4R)-1-((5-chloropyridin-2-yl)sulfonyl)-4-hydroxy-4-((R)-1-hydroxybutyl)pyrrolidin-3-yl)oxy)-2-fluorobenzonitrile | 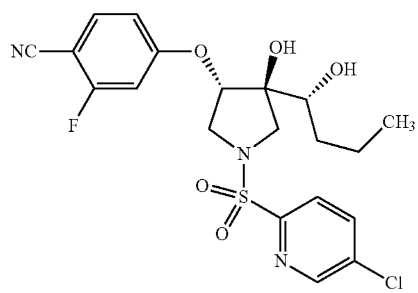 [SMILES: CCC[C@@H](O)[C@]1(O)CN(S(=O)(=O)c2ccc(Cl)cn2)C[C@@H]1Oc1ccc(C#N)c(F)c1] | 470.1 | 1H NMR (400 MHz, DMSO-d6) δ: 8.57 (d, J = 2.0 Hz, 1H), 8.11 (dd, J = 8.5, 2.5 Hz, 1H), 7.74-7.89 (m, 2H), 6.96 (dd, J = 11.5, 2.0 Hz, 1H), 6.67 (dd, J = 8.8, 2.3 Hz, 1H), 5.29 (s, 1H), 4.67 (d, J = 7.3 Hz, 1H), 4.51 (d, J = 2.5 Hz, 1H), 3.88 (dd, J = 12.2, 2.9 Hz, 1H), 3.50-3.68 (m, 4H), 1.28-1.51 (m, 2H), 1.11-1.20 (m, 1H), 0.93-1.04 (m, 1H), 0.70 (t, J = 7.3 Hz, 3H) |

Example 199

4-(((3S,4R)-1-((2-cyano-4-methoxyphenyl)sulfonyl)-4-hydroxy-4-((S)-1-hydroxyethyl)pyrrolidin-3-yl)oxy)-2-fluorobenzonitrile

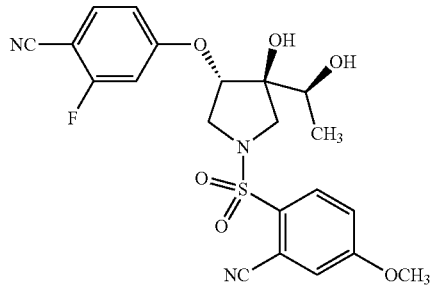 [SMILES: COc1ccc(S(=O)(=O)N2C[C@H](Oc3ccc(C#N)c(F)c3)[C@](O)([C@H](C)O)C2)c(C#N)c1]

Step 1: (3R,4S)-tert-butyl 4-(4-cyano-3-fluorophenoxy)-3-hydroxy-3-((S)-1-hydroxyethyl)pyrrolidine-1-carboxylate

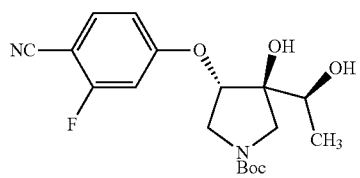 [SMILES: C[C@H](O)[C@]1(O)CN(C(=O)OC(C)(C)C)C[C@@H]1Oc1ccc(C#N)c(F)c1]

To a solution of (R,E)-tert-butyl 3-(4-cyano-3-fluorophenoxy)-4-ethylidenepyrrolidine-1-carboxylate (700 mg, 2.1 mmol) and NMO (345 mg, 2.95 mmol) in THF (20 mL) was added OsO4 (2.5% in t-BuOH, 1.3 mL, 0.10 mmol) and the reaction mixture was stirred at rt. The reaction was quenched with sat'd NaHSO3 (aq) followed by sat'd NaHCO3 (aq) and stirred 1 h. EtOAc (50 mL) was added and the biphasic mixture separated. The organic layer was washed with sat'd NaHCO3 (aq) and brine, dried over Na2SO4, filtered and concentrated under reduced pressure. The crude product was purified by flash column chromatography (SiO2) eluting with a gradient of 0-100% EtOAc in hexanes. The product fractions were pooled and concentrated to give the title compound (400 mg, 52% yield). MS (m/z) 389.2 (M+Na⁺).

Step 2: 2-fluoro-4-(((3S,4R)-4-hydroxy-4-((S)-1-hydroxyethyl)pyrrolidin-3-yl)oxy)benzonitrile Hydrochloride

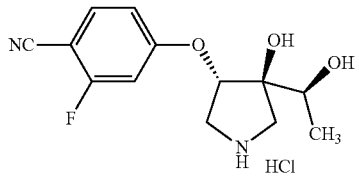 [SMILES: C[C@H](O)[C@]1(O)CNC[C@@H]1Oc1ccc(C#N)c(F)c1 ; Cl]

To a mixture of (3R,4S)-tert-butyl 4-(4-cyano-3-fluorophenoxy)-3-hydroxy-3-((S)-1-hydroxyethyl)pyrrolidine-1-carboxylate (400 mg, 1.1 mmol) in 1,4-dioxane (7 mL) was added 4 M HCl in dioxane (1.5 mL, 6.0 mmol) and the reaction mixture was stirred at rt overnight. The mixture was degassed by bubbling nitrogen through it then the solvent was removed by evaporation under reduced pressure to give the title compound. MS (m/z) 267.2 (M+H⁺).

Step 3: 4-(((3S,4R)-1-((2-cyano-4-methoxyphenyl)sulfonyl)-4-hydroxy-4-((S)-1-hydroxyethyl)pyrrolidin-3-yl)oxy)-2-fluorobenzonitrile To a solution of 2-fluoro-4-(((3S,4R)-4-hydroxy-4-((S)-1-hydroxyethyl)pyrrolidin-3-yl)oxy)benzonitrile Hydrochloride (47 mg, 0.16 mmol) in THF (3 mL) was added 2-cyano-4-methoxybenzene-1-sulfonyl chloride (90 mg, 0.39 mmol) and sat'd NaHCO₃ (aq) (1 mL) and the reaction mixture was stirred at rt overnight. The reaction mixture was diluted with EtOAc (20 mL), washed with brine, dried over Na₂SO₄, filtered and concentrated. The crude product was flash chromatographed (SiO₂) eluting with a gradient of 0-100% EtOAc in hexanes. The product fractions were pooled and concentrated to give the title compound (45 mg, 59% yield). ¹H NMR (400 MHz, DMSO-d₆) δ: 7.87 (d, J=8.8 Hz, 1H), 7.74-7.80 (m, 1H), 7.59 (d, J=2.8 Hz, 1H), 7.31 (dd, J=9.0, 2.8 Hz, 1H), 6.97 (dd, J=11.8, 2.3 Hz, 1H), 6.72 (dd, J=8.8, 2.3 Hz, 1H), 5.14-5.19 (m, 1H), 4.68 (d, J=5.8 Hz, 1H), 4.64 (d, J=2.8 Hz, 1H), 3.89 (s, 3H), 3.82-3.87 (m, 1H), 3.78 (dd, J=12.2, 2.9 Hz, 1H), 3.49 (d, J=12.3 Hz, 1H), 3.24-3.33 (m, 2H), 1.02 (d, J=6.5 Hz, 3H). MS (m/z) 462.2 (M+H⁺).

The following compounds were prepared using procedures analogous to those described in Example 199 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 200 | 4-(((3S,4R)-1-((2-cyanophenyl)sulfonyl)-4-hydroxy-4-((S)-1-hydroxyethyl)pyrrolidin-3-yl)oxy)-2-fluorobenzonitrile | 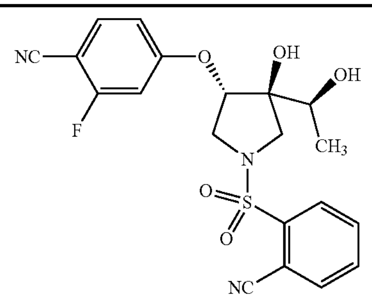 | 432.0 | ¹H NMR (400 MHz, DMSO-d₆) δ: 8.05 (d, J = 7.3 Hz, 1H), 8.00 (d, J = 8.0 Hz, 1H), 7.74-7.91 (m, 3H), 7.01 (d, J = 12.0 Hz, 1H), 6.70 (d, J = 9.0 Hz, 1H), 5.77 (s, 1H), 5.18 (s, 1H), 4.67-4.72 (m, 2H), 3.77-3.89 (m, 2H), 3.55 (d, J = 12.0 Hz, 1H), 3.31 (s, 1H), 1.01 (d, J = 6.3 Hz, 3H) |
| 201 | 4-(((3S,4R)-1-((2-cyano-4-fluorophenyl)sulfonyl)-4-hydroxy-4-((S)-1-hydroxyethyl)pyrrolidin-3-yl)oxy)-2-fluorobenzonitrile | 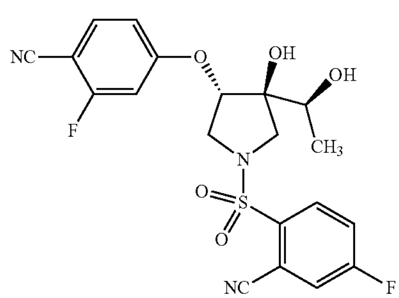 [SMILES: C[C@H](O)[C@]1(O)CN(S(=O)(=O)c2ccc(F)cc2C#N)C[C@@H]1Oc1ccc(C#N)c(F)c1] | 450.2 | ¹H NMR (400 MHz, DMSO-d₆) δ: 8.12 (dd, J = 8.5, 2.5 Hz, 1H), 8.05 (dd, J = 8.8, 5.3 Hz, 1H), 7.70-7.83 (m, 2H), 7.04 (d, J = 11.8 Hz, 1H), 6.76 (d, J = 8.5 Hz, 1H), 5.19 (s, 1H), 4.65-4.73 (m, 2H), 3.77-3.90 (m, 2H), 3.53 (d, J = 12.0 Hz, 1H), 3.28-3.33 (m, 2H, partially hidden by solvent peak), 1.02 (d, J = 6.3 Hz, 3H) |
| 202 | 4-(((3S,4R)-1-((4-chloro-2-cyanophenyl)sulfonyl)-4-hydroxy-4-((S)-1-hydroxyethyl)pyrrolidin-3-yl)oxy)-2-fluorobenzonitrile | 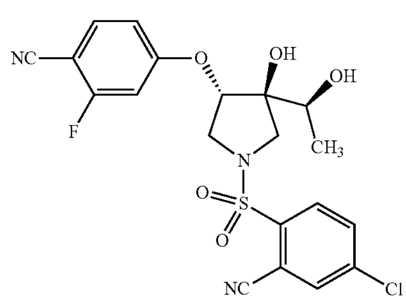 | 466.1 | ¹H NMR (400 MHz, DMSO-d₆) δ: 8.27 (d, J = 2.0 Hz, 1H), 7.95-7.99 (m, 1H), 7.89-7.94 (m, 1H), 7.78 (t, J = 8.3 Hz, 1H), 7.01 (dd, J = 11.8, 2.0 Hz, 1H), 6.74 (dd, J = 8.7, 1.9 Hz, 1H), 5.20 (s, 1H), 4.64-4.72 (m, 2H), 3.77-3.90 (m, 2H), 3.52 (d, J = 12.0 Hz, 1H), 3.33-3.37 (1H, partially hidden by solvent peak), 3.27-3.32 (m, 1H), 0.98-1.06 (m, 3H) |

-continued

| Ex. | Name | Structure | MS (m/z) (M + H⁺) | ¹H NMR |
|---|---|---|---|---|
| 203 | 3-(((3R,4S)-4-(4-cyano-3-fluorophenoxy)-3-hydroxy-3-((S)-1-hydroxyethyl)pyrrolidin-1-yl)sulfonyl)picolinonitrile | 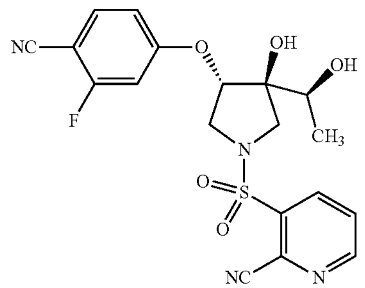 [SMILES: C[C@H](O)[C@]1(O)CN(S(=O)(=O)c2cccnc2C#N)C[C@@H]1Oc1ccc(C#N)c(F)c1] | 433.2 | $^1$H NMR (400 MHz, DMSO-$d_6$) δ: 8.96 (d, J = 4.5 Hz, 1H), 8.44 (d, J = 8.3 Hz, 1H), 7.93 (dd, J = 8.3, 4.8 Hz, 1H), 7.80 (t, J = 8.3 Hz, 1H), 7.04 (dd, J = 11.7, 1.9 Hz, 1H), 6.74 (dd, J = 8.8, 2.0 Hz, 1H), 5.19 (s, 1H), 4.66-4.72 (m, 2H), 3.79-3.90 (m, 2H), 3.58 (d, J = 12.0 Hz, 1H), 3.36 (s, 2H), 1.02 (d, J = 6.5 Hz, 3H) |
| 204 | 4-(((3S,4R)-1-((2,4-dichlorophenyl)sulfonyl)-4-hydroxy-4-((S)-1-hydroxyethyl)pyrrolidin-3-yl)oxy)-2-fluorobenzonitrile | 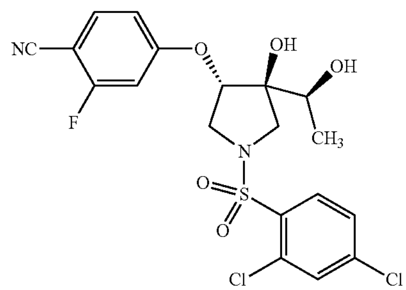 [SMILES: C[C@H](O)[C@]1(O)CN(S(=O)(=O)c2ccc(Cl)cc2Cl)C[C@@H]1Oc1ccc(C#N)c(F)c1] | 475.0 | $^1$H NMR (400 MHz, DMSO-$d_6$) δ: 7.92 (d, J = 8.5 Hz, 1H), 7.77-7.86 (m, 2H), 7.57 (dd, J = 8.4, 1.9 Hz, 1H), 7.09 (d, J = 11.8 Hz, 1H), 6.86 (d, J = 8.8 Hz, 1H), 5.22 (s, 1H), 4.68-4.74 (m, 2H), 3.81-3.95 (m, 2H), 3.51 (d, J = 11.8 Hz, 1H), 3.40 (d, J = 10.5 Hz, 1H), 3.26 (d, J = 10.3 Hz, 1H), 1.02 (d, J = 6.5 Hz, 3H) |
| 205 | 4-(((3S,4R)-1-((2-chloro-4-cyanophenyl)sulfonyl)-4-hydroxy-4-((S)-1-hydroxyethyl)pyrrolidin-3-yl)oxy)-2-fluorobenzonitrile | 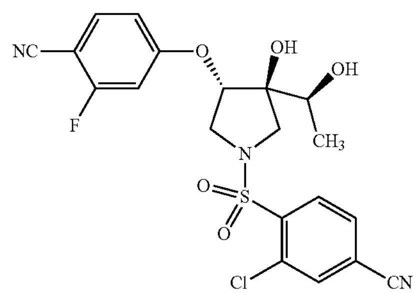 [SMILES: C[C@H](O)[C@]1(O)CN(S(=O)(=O)c2ccc(C#N)cc2Cl)C[C@@H]1Oc1ccc(C#N)c(F)c1] | 466.0 | $^1$H NMR (400 MHz, DMSO-$d_6$) δ: 8.28 (d, J = 1.5 Hz, 1H), 8.06-8.11 (m, 1H), 7.97-8.01 (m, 1H), 7.81 (t, J = 8.3 Hz, 1H), 7.12 (dd, J = 11.8, 2.3 Hz, 1H), 6.89 (dd, J = 8.8, 2.3 Hz, 1H), 5.33 (s, 1H), 4.71-4.80 (m, 2H), 3.84-3.96 (m, 2H), 3.55 (d, J = 11.8 Hz, 1H), 3.43 (d, J = 10.3 Hz, 1H), 3.29 (d, J = 10.3 Hz, 1H), 1.03 (d, J = 6.3 Hz, 3H) |

Example 206

2-fluoro-4-(((3S,4R)-4-hydroxy-4-((R)-1-hydroxyethyl)-1-((6-(trifluoromethyl)pyridin-3-yl)sulfonyl)pyrrolidin-3-yl)oxy)benzonitrile Step 1: (2S,3R,7S)-tert-butyl 7-(4-cyano-3-fluorophenoxy)-2-methyl-1-oxa-5-azaspiro[2.4]heptane-5-carboxylate

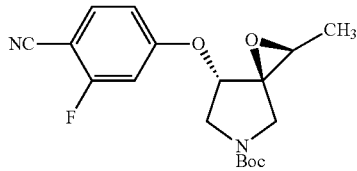

To a solution of (R,E)-tert-butyl 3-(4-cyano-3-fluorophenoxy)-4-ethylidenepyrrolidine-1-carboxylate (2.0 g, 6.0 mmol) in DCM (50 mL) was added m-CPBA (4.0 g, 18 mmol) and the reaction mixture was stirred at rt overnight. The reaction was quenched with sat'd NaHSO₃ (aq) followed by sat'd NaHCO₃ (aq) and stirred 1 h. The organic layer was separated, dried over Na₂SO₄, filtered and concentrated. The crude product was purified by flash column chromatography (SiO₂) eluting with a gradient of 0-100% EtOAc in hexanes. The product fractions were pooled and concentrated to give the title compound (400 mg, 19% yield). MS (m/z) 293.2 (M+H⁺-t-Bu).

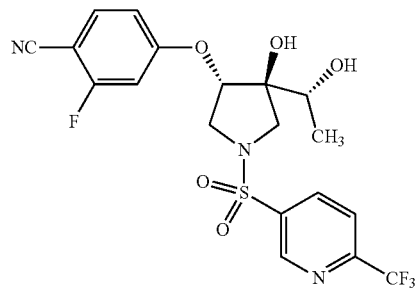 [SMILES: C[C@@H](O)[C@]1(O)CN(S(=O)(=O)c2ccc(C(F)(F)F)nc2)C[C@@H]1Oc1ccc(C#N)c(F)c1]

Step 2: 2-fluoro-4-(((3S,4R)-4-hydroxy-4-((R)-1-hydroxyethyl)pyrrolidin-3-yl)oxy)benzonitrile

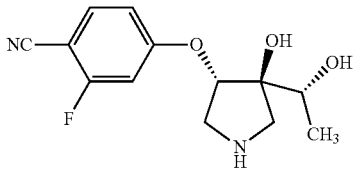

To a solution of (2S,3R,7S)-tert-butyl 7-(4-cyano-3-fluorophenoxy)-2-methyl-1-oxa-5-azaspiro[2.4]heptane-5-carboxylate (400 mg, 1.1 mmol) in THF (12 mL) was added 2 M $H_2SO_4$ (aq) (8 mL, 16 mmol) and the reaction mixture was stirred at 45° C. for 48 h. The reaction mixture was concentrated under reduced pressure to give the title compound which was used as is in step 3. MS (m/z) 267.1 (M+H$^+$).

Step 3: 2-fluoro-4-(((3S,4R)-4-hydroxy-4-((R)-1-hydroxyethyl)-1-((6-(trifluoromethyl)pyridin-3-yl)sulfonyl)pyrrolidin-3-yl)oxy)benzonitrile To a solution of 2-fluoro-4-(((3S,4R)-4-hydroxy-4-((R)-1-hydroxyethyl)pyrrolidin-3-yl)oxy)benzonitrile (100 mg, 0.38 mmol) in THF (8 mL) was added sat'd $NaHCO_3$ (aq) to neutralize the sulfuric acid and adjust the ph to 8. 6-(trifluoromethyl)pyridine-3-sulfonyl chloride (300 mg, 1.2 mmol) was added and the reaction mixture was stirred at rt for 72 h. The reaction mixture was concentrated under reduced pressure and partitioned between EtOAc (50 mL) and brine (25 mL). The organic layer was separated, dried over $Na_2SO_4$, filtered and concentrated. The residue was purified by flash column chromatography ($SiO_2$) eluting with a gradient of 0-100% EtOAc in hexanes. The product fractions were pooled and concentrated to give the title compound as a white solid (43 mg, 73% yield). $^1$H NMR (400 MHz, DMSO-d$_6$) δ: 9.09 (s, 1H), 8.40-8.46 (m, 1H), 8.06 (d, J=8.3 Hz, 1H), 7.74 (t, J=8.3 Hz, 1H), 6.91 (dd, J=11.5, 2.3 Hz, 1H), 6.66 (dd, J=8.7, 2.4 Hz, 1H), 5.35 (s, 1H), 4.76 (d, J=6.0 Hz, 1H), 4.52 (d, J=2.8 Hz, 1H), 3.86 (m, 1H), 3.78 (dd, J=12.4, 3.1 Hz, 1H), 3.49-3.61 (m, 2H), 3.44 (d, J=12.3 Hz, 1H), 0.90 (d, J=6.3 Hz, 3H). MS (m/z) 476.0 (M+H$^+$).

The following compounds were prepared using procedures analogous to those described in Example 206 using appropriately substituted starting materials. As is appreciated by those skilled in the art, these analogous examples may involve variations in general reaction conditions.

| Ex. | Name | Structure | MS (m/z) (M + H$^+$) | $^1$H NMR |
|---|---|---|---|---|
| 207 | 2-fluoro-4-(((3S,4R)-1-((5-fluoropyridin-2-yl)sulfonyl)-4-hydroxy-4-((R)-1-hydroxyethyl)pyrrolidin-3-yl)oxy)benzonitrile | 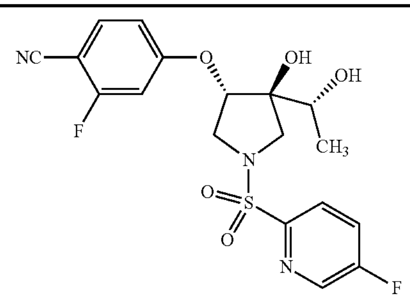 | 426.1 | $^1$H NMR (400 MHz, DMSO-d$_6$) δ: 8.55 (d, J = 2.5 Hz, 1H), 7.86-7.97 (m, 2H), 7.78 (t, J = 8.4 Hz, 1H), 6.98 (dd, J = 11.8, 2.3 Hz, 1H), 6.70 (dd, J = 8.8, 2.3 Hz, 1H), 5.28 (s, 1H), 4.74 (d, J = 6.0 Hz, 1H), 4.48 (d, J = 3.0 Hz, 1H), 3.81-3.92 (m, 2H), 3.51-3.61 (m, 3H), 0.91 (d, J = 6.5 Hz, 3H) |
| 208 | 2-fluoro-4-(((3S,4R)-4-hydroxy-4-((R)-1-hydroxyethyl)-1-((6-(trifluoromethoxy)pyridin-3-yl)sulfonyl)pyrrolidin-3-yl)oxy)benzonitrile | 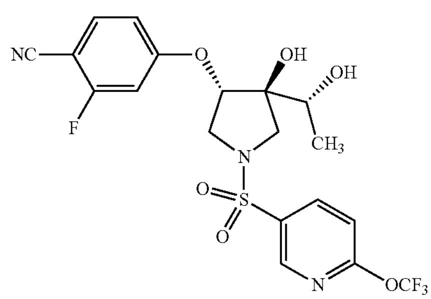 | 492.3 | $^1$H NMR (400 MHz, DMSO-d$_6$) δ: 8.68 (d, J = 2.3 Hz, 1H), 8.33 (dd, J = 8.7, 2.4 Hz, 1H), 7.77 (t, J = 8.2 Hz, 1H), 7.40 (d, J = 8.8 Hz, 1H), 6.90 (d, J = 11.3 Hz, 1H), 6.69 (d, J = 8.3 Hz, 1H), 5.36 (s, 1H), 4.76 (d, J = 5.8 Hz, 1H), 4.51 (s, 1H), 3.75 (d, J = 9.8 Hz, 1H), 3.46-3.58 (m, 2H), 3.40 (d, J = 12.3 Hz, 2H), 0.91 (d, J = 6.3 Hz, 3H) |
| 209 | 2-fluoro-4-(((3S,4R)-4-hydroxy-4-((R)-1-hydroxyethyl)-1-((4-iodophenyl)sulfonyl)pyrrolidin-3-yl)oxy)benzonitrile | 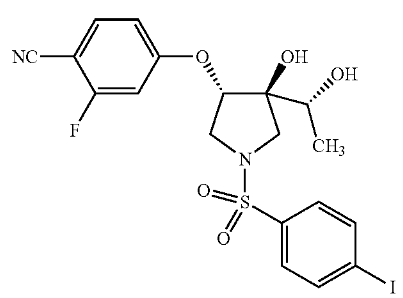 [SMILES: C[C@@H](O)[C@]1(O)CN(S(=O)(=O)c2ccc(I)cc2)C[C@@H]1Oc1ccc(C#N)c(F)c1] | 532.9 | $^1$H NMR (400 MHz, DMSO-d$_6$) δ: 7.86 (d, J = 8.0 Hz, 2H), 7.76 (t, J = 8.2 Hz, 1H), 7.43 (d, J = 8.0 Hz, 2H), 6.87 (d, J = 11.5 Hz, 1H), 6.62 (d, J = 8.3 Hz, 1H), 5.29 (s, 1H), 4.71 (d, J = 5.8 Hz, 1H), 4.47 (br s, 1H), 3.83 (t, J = 5.8 Hz, 1H), 3.71 (d, J = 12.0 Hz, 1H), 3.50 (d, J = 10.5 Hz, 1H), 3.37-3.45 (m, 1H), 3.28-3.30 (1H, partially hidden by solvent peak), 0.91 (d, J = 6.0 Hz, 3H) |

| Ex. | Name | Structure | MS (m/z) (M + H⁺) | ¹H NMR |
|---|---|---|---|---|
| 210 | 2-fluoro-4-(((3S,4R)-4-hydroxy-4-((R)-1-hydroxyethyl)-1-((5-(trifluoromethoxy)pyridin-2-yl)sulfonyl)pyrrolidin-3-yl)oxy)benzonitrile | 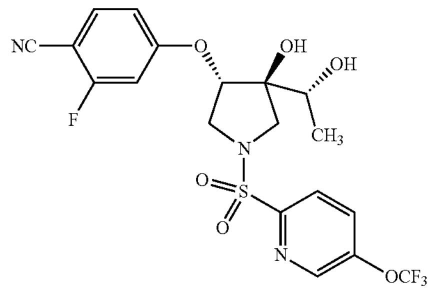 [SMILES: C[C@@H](O)[C@]1(O)CN(S(=O)(=O)c2ccc(OC(F)(F)F)cn2)C[C@@H]1Oc1ccc(C#N)c(F)c1] | 492.1 | $^1$H NMR (400 MHz, DMSO-$d_6$) δ: 8.64 (d, J = 2.8 Hz, 1H), 8.03-8.09 (m, 1H), 7.96-8.02 (m, 1H), 7.77 (t, J = 8.3 Hz, 1H), 6.96 (dd, J = 11.5, 2.3 Hz, 1H), 6.71 (dd, J = 8.8, 2.3 Hz, 1H), 5.32 (s, 1H), 4.77 (d, J = 6.0 Hz, 1H), 4.49 (d, J = 2.8 Hz, 1H), 3.81-3.94 (m, 2H), 3.51-3.64 (m, 3H), 0.91 (d, J = 6.5 Hz, 3H) |
| 211 | 4-(((3S,4R)-1-((5-(difluoromethyl)pyridin-2-yl)sulfonyl)-4-hydroxy-4-((R)-1-hydroxyethyl)pyrrolidin-3-yl)oxy)-2-fluorobenzonitrile | 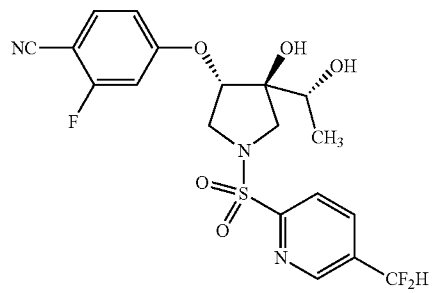 [SMILES: C[C@@H](O)[C@]1(O)CN(S(=O)(=O)c2ccc(C(F)F)cn2)C[C@@H]1Oc1ccc(C#N)c(F)c1] | 458.1 | $^1$H NMR (400 MHz, DMSO-$d_6$) δ: 8.73 (s, 1H), 8.20 (d, J = 8.0 Hz, 1H), 7.97 (d, J = 8.0 Hz, 1H), 7.69-7.79 (m, 1H), 7.08-7.40 (m, 1H), 6.93 (dd, J = 11.5, 2.3 Hz, 1H), 6.62 (dd, J = 8.7, 2.4 Hz, 1H), 5.31 (s, 1H), 4.75 (d, J = 6.0 Hz, 1H), 4.48 (d, J = 2.8 Hz, 1H), 3.91 (dd, J = 12.5, 3.0 Hz, 1H), 3.83 (m, 1H), 3.53-3.64 (m, 3H), 0.90 (d, J = 6.3 Hz, 3H) |
| 212 | 4-(((3S,4R)-1-((6-(difluoromethyl)pyridin-3-yl)sulfonyl)-4-hydroxy-4-((R)-1-hydroxyethyl)pyrrolidin-3-yl)oxy)-2-fluorobenzonitrile | 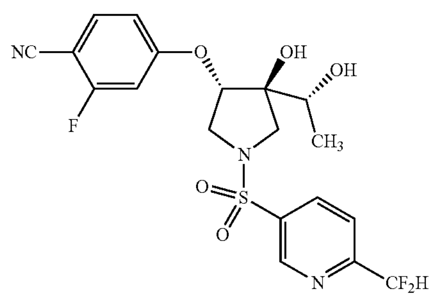 [SMILES: C[C@@H](O)[C@]1(O)CN(S(=O)(=O)c2ccc(C(F)F)nc2)C[C@@H]1Oc1ccc(C#N)c(F)c1] | 458.3 | $^1$H NMR (400 MHz, DMSO-$d_6$) δ: 8.99 (s, 1H), 8.33 (d, J = 8.0 Hz, 1H), 7.83 (d, J = 8.3 Hz, 1H), 7.74 (t, J = 8.3 Hz, 1H), 6.91-7.23 (m, 2H), 6.60 (d, J = 8.5 Hz, 1H), 5.34 (s, 1H), 4.76 (d, J = 6.0 Hz, 1H), 4.52 (d, J = 2.8 Hz, 1H), 3.81-3.88 (m, 1H), 3.72-3.79 (m, 1H), 3.38-3.60 (m, 3H), 0.90 (d, J = 6.3 Hz, 3H) |
| 213 | 4-(((3S,4R)-1-((6-(difluoromethoxy)pyridin-3-yl)sulfonyl)-4-hydroxy-4-((R)-1-hydroxyethyl)pyrrolidin-3-yl)oxy)-2-fluorobenzonitrile | 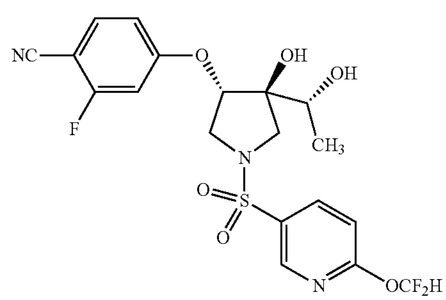 | 474.2 | $^1$H NMR (400 MHz, DMSO-$d_6$) δ: 8.58 (d, J = 2.0 Hz, 1H), 8.21 (dd, J = 8.8, 2.5 Hz, 1H), 7.55-7.94 (m, 2H), 7.19 (d, J = 8.8 Hz, 1H), 6.95 (dd, J = 11.5, 2.3 Hz, 1H), 6.68 (dd, J = 8.8, 2.3 Hz, 1H), 5.33 (s, 1H), 4.75 (d, J = 5.8 Hz, 1H), 4.50 (d, J = 3.0 Hz, 1H), 3.86 (quin, J = 6.3 Hz, 1H), 3.74 (dd, J = 12.4, 2.9 Hz, 1H), 3.43-3.56 (m, 2H), 3.38 (d, J = 12.3 Hz, 1H, partially hidden by solvent peak), 0.91 (d, J = 6.3 Hz, 3H) |

Example 214

4-(((3S,4S)-1-((5-chloropyridin-2-yl)sulfonyl)-4-hydroxy-4-(2-hydroxypropan-2-yl) pyrrolidin-3-yl)oxy)-2-fluorobenzonitrile

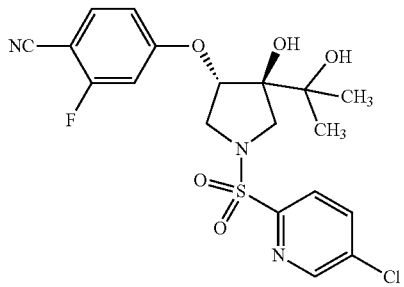 [SMILES: CC(C)(O)[C@]1(O)CN(S(=O)(=O)c2ccc(Cl)cn2)C[C@@H]1Oc1ccc(C#N)c(F)c1]

Step 1: (R,E)-4-((1-((5-chloropyridin-2-yl)sulfonyl)-4-ethylidenepyrrolidin-3-yl)oxy)-2-fluorobenzonitrile

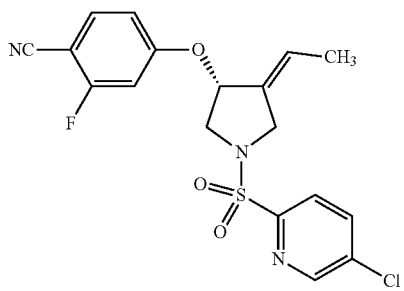 [SMILES: C/C=C1\CN(S(=O)(=O)c2ccc(Cl)cn2)C[C@@H]1Oc1ccc(C#N)c(F)c1]

To a mixture of (R)-4-((1-((5-chloropyridin-2-yl)sulfonyl)-4-methylenepyrrolidin-3-yl)oxy)-2-fluorobenzonitrile (1.3 g, 3.3 mmol) and 2-methylbut-2-ene (15 mL, 14 mmol) in DCM (10 mL) was added Grubbs Catalyst, $2^{nd}$ Generation (300 mg, 0.35 mmol) and the reaction mixture was stirred at rt overnight. The reaction mixture was concentrated and the residue was purified by flash column chromatography (SiO$_2$) eluting with a gradient of 0-70% EtOAc in hexanes. The product fractions were pooled and concentrated to give the title compound (600 mg, 44% yield). MS (m/z) 430.0 (M+Na$^+$).

Step 2: 4-(((3S,4S)-4-acetyl-1-((5-chloropyridin-2-yl)sulfonyl)-4-hydroxypyrrolidin-3-yl)oxy)-2-fluorobenzonitrile

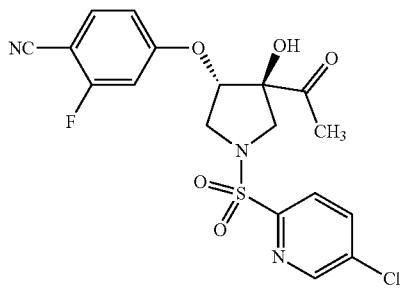 [SMILES: CC(=O)[C@]1(O)CN(S(=O)(=O)c2ccc(Cl)cn2)C[C@@H]1Oc1ccc(C#N)c(F)c1]

To a solution of (R,E)-4-((1-((5-chloropyridin-2-yl)sulfonyl)-4-ethylidenepyrrolidin-3-yl)oxy)-2-fluorobenzonitrile (600 mg, 1.4 mmol) in DCM (20 mL) was added m-CPBA (990 mg, 4.4 mmol) and the reaction mixture was stirred at rt for 48 h. The reaction was quenched with sat'd NaHSO$_3$ (aq) followed by sat'd NaHCO$_3$ (aq) and stirred 1 h. The organic layer was separated, dried over Na$_2$SO$_4$, filtered and concentrated. The crude product was purified by flash column chromatography (SiO$_2$) eluting with a gradient of 0-70% EtOAc in hexanes. The product fractions were pooled and concentrated to give the title compound (80 mg, 12% yield). $^1$H NMR (400 MHz, DMSO-d$_6$) δ: 8.57 (d, J=2.3 Hz, 1H), 8.13 (dd, J=8.3, 2.3 Hz, 1H), 7.88 (d, J=8.5 Hz, 1H), 7.79 (t, J=8.3 Hz, 1H), 6.97 (d, J=12.0 Hz, 1H), 6.70 (s, 1H), 6.65 (d, J=8.8 Hz, 1H), 4.99 (br s, 1H), 3.94 (d, J=11.0 Hz, 2H), 3.65 (d, J=12.5 Hz, 1H), 3.45 (d, J=11.0 Hz, 1H), 2.11 (s, 3H).

Step 3: 4-(((3S,4S)-1-((5-chloropyridin-2-yl)sulfonyl)-4-hydroxy-4-(2-hydroxypropan-2-yl) pyrrolidin-3-yl)oxy)-2-fluorobenzonitrile To a solution of 4-(((3S,4S)-4-acetyl-1-((5-chloropyridin-2-yl)sulfonyl)-4-hydroxypyrrolidin-3-yl)oxy)-2-fluorobenzonitrile (80 mg, 0.18 mmol) in THF (5 mL) was added 3 M methylmagnesium bromide in THF (2.3 mL) and the reaction mixture was stirred at rt for 6 min. The reaction was quenched with water and extracted with EtOAc. The organic layer was dried over Na$_2$SO$_4$, filtered and concentrated. The residue was purified by flash column chromatography (SiO$_2$) eluting with a gradient of 0-100% EtOAc in hexanes. The product fractions were pooled and concentrated to give the title compound (15 mg, 18% yield). $^1$H NMR (400 MHz, DMSO-d$_6$) δ: 8.58 (d, J=2.0 Hz, 1H), 8.11 (dd, J=8.3, 2.5 Hz, 1H), 7.85 (d, J=8.5 Hz, 1H), 7.79 (t, J=8.3 Hz, 1H), 6.97 (dd, J=11.8, 2.3 Hz, 1H), 6.69 (dd, J=8.8, 2.3 Hz, 1H), 5.29 (s, 1H), 4.60 (d, J=2.8 Hz, 1H), 4.24 (s, 1H), 3.85-3.93 (m, 2H), 3.40-3.50 (m, 2H), 1.14 (s, 3H), 1.08 (s, 3H). MS (m/z) 456.0 (M+H$^+$).

Example 215

4-(((3S,4S)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile

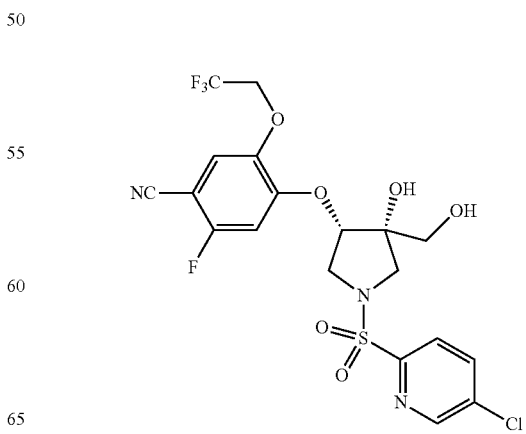

Step 1: (R)-2-((1-((5-chloropyridin-2-yl)sulfonyl)-4-methylenepyrrolidin-3-yl)oxy)-5-cyano-4-fluorophenylacetate

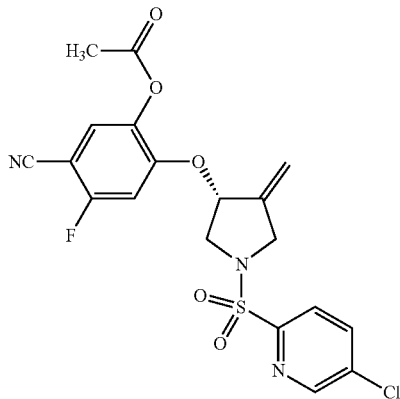 [SMILES: C=C1CN(S(=O)(=O)c2ccc(Cl)cn2)C[C@@H]1Oc1cc(F)c(C#N)cc1OC(C)=O]

To a cooled (0° C.) solution of (S)-1-((5-chloropyridin-2-yl)sulfonyl)-4-methylenepyrrolidin-3-ol (3.3 g, 12.0 mmol), 5-cyano-4-fluoro-2-hydroxyphenyl acetate (2.3 g, 12 mmol) and PS—PPh$_3$ (3 mmol/g) (6.0 g, 18 mmol) in DCM (100 mL) was added (E)-diisopropyl diazene-1,2-dicarboxylate (3.0 mL, 15 mmol) and the mixture was allowed to warm to rt with stirring overnight. The reaction mixture was filtered, concentrated, and purified by flash column chromatography (SiO$_2$) eluting with a gradient of 0-100% EtOAc in hexanes. The product fractions were pooled and concentrated to give the title compound as a yellow oil (4.2 g, 74% yield). MS (m/z) 452.2 (M+H$^+$).

Step 2: (R)-4-((1-((5-chloropyridin-2-yl)sulfonyl)-4-methylenepyrrolidin-3-yl)oxy)-2-fluoro-5-hydroxybenzonitrile

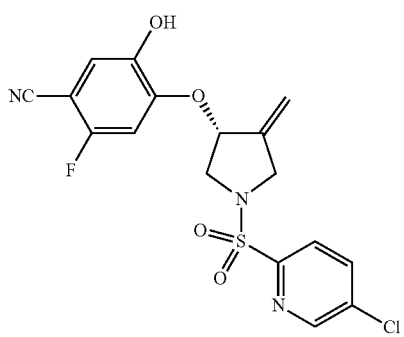 [SMILES: C=C1CN(S(=O)(=O)c2ccc(Cl)cn2)C[C@@H]1Oc1cc(F)c(C#N)cc1O]

To a solution of (R)-2-((1-((5-chloropyridin-2-yl)sulfonyl)-4-methylenepyrrolidin-3-yl)oxy)-5-cyano-4-fluorophenyl acetate (4.2 g, 9.3 mmol) in THF (200 mL) was added 2 M NaOH (aq) (65 mL, 130 mmol) and the reaction mixture was stirred at rt for 30 min. The reaction mixture was concentrated under reduced pressure. The residue was triturated with Et$_2$O and the title compound was collected by filtration as a white solid (2.4 g, 63% yield). MS (m/z) 410.1 (M+H$^+$).

Step 3: (R)-4-((1-((5-chloropyridin-2-yl)sulfonyl)-4-methylenepyrrolidin-3-yl)oxy)-2-fluoro-5-(2,2,2-trifluoroethoxy)benzonitrile

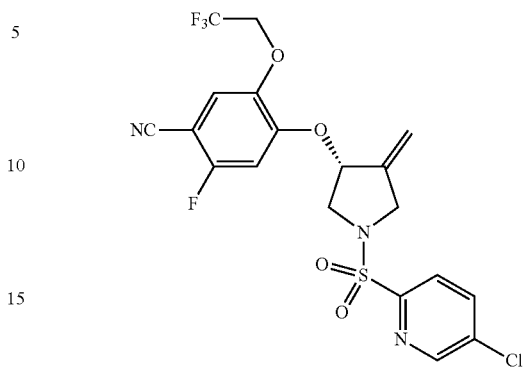

To a solution of (R)-4-((1-((5-chloropyridin-2-yl)sulfonyl)-4-methylenepyrrolidin-3-yl)oxy)-2-fluoro-5-hydroxybenzonitrile (1 g, 2.4 mmol) and K$_2$CO$_3$ (0.67 g, 4.9 mmol) in DMF (17 mL) was added 2,2,2-trifluoroethyl trifluoromethanesulfonate (1.13 g, 4.88 mmol) and the reaction mixture was stirred at rt for 2 h. The reaction mixture was diluted with EtOAc, washed with water and brine, dried over Na$_2$SO$_4$, filtered and concentrated. The crude product was purified by flash column chromatography (SiO$_2$) eluting with a gradient of 0-100% EtOAc in hexanes. The product fractions were pooled and concentrated to give the title compound as a white solid (1.2 g, 95% yield). MS (m/z) 492.2 (M+H$^+$).

Step 4: 4-(((3S,7S)-5-((5-chloropyridin-2-yl)sulfonyl)-1-oxa-5-azaspiro[2.4]heptan-7-yl)oxy)-2-fluoro-5-(2,2,2-trifluoroethoxy)benzonitrile

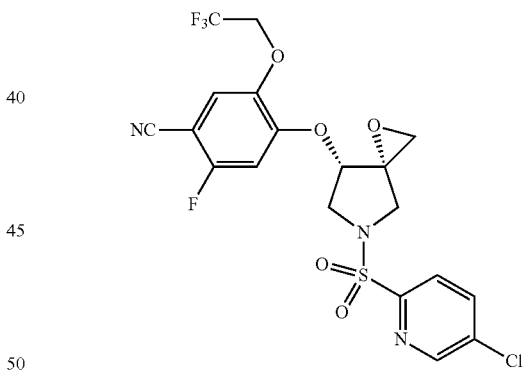

To a solution of (R)-4-((1-((5-chloropyridin-2-yl)sulfonyl)-4-methylenepyrrolidin-3-yl)oxy)-2-fluoro-5-(2,2,2-trifluoroethoxy)benzonitrile (1.2 g, 2.4 mmol) in DCE (24.4 mL) was added m-CPBA (1.6 g, 7.3 mmol) and the reaction mixture was stirred at 40° C. for 72 h. The reaction was quenched with sat'd NaHSO$_3$ (aq) followed by sat'd NaHCO$_3$ (aq) and stirred 1 h. The organic layer was separated, dried over Na$_2$SO$_4$, filtered and concentrated. The crude product was purified by flash column chromatography (SiO$_2$) eluting with a gradient of 0-100% EtOAc in hexanes. The product fractions were pooled and concentrated to give the title compound as a white solid (245 mg, 20% yield). $^1$H NMR (400 MHz, DMSO-d$_6$) δ: 8.66 (d, J=2.0 Hz, 1H), 8.21 (dd, J=8.4, 2.4 Hz, 1H), 7.96 (d, J=8.3 Hz, 1H), 7.69 (d, J=6.3 Hz, 1H), 7.29 (d, J=11.3 Hz, 1H), 4.90 (d, J=3.0 Hz, 1H), 4.59-4.75 (m, 2H), 3.95 (dd, J=12.7, 4.1 Hz, 1H), 3.79

(dd, J=12.5, 1.0 Hz, 1H), 3.60 (s, 2H), 3.09 (d, J=5.3 Hz, 1H), 3.03 (d, J=5.3 Hz, 1H). MS (m/z) 508.1 (M+H⁺).

Step 5: 4-(((3S,4S)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile To a solution of 4-(((3S,7S)-5-((5-chloropyridin-2-yl)sulfonyl)-1-oxa-5-azaspiro[2.4]heptan-7-yl)oxy)-2-fluoro-5-(2,2,2-trifluoroethoxy)benzonitrile (165 mg, 0.325 mmol) in THF (5 mL) was added 2 M H₂SO₄ (aq) (1.1 mL, 2.2 mmol) and the reaction mixture was stirred at 40° C. overnight. The reaction mixture was neutralized with 2 M NaOH (aq) (1 mL) and NaHCO₃ (aq), and then diluted with EtOAc. The organic layer was separated, dried over Na₂SO₄ and concentrated. The residue was purified by flash column chromatography (SiO₂) eluting with a gradient of 0-100% EtOAc in hexanes. The product fractions were pooled and concentrated to give the title compound as a colorless oil (123 mg, 69% yield). ¹H NMR (400 MHz, DMSO-d₆) δ: 8.75 (d, J=2.3 Hz, 1H), 8.23 (dd, J=8.4, 2.4 Hz, 1H), 7.96 (d, J=8.5 Hz, 1H), 7.65 (d, J=6.3 Hz, 1H), 7.39 (d, J=11.3 Hz, 1H), 5.29 (s, 1H), 5.19 (t, J=5.5 Hz, 1H), 4.84 (t, J=5.0 Hz, 1H), 4.61-4.76 (m, 2H), 3.91 (dd, J=11.0, 5.8 Hz, 1H), 3.56 (dd, J=11.2, 4.4 Hz, 1H), 3.48 (d, J=10.3 Hz, 1H), 3.32 (d, J=5.8 Hz, 2H), 3.25 (d, J=10.3 Hz, 1H). MS (m/z) 526.1 (M+H⁺).

Example 216

4-(((3S,4R)-1-((2-cyano-4-methylphenyl)sulfonyl)-4-hydroxy-4-(hydroxymethyl) pyrrolidin-3-yl)oxy)-2-fluorobenzonitrile

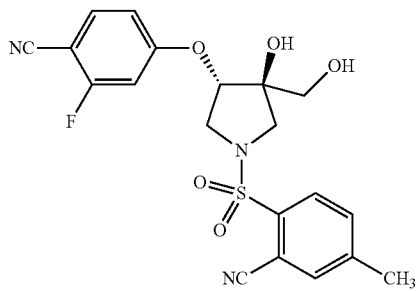 [SMILES: Cc1ccc(S(=O)(=O)N2C[C@H](Oc3ccc(C#N)c(F)c3)[C@](O)(CO)C2)c(C#N)c1]

A suspension of 4-(((3S,4R)-1-((4-bromo-2-cyanophenyl)sulfonyl)-4-hydroxy-4-(hydroxymethyl)pyrrolidin-3-yl)oxy)-2-fluorobenzonitrile (100 mg, 0.20 mmol), methylboronic acid (12 mg, 0.20 mmol), 1,1'-bis(diphenylphosphino)ferrocenedichloro palladium(II) dichloromethane complex (7.4 mg, 10.1 µmol) and 1 M K₂CO₃ (aq) (0.4 mL, 0.4 mmol) in 1,4-dioxane (1 mL) was subjected to microwave irradiation at 100° C. for 1 h.

The mixture was partitioned between EtOAc and water, the layers separated and the aqueous layer extracted with EtOAc. The organic layers were combined, washed with brine, dried over MgSO₄, filtered and concentrated under reduced pressure. The crude product was purified by reverse phase HPLC (C18 Sunfire OBD 19×100 mm preparatory column, eluting at 20 mL/min with a linear gradient running from 10-90% CH₃CN/H₂O (0.1% TFA)). The product fractions were pooled and concentrated under reduced pressure to give the title compound as a white solid (40.9 mg, 47% yield). ¹H NMR (400 MHz, DMSO-d₆) δ: 7.83-7.89 (m, 2H), 7.79 (t, J=8.3 Hz, 1H), 7.64 (d, J=8.0 Hz, 1H), 6.98 (d, J=11.8 Hz, 1H), 6.71 (d, J=8.8 Hz, 1H), 5.46 (s, 1H), 4.80 (t, J=5.5 Hz, 1H), 4.67 (d, J=2.3 Hz, 1H), 3.82 (dd, J=12.0, 2.8 Hz, 1H), 3.44-3.57 (m, 3H), 3.38 (1H, hidden under solvent peak), 3.27-3.32 (m, 1H), 2.43 (s, 3H). MS (m/z) 432.0 (M+H⁺).

The following compounds were prepared using procedures analogous to those described in Examples 215-216 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 217 | 4-(((3S,4R)-1-((2-cyano-4-ethylphenyl)sulfonyl)-4-hydroxy-4-(hydroxymethyl)pyrrolidin-3-yl)oxy)-2-fluorobenzonitrile | 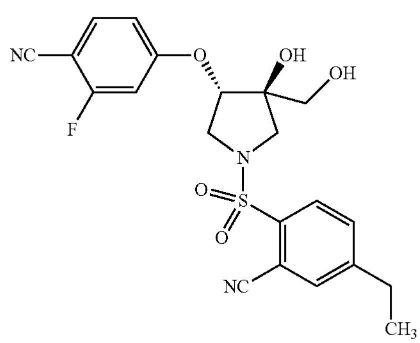 [SMILES: CCc1ccc(S(=O)(=O)N2C[C@H](Oc3ccc(C#N)c(F)c3)[C@](O)(CO)C2)c(C#N)c1] | 445.9 | ¹H NMR (400 MHz, DMSO-d₆) δ: 7.86-7.93 (m, 2H), 7.79 (t, J = 8.3 Hz, 1H), 7.69 (d, J = 8.3 Hz, 1H), 6.95-7.01 (m, 1H), 6.72 (dd, J = 8.8, 1.8 Hz, 1H), 5.47 (br s, 1H), 4.75 (br s, 1H), 4.68 (d, J = 2.5 Hz, 1H), 3.82 (dd, J = 12.0, 2.8 Hz, 1H), 3.23-3.76 (m, 5H), 2.74 (q, J = 7.5 Hz, 2H), 1.22 (t, J = 7.5 Hz, 3H) |

| Ex. | Name | Structure | MS (m/z) (M + H⁺) | ¹H NMR |
|---|---|---|---|---|
| 218 | 4-(((3R,4S)-4-(4-cyano-3-fluorophenoxy)-3-hydroxy-3-(hydroxymethyl)pyrrolidin-1-yl)sulfonyl)-[1,1'-biphenyl]-3-carbonitrile | 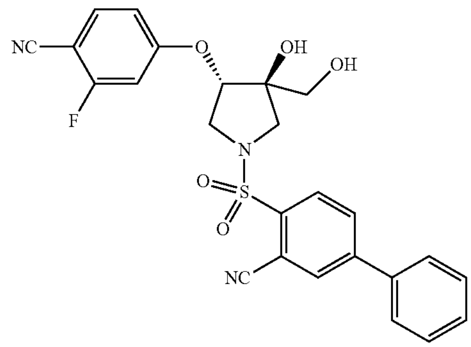 [SMILES: N#Cc1ccc(O[C@H]2CN(S(=O)(=O)c3ccc(-c4ccccc4)cc3C#N)C[C@@]2(O)CO)cc1F] | 494.1 | $^1$H NMR (400 MHz, DMSO-d$_6$) δ: 8.38 (s, 1H), 8.14 (d, J = 8.5 Hz, 1H), 8.02 (d, J = 8.5 Hz, 1H), 7.83 (d, J = 7.5 Hz, 2H), 7.67 (t, J = 8.3 Hz, 1H), 7.47-7.61 (m, 3H), 7.01 (d, J = 11.8 Hz, 1H), 6.76 (d, J = 8.8 Hz, 1H), 5.48 (br s, 1H), 4.70 (br s, 1H), 3.87 (dd, J = 11.9, 2.6 Hz, 1H), 3.51-3.59 (m, 2H), 3.41-3.50 (m, 3H) |
| 219 | 4-(((3S,4R)-1-((2-cyano-4-(prop-1-yn-1-yl)phenyl)sulfonyl)-4-hydroxy-4-(hydroxymethyl)pyrrolidin-3-yl)oxy)-2-fluorobenzonitrile | 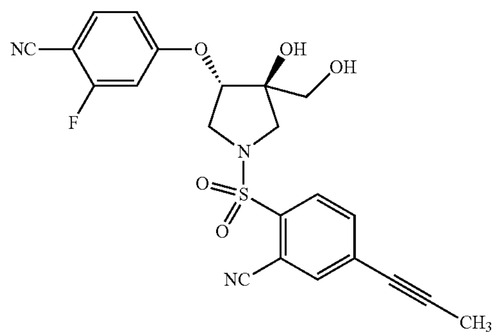 [SMILES: CC#Cc1ccc(S(=O)(=O)N2C[C@H](Oc3ccc(C#N)c(F)c3)[C@](O)(CO)C2)c(C#N)c1] | 456.0 | $^1$H NMR (400 MHz, CD$_3$OD) δ: 7.95 (d, J = 8.0 Hz, 1H), 7.86 (s, 1H), 7.60-7.75 (m, 2H), 6.80 (d, J = 11.3 Hz, 1H), 6.73 (d, J = 8.5 Hz, 1H), 5.51 (s, 1H), 4.84 (1H, under solvent peak) 4.71 (d, J = 2.5 Hz, 1H), 3.94 (dd, J = 12.2, 2.9 Hz, 1H), 3.77 (d, J = 11.5 Hz, 1H), 3.62-3.71 (m, 2H), 3.55 (m, 2H), 2.14 (s, 3H) |

Example 220

4-(((3S,4R)-1-((2-cyano-4-ethynylphenyl)sulfonyl)-4-hydroxy-4-(hydroxymethyl) pyrrolidin-3-yl)oxy)-2-fluorobenzonitrile

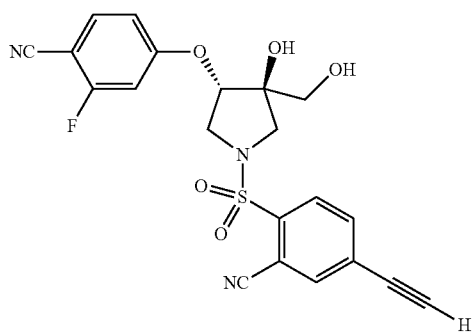 [SMILES: C#Cc1ccc(S(=O)(=O)N2C[C@H](Oc3ccc(C#N)c(F)c3)[C@](O)(CO)C2)c(C#N)c1]

A suspension of 4-(((3S,4R)-1-((4-bromo-2-cyanophenyl)sulfonyl)-4-hydroxy-4-(hydroxymethyl)pyrrolidin-3-yl)oxy)-2-fluorobenzonitrile (100 mg, 0.20 mmol), triphenylphosphine (11 mg, 0.04 mmol), copper(I) iodide (8 mg, 0.04 mmol), bis(triphenylphosphine)palladium(II) chloride (14 mg, 0.02 mmol) and triethylamine (0.084 mL, 0.60 mmol) in DMF (2 mL) was treated with ethynyltrimethylsilane (0.034 mL, 0.24 mmol) and subjected to microwave irradiation at 100° C. for 1 h. The solution was partitioned between EtOAc and water, the layers separated and the aqueous layer extracted with EtOAc (3×10 mL). The organic layers were combined, washed with brine, dried over MgSO$_4$, filtered and concentrated under reduced pressure. The crude product was purified by reverse phase HPLC (C18 Sunfire OBD 19×100 mm preparatory column, eluting at 20 mL/min with a linear gradient running from 30-90% CH$_3$CN/H$_2$O (0.1% TFA)). The product fractions were pooled and concentrated under reduced pressure to give 4-(((3S,4R)-1-((2-cyano-4-((trimethylsilyl)ethynyl)phenyl)sulfonyl)-4-hydroxy-4-(hydroxymethyl)pyrrolidin-3-yl)oxy)-2-fluorobenzonitrile. MS (m/z) 514 (M+H). The intermediate was treated with 1 M TBAF/THF (1.01 mL, 1.01 mmol) and stirred for 1 h. The solution was partitioned between EtOAc and water, the layers separated and the aqueous layer extracted with EtOAc (3×10 mL). The organic layers were combined, washed with brine, dried over MgSO$_4$, filtered and concentrated under reduced pressure. The crude product was purified by reverse phase HPLC (C18 Sunfire OBD 19×100 mm preparatory column, eluting at 20 mL/min with a linear gradient running from 10-90% CH$_3$CN/H$_2$O (0.1% TFA)). The product fractions were pooled and concentrated under reduced pressure to give the title compound as a tan solid (7 mg, 8% yield). $^1$H NMR (400 MHz, CD$_3$OD) δ: 7.99-8.07 (m, 2H), 7.84 (d, J=8.3 Hz, 1H), 7.53-7.72 (m, 1H), 6.69-6.89 (m, 2H), 4.72 (d, J=2.3 Hz, 1H), 4.06 (s, 1H), 3.96 (dd, J=11.9, 2.9 Hz, 1H), 3.61-3.83 (m, 3H), 3.49-3.60 (m, 2H). MS (m/z) 442.0 (M+H⁺).

The following compounds were prepared using procedures analogous to those described in Example 220 using appropriately substituted starting materials. As is appreciated by those skilled in the art, these analogous examples may involve variations in general reaction conditions.

| Ex. | Name | Structure | MS (m/z) (M + H+) | 1H NMR |
|---|---|---|---|---|
| 221 | 4-(((3S,4R)-1-((2-cyano-4-((trimethylsilyl)ethynyl)phenyl)sulfonyl)-4-hydroxy-4-(hydroxymethyl)pyrrolidin-3-yl)oxy)-2-fluorobenzonitrile | 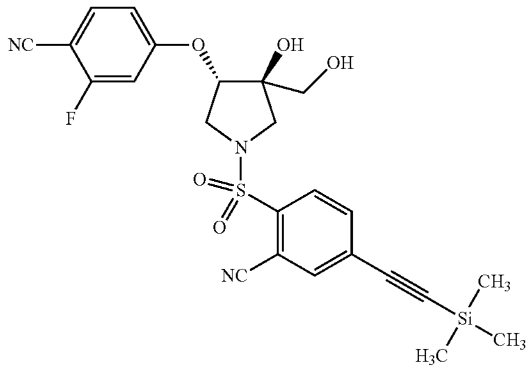 [SMILES: C[Si](C)(C)C#Cc1ccc(S(=O)(=O)N2C[C@H](Oc3ccc(C#N)c(F)c3)[C@](O)(CO)C2)c(C#N)c1] | 513.9 | 1H NMR (400 MHz, DMSO-d6) δ: 8.12 (s, 1H), 7.89-7.94 (m, 1H), 7.82 (d, J = 8.3 Hz, 1H), 7.75 (t, J = 8.2 Hz, 1H), 6.98 (d, J = 11.5 Hz, 1H), 6.78 (d, J = 8.8 Hz, 1H), 5.47 (s, 1H), 4.82 (t, J = 5.5 Hz, 1H), 4.66 (br s, 1H), 3.82 (dd, J = 12.2, 2.9 Hz, 1H), 3.37-3.58 (m, 5H), 0.29 (s, 9H) |
| 222 | 2-fluoro-4-(((3S,4R)-4-hydroxy-4-(hydroxymethyl)-1-((4-(prop-1-yn-1-yl)phenyl)sulfonyl)pyrrolidin-3-yl)oxy)benzonitrile | 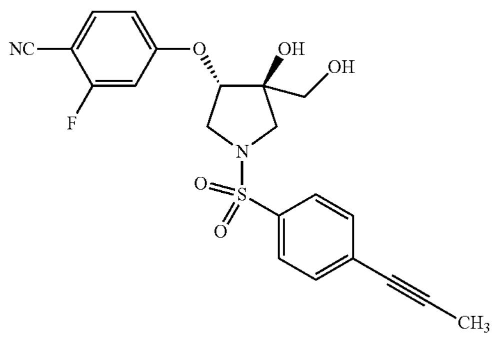 [SMILES: CC#Cc1ccc(S(=O)(=O)N2C[C@H](Oc3ccc(C#N)c(F)c3)[C@](O)(CO)C2)cc1] | 431.3 | 1H NMR (400 MHz, DMSO-d6) δ: 7.75 (t, J = 8.2 Hz, 1H), 7.65 (d, J = 8.0 Hz, 2H), 7.48 (d, J = 8.0 Hz, 2H), 6.88 (d, J = 11.8 Hz, 1H), 6.67 (d, J = 8.5 Hz, 1H), 4.60 (d, J = 2.3 Hz, 1H), 3.61-3.77 (m, 2H), 3.41-3.54 (m, 2H), 3.28-3.34 (2H, partially hidden by solvent peak), 2.12 (s, 3H) |
| 223 | 2-fluoro-4-(((3S,4R)-4-hydroxy-4-(hydroxymethyl)-1-((6-(prop-1-yn-1-yl)pyridin-3-yl)sulfonyl)pyrrolidin-3-yl)oxy)benzonitrile | 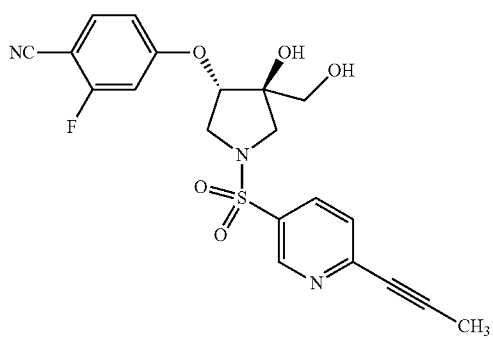 [SMILES: CC#Cc1ccc(S(=O)(=O)N2C[C@H](Oc3ccc(C#N)c(F)c3)[C@](O)(CO)C2)cn1] | 431.9 | 1H NMR (400 MHz, DMSO-d6) δ: 8.79 (s, 1H), 8.07 (d, J = 8.3 Hz, 1H), 7.77 (t, J = 8.3 Hz, 1H), 7.56 (d, J = 8.0 Hz, 1H), 6.92 (d, J = 11.8 Hz, 1H), 6.69 (d, J = 8.8 Hz, 1H), 4.62 (d, J = 2.3 Hz, 1H), 3.71 (dd, J = 12.2, 2.9 Hz, 1H), 3.42-3.55 (m, 2H), 3.31-3.40 (m, 3H, partially hidden by solvent peak), 2.16 (s, 3H) |
| 224 | 4-(((3S,4R)-1-((4-cyano-2-(prop-1-yn-1-yl)phenyl)sulfonyl)-4-hydroxy-4-(hydroxymethyl)pyrrolidin-3-yl)oxy)-2-fluorobenzonitrile | 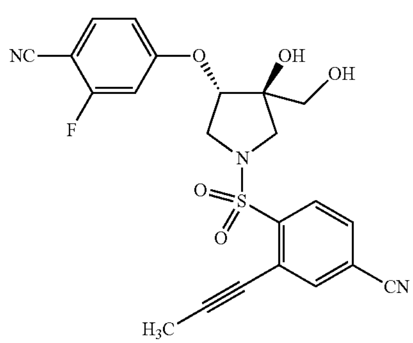 [SMILES: CC#Cc1cc(C#N)ccc1S(=O)(=O)N1C[C@H](Oc2ccc(C#N)c(F)c2)[C@](O)(CO)C1] | 455.9 | 1H NMR (400 MHz, CD3OD) δ: 8.03 (d, J = 8.3 Hz, 1H), 7.85 (s, 1H), 7.73 (d, J = 8.0 Hz, 1H), 7.62-7.69 (m, 1H), 6.83 (d, J = 11.5 Hz, 1H), 6.75 (d, J = 8.5 Hz, 1H), 4.72 (d, J = 2.3 Hz, 1H), 3.97 (dd, J = 12.0, 2.5 Hz, 1H), 3.73-3.87 (m, 2H), 3.62-3.68 (m, 1H), 3.47-3.59 (m, 2H), 2.05 (s, 3H) |

| Ex. | Name | Structure | MS (m/z) (M + H⁺) | ¹H NMR |
|---|---|---|---|---|
| 225 | 4-(((3S,4R)-1-((2-ethynyl-4-(trifluoromethyl)phenyl)sulfonyl)-4-hydroxy-4-(hydroxymethyl)pyrrolidin-3-yl)oxy)-2-fluorobenzonitrile | 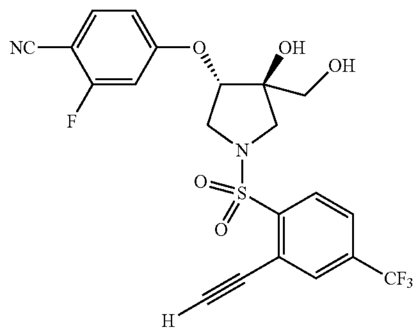 [SMILES: C#Cc1cc(C(F)(F)F)ccc1S(=O)(=O)N1C[C@H](Oc2ccc(C#N)c(F)c2)[C@](O)(CO)C1] | 485.2 | ¹H NMR (400 MHz, CD₃OD) δ: 8.13 (d, J = 8.3 Hz, 1H), 7.91 (s, 1H), 7.80 (d, J = 7.8 Hz, 1H), 7.61 (t, J = 8.2 Hz, 1H), 6.78 (d, J = 11.3 Hz, 1H), 6.72 (d, J = 8.8 Hz, 1H), 4.72 (br. s., 1H), 4.11 (s, 1H), 3.93-4.01 (m, 1H), 3.73-3.85 (m, 2H), 3.59-3.68 (m, 2H), 3.50-3.58 (m, 1H) |
| 226 | 4-(((3S,4R)-1-((6-(cyclopropylethynyl)pyridin-3-yl)sulfonyl)-4-hydroxy-4-(hydroxymethyl)pyrrolidin-3-yl)oxy)-2-fluorobenzonitrile | 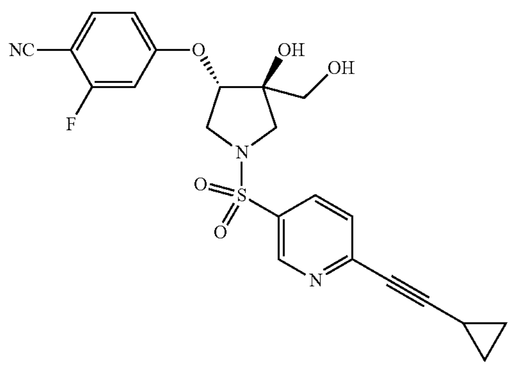 [SMILES: N#Cc1ccc(O[C@H]2CN(S(=O)(=O)c3ccc(C#CC4CC4)nc3)C[C@@]2(O)CO)cc1F] | 458.2 | ¹H NMR (400 MHz, DMSO-d₆) δ: 8.70-8.78 (m, 1H), 8.04 (dd, J = 8.2, 2.4 Hz, 1H), 7.71-7.80 (m, 1H), 7.52 (d, J = 8.3 Hz, 1H), 6.88 (dd, J = 11.8, 2.3 Hz, 1H), 6.69 (dd, J = 8.8, 2.3 Hz, 1H), 5.39 (s, 1H), 4.80 (t, J = 5.6 Hz, 1H), 4.60 (d, J = 3.0 Hz, 1H), 3.69 (dd, J = 12.3, 3.3 Hz, 1H), 3.41-3.54 (m, 2H), 3.31-3.40 (m, 3H, partially hidden by solvent peak), 1.67 (tt, J = 8.3, 5.0 Hz, 1H), 0.97-1.05 (m, 2H), 0.83-0.91 (m, 2H) |
| 227 | 2-fluoro-4-(((3S,4R)-4-hydroxy-4-(hydroxymethyl)-1-((5-(prop-1-yn-1-yl)pyridin-2-yl)sulfonyl)pyrrolidin-3-yl)oxy)benzonitrile | 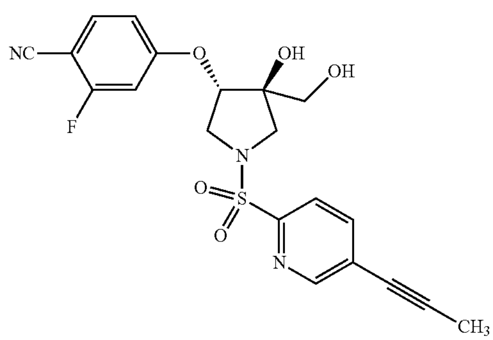 [SMILES: CC#Cc1ccc(S(=O)(=O)N2C[C@H](Oc3ccc(C#N)c(F)c3)[C@](O)(CO)C2)nc1] | 432.0 | ¹H NMR (400 MHz, DMSO-d₆) δ: 8.49(d, J = 1.5 Hz, 1H), 7.96 (dd, J = 8.3, 2.0 Hz, 1H), 7.73-7.84 (m, 2H), 6.93 (dd, J = 11.8, 2.3 Hz, 1H), 6.69 (dd, J = 8.7, 2.4 Hz, 1H), 5.39 (s, 1H), 4.78 (t, J = 5.6 Hz, 1H), 4.58 (d, J = 3.0 Hz, 1H), 3.85 (dd, J = 12.2, 3.4 Hz, 1H), 3.35-3.59 (m, 5H), 2.16 (s, 3H) |
| 228 | 4-(((3S,4R)-1-((5-ethynylpyridin-2-yl)sulfonyl)-4-hydroxy-4-(hydroxymethyl)pyrrolidin-3-yl)oxy)-2-fluorobenzonitrile | 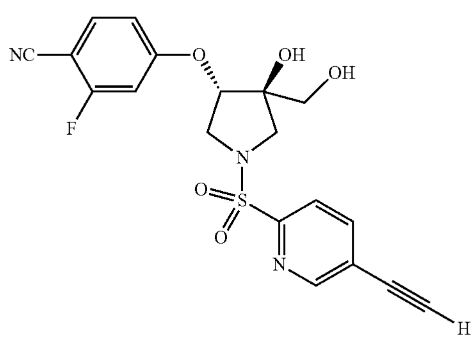 [SMILES: C#Cc1ccc(S(=O)(=O)N2C[C@H](Oc3ccc(C#N)c(F)c3)[C@](O)(CO)C2)nc1] | 418.0 | ¹H NMR (400 MHz, DMSO-d₆) δ: 8.60 (d, J = 1.5 Hz, 1H), 8.09 (dd, J = 8.0, 2.0 Hz, 1H), 7.81-7.88 (m, 1H), 7.72-7.80 (m, 1H), 6.94 (dd, J = 11.7, 2.4 Hz, 1H), 6.70 (dd, J = 8.8, 2.3 Hz, 1H), 5.39 (s, 1H), 4.76-4.82 (m, 2H), 4.59 (d, J = 3.0 Hz, 1H), 3.87 (dd, J = 12.2, 3.1 Hz, 1H), 3.41-3.57 (m, 4H), 3.38 (s, 1H) |

| Ex. | Name | Structure | MS (m/z) (M + H+) | 1H NMR |
|---|---|---|---|---|
| 229 | 4-(((3S,4R)-1-((5-(3,3-dimethylbut-1-yn-1-yl)pyridin-2-yl)sulfonyl)-4-hydroxy-4-(hydroxymethyl)pyrrolidin-3-yl)oxy)-2-fluorobenzonitrile | 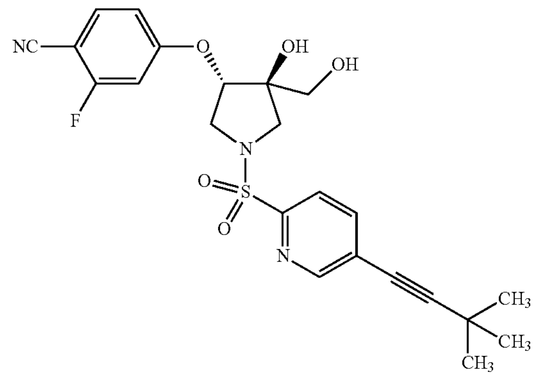 [SMILES: CC(C)(C)C#Cc1ccc(S(=O)(=O)N2C[C@H](Oc3ccc(C#N)c(F)c3)[C@](O)(CO)C2)nc1] | 474.2 | 1H NMR (400 MHz, DMSO-d6) δ: 8.38 (d, J = 1.8 Hz, 1H), 7.92 (dd, J = 8.0, 2.0 Hz, 1H), 7.70-7.79 (m, 2H), 6.86 (dd, J = 11.8, 2.0 Hz, 1H), 6.69 (dd, J = 8.8, 2.3 Hz, 1H), 5.40 (s, 1H), 4.78 (t, J = 5.6 Hz, 1H), 4.55 (d, J = 2.8 Hz, 1H), 3.83 (dd, J = 12.2, 2.9 Hz, 1H), 3.40-3.60 (m, 4H), 3.36 (br s, 1H), 1.32-1.38 (m, 9H) |
| 230 | 2-fluoro-4-(((3S,4R)-4-hydroxy-4-(hydroxymethyl)-1-((5-(phenylethynyl)pyridin-2-yl)sulfonyl)pyrrolidin-3-yl)oxy)benzonitrile | 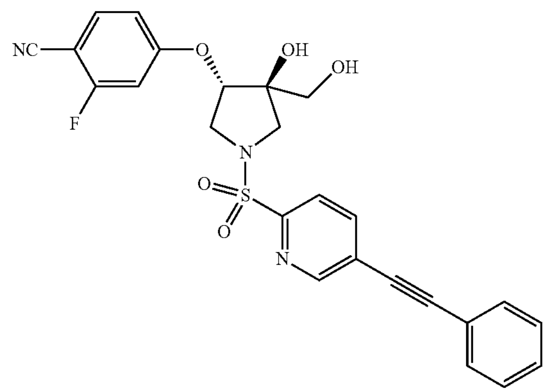 [SMILES: N#Cc1ccc(O[C@H]2CN(S(=O)(=O)c3ccc(C#Cc4ccccc4)cn3)C[C@@]2(O)CO)cc1F] | 494.2 | 1H NMR (400 MHz, DMSO-d6) δ: 8.65 (d, J = 1.3 Hz, 1H), 8.14 (dd, J = 8.0, 2.0 Hz, 1H), 7.87 (d, J = 8.0 Hz, 1H), 7.77 (t, J = 8.3 Hz, 1H), 7.61-7.71 (m, 2H), 7.46-7.57 (m, 3H), 6.94 (dd, J = 11.7, 1.9 Hz, 1H), 6.73 (dd, J = 8.8, 2.0 Hz, 1H), 5.41 (s, 1H), 4.80 (t, J = 5.6 Hz, 1H), 4.60 (d, J = 2.5 Hz, 1H), 3.88 (dd, J = 12.2, 2.9 Hz, 1H), 3.44-3.62 (m, 4H), 3.40 (1H, partially hidden by solvent peak) |

Example 231

6-(((3R,4S)-4-(4-cyano-3-fluorophenoxy)-3-hydroxy-3-(hydroxymethyl)pyrrolidin-1-yl)sulfonyl)nicotinonitrile

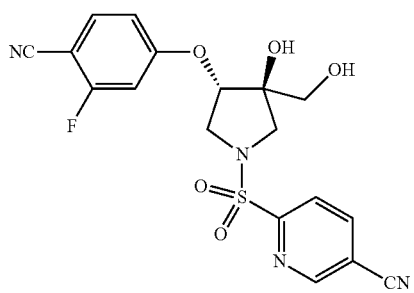 [SMILES: N#Cc1ccc(S(=O)(=O)N2C[C@H](Oc3ccc(C#N)c(F)c3)[C@](O)(CO)C2)nc1]

A mixture of 4-(((3S,4R)-1-((5-bromopyridin-2-yl)sulfonyl)-4-hydroxy-4-(hydroxymethyl)pyrrolidin-3-yl)oxy)-2-fluorobenzonitrile (132 mg, 0.28 mmol), Zn(CN)$_2$ (39 mg, 0.33 mmol) and Pd(Ph$_3$P)$_4$ (32 mg, 0.028 mmol) in DMF (2.5 mL) was subjected to microwave irradiation at 100° C. for 2 h. The reaction mixture was partitioned between DCM and water, the layers separated and the aqueous layer extracted with DCM. The organic layers were combined, washed with brine, dried over MgSO$_4$, filtered and concentrated under a steam of nitrogen at 40° C. The crude yellowish oil was purified by reverse phase HPLC (C18 Sunfire OBD 19×100 mm preparatory column, eluting at 20 mL/min with a linear gradient running from 10-90% CH$_3$CN/H$_2$O (0.1% TFA)). The product fractions were pooled and concentrated. The residue was treated with sat'd NaHCO$_3$ (aq) and extracted with DCM (2×25 mL). The organic extracts were combined, dried over MgSO$_4$, filtered and concentrated to near dryness. Hexane was added to form a precipitate and the title compound was obtained as a white solid (33 mg, 28% yield). 1H NMR (400 MHz, DMSO-d$_6$) δ: 9.02 (s, 1H), 8.55 (dd, J=8.0, 1.8 Hz, 1H), 8.02 (d, J=8.0 Hz, 1H), 7.78 (t, J=8.3 Hz, 1H), 6.99 (dd, J=11.8, 1.8 Hz, 1H), 6.74 (dd, J=8.8, 2.0 Hz, 1H), 5.41 (s, 1H), 4.80 (t, J=5.5 Hz, 1H), 4.60 (d, J=2.5 Hz, 1H), 3.90 (dd, J=12.2, 3.1 Hz, 1H), 3.43-3.59 (m, 4H), 3.36-3.40 (m, 1H, partially hidden by solvent peak). MS (m/z) 419.1 (M+H+).

The following compounds were prepared using procedures analogous to those described in Example 231 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 232 | 4-(((3S,4R)-1-((2-cyano-4-(trifluoromethoxy)phenyl)sulfonyl)-4-hydroxy-4-(hydroxymethyl)pyrrolidin-3-yl)oxy)-2-fluorobenzonitrile | 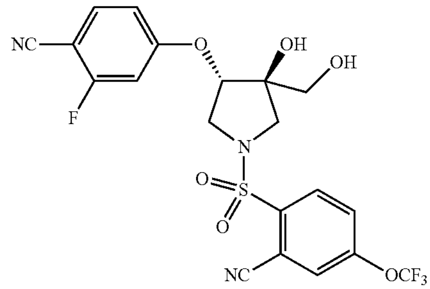 | 501.9 | $^1$H NMR (400 MHz, DMSO-d$_6$) δ: 8.23 (s, 1H), 8.11 (d, J = 8.8 Hz, 1H), 7.86 (d, J = 8.8 Hz, 1H), 7.78 (t, J = 8.3 Hz, 1H), 7.04 (d, J = 11.5 Hz, 1H), 6.79 (d, J = 8.8 Hz, 1H), 5.49 (br s, 1H), 4.71 (br s, 1H), 3.81-3.89 (m, 1H), 3.47-3.59 (m, 3H), 3.43 (m, 3H, partially hidden by solvent peak) |

Example 233

4-(((3S,4S)-4-(aminomethyl)-1-((5-chloropyridin-2-yl)sulfonyl)-4-hydroxypyrrolidin-3-yl)oxy)-2-fluorobenzonitrile, Hydrochloride

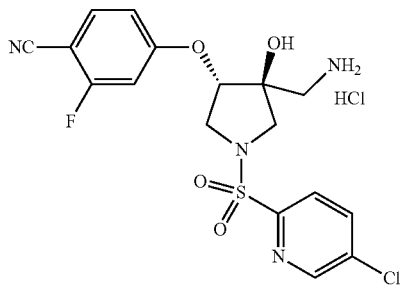 [SMILES: N#Cc1ccc(O[C@H]2CN(S(=O)(=O)c3ccc(Cl)cn3)C[C@@]2(O)CN)cc1F ; Cl]

Step 1: 4-(((3R,7S)-5-((5-chloropyridin-2-yl)sulfonyl)-1-oxa-5-azaspiro[2.4]heptan-7-yl)oxy)-2-fluorobenzonitrile OR 4-(((3S,7S)-5-((5-chloropyridin-2-yl)sulfonyl)-1-oxa-5-azaspiro[2.4]heptan-7-yl)oxy)-2-fluorobenzonitrile

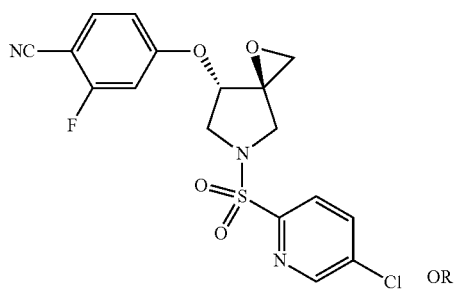

(R)-4-((1-((5-chloropyridin-2-yl)sulfonyl)-4-methylenepyrrolidin-3-yl)oxy)-2-fluorobenzonitrile (500 mg, 1.3 mmol) was dissolved in DCM (50 mL) and m-CPBA (880 mg, 5.1 mmol) was added. The mixture was stirred 5 days at rt, then treated with an additional portion of m-CPBA (2×200 mg, 2×1.2 mmol) and warmed to 40° C. for 6 h. The reaction mixture was poured into 10% Na$_2$S$_2$O$_3$ (aq) and extracted with DCM (2×). The organic layers were combined, dried over MgSO$_4$, filtered and concentrated. The crude mixture of cis/trans isomers was separated by flash column chromatography (SiO$_2$) eluting with a gradient of 0-100% EtOAc in hexanes. The separated isomer fractions were each pooled and concentrated to give the individual trans and cis isomers as the title compounds. Trans-isomer: (1$^{st}$ elutant, 80 mg as a white solid, 15% yield) $^1$H NMR (400 MHz, DMSO-d$_6$) δ: 8.73 (d, J=2.0 Hz, 1H), 8.18 (dd, J=8.5, 2.3 Hz, 1H), 7.93 (d, J=8.3 Hz, 1H), 7.82 (t, J=8.3 Hz, 1H), 7.03 (dd, J=11.5, 2.0 Hz, 1H), 6.77 (dd, J=8.7, 1.9 Hz, 1H), 4.74 (d, J=3.5 Hz, 1H), 4.06 (d, J=12.0 Hz, 1H), 3.95 (dd, J=12.8, 4.3 Hz, 1H), 3.64 (d, J=12.8 Hz, 1H), 3.32 (d, J=12.0 Hz, 1H), 3.08-3.16 (m, 2H). MS (m/z) 410.1 (M+H⁺). Cis-isomer: (2$^{nd}$ elutant, 200 mg as a white solid, 38% yield) $^1$H NMR (400 MHz, DMSO-d$_6$) δ: 8.76 (d, J=2.0 Hz, 1H), 8.22 (dd, J=8.5, 2.5 Hz, 1H), 7.96 (d, J=8.3 Hz, 1H), 7.80 (t, J=8.3 Hz, 1H), 6.96 (dd, J=11.8, 2.5 Hz, 1H), 6.74 (dd, J=8.8, 2.5 Hz, 1H), 4.90 (d, J=3.0 Hz, 1H), 3.92 (dd, J=12.8, 4.0 Hz, 1H), 3.67-3.76 (m, 2H), 3.59 (d, J=10.5 Hz, 1H), 3.12 (d, J=5.5 Hz, 1H), 3.03 (d, J=5.3 Hz, 1H). MS (m/z) 410.1 (M+H⁺).

Step 2: 4-(((3S,4S)-4-(aminomethyl)-1-((5-chloropyridin-2-yl)sulfonyl)-4-hydroxypyrrolidin-3-yl)oxy)-2-fluorobenzonitrile, Hydrochloride A mixture of 4-(((3R,7S)-5-((5-chloropyridin-2-yl)sulfonyl)-1-oxa-5-azaspiro[2.4]heptan-7-yl)oxy)-2-fluorobenzonitrile (80 mg, 0.2 mmol) and 2 M NH$_3$ in MeOH (10 mL, 20 mmol) was subjected to microwave irradiation at 60° C. for 20 min. The mixture was concentrated under reduced pressure, The mixture was concentrated under reduced pressure, and redissolved and concentrated from DCM several times. The residue was dissolved in CH$_3$CN (1.5 mL) and 1 M HCl in Et$_2$O (200 µl, 0.2 mmol) was added. Et$_2$O was then added dropwise with stirring and the resulting solid precipitate which was collected by filtration to give title compound (61 mg, 64% yield). $^1$H NMR (400 MHz, DMSO-d$_6$) δ: 8.52 (d, J=2.3 Hz, 1H), 8.03-8.15 (m, 4H), 7.76-7.86 (m, 2H), 6.99 (dd, J=11.5, 2.3 Hz, 1H), 6.70 (dd, J=8.8, 2.3 Hz, 1H), 6.32 (s, 1H), 4.72 (d, J=2.8 Hz, 1H), 3.92 (dd, J=12.8, 3.0 Hz, 1H), 3.49-3.64 (m, 3H), 2.96-3.16 (m, 2H). MS (m/z) 427.0 (M+H$^+$).

Example 233 A—Preparation of crystalline form 1 of 4-(((3S,4S)-4-(aminomethyl)-1-((5-chloropyridin-2-yl)sulfonyl)-4-hydroxypyrrolidin-3-yl)oxy)-2-fluorobenzonitrile, esylate anhydrate To a solution of 4-(((3S,4S)-4-(aminomethyl)-1-((5-chloropyridin-2-yl)sulfonyl)-4-hydroxypyrrolidin-3-yl)oxy)-2-fluorobenzonitrile (500 mg, 1.2 mmol) in acetonitrile (5 mL) at 40° C. was added ethanesulfonic acid (70% wt. solution in water) in three equal portions. The resulting reaction mixture was stirred at 40° C. for 30 minutes and then cooled to room temperature. Diethyl ether was added dropwise until the solution became cloudy and the resulting mixture was stirred at room temperature overnight. The solid was collected by filtration, washed with diethyl ether to provide crystalline 4-(((3S,4S)-4-(aminomethyl)-1-((5-chloropyridin-2-yl)sulfonyl)-4-hydroxypyrrolidin-3-yl)oxy)-2-fluorobenzonitrile, esyalte salt (550 mg, Form 1; 83% yield) as a white solid.

The crystalline form of 233 A that is characterized by an X-ray powder diffraction (XRPD) pattern has the representative peaks:

| Pos. [° 2Th.] | d-spacing [Å] |
| --- | --- |
| 3.914024 | 22.57524 |
| 7.812367 | 11.31684 |
| 11.14342 | 7.94031 |
| 11.743 | 7.53621 |
| 12.44405 | 7.11318 |
| 13.48035 | 6.5686 |
| 14.02824 | 6.31326 |
| 15.0946 | 5.86957 |
| 15.96048 | 5.55304 |
| 17.02008 | 5.20964 |
| 18.22626 | 4.86751 |
| 18.69867 | 4.74559 |
| 20.29148 | 4.37653 |
| 20.80948 | 4.26874 |
| 20.9931 | 4.23182 |
| 21.31421 | 4.16878 |
| 22.06551 | 4.02851 |
| 22.48512 | 3.95427 |
| 23.58871 | 3.77171 |
| 24.13811 | 3.6871 |
| 25.0223 | 3.55878 |
| 26.03558 | 3.42253 |
| 26.56074 | 3.35604 |
| 27.9287 | 3.19469 |
| 28.75653 | 3.10458 |
| 29.62728 | 3.01529 |
| 31.01127 | 2.88381 |
| 31.67233 | 2.82511 |
| 32.47341 | 2.75722 |
| 32.92414 | 2.7205 |
| 34.80934 | 2.57736 |
| 36.23697 | 2.47903 |
| 38.31221 | 2.34939 |
| 39.43937 | 2.28481 |

Example 233 B—Preparation of crystalline form 2 of 4-(((3S,4S)-4-(aminomethyl)-1-((5-chloropyridin-2-yl)sulfonyl)-4-hydroxypyrrolidin-3-yl)oxy)-2-fluorobenzonitrile, esylate monohydrate A slurry of 4-(((3S,4S)-4-(aminomethyl)-1-((5-chloropyridin-2-yl)sulfonyl)-4-hydroxypyrrolidin-3-yl)oxy)-2-fluorobenzonitrile, esyalte salt (148 grams, 273 mmol) in water (500 mL) was allowed to stand at room temperature overnight. The excess water was removed by evaporation under reduced pressure and further air dried by vacuum filtration overnight. The solid was then dried in vacuo to provide crystalline 4-(((3S,4S)-4-(aminomethyl)-1-((5-chloropyridin-2-yl)sulfonyl)-4-hydroxypyrrolidin-3-yl)oxy)-2-fluorobenzonitrile, esyalte salt monohydrate (149 g, Form 2; 97% yield).

The crystalline form of 233 B that is characterized by an X-ray powder diffraction (XRPD) pattern has the representative peaks (EXP127966):

| Position [° 2Theta] | d-spacing [Å] |
| --- | --- |
| 10.3463 | 8.55018 |
| 11.9959 | 7.37788 |
| 12.1689 | 7.27337 |
| 13.6074 | 6.50753 |
| 14.9044 | 5.94405 |
| 15.9738 | 5.54842 |
| 16.677 | 5.31604 |
| 17.8706 | 4.96358 |
| 18.2772 | 4.85404 |
| 18.8812 | 4.70011 |

Example 234

4-(((3S,4R)-4-(aminomethyl)-1-((5-chloropyridin-2-yl)sulfonyl)-4-hydroxypyrrolidin-3-yl)oxy)-2-fluorobenzonitrile, Hydrochloride

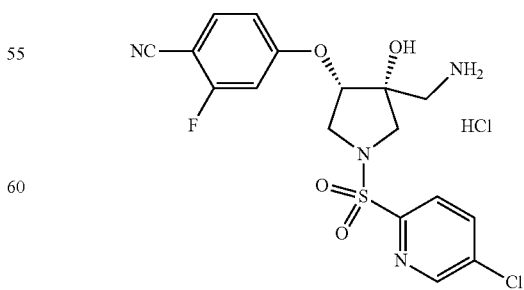

A mixture of 4-(((3S,7S)-5-((5-chloropyridin-2-yl)sulfonyl)-1-oxa-5-azaspiro[2.4]heptan-7-yl)oxy)-2-fluorobenzonitrile (90 mg, 0.22 mmol) in 2 M NH₃ in MeOH (11 mL, 22 mmol) was subjected to microwave irradiation at 60° C. for 20 min. The mixture was concentrated under reduced pressure, and redissolved and concentrated from DCM several times. The residue was then dissolved in CH₃CN (1.5 mL) and 1 M HCl in Et₂O (215 µl, 0.215 mmol) was added. Et₂O was added dropwise with stirring and the resulting solid precipitate was collected by filtration to give the title compound (61 mg, 64% yield). ¹H NMR (400 MHz, DMSO-d₆) δ: 8.76 (d, J=2.5 Hz, 1H), 8.25 (dd, J=8.3, 2.5 Hz, 1H), 8.15 (br s, 3H), 7.95 (d, J=8.3 Hz, 1H), 7.85 (t, J=8.3 Hz, 1H), 7.00 (dd, J=11.8, 2.3 Hz, 1H), 6.81 (dd, J=8.8, 2.3 Hz, 1H), 6.17 (s, 1H), 4.99 (dd, J=4.1, 2.9 Hz, 1H), 3.93 (dd, J=12.0, 4.5 Hz, 1H), 3.67 (d, J=10.3 Hz, 1H), 3.54 (dd, J=12.0, 2.5 Hz, 1H), 3.44 (d, J=10.3 Hz, 1H), 2.97-3.10 (m, 2H). MS (m/z) 427.0 (M+H⁺).

The following compounds were prepared using procedures analogous to those described in Example 233-234 using appropriately substituted starting materials. As is appreciated by those skilled in the art, these analogous examples may involve variations in general reaction conditions.

| Ex. | Name | Structure | MS (m/z) (M + H⁺) | ¹H NMR |
|---|---|---|---|---|
| 235 | 4-(((3S,4R)-4-(aminomethyl)-1-((4-chloro-2-cyanophenyl)sulfonyl)-4-hydroxypyrrolidin-3-yl)oxy)-2-fluorobenzonitrile, Hydrochloride | 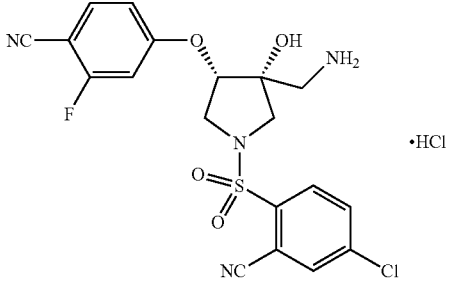 [SMILES: N#Cc1ccc(O[C@H]2CN(S(=O)(=O)c3ccc(Cl)cc3C#N)C[C@]2(O)CN)cc1F ; Cl] | 451.0 | ¹H NMR (400 MHz, DMSO-d₆) δ: 8.43 (s, 1H), 8.12 (br s, 3H), 7.96-8.05 (m, 2H), 7.85 (t, J = 8.3 Hz, 1H), 7.00 (d, J = 11.8 Hz, 1H), 6.80 (d, J = 8.8 Hz, 1H), 6.23 (s, 1H), 5.04 (br s, 1H), 3.96 (dd, J = 11.8, 4.3 Hz, 1H), 3.65 (d, J = 10.3 Hz, 1H), 3.48 (d, J = 12.0 Hz, 1H), 3.30-3.40 (1H, partially hidden by solvent peak), 2.97-3.14 (m, 2H) |
| 236 | 4-(((3S,4R)-1-((4-chloro-2-cyanophenyl)sulfonyl)-4-hydroxy-4-(((2-hydroxyethyl)amino)methyl)pyrrolidin-3-yl)oxy)-2-fluorobenzonitrile, 2,2,2-trifluoroacetate | 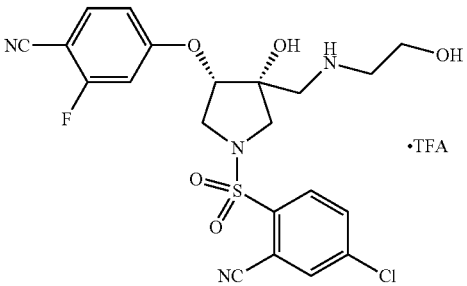 [SMILES: N#Cc1ccc(O[C@H]2CN(S(=O)(=O)c3ccc(Cl)cc3C#N)C[C@]2(O)CNCCO)cc1F ; "·TFA"] | 495.3 | ¹H NMR (400 MHz, DMSO-d₆) δ: 8.63 (br s, 1H), 8.43 (d, J = 2.0 Hz, 1H), 8.40 (br s, 1H), 7.97-8.05 (m, 2H), 7.86 (t, J = 8.4 Hz, 1H), 7.00 (dd, J = 11.5, 2.3 Hz, 1H), 6.80 (dd, J = 8.8, 2.3 Hz, 1H), 6.35 (s, 1H), 5.23 (br s, 1H), 4.98 (t, J = 4.1 Hz, 1H), 3.95 (dd, J = 11.8, 4.8 Hz, 1H), 3.68 (m, 3H), 3.21-3.48 (4H, partially hidden by solvent peak), 3.05 (br m, 2H) |
| 237 | 4-(((3S,4S)-1-((2-cyano-4-(trifluoromethyl)phenyl)sulfonyl)-4-hydroxy-4-((methylamino)methyl)pyrrolidin-3-yl)oxy)-2-fluorobenzonitrile, 2,2,2-trifluoroacetate | 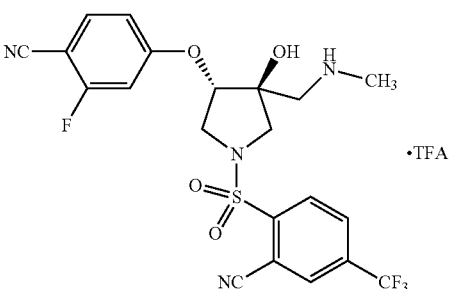 | 498.7 | ¹H NMR (400 MHz, DMSO-d₆) δ: 8.61-8.70 (br s, 1H), 8.59 (s, 1H), 8.41-8.53 (br s, 1H), 8.18-8.26 (m, 1H), 8.11-8.18 (m, 1H), 7.79 (t, J = 8.2 Hz, 1H), 7.00 (dd, J = 11.5, 1.8 Hz, 1H), 6.76 (dd, J = 8.8, 1.8 Hz, 1H), 6.58 (s, 1H), 4.74-4.82 (m, 1H), 3.90-3.98 (m, 1H), 3.59-3.68 (m, 2H), 3.48-3.55 (d, J = 11 Hz, 1H), 3.15-3.32 (m, 2H), 2.55 (s, 3H) |
| 238 | 4-(((3S,4S)-1-((2-cyano-4-(trifluoromethyl)phenyl)sulfonyl)-4-((ethylamino)methyl)-4-hydroxypyrrolidin-3-yl)oxy)-2-fluorobenzonitrile, 2,2,2-trifluoroacetate | 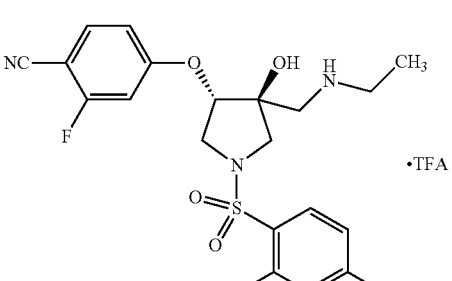 | 513.0 | ¹H NMR (400 MHz, DMSO-d₆) δ: 8.60 (d, J = 1.3 Hz, 1H), 8.43 (br s, 2H), 8.18-8.26 (m, 1H), 8.10-8.17 (m, 1H), 7.79 (t, J = 8.3 Hz, 1H), 7.02 (dd, J = 11.5, 2.3 Hz, 1H), 6.76 (dd, J = 8.8, 2.3 Hz, 1H), 6.55 (s, 1H), 4.79 (d, J = 2.5 Hz, 1H), 3.95 (dd, J = 12.9, 2.9 Hz, 1H), 3.65 (t, J = 11.8 Hz, 2H), 3.52 (d, J = 11.0 Hz, 1H), 3.14-3.34 (m, 2H), 2.88-3.01 (m, 2H), 1.15 (t, J = 7.2 Hz, 3H) |

| Ex. | Name | Structure | MS (m/z) (M + H⁺) | ¹H NMR |
|---|---|---|---|---|
| 239 | 4-(((3S,4S)-1-((2-cyano-4-(trifluoromethyl)phenyl)sulfonyl)-4-hydroxy-4-((isopropylamino)methyl)pyrrolidin-3-yl)oxy)-2-fluorobenzonitrile, 2,2,2-trifluoroacetate | 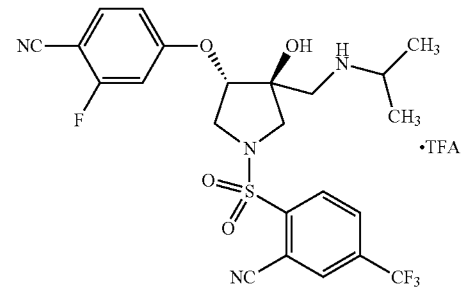 [SMILES: CC(C)NC[C@]1(O)CN(S(=O)(=O)c2ccc(C(F)(F)F)cc2C#N)C[C@@H]1Oc1ccc(C#N)c(F)c1 ; "·TFA"] | 526.7 | $^1$H NMR (400 MHz, DMSO-d$_6$) δ: 8.59 (d, J = 1.3 Hz, 1H), 8.36 (br s, 1H), 8.26 (br s, 1H), 8.18-8.23 (m, 1H), 8.10-8.16 (m, 1H), 7.79 (t, J = 8.3 Hz, 1H), 7.03 (dd, J = 11.5, 2.3 Hz, 1H), 6.77 (dd, J = 8.8, 2.3 Hz, 1H), 6.56 (s, 1H), 4.82 (d, J = 2.5 Hz, 1H), 3.97 (dd, J = 12.8, 2.8 Hz, 1H), 3.62-3.70 (m, 2H), 3.51 (d, J = 11.0 Hz, 1H), 3.23-3.36 (m, 2H), 3.12-3.22 (m, 1H), 1.18 (m, 6H) |

Example 240

4-(((3S,4S)-4-(aminomethyl)-1-((4-chloro-2-cyanophenyl)sulfonyl)-4-hydroxypyrrolidin-3-yl)oxy)-2-fluorobenzonitrile

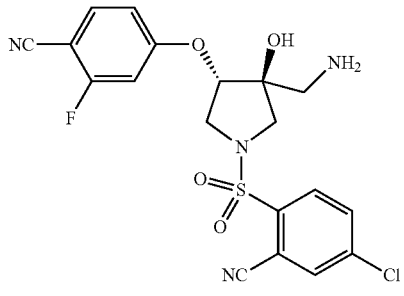 [SMILES: N#Cc1ccc(O[C@H]2CN(S(=O)(=O)c3ccc(Cl)cc3C#N)C[C@@]2(O)CN)cc1F]

Step 1: 4-(((3R,7S)-5-((4-chloro-2-cyanophenyl)sulfonyl)-1-oxa-5-azaspiro[2.4]heptan-7-yl)oxy)-2-fluorobenzonitrile

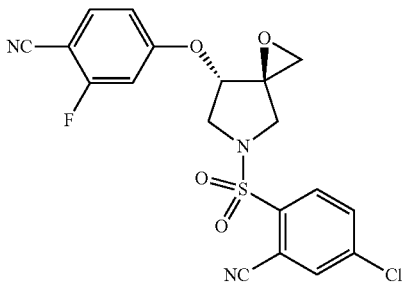 [SMILES: N#Cc1ccc(O[C@H]2CN(S(=O)(=O)c3ccc(Cl)cc3C#N)C[C@@]23CO3)cc1F]

A mixture of 4-(((3S,4R)-1-((4-chloro-2-cyanophenyl)sulfonyl)-4-hydroxy-4-(hydroxymethyl)pyrrolidin-3-yl)oxy)-2-fluorobenzonitrile (350 mg, 0.78 mmol) in DCM (20 mL) was treated with DIPEA (0.54 mL, 3.1 mmol) and MsCl (0.09 mL, 1.2 mmol) and stirred for 20 min. The mixture was concentrated and the residue was dissolved in THF (20 mL) and treated with 60% sodium hydride (120 mg, 3.1 mmol). The mixture was stirred for 15 minutes and then quenched with water, diluted with brine, and extracted with DCM (2×). The organic extracts were combined, dried over (Na$_2$SO$_4$), filtered and concentrated. The crude product was purified by flash column chromatography eluting with 40% EtOAc in hexanes. The product fractions were pooled and concentrated to give the title compound as a white solid (283 mg, 83% yield). $^1$H NMR (400 MHz, DMSO-d$_6$) δ: 8.36 (d, J=2.0 Hz, 1H), 7.99-8.06 (m, 1H), 7.93-7.98 (m, 1H), 7.83 (t, J=8.3 Hz, 1H), 7.08 (dd, J=11.7, 1.9 Hz, 1H), 6.81 (dd, J=8.8, 2.0 Hz, 1H), 4.81 (d, J=3.3 Hz, 1H), 3.99 (d, J=12.0 Hz, 1H), 3.89 (dd, J=12.5, 4.0 Hz, 1H), 3.65 (d, J=12.5 Hz, 1H), 3.29-3.36 (m, 3H), 3.16 (s, 2H).

Step 2: 4-(((3S,4S)-4-(aminomethyl)-1-((4-chloro-2-cyanophenyl)sulfonyl)-4-hydroxypyrrolidin-3-yl)oxy)-2-fluorobenzonitrile A mixture of 4-(((3R,7S)-5-((4-chloro-2-cyanophenyl)sulfonyl)-1-oxa-5-azaspiro[2.4]heptan-7-yl)oxy)-2-fluorobenzonitrile (280 mg, 0.64 mmol) and 2 M NH$_3$ in MeOH (2 mL, 4 mmol) was subjected to microwave irradiation at 75° C. for 20 min. The reaction mixture was concentrated and purified by reverse phase HPLC (C18 Sunfire 30×150 mm preparatory column, eluting at 50 mL/min with a gradient from 20-60% CH$_3$CN/H$_2$O (0.1% TFA)). The product fractions were pooled and lyophilized to give the title compound as a white solid (145 mg, 49% yield). $^1$H NMR (400 MHz, DMSO-d$_6$) δ: 8.28 (d, J=1.8 Hz, 1H), 7.88-7.99 (m, 2H), 7.79 (t, J=8.4 Hz, 1H), 7.05 (dd, J=11.8, 2.3 Hz, 1H), 6.76 (dd, J=8.7, 2.4 Hz, 1H), 4.67 (d, J=2.8 Hz, 1H), 3.84 (dd, J=12.2, 3.1 Hz, 1H), 3.51 (d, J=12.3 Hz, 1H), 3.35-3.47 (m, 2H), 2.64-2.80 (m, 2H). MS (m/z) 451.0 (M+H⁺).

The following compounds were prepared using procedures analogous to those described in Example 240 using appropriately substituted starting materials. As is appreciated by those skilled in the art, these analogous examples may involve variations in general reaction conditions.

| Ex. | Name | Structure | MS (m/z) (M + H+) | 1H NMR |
|---|---|---|---|---|
| 241 | 4-(((3S,4S)-4-(aminomethyl)-1-((4-chloro-1-methyl-1H-pyrazol-5-yl)sulfonyl)-4-hydroxypyrrolidin-3-yl)oxy)-2-fluorobenzonitrile, 2,2,2-trifluoroacetate | 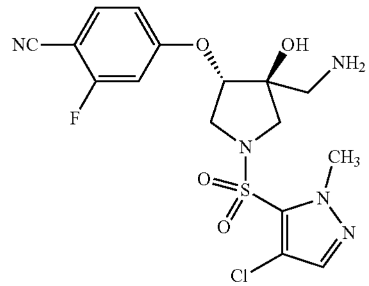 [SMILES: Cn1ncc(Cl)c1S(=O)(=O)N1C[C@H](Oc2ccc(C#N)c(F)c2)[C@](O)(CN)C1] | 430.0 | 1H NMR (400 MHz, DMSO-d6) δ: 7.93 (br s, 2H), 7.86 (t, J = 8.3 Hz, 1H), 7.73 (s, 1H), 7.14 (dd, J = 11.8, 2.3 Hz, 1H), 6.86 (dd, J = 8.8, 2.3 Hz, 1H), 6.38 (s, 1H), 4.81 (d, J = 2.8 Hz, 1H), 4.02 (s, 3H), 3.93 (dd, J = 12.5, 3.0 Hz, 1H), 3.57-3.64 (m, 2H), 3.48-3.53 (m, 1H), 3.05-3.22 (m, 2H) |
| 242 | 4-(((3S,4S)-4-(aminomethyl)-1-((5-fluoropyridin-2-yl)sulfonyl)-4-hydroxypyrrolidin-3-yl)oxy)-2-fluorobenzonitrile, 2,2,2-trifluoroacetate | 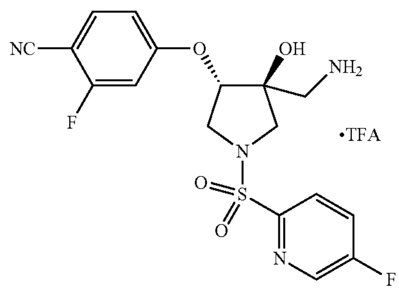 [SMILES: N#Cc1ccc(O[C@H]2CN(S(=O)(=O)c3ccc(F)cn3)C[C@@]2(O)CN)cc1F] | 411.0 | 1H NMR (400 MHz, DMSO-d6) δ: 8.50 (d, J = 2.0 Hz, 1H), 7.75-7.96 (m, 6H), 7.00 (dd, J = 11.8, 2.3 Hz, 1H), 6.72 (dd, J = 8.8, 2.3 Hz, 1H), 6.29 (s, 1H), 4.67 (d, J = 3.0 Hz, 1H), 3.93 (dd, J = 12.8, 3.0 Hz, 1H), 3.47-3.64 (m, 3H), 3.06-3.13 (m, 1H), 2.97-3.04 (m, 1H) |
| 243 | 5-(((3S,4S)-3-(aminomethyl)-4-(4-cyano-3-fluorophenoxy)-3-hydroxypyrrolidin-1-yl)sulfonyl)picolinonitrile, 2,2,2-trifluoroacetate | 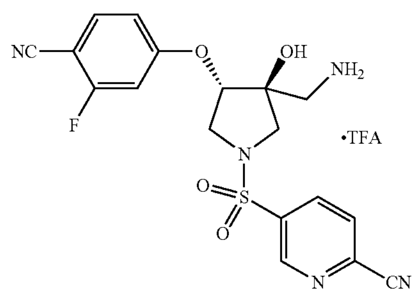 [SMILES: N#Cc1ccc(S(=O)(=O)N2C[C@H](Oc3ccc(C#N)c(F)c3)[C@](O)(CN)C2)cn1] | 418.2 | 1H NMR (400 MHz, DMSO-d6) δ: 9.01 (d, J = 1.8 Hz, 1H), 8.36 (dd, J = 8.0, 2.3 Hz, 1H), 8.21 (d, J = 8.0 Hz, 1H), 7.73-8.02 (m, 4H), 6.93 (dd, J = 11.5, 2.3 Hz, 1H), 6.68 (dd, J = 8.8, 2.3 Hz, 1H), 6.28 (br s, 1H), 4.69 (d, J = 2.8 Hz, 1H), 3.83 (dd, J = 12.9, 2.9 Hz, 1H), 3.54-3.63 (m, 1H), 3.42-3.53 (m, 2H), 3.07-3.14 (m, 1H), 2.95-3.04 (m, 1H) |
| 244 | 4-(((3S,4S)-4-(aminomethyl)-1-((5-(difluoromethyl)pyridin-2-yl)sulfonyl)-4-hydroxypyrrolidin-3-yl)oxy)-2-fluorobenzonitrile | 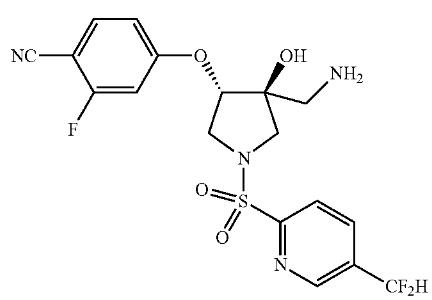 | 443.1 | 1H NMR (400 MHz, DMSO-d6) δ: 8.74 (s, 1H), 8.22 (d, J = 8.0 Hz, 1H), 7.98 (d, J = 8.0 Hz, 1H), 7.74 (t, J = 8.3 Hz, 1H), 7.07-7.39 (m, 1H), 6.94 (dd, J = 11.8, 2.3 Hz, 1H), 6.63 (dd, J = 8.5, 2.3 Hz, 1H), 5.42 (br s, 1H), 4.58 (d, J = 3.0 Hz, 1H), 3.90 (dd, J = 12.3, 3.3 Hz, 1H), 3.57 (d, J = 12.3 Hz, 1H), 3.39-3.48 (m, 2H), 2.60-2.73 (m, 2H), 1.45-1.84 (br s, 2H) |
| 245 | 4-(((3S,4S)-4-(aminomethyl)-4-hydroxy-1-((6-(trifluoromethyl)pyridin-3-yl)sulfonyl)pyrrolidin-3-yl)oxy)-2-fluorobenzonitrile, Hydrochloride | 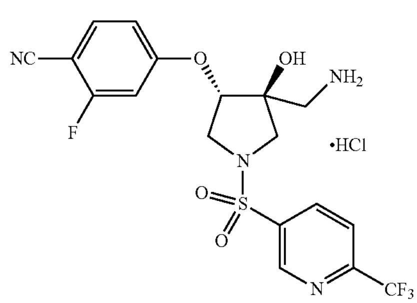 [SMILES: N#Cc1ccc(O[C@H]2CN(S(=O)(=O)c3ccc(C(F)(F)F)nc3)C[C@@]2(O)CN)cc1F ; Cl] | 461.0 | 1H NMR (400 MHz, DMSO-d6) δ: 9.07 (d, J = 2.0 Hz, 1H), 8.40 (dd, J = 8.2, 2.1 Hz, 1H), 8.00-8.12 (m, 4H), 7.76 (t, J = 8.3 Hz, 1H), 6.89 (dd, J = 11.5, 2.3 Hz, 1H), 6.66 (dd, J = 8.7, 2.1 Hz, 1H), 6.30 (s, 1H), 4.75 (d, J = 2.8 Hz, 1H), 3.83 (dd, J = 12.9, 2.9 Hz, 1H), 3.64 (d, J = 11.3 Hz, 1H), 3.53 (d, J = 11.3 Hz, 1H), 3.46 (d, J = 12.8 Hz, 1H), 3.07-3.16 (m, 1H), 2.96-3.04 (m, 1H) |

-continued

| Ex. | Name | Structure | MS (m/z) (M + H+) | 1H NMR |
|---|---|---|---|---|
| 246 | 4-(((3S,4S)-4-(aminomethyl)-1-((5-chloropyridin-2-yl)sulfonyl)-4-hydroxypyrrolidin-3-yl)oxy)benzonitrile | 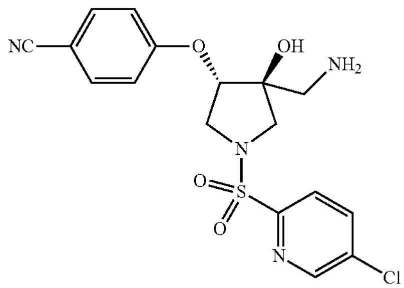 [SMILES: N#Cc1ccc(O[C@H]2CN(S(=O)(=O)c3ccc(Cl)cn3)C[C@@]2(O)CN)cc1] | 409.1 | 1H NMR (400 MHz, DMSO-d6) δ: 8.54 (d, J = 2.0 Hz, 1H), 8.10 (dd, J = 8.5, 2.5 Hz, 1H), 7.83 (d, J = 8.3 Hz, 1H), 7.68-7.74 (m, 2H), 6.84 (d, J = 9.0 Hz, 2H), 5.38 (br s, 1H), 4.55 (d, J = 3.0 Hz, 1H), 3.87 (dd, J = 12.0, 3.3 Hz, 1H), 3.37-3.54 (m, 3H), 2.61-2.77 (m, 2H), 1.68 (br s, 2H) |
| 247 | 4-(((3S,4S)-4-(aminomethyl)-1-((5-(difluoromethoxy)pyridin-2-yl)sulfonyl)-4-hydroxypyrrolidin-3-yl)oxy)-2-fluorobenzonitrile, 2,2,2-trifluoroacetate | 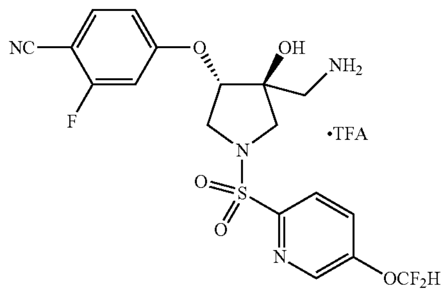 | 459.2 | 1H NMR (400 MHz, DMSO-d6) δ: 8.57 (d, J = 2.3 Hz, 1H), 8.17 (dd, J = 8.5, 2.5 Hz, 1H), 7.51-8.01 (m, 5H), 7.17 (d, J = 8.8 Hz, 1H), 6.93 (dd, J = 11.8, 2.3 Hz, 1H), 6.66 (dd, J = 8.8, 2.3 Hz, 1H), 6.33 (s, 1H), 4.69 (d, J = 2.8 Hz, 1H), 3.80 (dd, J = 12.9, 2.9 Hz, 1H), 3.52-3.61 (m, 1H), 3.38-3.50 (m, 2H), 2.94-3.22 (m, 2H) |
| 248 | 4-(((3S,4S)-4-(aminomethyl)-4-hydroxy-1-((5-(trifluoromethoxy)pyridin-2-yl)sulfonyl)pyrrolidin-3-yl)oxy)-2-fluorobenzonitrile | 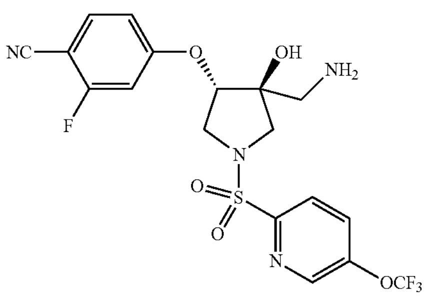 | 477.1 | 1H NMR (400 MHz, DMSO-d6) δ: 8.66 (d, J = 2.5 Hz, 1H), 8.04-8.13 (m, 1H), 7.95-8.02 (m, 1H), 7.77 (t, J = 8.3 Hz, 1H), 6.96 (dd, J = 11.8, 2.3 Hz, 1H), 6.71 (dd, J = 8.8, 2.3 Hz, 1H), 5.41 (br s, 1H), 4.59 (d, J = 3.0 Hz, 1H), 3.89 (dd, J = 12.4, 3.1 Hz, 1H), 3.53 (d, J = 12.3 Hz, 1H), 3.38-3.49 (m, 2H), 2.60-2.77 (m, 2H), 1.57 (br s, 2H) |
| 249 | 4-(((3S,4S)-4-(aminomethyl)-4-hydroxy-1-((6-(trifluoromethoxy)pyridin-3-yl)sulfonyl)pyrrolidin-3-yl)oxy)-2-fluorobenzonitrile, Hydrochloride | 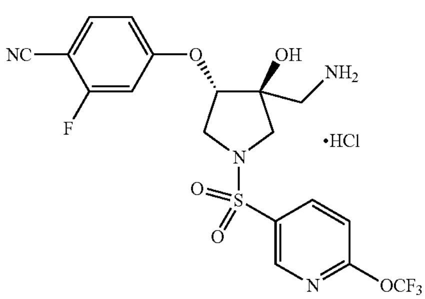 [SMILES: N#Cc1ccc(O[C@H]2CN(S(=O)(=O)c3ccc(OC(F)(F)F)nc3)C[C@@]2(O)CN)cc1F ; Cl] | 477.0 | 1H NMR (400 MHz, DMSO-d6) δ: 8.67 (d, J = 2.5 Hz, 1H), 8.30 (dd, J = 8.5, 2.5 Hz, 1H), 8.02 (br s, 3H), 7.78 (t, J = 8.3 Hz, 1H), 7.38 (d, J = 8.8 Hz, 1H), 6.88 (dd, J = 11.7, 2.1 Hz, 1H), 6.69 (dd, J = 8.8, 2.3 Hz, 1H), 6.31 (s, 1H), 4.73 (d, J = 2.8 Hz, 1H), 3.81 (dd, J = 12.9, 2.9 Hz, 1H), 3.57-3.64 (m, 1H), 3.48-3.54 (m, 1H), 3.41 (d, J = 12.8 Hz, 1H), 3.08-3.17 (m, 1H), 2.97-3.06 (m, 1H) |
| 250 | 4-(((3S,4S)-4-(aminomethyl)-4-hydroxy-1-((5-iodopyridin-2-yl)sulfonyl)pyrrolidin-3-yl)oxy)-2-fluorobenzonitrile, 2,2,2-trifluoroacetate | 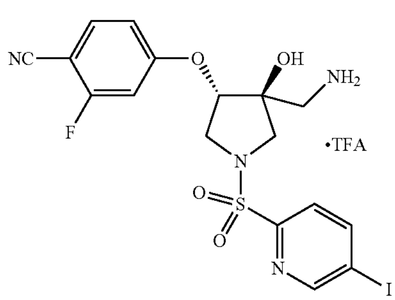 [SMILES: N#Cc1ccc(O[C@H]2CN(S(=O)(=O)c3ccc(I)cn3)C[C@@]2(O)CN)cc1F ; "·TFA"] | 519.0 | 1H NMR (400 MHz, DMSO-d6) δ: 8.65 (d, J = 1.5 Hz, 1H), 8.37 (dd, J = 8.3, 2.0 Hz, 1H), 8.00 (br s, 3H), 7.80 (t, J = 8.3 Hz, 1H), 7.59 (d, J = 8.0 Hz, 1H), 6.94 (dd, J = 11.5, 2.0 Hz, 1H), 6.67 (dd, J = 8.7, 1.9 Hz, 1H), 6.38 (br s, 1H), 4.68 (d, J = 2.3 Hz, 1H), 3.82-4.01 (m, 1H), 3.48-3.67 (m, 3H, partially hidden by solvent peak), 2.95-3.15 (m, 2H) |

| Ex. | Name | Structure | MS (m/z) (M + H⁺) | ¹H NMR |
|-----|------|-----------|-------------------|--------|
| 251 | 4-(((3S,4S)-4-(aminomethyl)-1-((5-bromopyridin-2-yl)sulfonyl)-4-hydroxypyrrolidin-3-yl)oxy)-2-fluorobenzonitrile, 2,2,2-trifluoroacetate | 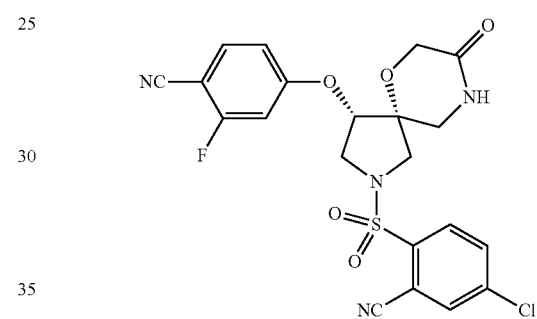 | 471.0 | ¹H NMR (400 MHz, DMSO-d₆) δ: 8.59 (d, J = 2.0 Hz, 1H), 8.24 (dd, J = 8.4, 2.4 Hz, 1H), 7.78-7.92 (m, 4H), 7.75 (d, J = 8.3 Hz, 1H), 6.97 (dd, J = 11.5, 2.3 Hz, 1H), 6.69 (dd, J = 8.8, 2.3 Hz, 1H), 6.29 (br s, 1H), 4.66 (d, J = 2.8 Hz, 1H), 3.87-3.99 (m, 1H), 3.48-3.66 (m, 3H), 2.97-3.14 (m, 2H) |

Example 252

4-(((4S,5R)-2-((4-chloro-2-cyanophenyl)sulfonyl)-9-methyl-6-oxa-2,9-diazaspiro[4.5]decan-4-yl)oxy)-2-fluorobenzonitrile

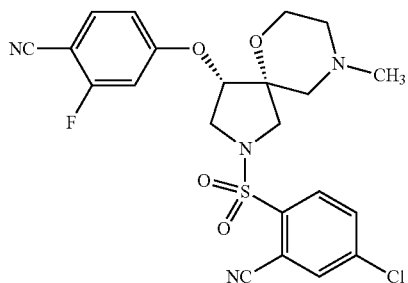 [SMILES: CN1CCO[C@]2(C1)CN(S(=O)(=O)c1ccc(Cl)cc1C#N)C[C@@H]2Oc1ccc(C#N)c(F)c1]

Step 1: 2-chloro-N-(((3R,4S)-1-((4-chloro-2-cyanophenyl)sulfonyl)-4-(4-cyano-3-fluorophenoxy)-3-hydroxypyrrolidin-3-yl)methyl)acetamide

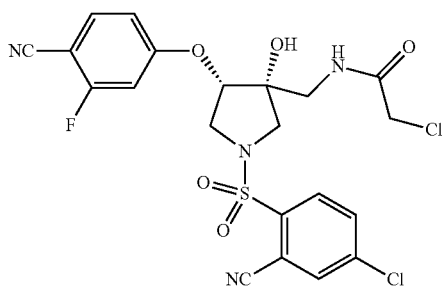 [SMILES: N#Cc1ccc(O[C@H]2CN(S(=O)(=O)c3ccc(Cl)cc3C#N)C[C@]2(O)CNC(=O)CCl)cc1F]

To a chilled (ice bath) mixture of 4-(((3S,4R)-4-(aminomethyl)-1-((4-chloro-2-cyanophenyl)sulfonyl)-4-hydroxypyrrolidin-3-yl)oxy)-2-fluorobenzonitrile (540 mg, 1.2 mmol) in DCM (10 mL) and Et₃N (0.50 mL, 3.6 mmol), was added 2-chloroacetyl chloride (0.12 mL, 1.6 mmol) and the reaction mixture was stirred for 25 min. The mixture was poured into 1 N HCl (aq) and extracted with EtOAc (3×). The organic layers were combined, dried, filtered, and concentrated to dryness to give the title compound (550 mg, 87% yield). MS (m/z) 527.1 (M+H⁺).

Step 2: 4-(((4S,5R)-2-((4-chloro-2-cyanophenyl)sulfonyl)-8-oxo-6-oxa-2,9-diazaspiro[4.5]decan-4-yl)oxy)-2-fluorobenzonitrile To a mixture of 2-chloro-N-(((3R,4S)-1-((4-chloro-2-cyanophenyl)sulfonyl)-4-(4-cyano-3-fluorophenoxy)-3-hydroxypyrrolidin-3-yl)methyl)acetamide (550 mg, 1.04 mmol) in THF (10 mL) was carefully added 60% sodium hydride (83 mg, 2.1 mmol) and the reaction mixture was at rt for 2 h. The mixture was chilled with an ice bath and carefully quenched with the dropwise addition of water. The mixture was then partitioned between EtOAc and water and the aqueous layer was removed and extracted with EtOAc (2×). The organic layers were combined, dried over MgSO₄, filtered and evaporated to dryness. The crude product was purified by flash column chromatography (SiO₂) eluting with a gradient of 0-10% MeOH in DCM. The product fractions were pooled and concentrated to give the title compound as a white solid (150 mg, 26% yield). ¹H NMR (400 MHz, DMSO-d₆) δ: 8.39 (d, J=2.0 Hz, 1H), 8.21 (brs, 1H), 8.03-8.08 (m, 1H), 7.96-8.02 (m, 1H), 7.80-7.85 (m, 1H), 7.11 (dd, J=11.8, 2.5 Hz, 1H), 6.84 (dd, J=8.8, 2.5 Hz, 1H), 5.16 (t, J=3.8 Hz, 1H), 3.93-4.00 (m, 3H), 3.59-3.65 (m, 1H), 3.48-3.57 (m, 2H), 3.39 (dd, J=7.0, 2.5 Hz, 2H). MS (m/z) 491.1 (M+H⁺).

Step 3: 4-(((4S,5R)-2-((4-chloro-2-cyanophenyl)sulfonyl)-6-oxa-2,9-diazaspiro[4.5]decan-4-yl)oxy)-2-fluorobenzonitrile,2,2,2-trifluoroacetate

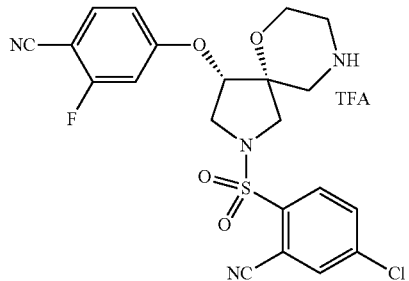 [SMILES: N#Cc1ccc(O[C@H]2CN(S(=O)(=O)c3ccc(Cl)cc3C#N)C[C@]23CNCCO3)cc1F]

0.84 mmol). This material was dissolved in DCM (0.5 mL) and formaldehyde (0.019 mL, 0.25 mmol) was added followed by sodium triacetoxyborohydride (36 mg, 0.17 mmol) and the mixture stirred at rt for 5 min. The mixture was poured into 1 N NaOH (aq) and extracted with DCM. The organic fractions were dried over $MgSO_4$, concentrated. The resulting residue was redissolved and concentrated from DCM several times and evaporated to dryness to give the title compound (25 mg, 58% yield). $^1$H NMR (400 MHz, DMSO-$d_6$) δ: 8.38 (d, J=2.0 Hz, 1H), 7.94-8.07 (m, 2H), 7.81 (t, J=8.3 Hz, 1H), 7.09 (dd, J=11.8, 2.3 Hz, 1H), 6.83 (dd, J=8.8, 2.3 Hz, 1H), 5.11 (br s, 1H), 3.89 (dd, J=12.3, 4.3 Hz, 1H), 3.62 (d, J=10.0 Hz, 1H), 3.43-3.54 (m, 4H), 2.19-2.40 (m, 4H), 2.15 (s, 3H). MS (m/z) 491.0 (M+H$^+$).

The following compound was prepared by isolating the trans isomer from the epoxidation and using procedures analogous to those described in Example 252. As is appreciated by those skilled in the art, this analogous example may involve variations in general reaction conditions.

| Ex. | Name | Structure | MS (m/z) (M + H$^+$) | $^1$H NMR |
|---|---|---|---|---|
| 253 | 4-(((4S,5S)-2-((4-chloro-2-cyanophenyl)sulfonyl)-6-oxa-2,9-diazaspiro[4.5]decan-4-yl)oxy)-2-fluorobenzonitrile, 2,2,2-trifluoroacetate | 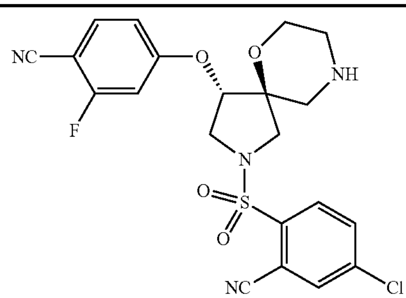 | 477.1 | $^1$H NMR (400 MHz, CDCl$_3$) δ: 7.96-8.06 (m, 1H), 7.83 (m, 1H), 7.68-7.75 (m, 1H), 7.52-7.64 (m, 1H), 6.65-6.82 (m, 2H), 4.76 (d, J = 18.6 Hz, 1H), 3.10-4.12 (m, 10H) |

To a solution of 4-(((4S,5R)-2-((4-chloro-2-cyanophenyl)sulfonyl)-8-oxo-6-oxa-2,9-diazaspiro[4.5]decan-4-yl)oxy)-2-fluorobenzonitrile (130 mg, 0.26 mmol) in THF (10 mL) was added 1 M BH$_3$ in THF (0.73 mL, 0.73 mmol) and the mixture was heated at 60° C. for 3 h. MeOH (5 mL) and 2 M HCl in MeOH (5 mL) were added and the mixture was heated at 60° C. for 90 min. The mixture was concentrated and purified by reverse phase HPLC chromatography with a gradient of 20-80% CH$_3$CN/H$_2$O (0.1% TFA). The product fractions were pooled, concentrated and lyophilized to give the title compound (44 mg, 27% yield). $^1$H NMR (400 MHz, DMSO-$d_6$) δ: 9.18 (br s, 2H), 8.43-8.45 (d, J=2.0 Hz, 1H), 7.97-8.09 (m, 2H), 7.82-7.92 (m, 1H), 7.07 (dd, J=11.7, 2.4 Hz, 1H), 6.84 (dd, J=8.8, 2.3 Hz, 1H), 5.23 (t, J=4.3 Hz, 1H), 3.98 (dd, J=11.7, 4.9 Hz, 1H), 3.75 (d, J=11.0 Hz, 1H), 3.62-3.71 (m, 3H), 3.47 (dd, J=11.5, 3.8 Hz, 1H), 3.34-3.41 (m, 1H), 3.24-3.33 (m, 1H), 3.02-3.17 (m, 2H). MS (m/z) 477.1 (M+H$^+$).

Step 4: 4-(((4S,5R)-2-((4-chloro-2-cyanophenyl)sulfonyl)-9-methyl-6-oxa-2,9-diazaspiro[4.5]decan-4-yl)oxy)-2-fluorobenzonitrile 4-(((4S,5R)-2-((4-chloro-2-cyanophenyl)sulfonyl)-6-oxa-2,9-diazaspiro[4.5]decan-4-yl)oxy)-2-fluorobenzonitrile, 2,2,2-trifluoroacetate (44 mg) was partitioned between NaHCO$_3$ (aq) and EtOAc. The organic layer was removed, dried, filtered and concentrated to give 4-(((4S,5R)-2-((4-chloro-2-cyanophenyl)sulfonyl)-6-oxa-2,9-diazaspiro[4.5]decan-4-yl)oxy)-2-fluorobenzonitrile (free base) (40 mg, Example 254

4-(((5S,9S)-7-((4-chloro-2-cyanophenyl)sulfonyl)-2-oxo-1-oxa-3,7-diazaspiro[4.4]nonan-9-yl)oxy)-2-fluorobenzonitrile

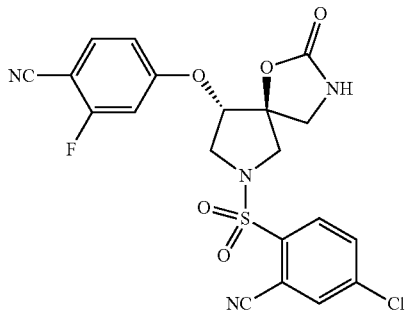 [SMILES: N#Cc1ccc(O[C@H]2CN(S(=O)(=O)c3ccc(Cl)cc3C#N)C[C@@]23CNC(=O)O3)cc1F]

To a solution of 4-(((3S,4S)-4-(aminomethyl)-1-((4-chloro-2-cyanophenyl)sulfonyl)-4-hydroxypyrrolidin-3-yl)oxy)-2-fluorobenzonitrile (75 mg, 0.17 mmol) in THF (15 mL) was added CDI (135 mg, 0.83 mmol) and the reaction mixture was stirred at rt overnight. The mixture was concentrated to dryness and purified by reverse phase HPLC (C18 Sunfire 30×150 mm preparatory column, eluting at 50 mL/min with a gradient of 30-70% CH$_3$CN/H$_2$O (0.1% TFA)). The product fractions were pooled and concentrated to give the title compound as a white solid (9 mg, 11% yield). ¹H NMR (400 MHz, DMSO-d₆) δ: 8.31 (d, J=2.3 Hz, 1H), 7.78-8.03 (m, 4H), 7.10 (dd, J=11.5, 2.3 Hz, 1H), 6.81 (dd, J=8.8, 2.3 Hz, 1H), 5.12 (d, J=2.8 Hz, 1H), 3.92 (d, J=11.8 Hz, 1H), 3.72-3.79 (m, 1H), 3.57-3.69 (m, 3H), 3.48-3.55 (m, 1H). MS (m/z) 477.1 (M+H⁺).

Example 255

4-(((5R,9S)-7-((4-chloro-2-cyanophenyl)sulfonyl)-2-oxo-1-oxa-3,7-diazaspiro[4.4]nonan-9-yl)oxy)-2-fluorobenzonitrile

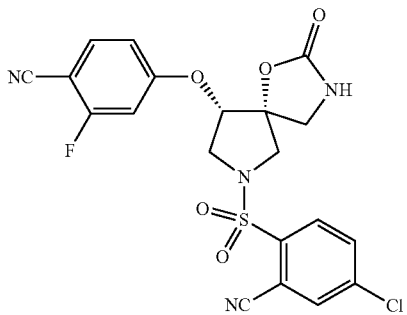 [SMILES: N#Cc1ccc(O[C@H]2CN(S(=O)(=O)c3ccc(Cl)cc3C#N)C[C@]23CNC(=O)O3)cc1F]

To a solution of 4-(((3S,4R)-4-(aminomethyl)-1-((4-chloro-2-cyanophenyl)sulfonyl)-4-hydroxypyrrolidin-3-yl)oxy)-2-fluorobenzonitrile (75 mg, 0.17 mmol) in THF (15 mL) was added CDI (135 mg, 0.83 mmol) and the reaction mixture was stirred at rt for 1 h. The mixture was concentrated to dryness and purified by reverse phase HPLC (C18 Sunfire 30×150 mm preparatory column, eluting at 50 mL/min with a gradient of 30-70% CH₃CN/H₂O (0.1% TFA)). The product fractions were pooled and concentrated to give the title compound as a white solid (9 mg, 11% yield). ¹H NMR (400 MHz, DMSO-d₆) δ: 8.41 (d, J=2.0 Hz, 1H), 8.03-8.11 (m, 1H), 7.97-8.02 (m, 1H), 7.81-7.91 (m, 2H), 7.15 (dd, J=11.7, 2.4 Hz, 1H), 6.89 (dd, J=8.8, 2.3 Hz, 1H), 5.21 (t, J=5.3 Hz, 1H), 4.00 (dd, J=11.3, 5.5 Hz, 1H), 3.66-3.77 (m, 2H), 3.47-3.58 (m, 2H), 3.35-3.41 (m, 1H, partially hidden by solvent peak). MS (m/z) 477.1 (M+H⁺).

Example 256

4-(((3S,4R)-4-((R)-1-aminoethyl)-1-((5-chloropyridin-2-yl)sulfonyl)-4-hydroxypyrrolidin-3-yl)oxy)-2-fluorobenzonitrile, 2,2,2-trifluoroacetate

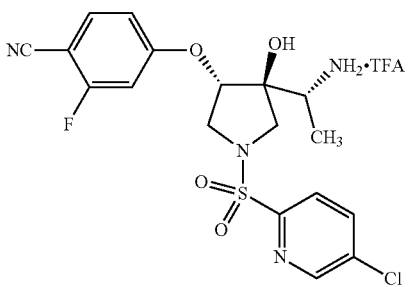

Step 1: 4-(((2S,3R,7S)-5-((5-chloropyridin-2-yl)sulfonyl)-2-methyl-1-oxa-5-azaspiro[2.4]heptan-7-yl)oxy)-2-fluorobenzonitrile or 4-(((2R,3S,7S)-5-((5-chloropyridin-2-yl)sulfonyl)-2-methyl-1-oxa-5-azaspiro[2.4]heptan-7-yl)oxy)-2-fluorobenzonitrile

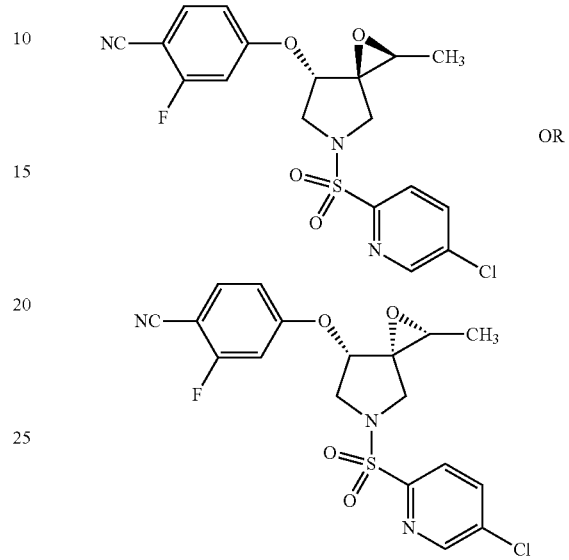

To a solution of (R,E)-4-((1-((5-chloropyridin-2-yl)sulfonyl)-4-ethylidenepyrrolidin-3-yl)oxy)-2-fluorobenzonitrile (600 m g, 4.4 mmol) in DCM (20 ml) was added m-CPBA (990 mg, 4.4 mmol) and the reaction mixture was stirred at rt for 48 h. The reaction was quenched with sat'd NaHSO₃ (aq) and sat'd NaHCO₃ (aq) and stirred 1 h. The organic layer was separated, dried over Na₂SO₄, filtered and concentrated. The crude trans/cis isomer mixture was purified and separated by flash column chromatography (SiO₂) eluting with a gradient of 0-70% EtOAc in hexanes. The individual trans and cis isomers of the title compounds were isolated. Trans-isomer (1ˢᵗ elutant, 240 mg, 38% yield): ¹H NMR (400 MHz, DMSO-d₆) δ: 8.75 (d, J=2.3 Hz, 1H), 8.20 (dd, J=8.4, 2.4 Hz, 1H), 7.94 (d, J=8.5 Hz, 1H), 7.82 (t, J=8.3 Hz, 1H), 7.03 (dd, J=11.8, 2.3 Hz, 1H), 6.77 (dd, J=8.8, 2.3 Hz, 1H), 4.72 (d, J=2.5 Hz, 1H), 3.88-4.01 (m, 2H), 3.60 (d, J=12.5 Hz, 1H), 3.41 (dd, J=8.8, 3.3 Hz, 2H), 1.27 (d, J=5.3 Hz, 3H), MS (m/z) 424.0 (M+H⁺). Cis-isomer (2ⁿᵈ elutant, 160 mg, 26% yield): ¹H NMR (400 MHz, DMSO-d₆) δ: 8.80 (s, 1H), 8.25 (d, J=8.3 Hz, 1H), 7.98 (d, J=8.3 Hz, 1H), 7.81 (t, J=8.0 Hz, 1H), 7.00 (d, J=11.5 Hz, 1H), 6.77 (d, J=9.0 Hz, 1H), 4.90 (br s, 1H), 3.79-3.86 (m, 1H), 3.54-3.71 (m, 3H), 3.41 (d, J=5.0 Hz, 1H), 1.18 (d, J=5.0 Hz, 3H), MS (m/z) 424.0 (M+H⁺).

Step 2: 4-(((3S,4R)-4-((R)-1-aminoethyl)-1-((5-chloropyridin-2-yl)sulfonyl)-4-hydroxypyrrolidin-3-yl)oxy)-2-fluorobenzonitrile, 2,2,2-trifluoroacetate 4-(((2S,3R,7S)-5-((5-chloropyridin-2-yl)sulfonyl)-2-methyl-1-oxa-5-azaspiro[2.4]heptan-7-yl)oxy)-2-fluorobenzonitrile (38 mg, 0.09 mmol) was mixed with 0.5 M NH₃ in dioxane (9.3 mL, 4.6 mmol) and ytterbium(III) trifluoromethanesulfonate (6 mg, 9 μmol) in a sealed tube and the mixture was heated at 75° C. for 72 h. A second portion of ytterbium(III) trifluoromethanesulfonate (55 mg, 0.09 mmol) was added and the reaction heated an additional 24 h at 75° C. The reaction mixture was concentrated, and the residue treated with water and extracted with EtOAc. The organic layer was dried, filtered and concentrated and the crude product was purified by reverse phase HPLC (C18 Sunfire 30×150 mm preparatory column, eluting at 50 mL/min with a gradient of 10-50% CH$_3$CN/H$_2$O (0.1% TFA)). The title compound was isolated as a white solid (5 mg, 10% yield). $^1$H NMR (400 MHz, DMSO-d$_6$) δ: 8.56 (d, J=2.3 Hz, 1H), 8.13 (dd, J=8.5, 2.5 Hz, 1H), 7.78-7.87 (m, 5H), 6.97 (dd, J=11.5, 2.3 Hz, 1H), 6.71 (dd, J=8.7, 2.4 Hz, 1H), 6.32 (s, 1H), 4.63 (d, J=2.8 Hz, 1H), 3.91 (dd, J=12.8, 3.0 Hz, 1H), 3.59-3.70 (m, 3H), 3.52 (d, J=5.5 Hz, 1H), 1.02 (d, J=6.5 Hz, 3H). MS (m/z) 441.1 (M+H$^+$).

Example 257

4-(((3S,4R)-4-((S)-1-aminoethyl)-1-((5-chloropyridin-2-yl)sulfonyl)-4-hydroxypyrrolidin-3-yl)oxy)-2-fluorobenzonitrile, 2,2,2-trifluoroacetate

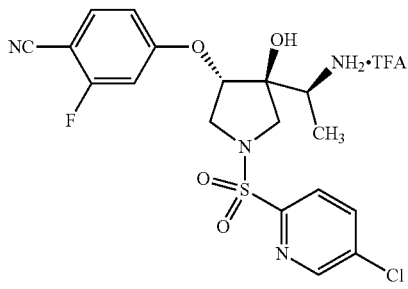

Step 1: 4-(((3S,4R)-1-((5-chloropyridin-2-yl)sulfonyl)-4-hydroxy-4-((S)-1-hydroxyethyl)pyrrolidin-3-yl)oxy)-2-fluorobenzonitrile

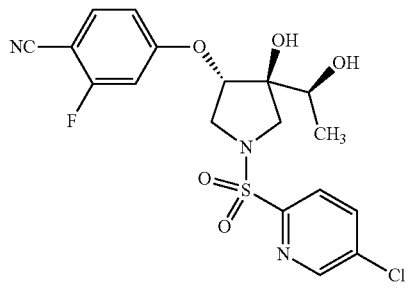 [SMILES: C[C@H](O)[C@]1(O)CN(S(=O)(=O)c2ccc(Cl)cn2)C[C@@H]1Oc1ccc(C#N)c(F)c1]

To a solution of (R,E)-4-((1-((5-chloropyridin-2-yl)sulfonyl)-4-ethylidenepyrrolidin-3-yl)oxy)-2-fluorobenzonitrile (500 mg, 1.1 mmol) and NMO (180 mg, 1.6 mmol) in water (2 mL), CH$_3$CN (2 mL), and acetone (2 mL) was added OsO$_4$ (2.5% in t-BuOH, 0.17 mL, 0.055 mmol) and the reaction mixture was stirred at rt overnight. The reaction was quenched with NaHSO$_3$ (aq) and extracted with EtOAc. The organic layer was dried, filtered and concentrated and the crude product was purified by flash column chromatography (SiO$_2$) eluting with a gradient of 0-100% EtOAc in hexanes. The title compound was isolated as a white solid (471 mg, 95% yield). $^1$H NMR (400 MHz, DMSO-d$_6$) δ: 8.57 (d, J=2.0 Hz, 1H), 8.11 (dd, J=8.4, 2.4 Hz, 1H), 7.85 (d, J=8.5 Hz, 1H), 7.77 (t, J=8.4 Hz, 1H), 6.91 (dd, J=11.8, 2.3 Hz, 1H), 6.65 (dd, J=8.8, 2.3 Hz, 1H), 5.13 (s, 1H), 4.63 (d, J=6.0 Hz, 1H), 4.57 (d, J=2.8 Hz, 1H), 3.78-3.89 (m, 2H), 3.54 (d, J=12.3 Hz, 1H), 3.38 (s, 1H), 3.25 (d, J=10.3 Hz, 1H), 1.01 (d, J=6.3 Hz, 3H). MS (m/z) 442.0 (M+H$^+$).

Step 2: 4-(((3S,4R)-4-((S)-1-aminoethyl)-1-((5-chloropyridin-2-yl)sulfonyl)-4-hydroxypyrrolidin-3-yl)oxy)-2-fluorobenzonitrile, 2,2,2-trifluoroacetate To a solution of 4-(((3S,4R)-1-((5-chloropyridin-2-yl)sulfonyl)-4-hydroxy-4-((S)-1-hydroxyethyl)pyrrolidin-3-yl)oxy)-2-fluorobenzonitrile (360 mg, 0.82 mmol) in DCM (2 mL) and THF (15 mL) was added TEA (0.4 mL, 2.8 mmol) followed by MsCl (0.07 mL, 0.9 mmol) and the reaction mixture was stirred at rt for 30 min. The reaction mixture was concentrated and the residue treated with EtOAc and washed with NaHCO3 (aq) (2×). The organic layers were combined, dried, filtered and concentrated to give (S)-1-((3S,4S)-1-((5-chloropyridin-2-yl)sulfonyl)-4-(4-cyano-3-fluorophenoxy)-3-hydroxypyrrolidin-3-yl)ethyl methanesulfonate which was treated with 2 M NH$_3$ in MeOH (18 mL, 36 mmol) and stirred at rt for 25 h. The reaction mixture was concentrated under reduced pressure, treated with water and extracted with EtOAc. The organic layer was dried, filtered and concentrated to give the corresponding epoxide 4-(((2S,3R,7S)-5-((5-chloropyridin-2-yl)sulfonyl)-2-methyl-1-oxa-5-azaspiro[2.4]heptan-7-yl)oxy)-2-fluorobenzonitrile which was treated with a 0.5 M NH$_3$ in dioxane (20 mL, 10 mmol) and ytterbium(III) trifluoromethanesulfonate (500 mg, 0.8 mmol) and stirred at 75° C. for 7 days. The reaction mixture was concentrated, treated with water and extracted with EtOAc (2×). The combined organic layers were dried, filtered and concentrated and the crude product purified by reverse phase HPLC (C18 Sunfire 30×150 mm preparatory column, eluting at 50 mL/min with a gradient of 10-50% CH$_3$CN/H$_2$O (0.1% TFA)). The desired product fractions were pooled and lyophilized to give the title compound as a white solid (84 mg, 23% yield). $^1$H NMR (400 MHz, DMSO-d$_6$) δ: 8.43 (d, J=2.3 Hz, 1H), 8.10 (dd, J=8.3, 2.5 Hz, 1H), 7.76-7.88 (m, 5H), 6.93 (dd, J=11.5, 2.3 Hz, 1H), 6.64 (dd, J=8.8, 2.3 Hz, 1H), 6.53 (s, 1H), 4.68 (d, J=2.5 Hz, 1H), 3.96 (dd, J=12.8, 2.8 Hz, 1H), 3.67 (d, J=12.8 Hz, 1H), 3.47-3.59 (m, 3H), 1.17 (d, J=6.8 Hz, 3H). MS (m/z) 441.1 (M+H$^+$).

Example 258—Capsule Composition

An oral dosage form for administering the present invention is produced by filing a standard two piece hard gelatin capsule with the ingredients in the proportions shown in Table 2, below.

TABLE 1

| INGREDIENTS | AMOUNTS |
| --- | --- |
| 4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile (Compound of Example 1) | 7 mg |
| Lactose | 53 mg |
| Talc | 16 mg |
| Magnesium Stearate | 4 mg |

Example 259—Injectable Parenteral Composition

An injectable form for administering the present invention is produced by stirring 1.7% by weight of 4-(((3S,4R)-1-

((2,4-dichlorophenyl)sulfonyl)-4-hydroxy-4-(hydroxymethyl)pyrrolidin-3-yl)oxy)-2-fluorobenzonitrile (Compound of Example 2) in 10% by volume propylene glycol in water.

Example 260 Tablet Composition

The sucrose, calcium sulfate dihydrate and a TRPV4 inhibitor as shown in Table 3 below, are mixed and granulated in the proportions shown with a 10% gelatin solution.

The wet granules are screened, dried, mixed with the starch, talc and stearic acid, screened and compressed into a tablet.

TABLE 3

| INGREDIENTS | AMOUNTS |
| --- | --- |
| 4-(((3S,4R)-1-((4-chloro-2-cyanophenyl)sulfonyl)-4-hydroxy-4-(hydroxymethyl)pyrrolidin-3-yl)oxy)-2-fluorobenzonitrile (Compound of Example 3) | 12 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A method of treating a disease selected from: ocular edema, glaucoma, and retinopathy, in a human subject which method comprises administering to a human subject in need thereof a therapeutically effective amount of a compound according to Formula (I)

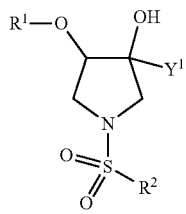

(I)

wherein:
$R^1$ is selected from:
aryl,
aryl substituted from 1 to 4 times by $R^a$,
heteroaryl,
heteroaryl substituted from 1 to 4 times by $R^a$,
bicycloheteroaryl, and
bicycloheteroaryl substituted from 1 to 4 times by $R^a$;
$R^2$ is selected from:
aryl,
aryl substituted from 1 to 4 times by $R^b$,
heteroaryl,
heteroaryl substituted from 1 to 4 times by $R^b$,
bicycloheteroaryl, and
bicycloheteroaryl substituted from 1 to 4 times by $R^b$,
and $Y^1$ is selected from:
$C_{1-6}$alkyl, and
$C_{1-6}$alkyl substituted with from: 1 to 9 substituents independently selected from:
fluoro,
chloro,
bromo,
iodo,
—$OC_{1-6}$alkyl,
—$OC_{1-6}$alkyl substituted with from 1 to 6 substituents independently selected from: fluoro, oxo, —OH, —$NH_2$, and CN,
mercapto,
—S(O)H,
—$S(O)_2$H,
oxo,
hydroxy,
amino,
—$NHR^{x11}$,
wherein $R^{x11}$ is selected from $C_{1-6}$ alkyl, and $C_{1-6}$alkyl substituted with from 1 to 6 substituents independently selected from: fluoro, oxo, —OH, —$NH_2$, CN, —$OC_{1-5}$alkyl,
—$OC_{1-5}$alkyl substituted from 1 to 6 times by fluoro and —$NH_2$, —$NR^{x12}R^{x13}$,
wherein $R^{x12}$ and $R^{x13}$ are each independently selected from $C_{1-6}$alkyl, and $C_{1-6}$ alkyl substituted with from 1 to 6 substituents independently selected from: fluoro, oxo, —OH, —$NH_2$, and —CN,
—$C(O)NH_2$,
aryl,
—Oaryl,
heteroaryl,
—Oheteroaryl,
—$S(O)_2NH_2$,
—$NHS(O)_2H$,
nitro, and
cyano, or
$Y^1$ is taken together with the adjacent —OH to form a heterocyclic ring selected from:
morpholinyl,
morpholinyl substituted by —$CH_3$, and
oxazolidin-2-one;
each $R^a$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo,—NO2, —$NH_2$ and —CN,
cyano,
—$OC_{1-6}$alkyl,
—$OC_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN,
—Ophenyl,
—$C(O)OC_{1-6}$alkyl,
—$C(O)OC_{1-6}$alkyl substituted 1 to 5 times by fluoro, and
—Ocycloalkyl; and
each $R^b$ is independently selected from:
fluoro,
chloro, bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN,
cyano,
—$OC_{1-6}$alkyl,
—$OC_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN,
phenyl,
$C_{1-4}$alkylphenyl,
—C≡C—Si(CH3)$_3$, and
—C≡C-cycloalkyl;
or a pharmaceutically acceptable salt thereof.

2. The method according to claim 1, wherein the compound is represented by the following Formula (II):

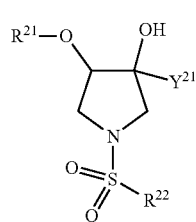

(II)

wherein:
$R^{21}$ is selected from:
aryl,
aryl substituted from 1 to 3 times by $R^{a2}$,
heteroaryl,
heteroaryl substituted from 1 to 3 times by $R^{a2}$,
bicycloheteroaryl, and
bicycloheteroaryl substituted from 1 to 3 times by $R^{a2}$;
$R^{22}$ is selected from:
aryl,
aryl substituted from 1 to 3 times by $R^{b2}$,
bicycloheteroaryl,
bicycloheteroaryl substituted from 1 to 3 times by $R^{b2}$;
heteroaryl, and
heteroaryl substituted from 1 to 3 times by $R^{b2}$, and
$Y^{21}$ is selected from:
$C_{1-6}$alkyl, and
$C_{1-6}$alkyl substituted with from: 1 to 9 substituents independently selected from:
fluoro,
chloro,
bromo,
iodo,
—$OC_{1-6}$alkyl,
—$OC_{1-6}$alkyl substituted with from 1 to 6 substituents independently selected from: fluoro, oxo, —OH, —$NH_2$, and —CN,
mercapto,
—S(O)H,
—S(O)$_2$H,
oxo,
hydroxy,
amino,
—$NHR^{x21}$, wherein $R^{x21}$ is selected from $C_{1-6}$alkyl, and $C_{1-6}$alkyl substituted with from 1 to 6 substituents independently selected from: fluoro, oxo, —OH, —$NH_2$, and —CN,
—$NR^{x22}R^{x23}$,
wherein $R^{x22}$ and $R^{x23}$ are each independently selected from $C_{1-6}$alkyl, and $C_{1-6}$alkyl substituted with from 1 to 6 substituents independently selected from: fluoro, oxo, —OH, —$NH_2$, and —CN,
—C(O)$NH_2$,
aryl,
—Oaryl,
heteroaryl,
—Oheteroaryl,
—S(O)$_2$$NH_2$,
—NHS(O)$_2$H,
nitro, and
cyano, or
$Y^{21}$ is taken together with the adjacent —OH to form a heterocyclic ring selected from:
morpholinyl,
morpholinyl substituted by —$CH_3$, and
oxazolidin-2-one;
each $R^{ae}$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$ alkyl, phenyl, oxo, —NO2, —$NH_2$ and —CN,
cyano,
—$OC_{1-6}$alkyl,
—$OC_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN,
—Ophenyl,
—C(O)$OC_{1-5}$alkyl,
—C(O)$OC_{1-5}$alkyl substituted 1 to 5 times by fluoro, and
—Ocycloalkyl; and
each $R^{b2}$ is independently selected from:
fluoro,
chloro,
bromo,
iodo,
—OH,
$C_{1-6}$alkyl,
$C_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN,
cyano,
—$OC_{1-6}$alkyl,
—$OC_{1-6}$alkyl substituted with from 1 to 5 substituents independently selected from: fluoro, chloro, bromo, iodo, $C_{1-4}$alkoxy, —OH, $C_{1-4}$alkyl, phenyl, oxo, —NO2, —$NH_2$ and —CN, phenyl,
C$_{1-4}$alkylphenyl,
—C≡C—Si(CH3)$_3$, and
—C≡C-cycloalkyl;
or a pharmaceutically acceptable salt thereof.

3. The method of claim 1, wherein the compound is represented by the following Formula (III):

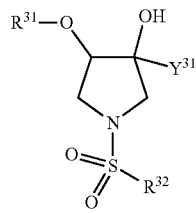

wherein:
R$^{31}$ is selected from:
  phenyl,
  phenyl substituted from 1 to 3 times by R$^{a3}$,
  benzo[c][1,2,5]oxadiazolyl,
  benzo[c][1,2,5]oxadiazolyl substituted from 1 to 3 times by R$^{a3}$,
  pyrimidinyl,
  pyrimidinyl substituted from 1 to 3 times by R$^{a3}$,
  naphthalenyl,
  naphthalenyl substituted from 1 to 3 times by R$^{a3}$,
  pyridinyl, and
  pyridinyl substituted from 1 to 3 times by R$^{a3}$;
R$^{32}$ is selected from:
  phenyl,
  phenyl substituted from 1 to 3 times by R$^{b3}$,
  pyridinyl,
  pyridinyl substituted from 1 to 3 times by R$^{b3}$,
  benzo[c][1,2,5]oxadiazolyl,
  benzo[c][1,2,5]oxadiazolyl substituted from 1 to 3 times by R$^{b3}$,
  thiophenyl,
  thiophenyl substituted from 1 to 3 times by R$^{b3}$,
  thiazolyl,
  thiazolyl substituted from 1 to 3 times by R$^{b3}$,
  pyrazolyl,
  pyrazolyl substituted from 1 to 3 times by R$^{b3}$,
  imidazo[2,1-b]thiazolyl,
  imidazo[2,1-b]thiazolyl substituted from 1 to 3 times by R$^{b3}$,
  pyrimidinyl,
  pyrimidinyl substituted from 1 to 3 times by R$^{b3}$,
  pyridazinyl, and
  pyridazinyl substituted from 1 to 3 times by R$^{b3}$; and
Y$^{31}$ is selected from:
  —CH$_2$OH,
  —CH(OH)CH$_3$,
  —CH(OH)CH$_2$CH$_3$,
  —CH(OH)CH$_2$CH$_2$CH$_3$,
  —CH(OH)CH$_2$CH(CH$_3$)$_2$,
  —C(OH)(CH$_3$)$_2$,
  —CH$_2$NH$_2$,
  —CH$_2$NHR$^{x30}$,
  —CH$_2$NR$^{x30}$R$^{x30}$, and
  —CH(NH$_2$)CH$_3$, or
Y$^{31}$ is taken together with the adjacent —OH to form a heterocyclic ring selected from:
  morpholinyl,
  morpholinyl substituted by —CH$_3$, and
  oxazolidin-2-one,
    wherein each R$^{x30}$ is independently selected from:
      C$_{1-6}$alkyl, and C$_{1-6}$alkyl substituted with from 1 to 6 substituents independently selected from: fluoro, oxo, —OH, —NH$_2$, and —CN;
  each R$^{a3}$ is independently selected from:
    fluoro,
    chloro,
    bromo,
    iodo,
    —OH,
    C$_{1-6}$alkyl,
    cyano,
    —CF$_3$,
    —C$_{1-5}$alkylCF$_3$,
    —CHF$_2$,
    —CH$_2$F,
    —OC$_{1-5}$alkyl,
    —OCF$_3$,
    —OC$_{1-5}$alkylCF$_3$,
    —Ophenyl,
    —Obenzyl,
    —C$_{1-5}$alkylCN,
    —C(O)OC$_{1-5}$alkyl,
    —C(O)OH, and
    —Ocycloalkyl; and
  each R$^{b3}$ is independently selected from:
    fluoro,
    chloro,
    bromo,
    iodo,
    —OH,
    C$_{1-6}$alkyl,
    cyano,
    —CF$_3$,
    —C$_{1-5}$alkylCF$_3$,
    —CHF$_2$,
    —CH$_2$F,
    —OC$_{1-5}$alkyl,
    —OCF$_3$,
    —OC$_{1-5}$alkylCF$_3$,
    —C(O)CH$_3$,
    —OCHF$_2$,
    phenyl,
    —C≡C—Si(CH$_3$)$_3$,
    —C≡C-cycloalkyl, and
    —C≡C-phenyl;
or a pharmaceutically acceptable salt thereof.

4. The method of claim 1, wherein the compound is represented by the following Formula (IV):

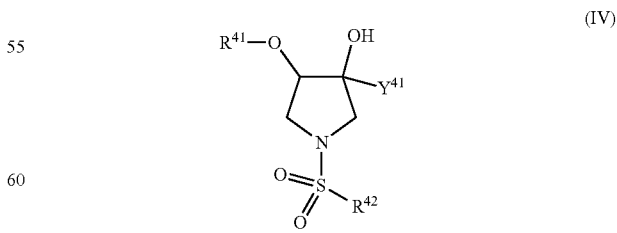

wherein:
R$^{41}$ is selected from:
  phenyl, and
  phenyl substituted from 1 to 3 times by R$^{a4}$;

$R^{42}$ is selected from:
  phenyl,
  phenyl substituted from 1 to 3 times by $R^{b4}$,
  pyridinyl, and
  pyridinyl substituted from 1 to 3 times by $R^{b4}$; and
$Y^{41}$ is selected from:
  —CH$_2$OH,
  —CH$_2$NH$_2$,
  —CH$_2$NHR$^{x40}$,
  —CH$_2$NR$^{x40}$R$^{x40}$, and
  —CH(NH$_2$)CH$_3$, or
$Y^{41}$ is taken together with the adjacent —OH to form a heterocyclic ring selected from:
  morpholinyl,
  morpholinyl substituted by —CH$_3$, and
  oxazolidin-2-one,
    wherein each $R^{x40}$ is independently selected from:
      $C_{1-6}$alkyl, and $C_{1-6}$alkyl substituted with from 1 to 6 substituents independently selected from: fluoro, oxo, —OH, —NH$_2$, and —CN;
each $R^{a4}$ is independently selected from:
  fluoro,
  chloro,
  bromo,
  iodo,
  —OH,
  $C_{1-6}$alkyl,
  cyano,
  —CF$_3$,
  —$C_{1-5}$alkylCF$_3$,
  —CHF$_2$,
  —CH$_2$F,
  —O$C_{1-5}$alkyl,
  —OCF$_3$,
  —O$C_{1-5}$alkylCF$_3$,
  —Ophenyl,
  —Obenzyl,
  —$C_{1-5}$alkylCN,
  —C(O)O$C_{1-5}$alkyl,
  —C(O)OH, and
  —Ocycloalkyl; and
each $R^{b4}$ is independently selected from:
  fluoro,
  chloro,
  bromo,
  iodo,
  —OH,
  $C_{1-6}$alkyl,
  cyano, —CF$_3$, —$C_{1-5}$alkylCF$_3$,
  —CHF$_2$,
  —CH$_2$F,
  —O$C_{1-5}$alkyl,
  —OCF$_3$,
  —O$C_{1-5}$alkylCF$_3$,
  —C(O)CH$_3$,
  —OCHF$_2$,
  phenyl,
  —C≡C—Si(CH$_3$)$_3$,
  —C≡C-cycloalkyl, and
  —C≡C-phenyl;
or a pharmaceutically acceptable salt thereof.

5. The method of claim 1 wherein the compound is selected from:
4-(((3S,4R)-1-((2-cyano-4-(trifluoromethyl)phenyl)sulfonyl)-4-hydroxy-4-(hydroxymethyl)pyrrolidin-3-yl)oxy)-2-fluorobenzonitrile;
4-(((3S,4R)-1-((2,4-dichlorophenyl)sulfonyl)-4-hydroxy-4-(hydroxymethyl)pyrrolidin-3-yl)oxy)-2-fluorobenzonitrile;
4-(((3S,4R)-1-((4-chloro-2-cyanophenyl)sulfonyl)-4-hydroxy-4-(hydroxymethyl)pyrrolidin-3-yl)oxy)-2-fluorobenzonitrile;
(3R,4S)-1-((2,4-dichlorophenyl)sulfonyl)-4-(3,4-difluorophenoxy)-3-(hydroxymethyl)pyrrolidin-3-ol;
2-fluoro-4-(((3S,4R)-4-hydroxy-4-(hydroxymethyl)-1-((6-(trifluoromethyl)pyridin-3-yl)sulfonyl)pyrrolidin-3-yl)oxy)benzonitrile;
2-(((3R,4S)-4-(4-chlorophenoxy)-3-hydroxy-3-(hydroxymethyl)pyrrolidin-1-yl) sulfonyl)-5-(trifluoromethyl)benzonitrile;
2-(((3R,4S)-4-(benzo[c][1,2,5]oxadiazol-5-yloxy)-3-hydroxy-3-(hydroxymethyl)pyrrolidin-1-yl)sulfonyl)-5-(trifluoromethyl)benzonitrile;
5-chloro-2-(((3R,4S)-4-(3,4-difluorophenoxy)-3-hydroxy-3-(hydroxymethyl)pyrrolidin-1-yl)sulfonyl)benzonitrile;
2-(((3R,4S)-4-(4-cyano-2-fluorophenoxy)-3-hydroxy-3-(hydroxymethyl)pyrrolidin-1-yl) sulfonyl)-5-(trifluoromethyl)benzonitrile;
2-(((3R,4S)-4-(4-cyano-2-methoxyphenoxy)-3-hydroxy-3-(hydroxymethyl)pyrrolidin-1-yl) sulfonyl)-5-(trifluoromethyl)benzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethyl)benzonitrile;
2-(((3R,4S)-4-(4-cyano-2-ethoxyphenoxy)-3-hydroxy-3-(hydroxymethyl)pyrrolidin-1-yl) sulfonyl)-5-(trifluoromethyl)benzonitrile;
5-(((3S,4R)-1-((2-cyano-4-(trifluoromethyl)phenyl)sulfonyl)-4-hydroxy-4-(hydroxymethyl)pyrrolidin-3-yl)oxy)pyrimidine-2-carbonitrile;
2-(((3R,4S)-4-(2-chloro-4-cyanophenoxy)-3-hydroxy-3-(hydroxymethyl)pyrrolidin-1-yl) sulfonyl)-5-(trifluoromethyl)benzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2,3-difluorobenzonitrile;
2-(((3R,4S)-4-(4-cyano-2-methylphenoxy)-3-hydroxy-3-(hydroxymethyl)pyrrolidin-1-yl)sulfonyl)-5-(trifluoromethyl)benzonitrile;
2-(((3R,4S)-4-(4-cyano-2-(trifluoromethyl)phenoxy)-3-hydroxy-3-(hydroxymethyl)pyrrolidin-1-yl)sulfonyl)-5-(trifluoromethyl)benzonitrile;
6-(((3S,4R)-1-((2-cyano-4-(trifluoromethyl)phenyl)sulfonyl)-4-hydroxy-4-(hydroxymethyl)pyrrolidin-3-yl)oxy)-2-naphthonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2,5-difluorobenzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2,6-difluorobenzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2-(trifluoromethoxy)benzonitrile;
5-chloro-2-(((3R,4S)-3-hydroxy-3-(hydroxymethyl)-4-(3,4,5-trifluorophenoxy)pyrrolidin-1-yl)sulfonyl)benzonitrile;
5-chloro-2-(((3R,4S)-3-hydroxy-3-(hydroxymethyl)-4-(2,3,4-trifluorophenoxy)pyrrolidin-1-yl)sulfonyl)benzonitrile;

5-chloro-2-(((3R,4S)-3-hydroxy-3-(hydroxymethyl)-4-(2,4,5-trifluorophenoxy)pyrrolidin-1-yl)sulfonyl)benzonitrile;

2-(((3R,4S)-4-(3,4-difluorophenoxy)-3-hydroxy-3-(hydroxymethyl)pyrrolidin-1-yl)sulfonyl)-5-(trifluoromethyl)benzonitrile;

2-(((3R,4S)-3-hydroxy-3-(hydroxymethyl)-4-(3,4,5-trifluorophenoxy)pyrrolidin-1-yl)sulfonyl)-5-(trifluoromethyl)benzonitrile;

2-(((3R,4S)-3-hydroxy-3-(hydroxymethyl)-4-(2,4,5-trifluorophenoxy)pyrrolidin-1-yl)sulfonyl)-5-(trifluoromethyl)benzonitrile;

2-(((3R,4S)-3-hydroxy-3-(hydroxymethyl)-4-(2,3,4-trifluorophenoxy)pyrrolidin-1-yl)sulfonyl)-5-(trifluoromethyl)benzonitrile;

2-(((3R,4S)-4-(4-cyanophenoxy)-3-hydroxy-3-(hydroxymethyl)pyrrolidin-1-yl)sulfonyl)-5-(trifluoromethyl)benzonitrile;

2-(((3R,4S)-4-(4-chloro-3-fluorophenoxy)-3-hydroxy-3-(hydroxymethyl)pyrrolidin-1-yl)sulfonyl)-5-(trifluoromethyl)benzonitrile;

2-(((3R,4S)-4-(3-fluoro-4-(trifluoromethyl)phenoxy)-3-hydroxy-3-(hydroxymethyl)pyrrolidin-1-yl)sulfonyl)-5-(trifluoromethyl)benzonitrile;

2-(((3R,4S)-4-(4-(cyanomethyl)phenoxy)-3-hydroxy-3-(hydroxymethyl)pyrrolidin-1-yl)sulfonyl)-5-(trifluoromethyl)benzonitrile;

2-(((3R,4S)-4-(3-(cyanomethyl)phenoxy)-3-hydroxy-3-(hydroxymethyl)pyrrolidin-1-yl)sulfonyl)-5-(trifluoromethyl)benzonitrile;

methyl 5-cyano-2-(((3S,4R)-1-((2-cyano-4-(trifluoromethyl)phenyl)sulfonyl)-4-hydroxy-4-(hydroxymethyl)pyrrolidin-3-yl)oxy)benzoate;

(3R,4S)-1-((2,4-dichlorophenyl)sulfonyl)-3-(hydroxymethyl)-4-((6-(trifluoromethyl)pyridin-3-yl)oxy)pyrrolidin-3-ol;

5-(((3S,4R)-1-((2,4-dichlorophenyl)sulfonyl)-4-hydroxy-4-(hydroxymethyl)pyrrolidin-3-yl)oxy)-3-fluoropicolinonitrile;

2-(((3R,4S)-3-hydroxy-3-(hydroxymethyl)-4-(4-(trifluoromethyl)phenoxy)pyrrolidin-1-yl)sulfonyl)-5-(trifluoromethyl)benzonitrile;

2-(((3R,4S)-4-(4-fluoro-3-(trifluoromethyl)phenoxy)-3-hydroxy-3-(hydroxymethyl)pyrrolidin-1-yl)sulfonyl)-5-(trifluoromethyl)benzonitrile;

2-(((3R,4S)-4-(3,4-dichlorophenoxy)-3-hydroxy-3-(hydroxymethyl)pyrrolidin-1-yl)sulfonyl)-5-(trifluoromethyl)benzonitrile;

2-(((3R,4S)-4-(3-fluoro-4-(trifluoromethoxy)phenoxy)-3-hydroxy-3-(hydroxymethyl)pyrrolidin-1-yl)sulfonyl)-5-(trifluoromethyl)benzonitrile;

2-(((3R,4S)-4-(3-chloro-4-fluorophenoxy)-3-hydroxy-3-(hydroxymethyl)pyrrolidin-1-yl)sulfonyl)-5-(trifluoromethyl)benzonitrile;

2-(((3R,4S)-3-hydroxy-3-(hydroxymethyl)-4-(6-(trifluoromethyl)pyridin-3-yl)oxy)pyrrolidin-1-yl)sulfonyl)-5-(trifluoromethyl)benzonitrile;

2-(((3R,4S)-4-(3-fluoro-4-methoxyphenoxy)-3-hydroxy-3-(hydroxymethyl)pyrrolidin-1-yl)sulfonyl)-5-(trifluoromethyl)benzonitrile;

2-(((3R,4S)-4-(4-cyano-2-isopropoxyphenoxy)-3-hydroxy-3-(hydroxymethyl)pyrrolidin-1-yl)sulfonyl)-5-(trifluoromethyl)benzonitrile;

2-(((3R,4S)-4-(4-cyano-2-cyclopropoxyphenoxy)-3-hydroxy-3-(hydroxymethyl)pyrrolidin-1-yl)sulfonyl)-5-(trifluoromethyl)benzonitrile;

2-(((3R,4S)-3-hydroxy-3-(hydroxymethyl)-4-phenoxypyrrolidin-1-yl)sulfonyl)-5-(trifluoromethyl)benzonitrile;

2-(((3R,4S)-4-(4-fluorophenoxy)-3-hydroxy-3-(hydroxymethyl)pyrrolidin-1-yl)sulfonyl)-5-(trifluoromethyl)benzonitrile;

2-(((3R,4S)-4-(4-chloro-2-methoxyphenoxy)-3-hydroxy-3-(hydroxymethyl)pyrrolidin-1-yl)sulfonyl)-5-(trifluoromethyl)benzonitrile;

4-(((3S,4R)-1-((2-chloro-4-(trifluoromethyl)phenyl)sulfonyl)-4-hydroxy-4-(hydroxymethyl)pyrrolidin-3-yl)oxy)benzonitrile;

2-(((3R,4S)-3-hydroxy-3-(hydroxymethyl)-4-(4-(trifluoromethoxy)phenoxy)pyrrolidin-1-yl)sulfonyl)-5-(trifluoromethyl)benzonitrile;

2-(((3R,4S)-3-hydroxy-3-(hydroxymethyl)-4-(p-tolyloxy)pyrrolidin-1-yl)sulfonyl)-5-(trifluoromethyl)benzonitrile;

2-(((3R,4S)-3-hydroxy-3-(hydroxymethyl)-4-(4-methoxyphenoxy)pyrrolidin-1-yl)sulfonyl)-5-(trifluoromethyl)benzonitrile;

2-(((3R,4S)-4-(3-cyanophenoxy)-3-hydroxy-3-(hydroxymethyl)pyrrolidin-1-yl)sulfonyl)-5-(trifluoromethyl)benzonitrile;

2-(((3R,4S)-4-(5-cyano-2-methoxyphenoxy)-3-hydroxy-3-(hydroxymethyl)pyrrolidin-1-yl)sulfonyl)-5-(trifluoromethyl)benzonitrile;

2-(((3R,4S)-3-hydroxy-3-(hydroxymethyl)-4-((2-(trifluoromethyl)pyrimidin-5-yl)oxy)pyrrolidin-1-yl)sulfonyl)-5-(trifluoromethyl)benzonitrile;

2-(((3R,4S)-3-hydroxy-3-(hydroxymethyl)-4-(4-(trifluoromethyl)phenoxy)pyrrolidin-1-yl)sulfonyl)benzonitrile;

4-(((3S,4R)-1-((5-chloropyridin-2-yl)sulfonyl)-4-hydroxy-4-(hydroxymethyl)pyrrolidin-3-yl)oxy)-1-naphthonitrile;

4-(((3S,4R)-1-((5-chloropyridin-2-yl)sulfonyl)-4-hydroxy-4-(hydroxymethyl)pyrrolidin-3-yl)oxy)-2-fluorobenzonitrile;

4-(((3S,4R)-1-((7-chlorobenzo[c][1,2,5]oxadiazol-4-yl)sulfonyl)-4-hydroxy-4-(hydroxymethyl)pyrrolidin-3-yl)oxy)-2-fluorobenzonitrile;

4-(((3S,4R)-1-(benzo[c][1,2,5]oxadiazol-5-ylsulfonyl)-4-hydroxy-4-(hydroxymethyl)pyrrolidin-3-yl)oxy)-2-fluorobenzonitrile;

4-(((3S,4R)-1-((2-cyanophenyl)sulfonyl)-4-hydroxy-4-(hydroxymethyl)pyrrolidin-3-yl)oxy)-2-fluorobenzonitrile;

3-(((3R,4S)-4-(4-cyano-3-fluorophenoxy)-3-hydroxy-3-(hydroxymethyl)pyrrolidin-1-yl)sulfonyl)picolinonitrile;

4-(((3S,4R)-1-((2-chloro-4-(trifluoromethyl)phenyl)sulfonyl)-4-hydroxy-4-(hydroxymethyl)pyrrolidin-3-yl)oxy)-2-fluorobenzonitrile;

4-(((3S,4R)-1-((2-bromo-4-methoxyphenyl)sulfonyl)-4-hydroxy-4-(hydroxymethyl)pyrrolidin-3-yl)oxy)-2-fluorobenzonitrile;

4-(((3S,4R)-1-((2-bromo-4-(trifluoromethoxy)phenyl)sulfonyl)-4-hydroxy-4-(hydroxymethyl)pyrrolidin-3-yl)oxy)-2-fluorobenzonitrile;

4-(((3S,4R)-1-((2-chloro-4-(trifluoromethoxy)phenyl)sulfonyl)-4-hydroxy-4-(hydroxymethyl)pyrrolidin-3-yl)oxy)-2-fluorobenzonitrile;

4-(((3S,4R)-1-((4-bromo-2-cyanophenyl)sulfonyl)-4-hydroxy-4-(hydroxymethyl)pyrrolidin-3-yl)oxy)-2-fluorobenzonitrile;

4-(((3S,4R)-1-((4-cyano-2-(trifluoromethyl)phenyl) sulfonyl)-4-hydroxy-4-(hydroxymethyl)pyrrolidin-3-yl)oxy)-2-fluorobenzonitrile;

5-(((3S,4R)-1-((2-cyano-4-(trifluoromethyl)phenyl) sulfonyl)-4-hydroxy-4-(hydroxymethyl)pyrrolidin-3-yl)oxy)picolinonitrile;

2-fluoro-4-(((3S,4R)-4-hydroxy-4-(hydroxymethyl)-1-((4-(trifluoromethyl)phenyl)sulfonyl)pyrrolidin-3-yl) oxy)benzonitrile;

4-(((3S,4R)-1-((4-cyanophenyl)sulfonyl)-4-hydroxy-4-(hydroxymethyl)pyrrolidin-3-yl)oxy)-2-fluorobenzonitrile;

4-(((3S,4R)-1-((4-acetyl-2-cyanophenyl)sulfonyl)-4-hydroxy-4-(hydroxymethyl)pyrrolidin-3-yl)oxy)-2-fluorobenzonitrile;

5-(((3S,4R)-1-((2,4-dichlorophenyl)sulfonyl)-4-hydroxy-4-(hydroxymethyl)pyrrolidin-3-yl)oxy)picolinonitrile;

5-(((3S,4R)-1-((2-chloro-4-(trifluoromethyl)phenyl) sulfonyl)-4-hydroxy-4-(hydroxymethyl)pyrrolidin-3-yl)oxy)picolinonitrile;

5-(((3S,4R)-1-((2-chloro-4-methylphenyl)sulfonyl)-4-hydroxy-4-(hydroxymethyl)pyrrolidin-3-yl)oxy)picolinonitrile;

5-(((3S,4R)-4-hydroxy-4-(hydroxymethyl)-1-((2,4,6-trichlorophenyl)sulfonyl)pyrrolidin-3-yl)oxy)picolinonitrile;

2-fluoro-4-(((3S,4R)-4-hydroxy-4-(hydroxymethyl)-1-((2,4,6-trichlorophenyl)sulfonyl)pyrrolidin-3-yl)oxy) benzonitrile;

4-(((3S,4R)-1-((2-chloro-4-methylphenyl)sulfonyl)-4-hydroxy-4-(hydroxymethyl)pyrrolidin-3-yl)oxy)-2-fluorobenzonitrile;

5-(((3R,4S)-4-(4-cyano-3-fluorophenoxy)-3-hydroxy-3-(hydroxymethyl)pyrrolidin-1-yl)sulfonyl)picolinonitrile;

4-(((3S,4R)-1-((4-cyano-2-methylphenyl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((2-methyl-4-(trifluoromethyl)phenyl)sulfonyl)pyrrolidin-3-yl)oxy)benzonitrile;

5-(((3R,4S)-4-(4-cyano-2,5-difluorophenoxy)-3-hydroxy-3-(hydroxymethyl)pyrrolidin-1-yl)sulfonyl)picolinonitrile;

2-fluoro-4-(((3S,4R)-4-hydroxy-4-(hydroxymethyl)-1-((2-methyl-6-(trifluoromethyl)pyridin-3-yl)sulfonyl) pyrrolidin-3-yl)oxy)benzonitrile;

2-fluoro-4-(((3S,4R)-4-hydroxy-4-(hydroxymethyl)-1-((5-(trifluoromethyl)pyridin-2-yl)sulfonyl)pyrrolidin-3-yl)oxy)benzonitrile;

4-(((3S,4R)-1-((2-chlorophenyl)sulfonyl)-4-hydroxy-4-(hydroxymethyl)pyrrolidin-3-yl)oxy)-2-fluorobenzonitrile;

4-(((3S,4R)-1-((5-chlorothiophen-2-yl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((2-methyl-4-(trifluoromethyl)thiazol-5-yl)sulfonyl) pyrrolidin-3-yl)oxy)benzonitrile;

4-(((3S,4R)-1-((2,4-dichlorothiazol-5-yl)sulfonyl)-4-hydroxy-4-(hydroxymethyl)pyrrolidin-3-yl)oxy)-2-fluorobenzonitrile;

4-(((3S,4R)-1-((4-chloro-1-methyl-1H-pyrazol-5-yl) sulfonyl)-4-hydroxy-4-(hydroxymethyl)pyrrolidin-3-yl)oxy)-2-fluorobenzonitrile;

4-(((3S,4R)-1-((6-chloroimidazo[2,1-b]thiazol-5-yl) sulfonyl)-4-hydroxy-4-(hydroxymethyl)pyrrolidin-3-yl)oxy)-2-fluorobenzonitrile;

4-(((3S,4R)-1-((6-chloropyridin-3-yl)sulfonyl)-4-hydroxy-4-(hydroxymethyl)pyrrolidin-3-yl)oxy)-2-fluorobenzonitrile;

4-(((3S,4R)-1-((2,6-dichloropyridin-3-yl)sulfonyl)-4-hydroxy-4-(hydroxymethyl)pyrrolidin-3-yl)oxy)-2-fluorobenzonitrile;

4-(((3S,4R)-1-((2-ethynylphenyl)sulfonyl)-4-hydroxy-4-(hydroxymethyl)pyrrolidin-3-yl)oxy)-2-fluorobenzonitrile;

4-(((3S,4R)-1-((2,3-dichlorophenyl)sulfonyl)-4-hydroxy-4-(hydroxymethyl)pyrrolidin-3-yl)oxy)-2-fluorobenzonitrile;

4-(((3S,4R)-1-((3-chloro-2-cyanophenyl)sulfonyl)-4-hydroxy-4-(hydroxymethyl)pyrrolidin-3-yl)oxy)-2-fluorobenzonitrile;

4-(((3S,4R)-1-((2,6-dichloro-4-(trifluoromethyl)phenyl) sulfonyl)-4-hydroxy-4-(hydroxymethyl)pyrrolidin-3-yl)oxy)-2-fluorobenzonitrile;

4-(((3S,4R)-1-((2-chloro-4-cyanophenyl)sulfonyl)-4-hydroxy-4-(hydroxymethyl)pyrrolidin-3-yl)oxy)-2-fluorobenzonitrile;

4-(((3S,4R)-1-((4-(difluoromethyl)phenyl)sulfonyl)-4-hydroxy-4-(hydroxymethyl)pyrrolidin-3-yl)oxy)-2-fluorobenzonitrile;

4-(((3S,4R)-1-((6-bromopyridin-3-yl)sulfonyl)-4-hydroxy-4-(hydroxymethyl)pyrrolidin-3-yl)oxy)-2-fluorobenzonitrile;

4-(((3S,4R)-1-((2-chloro-6-(trifluoromethyl)pyridin-3-yl) sulfonyl)-4-hydroxy-4-(hydroxymethyl)pyrrolidin-3-yl)oxy)-2-fluorobenzonitrile;

4-(((3S,4R)-1-((4-chlorophenyl)sulfonyl)-4-hydroxy-4-(hydroxymethyl)pyrrolidin-3-yl)oxy)-2-fluorobenzonitrile;

4-(((3S,4R)-1-((4-bromophenyl)sulfonyl)-4-hydroxy-4-(hydroxymethyl)pyrrolidin-3-yl)oxy)-2-fluorobenzonitrile;

2-fluoro-4-(((3S,4R)-4-hydroxy-4-(hydroxymethyl)-1-((4-iodophenyl)sulfonyl)pyrrolidin-3-yl)oxy)benzonitrile;

4-(((3S,4R)-1-((4-cyano-2-methoxyphenyl)sulfonyl)-4-hydroxy-4-(hydroxymethyl)pyrrolidin-3-yl)oxy)-2-fluorobenzonitrile;

4-(((3S,4R)-1-((5-bromopyridin-2-yl)sulfonyl)-4-hydroxy-4-(hydroxymethyl)pyrrolidin-3-yl)oxy)-2-fluorobenzonitrile;

3-chloro-4-(((3R,4S)-4-(4-chlorophenoxy)-3-hydroxy-3-(hydroxymethyl)pyrrolidin-1-yl)sulfonyl)benzonitrile;

2-(((3R,4S)-4-(4-chlorophenoxy)-3-hydroxy-3-(hydroxymethyl)pyrrolidin-1-yl)sulfonyl)benzonitrile;

3-bromo-4-(((3R,4S)-4-(4-chlorophenoxy)-3-hydroxy-3-(hydroxymethyl)pyrrolidin-1-yl)sulfonyl)benzonitrile;

5-(((3R,4S)-4-(4-chlorophenoxy)-3-hydroxy-3-(hydroxymethyl)pyrrolidin-1-yl)sulfonyl)picolinonitrile;

3-(((3R,4S)-4-(4-chlorophenoxy)-3-hydroxy-3-(hydroxymethyl)pyrrolidin-1-yl)sulfonyl)picolinonitrile;

2-fluoro-4-(((3S,4R)-4-hydroxy-4-(hydroxymethyl)-1-((4-(2,2,2-trifluoroethyl)phenyl)sulfonyl)pyrrolidin-3-yl)oxy)benzonitrile;

2-fluoro-4-(((3S,4R)-4-hydroxy-4-(hydroxymethyl)-1-((5-(trifluoromethyl)thiophen-2-yl)sulfonyl)pyrrolidin-3-yl)oxy)benzonitrile;

4-(((3S,4R)-1-((4-cyano-2-fluorophenyl)sulfonyl)-4-hydroxy-4-(hydroxymethyl)pyrrolidin-3-yl)oxy)-2-fluorobenzonitrile;

4-(((3S,4R)-1-((2-cyano-4-iodophenyl)sulfonyl)-4-hydroxy-4-(hydroxymethyl)pyrrolidin-3-yl)oxy)-2-fluorobenzonitrile;
4-(((3S,4R)-1-((2-chloro-4-iodophenyl)sulfonyl)-4-hydroxy-4-(hydroxymethyl)pyrrolidin-3-yl)oxy)-2-fluorobenzonitrile;
2-fluoro-4-(((3S,4R)-1-((3-fluoro-4-(trifluoromethyl)phenyl)sulfonyl)-4-hydroxy-4-(hydroxymethyl)pyrrolidin-3-yl)oxy)benzonitrile;
4-(((3S,4R)-1-((2-bromophenyl)sulfonyl)-4-hydroxy-4-(hydroxymethyl)pyrrolidin-3-yl)oxy)-2-fluorobenzonitrile;
2-fluoro-4-(((3S,4R)-1-((3-fluoro-4-methylphenyl)sulfonyl)-4-hydroxy-4-(hydroxymethyl)pyrrolidin-3-yl)oxy)benzonitrile;
2-fluoro-4-(((3S,4R)-4-hydroxy-4-(hydroxymethyl)-1-((2-iodophenyl)sulfonyl)pyrrolidin-3-yl)oxy)benzonitrile;
4-(((3S,4R)-1-((2-bromo-4-chlorophenyl)sulfonyl)-4-hydroxy-4-(hydroxymethyl)pyrrolidin-3-yl)oxy)-2-fluorobenzonitrile;
4-(((3S,4R)-1-((4-bromo-2-(trifluoromethyl)phenyl)sulfonyl)-4-hydroxy-4-(hydroxymethyl)pyrrolidin-3-yl)oxy)-2-fluorobenzonitrile;
4-(((3S,4R)-1-((2-(difluoromethoxy)pyridin-3-yl)sulfonyl)-4-hydroxy-4-(hydroxymethyl)pyrrolidin-3-yl)oxy)-2-fluorobenzonitrile;
4-(((3S,4R)-1-((4-bromo-1-methyl-1H-pyrazol-5-yl)sulfonyl)-4-hydroxy-4-(hydroxymethyl)pyrrolidin-3-yl)oxy)-2-fluorobenzonitrile;
4-(((3S,4R)-1-((4-chloro-1,3-dimethyl-1H-pyrazol-5-yl)sulfonyl)-4-hydroxy-4-(hydroxymethyl)pyrrolidin-3-yl)oxy)-2-fluorobenzonitrile;
(3R,4S)-4-(benzo[c][1,2,5]oxadiazol-5-yloxy)-1-((2-fluoro-4-(trifluoromethyl)phenyl)sulfonyl)-3-(hydroxymethyl)pyrrolidin-3-ol;
4-(((3S,4R)-1-((6-(difluoromethoxy)pyridin-3-yl)sulfonyl)-4-hydroxy-4-(hydroxymethyl)pyrrolidin-3-yl)oxy)-2-fluorobenzonitrile;
2-fluoro-4-(((3S,4R)-4-hydroxy-4-(hydroxymethyl)-1-((5-(trifluoromethoxy)pyridin-2-yl)sulfonyl)pyrrolidin-3-yl)oxy)benzonitrile;
2-fluoro-4-(((3S,4R)-4-hydroxy-4-(hydroxymethyl)-1-((2-(trifluoromethyl)pyrimidin-5-yl)sulfonyl)pyrrolidin-3-yl)oxy)benzonitrile;
4-(((3S,4R)-1-((4-chloro-3-(trifluoromethoxy)phenyl)sulfonyl)-4-hydroxy-4-(hydroxymethyl)pyrrolidin-3-yl)oxy)-2-fluorobenzonitrile;
2-fluoro-4-(((3S,4R)-4-hydroxy-4-(hydroxymethyl)-1-((5-iodopyridin-2-yl)sulfonyl)pyrrolidin-3-yl)oxy)benzonitrile;
5-(((3R,4S)-4-(4-cyano-3-fluorophenoxy)-3-hydroxy-3-(hydroxymethyl)pyrrolidin-1-yl)sulfonyl)-6-methylpicolinonitrile;
2-fluoro-4-(((3S,4R)-4-hydroxy-4-(hydroxymethyl)-1-((6-(trifluoromethoxy)pyridin-2-yl)sulfonyl)pyrrolidin-3-yl)oxy)benzonitrile;
2-fluoro-4-(((3S,4R)-4-hydroxy-4-(hydroxymethyl)-1-((6-(2,2,2-trifluoroethoxy)pyridazin-3-yl)sulfonyl)pyrrolidin-3-yl)oxy)benzonitrile;
4-(((3S,4R)-1-((6-(difluoromethoxy)pyridin-2-yl)sulfonyl)-4-hydroxy-4-(hydroxymethyl)pyrrolidin-3-yl)oxy)-2-fluorobenzonitrile;
4-(((3S,4S)-1-((2-cyano-4-(trifluoromethyl)phenyl)sulfonyl)-4-hydroxy-4-(hydroxymethyl)pyrrolidin-3-yl)oxy)-2-fluorobenzonitrile;
4-(((3S,4S)-1-((5-chloropyridin-2-yl)sulfonyl)-4-hydroxy-4-(hydroxymethyl)pyrrolidin-3-yl)oxy)-2-fluorobenzonitrile;
4-(((3S,4S)-1-((2-cyanophenyl)sulfonyl)-4-hydroxy-4-(hydroxymethyl)pyrrolidin-3-yl)oxy)-2-fluorobenzonitrile;
4-(((3S,4S)-1-((2-cyano-4-fluorophenyl)sulfonyl)-4-hydroxy-4-(hydroxymethyl)pyrrolidin-3-yl)oxy)-2-fluorobenzonitrile;
4-(((3S,4S)-1-((4-chloro-2-cyanophenyl)sulfonyl)-4-hydroxy-4-(hydroxymethyl)pyrrolidin-3-yl)oxy)-2-fluorobenzonitrile;
3-(((3S,4S)-4-(4-cyano-3-fluorophenoxy)-3-hydroxy-3-(hydroxymethyl)pyrrolidin-1-yl)sulfonyl)picolinonitrile;
4-(((3S,4S)-1-((2-chloro-4-cyanophenyl)sulfonyl)-4-hydroxy-4-(hydroxymethyl)pyrrolidin-3-yl)oxy)-2-fluorobenzonitrile;
4-(((3S,4S)-1-((2,4-dichlorophenyl)sulfonyl)-4-hydroxy-4-(hydroxymethyl)pyrrolidin-3-yl)oxy)-2-fluorobenzonitrile;
4-(((3S,4S)-1-((4-bromo-2-cyanophenyl)sulfonyl)-4-hydroxy-4-(hydroxymethyl)pyrrolidin-3-yl)oxy)-2-fluorobenzonitrile;
4-(((3S,4S)-1-((2-bromo-4-fluorophenyl)sulfonyl)-4-hydroxy-4-(hydroxymethyl)pyrrolidin-3-yl)oxy)-2-fluorobenzonitrile;
4-(((3S,4S)-1-((2-cyano-4-methoxyphenyl)sulfonyl)-4-hydroxy-4-(hydroxymethyl)pyrrolidin-3-yl)oxy)-2-fluorobenzonitrile;
2-(((3S,4S)-4-(4-chlorophenoxy)-3-hydroxy-3-(hydroxymethyl)pyrrolidin-1-yl)sulfonyl)-5-(trifluoromethyl)benzonitrile;
2-(((3S,4S)-4-(4-chlorophenoxy)-3-hydroxy-3-(hydroxymethyl)pyrrolidin-1-yl)sulfonyl)-5-fluorobenzonitrile;
2-(((3S,4S)-3-hydroxy-3-(hydroxymethyl)-4-(4-(trifluoromethyl)phenoxy)pyrrolidin-1-yl)sulfonyl)-5-(trifluoromethyl)benzonitrile;
5-fluoro-2-(((3S,4S)-3-hydroxy-3-(hydroxymethyl)-4-(4-(trifluoromethyl)phenoxy)pyrrolidin-1-yl)sulfonyl)benzonitrile;
3-chloro-4-(((3R,4S)-3-hydroxy-3-(hydroxymethyl)-4-(4-(trifluoromethyl)phenoxy)pyrrolidin-1-yl)sulfonyl)benzonitrile;
5-chloro-2-(((3S,4S)-4-(4-chlorophenoxy)-3-hydroxy-3-(hydroxymethyl)pyrrolidin-1-yl)sulfonyl)benzonitrile;
5-chloro-2-(((3S,4S)-3-hydroxy-3-(hydroxymethyl)-4-(4-(trifluoromethyl)phenoxy)pyrrolidin-1-yl)sulfonyl)benzonitrile;
5-fluoro-2-(((3R,4S)-3-hydroxy-3-(hydroxymethyl)-4-(4-(trifluoromethyl)phenoxy)pyrrolidin-1-yl)sulfonyl)benzonitrile;
5-chloro-2-(((3R,4S)-4-(4-chlorophenoxy)-3-hydroxy-3-(hydroxymethyl)pyrrolidin-1-yl)sulfonyl)benzonitrile;
2-(((3R,4S)-4-(4-chlorophenoxy)-3-hydroxy-3-(hydroxymethyl)pyrrolidin-1-yl)sulfonyl)-5-fluorobenzonitrile;
5-chloro-2-(((3R,4S)-3-hydroxy-3-(hydroxymethyl)-4-(4-(trifluoromethyl)phenoxy)pyrrolidin-1-yl)sulfonyl)benzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-(2,2,2-trifluoroethoxy)benzonitrile;
4-(((3S,4R)-1-((2-cyano-4-(trifluoromethyl)phenyl)sulfonyl)-4-hydroxy-4-(hydroxymethyl)pyrrolidin-3-yl)oxy)-2-fluoro-5-methoxybenzonitrile;

4-(((3S,4R)-1-((2-cyano-4-(trifluoromethyl)phenyl)
sulfonyl)-4-hydroxy-4-(hydroxymethyl)pyrrolidin-3-
yl)oxy)-5-ethoxy-2-fluorobenzonitrile;
4-(((3S,4R)-1-((2-cyano-4-(trifluoromethyl)phenyl)
sulfonyl)-4-hydroxy-4-(hydroxymethyl)pyrrolidin-3-
yl)oxy)-2-fluoro-5-propoxybenzonitrile;
4-(((3S,4R)-1-((2-cyano-4-(trifluoromethyl)phenyl)
sulfonyl)-4-hydroxy-4-(hydroxymethyl)pyrrolidin-3-
yl)oxy)-2-fluoro-5-isopropoxybenzonitrile;
4-(((3S,4R)-1-((2-cyano-4-(trifluoromethyl)phenyl)
sulfonyl)-4-hydroxy-4-(hydroxymethyl)pyrrolidin-3-
yl)oxy)-2-fluoro-5-hydroxybenzonitrile;
5-(benzyloxy)-4-(((3S,4R)-1-((2-cyano-4-(trifluorom-
ethyl)phenyl)sulfonyl)-4-hydroxy-4-(hydroxymethyl)
pyrrolidin-3-yl)oxy)-2-fluorobenzonitrile;
5-butoxy-4-(((3S,4R)-1-((2-cyano-4-(trifluoromethyl)
phenyl)sulfonyl)-4-hydroxy-4-(hydroxymethyl)pyrro-
lidin-3-yl)oxy)-2-fluorobenzonitrile;
4-(((3S,4R)-1-((2-cyano-4-(trifluoromethyl)phenyl)
sulfonyl)-4-hydroxy-4-(hydroxymethyl)pyrrolidin-3-
yl)oxy)-2-fluoro-5-isobutoxybenzonitrile;
2-(((3R,4S)-4-(4-cyano-2-propoxyphenoxy)-3-hydroxy-
3-(hydroxymethyl)pyrrolidin-1-yl)sulfonyl)-5-(trifluo-
romethyl)benzonitrile;
2-(((3R,4S)-4-(4-cyano-2-(2,2,2-trifluoroethoxy)phe-
noxy)-3-hydroxy-3-(hydroxymethyl)pyrrolidin-1-yl)
sulfonyl)-5-(trifluoromethyl)benzonitrile;
2-(((3R,4S)-4-(4-cyano-2-hydroxyphenoxy)-3-hydroxy-
3-(hydroxymethyl)pyrrolidin-1-yl)sulfonyl)-5-(trifluo-
romethyl)benzonitrile;
2-(((3R,4S)-4-(2-butoxy-4-cyanophenoxy)-3-hydroxy-3-
(hydroxymethyl)pyrrolidin-1-yl)sulfonyl)-5-(trifluo-
romethyl)benzonitrile;
2-(((3R,4S)-4-(4-cyano-2-isobutoxyphenoxy)-3-hy-
droxy-3-(hydroxymethyl)pyrrolidin-1-yl)sulfonyl)-5-
(trifluoromethyl)benzonitrile;
2-(((3R,4S)-4-(2-(benzyloxy)-4-cyanophenoxy)-3-hy-
droxy-3-(hydroxymethyl)pyrrolidin-1-yl)sulfonyl)-5-
(trifluoromethyl)benzonitrile;
4-(((3S,4R)-1-((4-cyanophenyl)sulfonyl)-4-hydroxy-4-
(hydroxymethyl)pyrrolidin-3-yl)oxy)-3-(2,2,2-trifluo-
roethoxy)benzonitrile;
4-(((3S,4R)-1-((2-cyanophenyl)sulfonyl)-4-hydroxy-4-
(hydroxymethyl)pyrrolidin-3-yl)oxy)-2-fluoro-5-(2,2,
2-trifluoroethoxy)benzonitrile;
5-(((3R,4S)-4-(4-cyano-5-fluoro-2-(2,2,2-trifluoroeth-
oxy)phenoxy)-3-hydroxy-3-(hydroxymethyl)pyrroli-
din-1-yl)sulfonyl)picolinonitrile;
2-fluoro-4-(((3S,4R)-4-hydroxy-4-(hydroxymethyl)-1-
((6-(trifluoromethyl)pyridin-3-yl)sulfonyl)pyrrolidin-
3-yl)oxy)-5-(2,2,2-trifluoroethoxy)benzonitrile;
2-fluoro-4-(((3S,4R)-4-hydroxy-4-(hydroxymethyl)-1-
(phenylsulfonyl)pyrrolidin-3-yl)oxy)-5-(2,2,2-trifluo-
roethoxy)benzonitrile;
4-(((3S,4R)-1-((2,4-dichlorophenyl)sulfonyl)-4-hydroxy-
4-(hydroxymethyl)pyrrolidin-3-yl)oxy)-2-fluoro-5-(2,
2,2-trifluoroethoxy)benzonitrile;
4-(((3S,4R)-1-((4-cyanophenyl)sulfonyl)-4-hydroxy-4-
(hydroxymethyl)pyrrolidin-3-yl)oxy)-2-fluoro-5-(2,2,
2-trifluoroethoxy)benzonitrile;
4-(((3S,4R)-1-((2-cyanophenyl)sulfonyl)-4-hydroxy-4-
(hydroxymethyl)pyrrolidin-3-yl)oxy)-2-fluoro-5-
isobutoxybenzonitrile;
4-(((3S,4R)-1-((4-cyanophenyl)sulfonyl)-4-hydroxy-4-
(hydroxymethyl)pyrrolidin-3-yl)oxy)-2-fluoro-5-
isobutoxybenzonitrile;
5-(((3R,4S)-4-(4-cyano-5-fluoro-2-isobutoxyphenoxy)-
3-hydroxy-3-(hydroxymethyl)pyrrolidin-1-yl)sulfonyl)
picolinonitrile;
2-fluoro-4-(((3S,4R)-4-hydroxy-4-(hydroxymethyl)-1-
((4-(trifluoromethyl)phenyl)sulfonyl)pyrrolidin-3-yl)
oxy)-5-isobutoxybenzonitrile;
2-fluoro-4-(((3S,4R)-4-hydroxy-4-(hydroxymethyl)-1-
((6-(trifluoromethyl)pyridin-3-yl)sulfonyl)pyrrolidin-
3-yl)oxy)-5-isobutoxybenzonitrile;
5-(((3R,4S)-4-(4-cyano-2-(2,2,2-trifluoroethoxy)phe-
noxy)-3-hydroxy-3-(hydroxymethyl)pyrrolidin-1-yl)
sulfonyl)picolinonitrile;
4-(((3S,4R)-1-((2-cyanophenyl)sulfonyl)-4-hydroxy-4-
(hydroxymethyl)pyrrolidin-3-yl)oxy)-3-(2,2,2-trifluo-
roethoxy)benzonitrile;
4-(((3S,4R)-1-((5-chloropyridin-2-yl)sulfonyl)-4-hy-
droxy-4-(hydroxymethyl)pyrrolidin-3-yl)oxy)-3-(2,2,
2-trifluoroethoxy)benzonitrile;
4-(((3S,4R)-1-((5-chloropyridin-2-yl)sulfonyl)-4-hy-
droxy-4-(hydroxymethyl)pyrrolidin-3-yl)oxy)-2-
fluoro-5-(2,2,2-trifluoroethoxy)benzonitrile;
2-fluoro-4-(((3S,4R)-4-hydroxy-4-(hydroxymethyl)-1-
((6-methylpyridazin-3-yl)sulfonyl)pyrrolidin-3-yl)
oxy)-5-isobutoxybenzonitrile;
4-(((3S,4R)-1-((5-chloropyridin-2-yl)sulfonyl)-4-hy-
droxy-4-((S)-1-hydroxybutyl)pyrrolidin-3-yl)oxy)-2-
fluorobenzonitrile;
4-(((3S,4R)-1-((2-cyano-4-(trifluoromethyl)phenyl)
sulfonyl)-4-hydroxy-4-((R)-1-hydroxyethyl)pyrroli-
din-3-yl)oxy)-2-fluorobenzonitrile;
4-(((3S,4R)-1-((5-chloropyridin-2-yl)sulfonyl)-4-hy-
droxy-4-(1-hydroxyethyl)pyrrolidin-3-yl)oxy)-2-fluo-
robenzonitrile;
4-(((3S,4R)-1-((5-chloropyridin-2-yl)sulfonyl)-4-hy-
droxy-4-((S)-1-hydroxy-3-methylbutyl)pyrrolidin-3-
yl)oxy)-2-fluorobenzonitrile;
4-(((3S,4R)-1-((2-cyano-4-(trifluoromethyl)phenyl)
sulfonyl)-4-hydroxy-4-(1-hydroxyethyl)pyrrolidin-3-
yl)oxy)-2-fluorobenzonitrile;
4-(((3S,4S)-1-((2-cyano-4-(trifluoromethyl)phenyl)sulfo-
nyl)-4-hydroxy-4-((S)-1-hydroxyethyl)pyrrolidin-3-yl)
oxy)-2-fluorobenzonitrile;
4-(((3S,4R)-1-((5-chloropyridin-2-yl)sulfonyl)-4-hy-
droxy-4-((R)-1-methoxyethyl)pyrrolidin-3-yl)oxy)-2-
fluorobenzonitrile;
4-(((3S,4R)-1-((5-chloropyridin-2-yl)sulfonyl)-4-hy-
droxy-4-((R)-1-hydroxypropyl)pyrrolidin-3-yl)oxy)-2-
fluorobenzonitrile;
4-(((3S,4R)-1-((5-chloropyridin-2-yl)sulfonyl)-4-hy-
droxy-4-((R)-1-hydroxy-3-methylbutyl)pyrrolidin-3-
yl)oxy)-2-fluorobenzonitrile;
4-(((3S,4R)-1-((5-chloropyridin-2-yl)sulfonyl)-4-hy-
droxy-4-((R)-1-hydroxybutyl)pyrrolidin-3-yl)oxy)-2-
fluorobenzonitrile;
4-(((3S,4R)-1-((2-cyano-4-methoxyphenyl)sulfonyl)-4-
hydroxy-4-((S)-1-hydroxyethyl)pyrrolidin-3-yl)oxy)-
2-fluorobenzonitrile;
4-(((3S,4R)-1-((2-cyanophenyl)sulfonyl)-4-hydroxy-4-
((S)-1-hydroxyethyl)pyrrolidin-3-yl)oxy)-2-fluoroben-
zonitrile;
4-(((3S,4R)-1-((2-cyano-4-fluorophenyl)sulfonyl)-4-hy-
droxy-4-((S)-1-hydroxyethyl)pyrrolidin-3-yl)oxy)-2-
fluorobenzonitrile;
4-(((3S,4R)-1-((4-chloro-2-cyanophenyl)sulfonyl)-4-hy-
droxy-4-((S)-1-hydroxyethyl)pyrrolidin-3-yl)oxy)-2-
fluorobenzonitrile;

3-(((3R,4S)-4-(4-cyano-3-fluorophenoxy)-3-hydroxy-3-((S)-1-hydroxyethyl)pyrrolidin-1-yl)sulfonyl)picolinonitrile;
4-(((3S,4R)-1-((2,4-dichlorophenyl)sulfonyl)-4-hydroxy-4-((S)-1-hydroxyethyl)pyrrolidin-3-yl)oxy)-2-fluorobenzonitrile;
4-(((3S,4R)-1-((2-chloro-4-cyanophenyl)sulfonyl)-4-hydroxy-4-((S)-1-hydroxyethyl)pyrrolidin-3-yl)oxy)-2-fluorobenzonitrile;
2-fluoro-4-(((3S,4R)-4-hydroxy-4-((R)-1-hydroxyethyl)-1-((6-(trifluoromethyl)pyridin-3-yl)sulfonyl)pyrrolidin-3-yl)oxy)benzonitrile;
2-fluoro-4-(((3S,4R)-1-((5-fluoropyridin-2-yl)sulfonyl)-4-hydroxy-4-((R)-1-hydroxyethyl)pyrrolidin-3-yl)oxy)benzonitrile;
2-fluoro-4-(((3S,4R)-4-hydroxy-4-((R)-1-hydroxyethyl)-1-((6-(trifluoromethoxy)pyridin-3-yl)sulfonyl)pyrrolidin-3-yl)oxy)benzonitrile;
2-fluoro-4-(((3S,4R)-4-hydroxy-4-((R)-1-hydroxyethyl)-1-((4-iodophenyl)sulfonyl)pyrrolidin-3-yl)oxy)benzonitrile;
2-fluoro-4-(((3S,4R)-4-hydroxy-4-((R)-1-hydroxyethyl)-1-((5-(trifluoromethoxy)pyridin-2-yl)sulfonyl)pyrrolidin-3-yl)oxy)benzonitrile;
4-(((3S,4R)-1-((5-(difluoromethyl)pyridin-2-yl)sulfonyl)-4-hydroxy-4-((R)-1-hydroxyethyl)pyrrolidin-3-yl)oxy)-2-fluorobenzonitrile;
4-(((3S,4R)-1-((6-(difluoromethyl)pyridin-2-yl)sulfonyl)-4-hydroxy-4-((R)-1-hydroxyethyl)pyrrolidin-3-yl)oxy)-2-fluorobenzonitrile;
4-(((3S,4R)-1-((6-(difluoromethoxy)pyridin-3-yl)sulfonyl)-4-hydroxy-4-((R)-1-hydroxyethyl)pyrrolidin-3-yl)oxy)-2-fluorobenzonitrile;
4-(((3S,4S)-1-((5-chloropyridin-2-yl)sulfonyl)-4-hydroxy-4-(2-hydroxypropan-2-yl)pyrrolidin-3-yl)oxy)-2-fluorobenzonitrile;
4-(((3S,4S)-1-((5-chloropyridin-2-yl)sulfonyl)-4-hydroxy-4-(hydroxymethyl)pyrrolidin-3-yl)oxy)-2-fluoro-5-(2,2,2-trifluoroethoxy)benzonitrile;
4-(((3S,4R)-1-((2-cyano-4-methylphenyl)sulfonyl)-4-hydroxy-4-(hydroxymethyl)pyrrolidin-3-yl)oxy)-2-fluorobenzonitrile;
4-(((3S,4R)-1-((2-cyano-4-ethylphenyl)sulfonyl)-4-hydroxy-4-(hydroxymethyl)pyrrolidin-3-yl)oxy)-2-fluorobenzonitrile;
4-(((3R,4S)-4-(4-cyano-3-fluorophenoxy)-3-hydroxy-3-(hydroxymethyl)pyrrolidin-1-yl) sulfonyl)-[1,1'-biphenyl]-3-carbonitrile;
4-(((3S,4R)-1-((2-cyano-4-(prop-1-yn-1-yl)phenyl)sulfonyl)-4-hydroxy-4-(hydroxymethyl)pyrrolidin-3-yl)oxy)-2-fluorobenzonitrile;
4-(((3S,4R)-1-((2-cyano-4-ethynylphenyl)sulfonyl)-4-hydroxy-4-(hydroxymethyl)pyrrolidin-3-yl)oxy)-2-fluorobenzonitrile;
4-(((3S,4R)-1-((2-cyano-4-((trimethylsilyl)ethynyl)phenyl)sulfonyl)-4-hydroxy-4-(hydroxymethyl)pyrrolidin-3-yl)oxy)-2-fluorobenzonitrile;
2-fluoro-4-(((3S,4R)-4-hydroxy-4-(hydroxymethyl)-1-((4-(prop-1-yn-1-yl)phenyl)sulfonyl)pyrrolidin-3-yl)oxy)benzonitrile;
2-fluoro-4-(((3S,4R)-4-hydroxy-4-(hydroxymethyl)-1-((6-(prop-1-yn-1-yl)pyridin-3-yl)sulfonyl)pyrrolidin-3-yl)oxy)benzonitrile;
4-(((3S,4R)-1-((4-cyano-2-(prop-1-yn-1-yl)phenyl)sulfonyl)-4-hydroxy-4-(hydroxymethyl)pyrrolidin-3-yl)oxy)-2-fluorobenzonitrile;
4-(((3S,4R)-1-((2-ethynyl-4-(trifluoromethyl)phenyl)sulfonyl)-4-hydroxy-4-(hydroxymethyl)pyrrolidin-3-yl)oxy)-2-fluorobenzonitrile;
4-(((3S,4R)-1-((6-(cyclopropylethynyl)pyridin-3-yl)sulfonyl)-4-hydroxy-4-(hydroxymethyl)pyrrolidin-3-yl)oxy)-2-fluorobenzonitrile;
2-fluoro-4-(((3S,4R)-4-hydroxy-4-(hydroxymethyl)-1-((5-(prop-1-yn-1-yl)pyridin-2-yl)sulfonyl)pyrrolidin-3-yl)oxy)benzonitrile;
4-(((3S,4R)-1-((5-ethynylpyridin-2-yl)sulfonyl)-4-hydroxy-4-(hydroxymethyl)pyrrolidin-3-yl)oxy)-2-fluorobenzonitrile;
4-(((3S,4R)-1-((5-(3,3-dimethylbut-1-yn-1-yl)pyridin-2-yl)sulfonyl)-4-hydroxy-4-(hydroxymethyl)pyrrolidin-3-yl)oxy)-2-fluorobenzonitrile;
2-fluoro-4-(((3S,4R)-4-hydroxy-4-(hydroxymethyl)-1-((5-(phenylethynyl)pyridin-2-yl)sulfonyl)pyrrolidin-3-yl)oxy)benzonitrile;
6-(((3R,4S)-4-(4-cyano-3-fluorophenoxy)-3-hydroxy-3-(hydroxymethyl)pyrrolidin-1-yl)sulfonyl)nicotinonitrile;
4-(((3S,4R)-1-((2-cyano-4-(trifluoromethoxy)phenyl)sulfonyl)-4-hydroxy-4-(hydroxymethyl)pyrrolidin-3-yl)oxy)-2-fluorobenzonitrile;
4-(((3S,4S)-4-(aminomethyl)-1-((5-chloropyridin-2-yl)sulfonyl)-4-hydroxypyrrolidin-3-yl)oxy)-2-fluorobenzonitrile;
4-(((3S,4R)-4-(aminomethyl)-1-((5-chloropyridin-2-yl)sulfonyl)-4-hydroxypyrrolidin-3-yl)oxy)-2-fluorobenzonitrile;
4-(((3S,4R)-4-(aminomethyl)-1-((4-chloro-2-cyanophenyl)sulfonyl)-4-hydroxypyrrolidin-3-yl)oxy)-2-fluorobenzonitrile;
4-(((3S,4R)-1-((4-chloro-2-cyanophenyl)sulfonyl)-4-hydroxy-4-(((2-hydroxyethyl)amino)methyl)pyrrolidin-3-yl)oxy)-2-fluorobenzonitrile;
4-(((3S,4S)-1-((2-cyano-4-(trifluoromethyl)phenyl)sulfonyl)-4-hydroxy-4-((methylamino)methyl)pyrrolidin-3-yl)oxy)-2-fluorobenzonitrile;
4-(((3S,4S)-1-((2-cyano-4-(trifluoromethyl)phenyl)sulfonyl)-4-((ethylamino)methyl)-4-hydroxypyrrolidin-3-yl)oxy)-2-fluorobenzonitrile;
4-(((3S,4S)-1-((2-cyano-4-(trifluoromethyl)phenyl)sulfonyl)-4-hydroxy-4-((isopropylamino)methyl)pyrrolidin-3-yl)oxy)-2-fluorobenzonitrile;
4-(((3S,4S)-4-(aminomethyl)-1-((4-chloro-2-cyanophenyl)sulfonyl)-4-hydroxypyrrolidin-3-yl)oxy)-2-fluorobenzonitrile;
4-(((3S,4S)-4-(aminomethyl)-1-((4-chloro-1-methyl-1H-pyrazol-5-yl)sulfonyl)-4-hydroxypyrrolidin-3-yl)oxy)-2-fluorobenzonitrile, 2,2,2-trifluoroacetate;
4-(((3S,4S)-4-(aminomethyl)-1-((5-fluoropyridin-2-yl)sulfonyl)-4-hydroxypyrrolidin-3-yl)oxy)-2-fluorobenzonitrile, 2,2,2-trifluoroacetate;
5-(((3S,4S)-3-(aminomethyl)-4-(4-cyano-3-fluorophenoxy)-3-hydroxypyrrolidin-1-yl)sulfonyl)picolinonitrile, 2,2,2-trifluoroacetate;
4-(((3S,4S)-4-(aminomethyl)-1-((5-(difluoromethyl)pyridin-2-yl)sulfonyl)-4-hydroxypyrrolidin-3-yl)oxy)-2-fluorobenzonitrile;
4-(((3S,4S)-4-(aminomethyl)-4-hydroxy-1-((6-(trifluoromethyl)pyridin-3-yl)sulfonyl)pyrrolidin-3-yl)oxy)-2-fluorobenzonitrile;
4-(((3S,4S)-4-(aminomethyl)-1-((5-chloropyridin-2-yl)sulfonyl)-4-hydroxypyrrolidin-3-yl)oxy)benzonitrile;

4-(((3S,4S)-4-(aminomethyl)-1-((5-(difluoromethoxy) pyridin-2-yl)sulfonyl)-4-hydroxypyrrolidin-3-yl)oxy)-2-fluorobenzonitrile;

4-(((3S,4S)-4-(aminomethyl)-4-hydroxy-1-((5-(trifluoromethoxy)pyridin-2-yl)sulfonyl)pyrrolidin-3-yl)oxy)-2-fluorobenzonitrile;

4-(((3S,4S)-4-(aminomethyl)-4-hydroxy-1-((6-(trifluoromethoxy)pyridin-3-yl)sulfonyl)pyrrolidin-3-yl)oxy)-2-fluorobenzonitrile;

4-(((3S,4S)-4-(aminomethyl)-4-hydroxy-1-((5-iodopyridin-2-yl)sulfonyl)pyrrolidin-3-yl)oxy)-2-fluorobenzonitrile;

4-(((3S,4S)-4-(aminomethyl)-1-((5-bromopyridin-2-yl)sulfonyl)-4-hydroxypyrrolidin-3-yl)oxy)-2-fluorobenzonitrile;

4-(((4S,5R)-2-((4-chloro-2-cyanophenyl)sulfonyl)-9-methyl-6-oxa-2,9-diazaspiro[4.5]decan-4-yl)oxy)-2-fluorobenzonitrile;

4-(((4S,5S)-2-((4-chloro-2-cyanophenyl)sulfonyl)-6-oxa-2,9-diazaspiro[4.5]decan-4-yl)oxy)-2-fluorobenzonitrile;

4-(((5S,9S)-7-((4-chloro-2-cyanophenyl)sulfonyl)-2-oxo-1-oxa-3,7-diazaspiro[4.4]nonan-9-yl)oxy)-2-fluorobenzonitrile;

4-(((5R,9S)-7-((4-chloro-2-cyanophenyl)sulfonyl)-2-oxo-1-oxa-3,7-diazaspiro [4.4]nonan-9-yl)oxy)-2-fluorobenzonitrile;

4-(((3S,4R)-4-((R)-1-aminoethyl)-1-((5-chloropyridin-2-yl) sulfonyl)-4-hydroxypyrrolidin-3-yl)oxy)-2-fluorobenzonitrile;

4-(((3S,4R)-4-((S)-1-aminoethyl)-1-((5-chloropyridin-2-yl)sulfonyl)-4-hydroxypyrrolidin-3-yl)oxy)-2-fluorobenzonitrile; and ((3R,4S)-1-((5-chloropyridin-2-yl) sulfonyl)-4-(4-cyano-3-fluorophenoxy)-3-hydroxypyrrolidin-3-yl)methyl 2-aminoacetate;

or a pharmaceutically acceptable salt thereof.

6. The method of claim 1 wherein the compound is 4-(((3S,4S)-4-(aminomethyl)-1-((5-chloropyridin-2-yl)sulfonyl)-4-hydroxypyrrolidin-3-yl)oxy)-2-fluorobenzonitrile illustrated by a chemical structure of

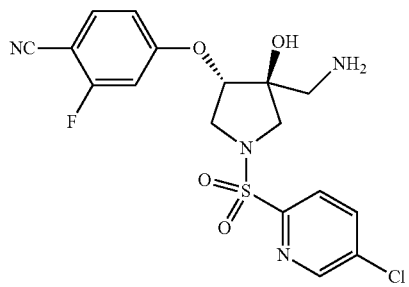 [SMILES: N#Cc1ccc(O[C@H]2CN(S(=O)(=O)c3ccc(Cl)cn3)C[C@@]2(O)CN)cc1F]

or a pharmaceutically acceptable salt thereof.

7. The method of claim 1 wherein the compound or pharmaceutically acceptable salt thereof is administered orally.

8. The method of claim 1 wherein the compound or pharmaceutically acceptable salt thereof is administered intravenously.

9. The method of claim 1 wherein the compound or pharmaceutically acceptable salt thereof is administered by inhalation.

10. The method of claim 1 wherein the disease is ocular edema.

11. The method of claim 1 wherein the disease is glaucoma.

12. The method of claim 1 wherein the disease is retinopathy.

13. The method of claim 6 wherein the disease is ocular edema.

14. The method of claim 6 wherein the disease is glaucoma.

15. The method of claim 6 wherein the disease is retinopathy.

16. The method of claim 6 wherein the compound is

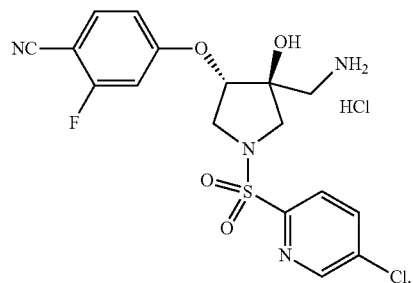 [SMILES: N#Cc1ccc(O[C@H]2CN(S(=O)(=O)c3ccc(Cl)cn3)C[C@@]2(O)CN)cc1F ; Cl]

17. The method of claim 16 wherein the disease is ocular edema.

18. The method of claim 16 wherein the disease is glaucoma.

19. The method of claim 16 wherein the disease is retinopathy.

20. The method of claim 1 wherein the compound is 4-(((3S,4R)-4-(aminomethyl)-1-((5-chloropyridin-2-yl) sulfonyl)-4-hydroxypyrrolidin-3-yl)oxy)benzonitrile illustrated by a chemical structure of

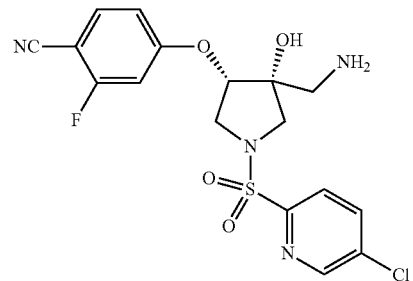 [SMILES: N#Cc1ccc(O[C@H]2CN(S(=O)(=O)c3ccc(Cl)cn3)C[C@]2(O)CN)cc1F]

or a pharmaceutically acceptable salt thereof.

21. The method of claim 20 wherein the compound is

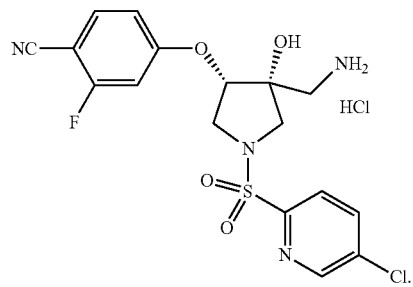 [SMILES: N#Cc1ccc(O[C@H]2CN(S(=O)(=O)c3ccc(Cl)cn3)C[C@]2(O)CN)cc1F ; Cl]

* * * * *